US012280123B2

(12) United States Patent
Larson et al.

(10) Patent No.: US 12,280,123 B2
(45) Date of Patent: *Apr. 22, 2025

(54) RECOMBINANT ADENOVIRUSES CARRYING TRANSGENES

(71) Applicant: EpicentRx, Inc., La Jolla, CA (US)

(72) Inventors: Christopher Larson, San Diego, CA (US); Bryan Oronsky, Los Altos Hills, CA (US); Tony R. Reid, San Diego, CA (US)

(73) Assignee: EPICENTRX, INC., La Jolla, CA (US)

(*) Notice: Subject to any disclaimer, the term of this patent is extended or adjusted under 35 U.S.C. 154(b) by 227 days.

This patent is subject to a terminal disclaimer.

(21) Appl. No.: 17/575,488

(22) Filed: Jan. 13, 2022

(65) Prior Publication Data

US 2022/0125946 A1 Apr. 28, 2022

Related U.S. Application Data

(63) Continuation of application No. 15/991,745, filed on May 29, 2018, now Pat. No. 11,253,608.

(60) Provisional application No. 62/511,822, filed on May 26, 2017.

(51) Int. Cl.
| *A61K 35/761* | (2015.01) |
| *A61K 47/68* | (2017.01) |
| *A61K 47/69* | (2017.01) |
| *A61K 48/00* | (2006.01) |
| *A61P 35/00* | (2006.01) |
| *C12N 7/02* | (2006.01) |
| *C12N 7/04* | (2006.01) |
| *C12N 15/62* | (2006.01) |
| *C12N 15/85* | (2006.01) |
| *C12N 15/86* | (2006.01) |

(52) U.S. Cl.
CPC ........ *A61K 47/6829* (2017.08); *A61K 35/761* (2013.01); *A61K 47/6851* (2017.08); *A61K 47/6901* (2017.08); *A61K 48/0025* (2013.01); *A61K 48/0066* (2013.01); *A61K 48/0083* (2013.01); *A61P 35/00* (2018.01); *C12N 7/025* (2013.01); *C12N 7/045* (2013.01); *C12N 15/62* (2013.01); *C12N 15/85* (2013.01); *C12N 15/86* (2013.01); *C12N 2710/10343* (2013.01)

(58) Field of Classification Search
CPC ............ A61K 47/6829; A61K 47/6851; A61K 47/6901; A61K 48/0025; A61K 48/0066; A61K 48/0083; A61P 35/00; C12N 7/025; C12N 7/045; C12N 15/62; C12N 15/85; C12N 15/86; C12N 2710/10343
See application file for complete search history.

(56) References Cited

U.S. PATENT DOCUMENTS

| 11,253,608 | B2 | 2/2022 | Larson et al. | |
| 2003/0104625 | A1 | 6/2003 | Cheng et al. | |
| 2003/0133912 | A1* | 7/2003 | Davidson | C07K 14/005 435/235.1 |
| 2004/0091456 | A1* | 5/2004 | Nakai | A61K 48/00 435/456 |
| 2005/0158278 | A1 | 7/2005 | Vogels et al. | |
| 2006/0292682 | A1* | 12/2006 | Hawkins | C12N 15/86 435/235.1 |
| 2016/0017294 | A1 | 1/2016 | Reid et al. | |
| 2016/0319304 | A1* | 11/2016 | Brown | C12N 15/86 |
| 2020/0123571 | A1* | 4/2020 | Burny | C12N 15/86 |

FOREIGN PATENT DOCUMENTS

| CN | 1298451 A | 6/2001 |
| CN | 102108355 A | 6/2011 |
| JP | 2008-507279 A | 3/2008 |
| JP | 2017-501695 A | 1/2017 |
| WO | WO-1999055831 A2 | 11/1999 |
| WO | WO-2000003029 A2 | 1/2000 |
| WO | WO-2000031285 A1 | 6/2000 |
| WO | WO-2000052186 A1 | 9/2000 |
| WO | WO-2006012393 A2 | 2/2006 |
| WO | WO-2010101921 A2 | 9/2010 |
| WO | WO-2015097220 A1 | 7/2015 |
| WO | WO-2016174200 A1 | 11/2016 |
| WO | WO-2018218240 A1 | 11/2018 |

OTHER PUBLICATIONS

Genbank Accession AY601635.1 (Human adenovirus type 5 strain NHRC Ad5FS 7151, complete genome, Apr. 12, 2006 [online], [Retrieved on Aug. 14, 2018]. IDS reference). (Year: 2006).*
Bett Dissertation, 1995, McMaster University, Ontario, Canada. (Year: 1995).*
Choi et al., (2013). "Oncolytic Adenovirus Expressing IL-23 and p35 Elicits IFN-[gamma]- and TNF-[alpha]-Co-Producing T Cell-Mediated Antitumor Immunity," PLoS One, 8(7):1-15.
Extended European Search Report and Written Opinion mailed Feb. 22, 2021, for European Patent Application No. 18806954.6, 11 pages.
GenBank Accession No. AY601635.1, Human adenovirus type 5 strain NHRC Ad5FS 7151, complete genome, Apr. 12, 2006 [online]. [Retrieved on Aug. 14, 2018). Available online at <https://www.ncbi.nlm.nih.gov/nuccore/AY601635.1?&feature=CDS>, 18 pages.
International Search Report and Written Opinion mailed Oct. 16, 2018, for International Application No. PCT/2018/034888, 11 pages.
Larson et al., (2015). "Going Viral: A Review Of Replication-Selective Oncolytic Adenoviruses," Oncotarget, 6(24):19976-89.

(Continued)

Primary Examiner — Catherine S Hibbert
(74) Attorney, Agent, or Firm — Morrison & Foerster LLP

(57) ABSTRACT

Disclosed herein are recombinant adenoviruses with one or more nucleotide sequences inserted between two viral transcription units, formulations comprising the recombinant adenoviruses, and methods of treatment using the recombinant adenoviruses. In some embodiments, the one or more nucleotide sequences are inserted in an IX-E2 insertion site and/or an L5-E4 insertion site.

17 Claims, 14 Drawing Sheets

Specification includes a Sequence Listing.

(56) References Cited

OTHER PUBLICATIONS

Leppard et al., (1997). "E4 Gene Function In Adenovirus, Adenovirus Vector And Adeno-Associated Virus Infections," J. Gen. Virol., 78:2131-8.

Mizuguchi et al., (2000). "IRES-Dependent Second Gene Expression Is Significantly Lower Than Cap-Dependent First Gene Expression In A Bicistronic Vector," Mol. Ther., 1(4):376-82.

NCBI Reference Sequence AC_000008.1, "Human Adenovirus 5, Complete Genome," Aug. 13, 2018, Retrieved on May 8, 2020, Available online at <https://www.ncbi.nlm.nih.gov/nuccore/AC_000008>, 14 pages.

Seila et al., (2008). "Divergent Transcription From Active Promoters," Science, 322(5909):1849-51.

\* cited by examiner

Initial IX-E2 design

Revised IX-E2 design

A549 Cells

HT29 Cells

ADS12 Cells

F244 Cells

RECOMBINANT ADENOVIRUSES CARRYING TRANSGENES

CROSS-REFERENCE TO RELATED APPLICATIONS

This application is a Continuation of U.S. patent application Ser. No. 15/991,745, filed May 29, 2018, now U.S. Pat. No. 11,253,608, which claims priority to U.S. Provisional Patent Application No. 62/511,822, filed May 26, 2017, all of which are hereby incorporated by reference in the present disclosure in their entirety.

STATEMENT REGARDING SEQUENCE LISTING

The content of the following submission on ASCII text file is incorporated herein by reference in its entirety: a computer readable form (CRF) of the Sequence Listing (file name: 203592000301SEQLIST.TXT, date recorded: Jan. 12, 2022, size: 130,855 bytes).

FIELD OF THE INVENTION

The invention described herein generally relates to the fields of virology, virotherapy, and molecular biology.

BACKGROUND

The uses of virotherapy to treat diseases such as cancer encompass employing replication-selective viruses armed with therapeutic genes or transgenes. Of the variety of infectious viral species developed as virotherapy agents, adenoviruses have emerged as one of the most promising because not only are they minimally toxic to normal non-transformed cells but their genomes, comprised of multiple endogenous genes, are amenable to manipulation, which generally takes the form of deletion of endogenous genes and insertion of exogenous ones. The downside to this manipulation is that most endogenous gene deletions or exogenous gene additions slow down or attenuate the replicative and infectivity potential of the virus. (Larson et al., Oncotarget, 6(24):19976-89 (2015))

The reduced replication efficiency of viruses carrying transgenes in these regions is undesirable because, such as in the case of an oncolytic virus for the treatment of cancer, it impairs the ability of the virus to multiply within tumors and infect neighboring cancerous cells, decreases the number of viral genome copies within infected cells and therefore likely reduces transcription of the therapeutic transgene, and increases the size of production cultures required to manufacture the virus. Therefore, a need exists for a new method to improve the ability of recombinant adenoviruses to replicate to high levels in targeted cells or tissues such as in tumors, thereby rapidly turning the targeted cells or tissues into a "factory" for the production of particular exogenous gene products.

Typically, to have oncolytic viruses express two or more separate protein or polypeptide chains requires the use of more than one virus vector or the use of linker, such as an internal ribosome entry site (IRES), between two transgenes. Both methods have significant drawbacks. Two or more virus vectors may not all express well within a single cell or tissue. As known in the art, the sequence downstream of the IRES is expressed at much lower levels than the sequence upstream. (Mizuguchi et al., Mol. Ther. 1(4):376-82 (2000)) In addition, the linker, being non-endogenous, has the potential for immunogenicity. Therefore, a need exists for more efficient viral vectors to express more than one peptide chain within a single virus.

SUMMARY OF THE INVENTION

The invention is based, in part, upon the discovery that recombinant adenoviruses with one or more nucleotide sequences inserted between two viral transcription units in the viral genome can efficiently replicate and express the nucleotide sequences in targeted cells or tissues, do not significantly impact the oncolytic activity of the virus. The vectors of this invention can be advantageously used where equal levels of two or more transgenes are desired or to express completely native chains from dual chain proteins.

In one aspect, the invention provides a recombinant adenovirus comprising a nucleotide sequence inserted in an insertion site, wherein the insertion site is located between the stop codon of a first viral transcription unit and the stop codon of a second viral transcription unit, wherein the stop codon of the first viral transcription unit is nearer to the stop codon of the second viral transcription unit than the start site of the first viral transcription unit is to the stop codon of the second viral transcription unit, wherein the stop codon of the second viral transcription is nearer to the stop codon of the first viral transcription unit than the start site of the second viral transcription unit is to the stop codon of the first viral transcription unit, and wherein there is no viral transcription unit between the first viral transcription unit and the second viral transcription unit before the nucleotide sequence is inserted.

In certain embodiments, the first viral transcription unit is adenovirus IX gene and the second viral transcription unit is adenovirus IVa2 gene. In certain embodiments, the first viral transcription unit is adenovirus fiber gene and the second viral transcription unit is ORF6 or ORF6/7 of adenovirus E4 gene. In certain embodiments, the recombinant adenovirus is a type 5 adenovirus (Ad5). In certain embodiments, the recombinant adenovirus is a type 35 adenovirus (Ad35).

In certain embodiments, a nucleotide sequence in inserted in the IX-E2 insertion site. In certain embodiments, the IX-E2 insertion site is located between the stop codon of adenovirus IX gene and the stop codon of adenovirus IVa2 gene. In certain embodiments, the nucleotide sequence is inserted between nucleotides corresponding to about 4029 and 4093 of the Ad5 genome (SEQ ID NO: 1). In certain embodiments, the nucleotide sequence is inserted between nucleotides corresponding to 4029 and 4050, nucleotides corresponding to 4050 and 4070, or nucleotides corresponding to 4070 and 4093 of the Ad5 genome (SEQ ID NO: 1). In certain embodiments, the nucleotide sequence is inserted between nucleotides corresponding to about 3899 and 3970 of the Ad35 genome (SEQ ID NO: 41). In certain embodiments, the nucleotide sequence is inserted between nucleotides corresponding to 3899 and 3920, nucleotides corresponding to 3920 and 3940, or nucleotides corresponding to 3940 and 3970 of the Ad35 genome (SEQ ID NO: 41).

In certain embodiments, a nucleotide sequence is inserted in an L5-E4 insertion site. In certain embodiments, the L5-E4 insertion site is located between the stop codon of adenovirus fiber gene and the stop codon of ORF6 or ORF6/7 of the adenovirus E4 gene. In certain embodiments, the nucleotide sequence is inserted between nucleotides corresponding to 32785 to 32916 of the Ad5 genome (SEQ ID NO: 1). In certain embodiments, the nucleotide sequence is inserted between nucleotides corresponding to 32785 and 32800, nucleotides corresponding to 32800 and 32820, nucleotides corresponding to 32820 and 32840, nucleotides corresponding to 32840 and 32860, nucleotides corresponding to 32860 and 32880, nucleotides corresponding to 32880 and 32900, or nucleotides corresponding to about 32901 and 32916 of the Ad5 genome (SEQ ID NO: 1). In certain embodiments, the nucleotide sequence is inserted between nucleotides corresponding to about 31799 and 31821 of the Ad35 genome (SEQ ID NO: 41). In certain embodiments, the nucleotide sequence is inserted between nucleotides corresponding to 31799 and 32810, or nucleotides corresponding to 32810 and 31821 of the Ad35 genome (SEQ ID NO: 41).

In certain embodiments, the foregoing recombinant adenovirus further comprises a nucleotide sequence inserted in an E1b-19K insertion site, an E3 insertion site, or an E4 insertion site. In certain embodiments, the E1b-19K insertion site is located between the start site of E1b-19K and the start site of E1b-55K. In certain embodiments, the E1b-19k insertion site is located between the start site of E1b-19K and the stop codon of E1b-19K. In certain embodiments, the E3 insertion site is located between the stop codon of adenovirus pVIII gene and the start site of adenovirus Fiber gene.

In certain embodiments, the invention provides a recombinant adenovirus comprising a first nucleotide sequence inserted in an IX-E2 insertion site and a second nucleotide sequence inserted in an L5-E4 insertion site.

In certain embodiments, the first nucleotide sequence is inserted between nucleotides corresponding to about 4029 and 4093 of the Ad5 genome (SEQ ID NO: 1). In certain embodiments, the first nucleotide sequence is inserted between nucleotides corresponding to 4029 and 4050, nucleotides corresponding to 4050 and 4070, or nucleotides corresponding to 4070 and 4093 of the Ad5 genome (SEQ ID NO: 1). In certain embodiments, the first nucleotide sequence is inserted between nucleotides corresponding to about 3899 and 3970 of the Ad35 genome (SEQ ID NO: 41). In certain embodiments, the first nucleotide sequence is inserted between nucleotides corresponding to 3899 and 3920, nucleotides corresponding to 3920 and 3940, or nucleotides corresponding to 3940 and 3970 of the Ad35 genome (SEQ ID NO: 41).

In certain embodiments, the second nucleotide sequence is inserted between nucleotides corresponding to 32785 to 32916 of the Ad5 genome (SEQ ID NO: 1). In certain embodiments, the second nucleotide sequence is inserted between nucleotides corresponding to 32785 and 32800, nucleotides corresponding to 32800 and 32820, nucleotides corresponding to 32820 and 32840, nucleotides corresponding to 32840 and 32860, nucleotides corresponding to 32860 and 32880, nucleotides corresponding to 32880 and 32900, or nucleotides corresponding to about 32901 and 32916 of the Ad5 genome (SEQ ID NO: 1). In certain embodiments, the second nucleotide sequence is inserted between nucleotides corresponding to about 31799 and 31821 of the Ad35 genome (SEQ ID NO: 41). In certain embodiments, the second nucleotide sequence is inserted between nucleotides corresponding to 31799 and 32810, or nucleotides corresponding to 32810 and 31821 of the Ad35 genome (SEQ ID NO: 41).

In certain embodiments, the nucleotide sequence, the first nucleotide sequence, and/or the second nucleotide sequence comprises at least one transgene. In certain embodiments, the nucleotide sequence further comprises a promoter, wherein the transgene is operably linked to the promoter.

In certain embodiments, the recombinant adenovirus comprises, in a 5' to 3' orientation: (i) a first polyadenylation signal; (ii) a promoter; (iii) a transgene; (iv) a second polyadenylation signal; and (v) a third polyadenylation signal; wherein the transgene is operably linked to the promoter. In some embodiments, the nucleotide sequence, the first nucleotide sequence, and/or the second nucleotide sequence (comprising one or more transgenes) is inserted between the first polyadenylation signal and the third polyadenylation signal. In some embodiments, the one or more transgenes is inserted between the first polyadenylation signal and the third polyadenylation signal. In certain embodiments, wherein the second polyadenylation signal is in the opposite transcriptional direction of the third polyadenylation signal.

In certain embodiments, the nucleotide sequence is inserted in the L5-E4 insertion site, and the first polyadenylation signal is the polyadenylation signal of the fiber (L5) gene, the second polyadenylation signal is the polyadenylation signal of the transgene, and the third polyadenylation signal is the polyadenylation signal of the ORF6 or ORF6/7 of the adenovirus E4 gene. In certain embodiments, the nucleotide sequence is inserted in the IX-E2 insertion site, and the first polyadenylation signal is the polyadenylation signal of the IX gene, the second polyadenylation signal is the polyadenylation signal of the transgene, and the third polyadenylation signal is the polyadenylation signal of the adenovirus IVa2 gene.

In certain embodiments, the recombinant adenovirus comprises, in a 5' to 3' orientation: (i) a first polyadenylation signal; (ii) a second polyadenylation signal; (iii) a promoter; (iv) a transgene; (v) a third polyadenylation signal; and (vi) a fourth polyadenylation signal, and the transgene is operably linked to the promoter. In some embodiments, the nucleotide sequence, the first nucleotide sequence, and/or the second nucleotide sequence (comprising one or more transgenes) is inserted between the first polyadenylation signal and the fourth polyadenylation signal. In some embodiments, the one or more transgenes is inserted between the first polyadenylation signal and the fourth polyadenylation signal. In certain embodiments, wherein the second polyadenylation signal is in the opposite transcriptional direction of the first polyadenylation signal. In certain embodiments, wherein the fourth polyadenylation signal is in the opposite transcriptional direction of the third polyadenylation signal.

In certain embodiments, the nucleotide sequence is inserted in the L5-E4 insertion site, and the first polyadenylation signal is the polyadenylation signal of the fiber (L5) gene, the third polyadenylation signal is the polyadenylation signal of the transgene, and the fourth polyadenylation signal is the polyadenylation signal of the ORF6 or ORF6/7 of the adenovirus E4 gene. In certain embodiments, the nucleotide sequence is inserted in the IX-E2 insertion site, the first polyadenylation signal is the polyadenylation signal of the IX gene, the third polyadenylation signal is the polyadenylation signal of the transgene, and the fourth polyadenylation signal is the polyadenylation signal of the adenovirus IVa2 gene.

In certain embodiments, the promoter is a ubiquitous promoter, a tissue-specific promoter, or tumor-specific promoter.

In certain embodiments, the IX-E2 insertion site comprises a deletion of about 5, 10, 15, 20, 25, 30, 35, 40, 45, 50, 55, or 60 nucleotides. In certain embodiments, the L5-E4 insertion site comprises a deletion of about 5, 10, 15, 20, 25, 30, 35, 40, 45, 50, 55, 60, 65, 70, 75, 80, 85, 90, 95, 100, 105, 110, 115, 120, 125, or 130 nucleotides.

In certain embodiments, the nucleotide sequence further comprises a consensus Kozak sequence. In certain embodiments, the recombinant adenovirus comprises a partial or complete deletion of the nucleotide sequence encoding the adenoviral death protein (ADP).

In certain embodiments, the foregoing recombinant adenovirus further comprises a nucleotide sequence inserted in an E1b-19K insertion site, an E3 insertion site, or an E4 insertion site. In certain embodiments, the E1b-19K insertion site is located between the start site of E1b-19K and the start site of E1b-55K. In certain embodiments, the E1b-19k insertion site is located between the start site of E1b-19K and the stop codon of E1b-19K. In certain embodiments, the E3 insertion site is located between the stop codon of adenovirus pVIII gene and the start site of adenovirus Fiber gene.

In certain embodiments, the E1b-19K insertion site comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent the start site of E1b-19K. In certain embodiments, the E1b-19K insertion site comprises a deletion of about 200 nucleotides, e.g., 202 nucleotides adjacent the start site of E1b-19K. In certain embodiments, the E1b-19K insertion site comprises a deletion corresponding to nucleotides 1714-1917 of the Ad5 genome (SEQ ID NO: 1), or the first therapeutic transgene is inserted between nucleotides corresponding to 1714 and 1917 of the Ad5 genome (SEQ ID NO: 1). In certain embodiments, the first therapeutic transgene is inserted between CTGACCTC (SEQ ID NO: 3) and TCACCAGG (SEQ ID NO: 2), e.g., the recombinant adenovirus comprises, in a 5' to 3' orientation, CTGACCTC (SEQ ID NO: 3), the first therapeutic transgene, and TCACCAGG (SEQ ID NO: 2).

In certain embodiments, the E3 insertion site comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or about 3000 to about 3185 nucleotides. In certain embodiments, the E3 insertion site is located between the stop codon of E3-10.5K and the stop codon of E3-14.7K. In certain embodiments, the E3 insertion site comprises a deletion of from about 500 to about 1551, from about 500 to about 1500, from about 500 to about 1000, from about 1000 to about 1551, from about 1000 to about 1500, or from about 1500 to about 1551 nucleotides adjacent the stop codon of E3-10.5K. In certain embodiments, the E3 insertion site comprises a deletion of about 1050 nucleotides adjacent the stop codon of E3-10.5K, e.g., the E3 insertion site comprises a deletion of 1063 nucleotides adjacent the stop codon of E3-10.5K. In certain embodiments, the E3 insertion site comprises a deletion corresponding to the Ad5 dl309 E3 deletion. In certain embodiments, the E3 insertion site comprises a deletion corresponding to nucleotides 29773-30836 of the Ad5 genome (SEQ ID NO: 1), or the second therapeutic transgene is inserted between nucleotides corresponding to 29773 and 30836 of the Ad5 genome (SEQ ID NO: 1). In certain embodiments, the E3 insertion site comprises a deletion corresponding to nucleotides 29119-30622 of the Ad35 genome (SEQ ID NO: 41).

In certain embodiments, the recombinant adenovirus comprises an E1a promoter having a deletion of a functional Pea3 binding site. For example, the virus may comprise a deletion of nucleotides corresponding to about −300 to about −250 upstream of the initiation site of E1a or a deletion of nucleotides corresponding to −305 to −255 upstream of the initiation site of E1a. In certain embodiments, the deletion comprises a deletion of nucleotides corresponding to 195-244 of the Ad5 genome (SEQ ID NO: 1), and/or the E1a promoter comprises the sequence GGTGTTTTGG (SEQ ID NO: 4).

In certain embodiments, the recombinant adenovirus comprises a modified TATA box-based promoter operably linked to a gene, wherein the modified TATA box-based promoter lacks a functional TATA box and permits selective expression of the gene in a hyperproliferative cell and/or a modified CAAT box-based promoter operably linked to a gene, wherein the modified CAAT box-based promoter lacks a functional CAAT box and permits selective expression of the gene in a hyperproliferative cell.

In certain embodiments, wherein the modified TATA box-based promoter is an early gene promoter. In certain embodiments, the modified TATA box-based promoter is an E1a promoter, E1b promoter, or E4 promoter. In certain embodiments, the modified TATA box-based promoter is an E1a promoter.

In certain embodiments, the modification included in the modified TATA box-based promoter comprises a deletion of the entire TATA box. In certain embodiments, the recombinant adenovirus comprises a deletion of nucleotides corresponding to −27 to −24, −31 to −24, −44 to +54, or −146 to +54 of the E1a promoter. In certain embodiments, the deletion comprises a deletion of nucleotides corresponding to 472 to 475, 468 to 475, 455 to 552, or 353 to 552 of the Ad5 genome (SEQ ID NO: 1).

In certain embodiments, the recombinant adenovirus comprises a polynucleotide deletion that results in a virus comprising the sequence CTAGGACTG (SEQ ID NO: 5), AGTGCCCG (SEQ ID NO: 44) and/or TATTCCCG (SEQ ID NO: 45).

In certain embodiments, the modified CAAT box-based promoter is an early gene promoter. In certain embodiments, the modified CAAT box-based promoter is an E1a promoter, E1b promoter, or E4 promoter. In certain embodiments, the modified CAAT box-based promoter is an E1a promoter.

In certain embodiments, the modification included in the modified CAAT box-based promoter comprises a deletion of the entire CAAT box. In certain embodiments, the recombinant adenovirus comprises a deletion of nucleotides corresponding to −76 to −68 of the E1a promoter.

In certain embodiments, the recombinant adenovirus comprises a deletion of nucleotides corresponding to 423 to 431 of the Ad5 genome (SEQ ID NO: 1). In certain embodiments, the recombinant adenovirus comprises a polynucleotide deletion that results in a virus comprising the sequence TTCCGTGGCG (SEQ ID NO: 46). In certain embodiments, the recombinant adenovirus comprises a deletion of nucleotides corresponding to 477 to 484 of the Ad35 genome (SEQ ID NO: 41).

In certain embodiments, the inserted nucleotide sequence comprises a first nucleotide sequence comprising a first transgene, and a second nucleotide sequence comprising a second transgene, wherein the first nucleotide sequence and the second nucleotide sequence are separated by a linker. In certain embodiments, the linker encodes a peptide cleavable by a protease or proteases. In certain embodiments, the linker encodes an internal ribosome entry site (IRES) or a self-cleaving 2A peptide. The IRES may, e.g., be selected from the group consisting of the encephalomyocarditis virus IRES, the foot-and-mouth disease virus IRES, and the poliovirus IRES. In certain embodiments, wherein the nucleotide sequence is inserted in the IX-E2 insertion or the L5-E4 insertion site, wherein the recombinant adenovirus further comprise a third nucleotide sequence comprising a third transgene inserted in an E1b-19K insertion site, an E3 insertion site, or an E4 insertion site.

In certain embodiments, one or more of the nucleotide sequence, the first nucleotide sequence, the second nucleotide sequence, and the third nucleotide sequence comprises one or more transgenes.

In certain embodiments, one or more of the transgene, the first transgene, and the second transgene encodes a monomeric, dimeric, trimeric, tetrameric, or multimeric protein, or a part thereof. In certain embodiments, one or more of the transgene, the first transgene, and/or the second transgene encodes a RNA that has a therapeutic activity. In certain embodiments, one or more of the transgene, the first transgene, and/or the second transgene encodes a fusion protein comprising at least one binding domain.

In certain embodiments, one or more of the transgene, the first transgene, and the second transgene encodes an immunomodulatory molecule. In certain embodiments, the immunomodulatory molecule is a costimulatory ligand, a cytokine, or a cytokine receptor. In certain embodiments, the immunomodulatory molecule is selected from the group consisting of IL-1, IL-2, IL-3, IL-4, IL-5, IL-6, IL-7, IL-8, IL-9, IL-7, IL-10, IL-10 trap, IL-10R, IL-12A/p35, IL-12B/p40, IL-15, IL-15 receptor fusion protein, IL-23A/p19, IL24, IL-27, IL-33, IL-35, IL-15, an IL-15 receptor fusion protein, TGF-β, a TGF-β trap, an IL-10 trap, VEGF, indoleamin-2,3-dioxygenase (IDO), inducible T-cell co-stimulator ligand (ICOS-L), CD80, CD137L, TNF-α, IFN-α, IFN-β, IFN-γ, or GM-CSF, GITR ligand (GITRL), OX40 ligand (OX40L), CD40 ligand (CD40L), drug-inducible CD40 (iCD40), CD154, CD70, CD86, CD137, CD137L, BORIS/CTCFL, TNFSF9, FGF, ICAM, Podocalyxin, functional fragments thereof, and derivatives thereof.

In certain embodiments, one or more of the transgenes, the first transgene, and the second transgene encodes an antigen-binding molecule. In certain embodiments, the antigen-binding molecule is an anti-PD-1 antibody, an anti-TGF-β antibody, an anti-PD-L1 antibody, and an anti-CTLA-4 antibody, or functional fragments thereof.

In certain embodiments, one or more of the transgenes, the first transgene, and the second transgene encodes an antigen or a ligand to the antigen. In certain embodiments, the antigen is selected from the group consisting of CAIX, CEA, CDS, CD7, CD10, CD19, CD20, CD22, CD30, CD33, CD34, CD38, CD41, CD44, CD49f, CD56, CD74, CD80, CD133, CD138, a cytomegalovirus (CMV) infected cell antigen, 4-1BB, EGP-2, EGP-40, EpCAM, erbB2, erbB3, erbB4, FBP, Fetal acetylcholine receptor, KRAS, HPV E6, E7, BING-4, EphA3, calcium activated chloride channel-2, cyclin B 1, 9D7, Ep-CAM, PRAME, SSX-2, immature laminin receptor, folate receptor-a, telomerase, tyrosinase, melan-A, NY-ESO-1, GD2, GD3, hTERT, IL13R-a2, x-light chain, KDR, LeY, LI cell adhesion molecule, MAGE-AL MAGE-A3, MART1, MART2, MUC1, Mesothelin, HER-2/neu, EGFRvIII, NKG2D ligands, NY-ESO-1, gp100, TRP-1/-2, TRP-1/-2, P polypeptide, MC1R, prostate specific antigen, BRAF, androgen-receptor, β-catenin, BRCA1/2, CDK4, CML66, fibronectin, p53, TGF-βRII, T cell receptor, oncofetal antigen, 5T4, PSCA, PSMA, ROR1, TAG-72, VEGF-R2, WT-1, functional fragments thereof, and derivatives thereof.

In certain embodiments, one or more of the transgenes, the first transgene, and the second transgene encodes a toxin. In certain embodiments, the toxin is pseudomonas exotoxin, ricin toxin, or diphtheria toxin.

In certain embodiments, one or more of the transgenes, the first transgene, and the second transgene encodes an enzyme. In certain embodiments, the enzyme is selected from the group consisting of beta-glucuronidase, beta-galactosidase, beta-glucosidase, carboxypeptidase, beta-lactamase, esterase, metalloproteinase, relaxin, collagenase, streptokinase, arginase, NOS-2, fragments thereof, and derivatives thereof.

In certain embodiments, one or more of the transgenes, the first transgene, and the second transgene encodes a cell cycle control agent, a growth factor, an anticoagulant, a pro-drug activating gene, a tumor suppressor gene, an apoptotic gene, an anti-platelet agent, a clotting factor, a cystic fibrosis transmembrane conductance regulator (CFTR) protein, fragments thereof, or derivatives thereof.

In certain embodiments, one or more of the transgenes, the first transgene, and the second transgene encodes angiostatin, endostatin, acetylcholine, DKK1/Wnt, Ox40L, GITRL, secreted flagellin, thymidine kinase, functional fragments thereof, or derivatives thereof.

In certain embodiments, the recombinant adenovirus is oncolytic. In certain embodiments, the recombinant adenovirus selectively replicates in a hyperproliferative cell. In certain embodiments, the recombinant adenovirus selectively expresses a transgene in a hyperproliferative cell. In certain embodiments, the hyperproliferative cell is a tumor cell.

In another aspect, the invention provides an isolated nucleotide sequence comprising any of the foregoing recombinant adenovirus sequence, optionally wherein the nucleotide sequence is cDNA. In another aspect, the invention provides an isolated vector comprising the adenovirus nucleotide sequence. In another aspect, the invention provides an isolated cell comprising the adenovirus nucleotide sequence or the vector.

In another aspect, the invention provides a method of inhibiting proliferation of a tumor cell comprising exposing the tumor cell to an effective amount of any of the foregoing recombinant adenoviruses to inhibit proliferation of the tumor cell.

In another aspect, the invention provides a method of treating a condition in a subject. In some embodiments, the condition is cancer. The method comprises administering to the subject an effective amount of a recombinant adenoviruses described herein to treat the cancer disease in the subject.

In another aspect, the invention provides a method of inhibiting tumor growth in a subject in need thereof, wherein the method comprising administering to the subject to an effective amount of any of the foregoing recombinant adenoviruses to inhibit tumor growth. In certain embodiments, the tumor is selected from the group consisting of melanoma, squamous cell carcinoma of the skin, basal cell carcinoma, head and neck tumor, breast tumor, anal cancer, cervical cancer, non-small cell lung cancer, mesothelioma, small cell lung tumor, renal cell carcinoma, prostate tumor, gastroesophageal tumor, colorectal tumor, testicular tumor, bladder tumor, ovarian tumor, hepatocellular carcinoma, cholangiocarcinoma, brain tumor, endometrial tumor, neuroendocrine tumor, merkel cell carcinoma, gastrointestinal stromal tumor, a sarcoma, and pancreatic tumor.

In another aspect, the invention provides a method of treating a disease or condition in a subject in need thereof, wherein the method comprising administering to the subject an effective amount of any of the foregoing recombinant adenoviruses. In certain embodiments, the disease or condition is selected from the group consisting of an infection, diabetic retinopathy, psoriasis, rheumatoid arthritis, endometriosis, macular degenerative disorders and benign growth disorders such as prostate enlargement and lipomas, a vascular disorder, a cardiovascular disease, cirrhosis of the liver, a connective tissue disorder, a tumor, a vascular lesion, an ulcerative lesion, an inflammation, thrombosis, and neointima formation.

In certain embodiments, the subject is a mammal. In certain embodiments, the subject is a human. In certain embodiments, the subject is a pediatric human In certain embodiments, the subject is an adult human.

In certain embodiments, the recombinant adenovirus is administered by intramuscular, intravenous, intraarterial, intratumoral, intradermal, inhalation, transdermal, topical, eye drops, intranasal, transmucosal, and/or rectal administration.

In certain embodiments, the foregoing methods further comprising administering to the subject one or more therapies selected from the group consisting of surgery, radiation, chemotherapy, immunotherapy, hormone therapy, and virotherapy.

In certain embodiments, the foregoing methods further comprise administering to the subject one or more immune checkpoint modulators. In certain embodiments, the immune checkpoint modulator is an inhibitor, an antagonist, or an agonist of one or more molecules selected from the group consisting of PD-1, PD-L1, PD-L2, 2B4, TIGIT, LAG3, Tim3, BTLA, CD160, GITR, KIR, 4-1BB, and CTLA4.

In another aspect, the invention provides a pharmaceutical composition comprising any of the foregoing recombinant adenoviruses and at least one pharmaceutically acceptable carrier or diluent.

In another aspect, the invention provides a formulation for adenoviruses comprising:
a) one or more of any of the foregoing recombinant adenoviruses;
b) at least one buffer;
c) at least one tonicity modifier;
d) at least one sugar or at least one stabilizing agent, or both; and
wherein the formulation has a pH ranging between about 7.0 and about 9.0.

In certain embodiments, any of the foregoing formulations has an osmolarity of about 200 mOs/L to about 800 mOs/L. In certain embodiments, the recombinant adenovirus in any of the foregoing formulations is at concentration from about $1\times10^7$ vp/mL to $1\times10^{13}$ vp/mL.

These and other aspects and advantages of the invention are illustrated by the following figures, detailed description and claims.

DESCRIPTION OF THE DRAWINGS

The invention can be more completely understood with reference to the following drawings.

mCD80-(IX)mCD137L-(L5)mICAM1, labeled as 19K-IX-5], or the control virus [TAV-(19k)Empty-(IX)Empty-(L5) Empty, labeled as Empty].

Figure 13:
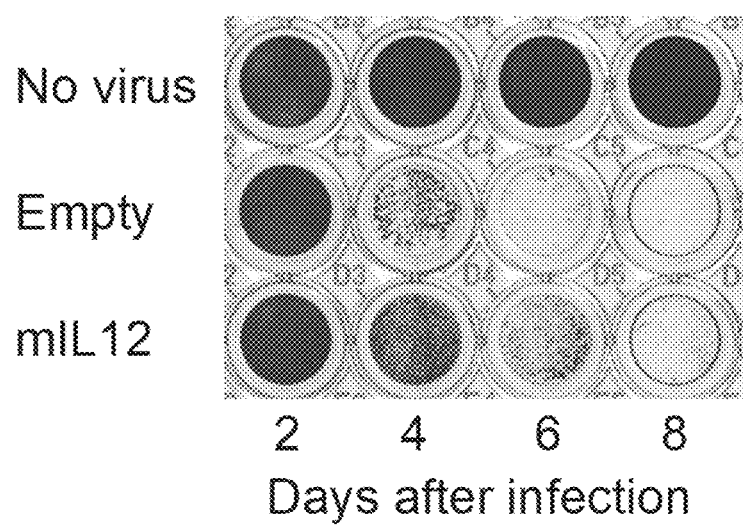

FIG. 13 depicts oncolytic activity of the viruses TAV-IX5-Empty (labeled "Empty") and TAV-IX5-mIL12 (labeled "mIL12") in A549 cells after infection at an MOI of 5. Wells were stained with crystal violet on the indicated days after infection.

Figure 14:
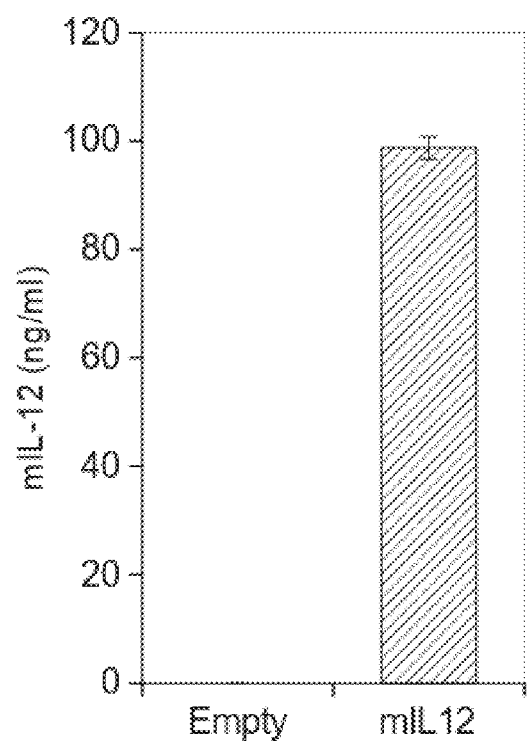

FIG. 14 transgene expression of the virus TAV-IX5-mIL12. A549 cells were infected with TAV-IX5-Empty (labeled "Empty") or TAV-IX5-mIL12 (labeled "mIL12") at an MOI of 5, and conditioned media was collected five days after infection and used in an ELISA to measure heterodimeric mouse IL-12. High levels of mouse IL-12 were expressed with the TAV-IX5-mIL12 virus and not the control TAV-IX5-Empty virus. Bars depict the mean IL-12 level of triplicate samples and error bars depict standard deviation.

DETAILED DESCRIPTION

The invention is based, in part, upon the discovery that recombinant adenoviruses with one or more nucleotide sequences inserted between two viral transcription units in the viral genome can efficiently replicate and express the nucleotide sequences in targeted cells or tissues.

I. Recombinant Adenovirus

Adenoviruses are non-enveloped and icosahedral viruses composed of a nucleocapsid and a double-stranded linear DNA genome. Adenoviruses replicate in the nucleus of mammalian cells using the host's replication machinery. The term "adenovirus" refers to any virus in the genus Adenoviridae including, but not limited to, human, bovine, ovine, equine, canine, porcine, murine, and simian adenovirus subgenera. In particular, human adenoviruses includes the A-F subgenera as well as the individual serotypes thereof, the individual serotypes and A-F subgenera including but not limited to human adenovirus types 1, 2, 3, 4, 4a, 5, 6, 7, 8, 9, 10, 11 (Ad11a and Ad11p), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. The term bovine adenoviruses includes, but is not limited to, bovine adenovirus types 1, 2, 3, 4, 7, and 10. The term canine adenoviruses includes, but is not limited to, canine types 1 (strains CLL, Glaxo, RI261, Utrect, Toronto 26-61) and 2. The term equine adenoviruses includes, but is not limited to, equine types 1 and 2. The term porcine adenoviruses includes, but is not limited to, porcine types 3 and 4.

In some embodiments, provided are recombinant viruses derived from human adenovirus types 5 and 35. The terms "viral vector" and "virus" are used interchangeably herein to refer to any of the obligate intracellular parasites having no protein-synthesizing or energy-generating mechanism.

The adenovirus replication cycle has two phases: an early phase, during which transcription units E1A, E1B, E2A, E2B, E3, and E4 are expressed. The proteins coded for by genes within these transcription units are mostly involved in regulation of viral transcription, in replication of viral DNA, and in suppression of the host response to infection. The L1-L5 transcription units are transcribed later in the viral reproductive cycle, and code mostly for proteins that make up components of the viral capsid or are involved in assembly of the capsid. The L1-L5 transcription units are expressed primarily from the major late promoter (MLP).

The general structure of the mature Adenovirion is conserved among different Adenoviral species. The Adenoviral capsid is composed of three major proteins (II, III, and IV) and five minor proteins, VI, VIII, IX, Ma, and IVa2. "IVa2 gene" used herein refers to the gene encoding the IVa2 protein, modified versions, and/or fragment thereof. "IX gene" used herein refers to the gene encoding the IX protein, modified versions, and/or fragment thereof.

Figure 1:
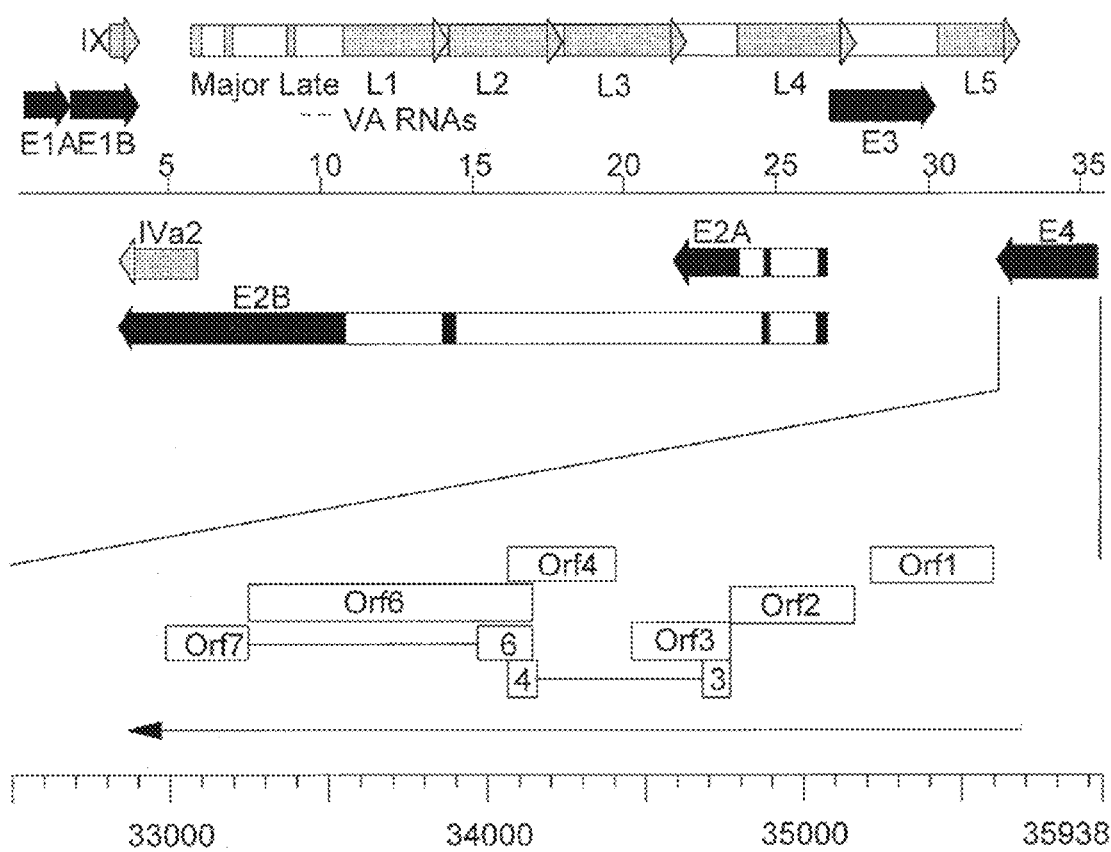
FIG. 1 is a graph depicting the genome organization of human Ad5. At the top of the figure the genome is represented as a line with lengths marked in kbp from the conventional left end. Thick arrows represent early and late transcription units (black and grey, respectively). Open boxes represent the major introns. The E4 gene is enlarged as a line scale with lengths in bp. The primary transcript is shown as a black arrow in a 5' to 3' direction and each of the potential encoded proteins is shown as an open box; proteins whose coding regions are split by intron sequences are shown as boxes linked by a line.

A schematic representation of the Ad5 genome and a detail of the E4 gene are shown in FIG. 1. Primary transcripts from E4 are subject to alternative splicing events and are predicted to encode seven different polypeptides: ORF1, ORF2, ORF3, ORF3/4, ORF4, ORFS, ORF6, and ORF6/7. (Leppard et al., Journal of General Virology, 78:2131-8 (1997)) "ORF" is used herein to refer to either the polypeptide or the nucleotide sequence encoding the polypeptide, modified versions, and/or fragment thereof.

In addition, the fiber protein (also known as protein IV or SPIKE) forms spikes that protrude from each vertex of the icosahedral capsid. "Fiber gene" used herein refers to the gene encoding the fiber protein, also known as L5 gene, modified versions, and/or fragment thereof.

A. Insertion Sites

In one aspect, the invention provides a recombinant adenovirus comprising a nucleotide sequence inserted in an insertion site, wherein the insertion site is located between the stop codon of a first viral transcription unit and the stop codon of a second viral transcription unit, wherein the stop codon of the first viral transcription unit is nearer to the stop codon of the second viral transcription unit than the start site of the first viral transcription unit is to the stop codon of the second viral transcription unit, wherein the stop codon of the second viral transcription is nearer to the stop codon of the first viral transcription unit than the start site of the second viral transcription unit is to the stop codon of the first viral transcription unit. In some embodiments, the first viral transcription unit and the second viral transcription unit are adjacent to each other in the adenoviral genome, e.g., there is no viral transcription unit between the first viral transcription unit and the second viral transcription unit before the nucleotide sequence is inserted.

The term "viral transcription unit" used herein refers a linear sequence of nucleotide sequence that extends from a transcription start site to a transcription stop site in the viral genome. The viral transcription unit may be naturally occurring, modified, or fragment thereof. The terms "viral transcription unit" and "virus gene" are used interchangeably herein.

In certain embodiments, the recombinant adenovirus is a human adenovirus. In some embodiments, the recombinant adenovirus is a human adenovirus type 1, 2, 3, 4, 4a, 5, 6, 7, 8, 9, 10, 11, 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, or 91. In some embodiment, the recombinant adenovirus is a type 5 adenovirus (Ad5) or a type 35 adenovirus (Ad35).

In certain embodiments, the first viral transcription unit is adenovirus IX gene and the second viral transcription unit is adenovirus IVa2 gene. In certain embodiments, the first viral transcription unit is adenovirus fiber gene and the second viral transcription unit is ORF6 or ORF6/7 of adenovirus E4 gene.

In certain embodiments, the insertion site is the IX-E2 insertion site. In certain embodiments, the IX-E2 insertion site is located between the stop codon of adenovirus IX gene and the stop codon of adenovirus IVa2 gene. In certain embodiments, the nucleotide sequence is inserted between nucleotides corresponding to 4029 and 4093 of the Ad5 genome (SEQ ID NO: 1). In certain embodiments, the nucleotide sequence is inserted between nucleotides corresponding to 4029 and 4050, nucleotides corresponding to 4051 and 4070, or nucleotides corresponding to 4071 and 4093 of the Ad5 genome (SEQ ID NO: 1). In certain embodiments, the nucleotide sequence is inserted between nucleotides corresponding to 3899 and 3970 of the Ad35 genome (SEQ ID NO: 41). In certain embodiments, the nucleotide sequence is inserted between nucleotides corresponding to 3899 and 3920, nucleotides corresponding to 3920 and 3940, or nucleotides corresponding to 3940 and 3970 of the Ad35 genome (SEQ ID NO: 41).

In some embodiments, the IX-E2 insertion site has at least 60%, at least 70%, at least 80%, at least 90%, at least 95%, or at least 99% identity to nucleotides corresponding to 4029 and 4093 of the Ad5 genome (SEQ ID NO: 1). In some embodiments, the IX-E2 insertion site has at least 60%, at least 70%, at least 80%, at least 90%, at least 95%, or at least 99% identity to nucleotides corresponding to 3899 and 3970 of the Ad35 genome (SEQ ID NO: 41).

In certain embodiments, the insertion site is an L5-E4 insertion site. In certain embodiments, the L5-E4 insertion site is located between the stop codon of adenovirus fiber gene and the stop codon of ORF6 or ORF6/7 of the adenovirus E4 gene. In certain embodiments, the nucleotide sequence is inserted between nucleotides corresponding to 32785 to 32916 of the Ad5 genome (SEQ ID NO: 1). In certain embodiments, the nucleotide sequence is inserted between nucleotides corresponding to 32785 and 32800, nucleotides corresponding to 32801 and 32820, nucleotides corresponding to 32821 and 32840, nucleotides corresponding to 32841 and 32860, nucleotides corresponding to 32861 and 32880, nucleotides corresponding to 32881 and 32900, or nucleotides corresponding to 32901 and 32916 of the Ad5 genome (SEQ ID NO: 1). In certain embodiments, the nucleotide sequence is inserted between nucleotides corresponding to 31799 and 31821 of the Ad35 genome (SEQ ID NO: 41). In certain embodiments, the nucleotide sequence is inserted between nucleotides corresponding to 31799 and 32810, or nucleotides corresponding to 32810 and 31821 of the Ad35 genome (SEQ ID NO: 41).

In some embodiments, the L5-E4 insertion site has at least 60%, at least 70%, at least 80%, at least 90%, at least 95%, or at least 99% identity to nucleotides corresponding to 32785 to 32916 of the Ad5 genome (SEQ ID NO: 1). In some embodiments, the L5-E4 insertion site has at least 60%, at least 70%, at least 80%, at least 90%, at least 95%, or at least 99% identity to nucleotides corresponding to 31799 and 31821 of the Ad35 genome (SEQ ID NO: 41).

Recombinant adenoviruses with insertions of exogenous nucleotide sequence in the IX-E2 insertion site and/or the L5-E4 insertion site have not been previously described. Such recombinant adenoviruses unexpectedly show very good tumor selective expression in tumor cells compared with in normal cells. In one aspect, the invention provides a method of expressing native proteins. In another aspect, the invention provides a method of expressing native structure, sush as dimeric or multimeric proteins.

In another aspect, the invention provides a method of expressing two or more therapeutic transgenes in a target cell. The method comprises exposing the cell to an effective amount of the recombinant virus described herein to express the target transgenes.

In certain embodiments, the nucleotide sequence comprises at least one transgene. In certain embodiments, the nucleotide sequence further comprises a promoter, wherein the transgene is operably linked to the promoter.

In certain embodiments, the recombinant adenovirus comprises, in a 5' to 3' orientation: (i) a first polyadenylation signal; (ii) a promoter; (iii) a transgene; (iv) a second polyadenylation signal; and (v) a third polyadenylation signal; wherein the transgene is operably linked to the promoter. In some embodiments, the nucleotide sequence, the first nucleotide sequence, and/or the second nucleotide sequence is inserted between the first polyadenylation signal and the third polyadenylation signal. In certain embodiments, wherein the second polyadenylation signal is in the opposite transcriptional direction of the third polyadenylation signal. In certain embodiments, the nucleotide sequence is inserted in the L5-E4 insertion site, and the first polyadenylation signal is the polyadenylation signal of the fiber (L5) gene, the second polyadenylation signal is the polyadenylation signal of the transgene, and the third polyadenylation signal is the polyadenylation signal of the ORF6 or ORF6/7 of the adenovirus E4 gene. In certain embodiments, the nucleotide sequence is inserted in the IX-E2 insertion site, and the first polyadenylation signal is the polyadenylation signal of the IX gene, the second polyadenylation signal is the polyadenylation signal of the transgene, and the third polyadenylation signal is the polyadenylation signal of the adenovirus IVa2 gene.

In certain embodiments, the recombinant adenovirus comprises, in a 5' to 3' orientation: (i) a first polyadenylation signal; (ii) a second polyadenylation signal; (iii) a promoter; (iv) a transgene; (v) a third polyadenylation signal; and (vi) a fourth polyadenylation signal, and the transgene is operably linked to the promoter. In some embodiments, the nucleotide sequence, the first nucleotide sequence, and/or the second nucleotide sequence is inserted between the first polyadenylation signal and the fourth polyadenylation signal. In certain embodiments, wherein the second polyadenylation signal is in the opposite transcriptional direction of the first polyadenylation signal. In certain embodiments, wherein the fourth polyadenylation signal is in the opposite transcriptional direction of the third polyadenylation signal. In certain embodiments, the nucleotide sequence is inserted in the L5-E4 insertion site, and the first polyadenylation signal is the polyadenylation signal of the fiber (L5) gene, the third polyadenylation signal is the polyadenylation signal of the transgene, and the fourth polyadenylation signal is the polyadenylation signal of the ORF6 or ORF6/7 of the adenovirus E4 gene. In certain embodiments, the nucleotide sequence is inserted in the IX-E2 insertion site, and the first polyadenylation signal is the polyadenylation signal of the IX gene, the third polyadenylation signal is the polyadenylation signal of the transgene, and the fourth polyadenylation signal is the polyadenylation signal of the adenovirus IVa2 gene.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of affecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

In certain embodiments, the promoter is a ubiquitous promoter, a tissue-specific promoter, or tumor-specific promoter.

In some embodiments, the transgene is operably linked to a ubiquitous promoter, such as βAct promoter, EF1 promoter, EGR1 promoter, eIF4A1 promoter, FerH promoter, FerL promoter, GAPDH promoter, GRP78 promoter, GRP94 promoter, HSP70 promoter, β-Kin promoter, PGK-1 promoter, ROSA promoter, Ubiquitin B promoter, SV40 promoter, or CMV promoter. In one embodiment, high-level constitutive expression will be desired. Examples of useful constitutive promoters include, without limitation, the retroviral Rous sarcoma virus (RSV) LTR promoter (optionally with the RSV enhancer), the cytomegalovirus (CMV) promoter (optionally with the CMV enhancer) (see, e.g. Boshart et al, Cell, 41:521-530 (1985)), the SV40 promoter, the dihydrofolate reductase promoter, the β-actin promoter, the phosphoglycerol kinase (PGK) promoter, and the EF1α promoter (Invitrogen). Inducible promoters, regulated by exogenously supplied compounds, are also useful and include, the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al. Proc. Natl. Acad. Sci. USA, 93:3346-3351 (1996)), the tetracycline-repressible system (Gossen et al, Proc. Natl. Acad Sci. USA, 89:5547-5551 (1992)), the tetracycline-inducible system (Gossen et al, Science. 268: 1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Other types of inducible promoters which may be useful in this context are those which are regulated by a specific physiological state, e.g., temperature, acute phase, a particular differentiation state of the cell, or in replicating cells only.

In another embodiment, a native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter, such as B29 promoter (B cells), CD14 promoter (Monocytic cells), CD43 promoter (Leukocytes & platelets), CD45 promoter (Haematopoietic cells), CD68 promoter (Macrophages), Desmin promoter (Muscle), Elastase-1 promoter (Pancreatic acinar cells), Endoglin promoter (Endothelial cells), Endoglin promoter (Endothelial cells), Flt-1 promoter (Endothelial cells) GFAP promoter (Astrocytes), GPIIb promoter (Megakaryocytes), ICAM-2 promoter (Endothelial cells), mouse INF-β promoter (Hematopoietic cells), Mb promoter (Muscle), Nphsl promoter (Podocytes), OG-2 promoter (Osteoblasts, Odonblasts), SP-B promoter (Lung), SYN1 promoter (Neurons), WASP promoter (Hematopoietic cells), SV40/bAlb promoter (Liver), or SV40/hAlb promoter (Liver). Tissue-specific promoters are active in a specific type of cells or tissues. For instance, if expression in skeletal muscle is desired, a promoter active in muscle should be used. These include the promoters from genes encoding skeletal α-actin, myosin light chain 2A, dystrophin, muscle creatine kinase, as well as synthetic muscle promoters with activities higher than naturally-occurring promoters (see Li et al., Nat. Biotech., 17:241-245 (1999)). Examples of promoters that are tissue-specific are known for liver (albumin, Miyatake et al. J. Virol. 71:5124-32 (1997); hepatitis B virus core promoter, Sandig et al., Gene Ther., 3:1002-9 (1996); alpha-fetoprotein (AFP). Arbuthnot et al., Hum. Gene Ther., 7:1503-14 (1996)), bone osteocalcin (Stein et al., Mol. Biol. Rep., 24:185-96 (1997)), bone sialoprotein (Chen et al., J. Bone Miner. Rep., 11:654-64 (1996)), lymphocytes (CD2, Hansal et al., J. Immumnol., 161:1063-8 (1998); immunogllobulin heavy chain; T cell receptor a chain), neuronal such as neuron-specific enolase (NSE) promoter (Andersen et al., Cell. Mol. Neurobiol., 13:503-15 (1993)), neurofilament light-chain gene (Piccioli et al., Proc. Natl. Acad. Sci. USA, 88:5611-5 (1991)), and the neuron-specific vgf gene (Piccioli et al., Neuron. 15:373-84 (1995)), among others.

Another embodiment of the transgene includes a transgene operably linked to a tumor-specific promoter, such as AFP promoter (Hepatocellular carcinoma), CCKAR promoter (Pancreatic cancer), CEA promoter (Epithelial cancers), c-erbB2 promoter (Breast & pancreas cancer), COX-2 promoter (Tumor), E2F-1 promoter (Tumor), HE4 promoter (Tumor), LP promoter (Tumor), MUC1 promoter (Carcinoma cells), PSA promoter (Prostate and prostate cancers), Survivin promoter (Tumor), TRP1 promoter (Melanocytes & melanoma), Tyr promoter (Melanocytes & melanoma), CXCR4 promoter (Tumor), or AFP/hAFP promoter (Hepatocellular carcinoma). Tumor-specific promoter are active specifically in tumor cells.

In certain embodiments, the nucleotide sequence further comprises a consensus Kozak sequence. In certain embodiments, the recombinant adenovirus comprises a partial or complete deletion of the nucleotide sequence encoding the adenoviral death protein (ADP).

In certain embodiments, the invention provides a recombinant adenovirus comprising a first nucleotide sequence inserted in an IX-E2 insertion site and a second nucleotide sequence inserted in an L5-E4 insertion site. These embodiments enable the adenoviruses to express two or more separate exogenous transgenes. This approach has certain advantages over adenoviruses expressing a fusion protein comprising two transgenes with a self-cleavable linker joining them because the cleaved linker may be potentially immunogenic.

In certain embodiments, the recombinant adenovirus comprises, in a 5' to 3' orientation: (i) a first polyadenylation signal; (ii) a promoter; (iii) a first nucleotide sequence comprising a first transgene; (iv) a linker; (v) a second nucleotide sequence comprising a second transgene; (vi) a second polyadenylation signal; and (vii) a third polyadenylation signal; wherein the transgene is operably linked to the promoter. In certain embodiments, wherein the second polyadenylation signal is in the opposite transcriptional direction of the third polyadenylation signal. In certain embodiments, the recombinant adenovirus comprises, in a 5' to 3' orientation: (i) a first polyadenylation signal; (ii) a second polyadenylation signal; (iii) a promoter; (iv) a first nucleotide sequence comprising a first transgene; (v) a linker; (vi) a second nucleotide sequence comprising a second transgene; (vii) a third polyadenylation signal; and (viii) a fourth polyadenylation signal; wherein the transgene is operably linked to the promoter. In certain embodiments, wherein the second polyadenylation signal is in the opposite transcriptional direction of the first polyadenylation signal. In certain embodiments, wherein the fourth polyadenylation signal is in the opposite transcriptional direction of the third polyadenylation signal.

In certain embodiments, the IX-E2 insertion site comprises a deletion of about 5, 10, 15, 20, 25, 30, 35, 40, 45, 50, 55, or 60 nucleotides. In certain embodiments, the L5-E4 insertion site comprises a deletion of about 5, 10, 15, 20, 25, 30, 35, 40, 45, 50, 55, 60, 65, 70, 75, 80, 85, 90, 95, 100, 105, 110, 115, 120, 125, or 130 nucleotides.

In certain embodiments, the recombinant adenovirus further comprises a nucleotide sequence inserted in an E1b-19K insertion site, an E3 insertion site, or an E4 insertion site. In certain embodiments, the E1b-19K insertion site is located between the start site of E1b-19K and the start site of E1b-55K. In certain embodiments, the E3 insertion site is located between the stop codon of adenovirus pVIII gene and the start site of adenovirus Fiber gene (L5). In certain embodiments, an E4 insertion site is located between the start codon of ORF1 to the stop codon of ORF6/7 of the adenovirus E4 gene.

In certain embodiments, the recombinant adenovirus further comprises a first nucleotide sequence inserted in the IX-E2 insertion site and a second nucleotide sequence inserted in the E1b-19K insertion site. In certain embodiments, the recombinant adenovirus further comprises a first nucleotide sequence inserted in the IX-E2 insertion site and a second nucleotide sequence inserted in the E3 insertion site. In certain embodiments, the recombinant adenovirus further comprises a first nucleotide sequence inserted in the IX-E2 insertion site and a second nucleotide sequence inserted in the E4 insertion site.

In certain embodiments, the recombinant adenovirus further comprises a first nucleotide sequence inserted in the L5-E4 insertion site and a second nucleotide sequence inserted in the E1b-19K insertion site. In certain embodiments, the recombinant adenovirus further comprises a first nucleotide sequence inserted in the L5-E4 insertion site and a second nucleotide sequence inserted in the E3 insertion site. In certain embodiments, the recombinant adenovirus further comprises a first nucleotide sequence inserted in the L5-E4 insertion site and a second nucleotide sequence inserted in the E4 insertion site.

In certain embodiments, the recombinant adenovirus further comprises a first nucleotide sequence inserted in the IX-E2 insertion site and a second nucleotide sequence inserted in the L5-E4 insertion site, and a third nucleotide sequence inserted in the E1b-19K insertion site, the E3 insertion site, or the E4 insertion site.

The adenoviral E1b-19k gene functions primarily as an anti-apoptotic gene and is a homolog of the cellular anti-apoptotic gene, BCL-2. Since host cell death prior to maturation of the progeny viral particles would restrict viral replication, E1b-19k is expressed as part of the E1 cassette to prevent premature cell death thereby allowing the infection to proceed and yield mature virions. Accordingly, in certain embodiments, a recombinant virus is provided that includes an E1b-19K insertion site, e.g., the adenovirus has an exogenous nucleotide sequence inserted into an E1b-19K insertion site. In certain embodiments, the insertion site is located between the start site of E1b-19K and the stop codon of E1b-19K.

In certain embodiments, the E1b-19K insertion site comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent to the start site of E1b-19K. In certain embodiments, the E1b-19K insertion site comprises a deletion of about 200 nucleotides, e.g., 202 nucleotides adjacent to the start site of E1b-19K. In certain embodiments, the E1b-19K insertion site comprises a deletion corresponding to nucleotides 1714-1917 of the Ad5 genome (SEQ ID NO: 1), or, an exogenous nucleotide sequence encoding a transgene is inserted between nucleotides corresponding to 1714 and 1917 of the Ad5 genome (SEQ ID NO: 1). In certain embodiments, an exogenous nucleotide sequence encoding a transgene is inserted between CTGACCTC (SEQ ID NO: 3) and TCACCAGG (SEQ ID NO: 2), e.g., the recombinant adenovirus comprises, in a 5' to 3' orientation, CTGACCTC (SEQ ID NO: 3), an exogenous nucleotide sequence encoding a transgene, and TCACCAGG (SEQ ID NO: 2). In certain embodiments, the E1b-19K insertion site comprises a deletion corresponding to nucleotides 1611-2153 or 1611-1915 of the Ad35 genome (SEQ ID NO: 41).

In certain embodiments, the E1b-19K insertion site comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent the start site of E1b-19K. In certain embodiments, the E1b-19K insertion site comprises a deletion of about 200 nucleotides, e.g., 202 nucleotides adjacent the start site of E1b-19K. In certain embodiments, the E1b-19K insertion site comprises a deletion corresponding to nucleotides 1714-1917 of the Ad5 genome (SEQ ID NO: 1), or the first therapeutic transgene is inserted between nucleotides corresponding to 1714 and 1917 of the Ad5 genome (SEQ ID NO: 1). In certain embodiments, the first therapeutic transgene is inserted between CTGACCTC (SEQ ID NO: 3) and TCACCAGG (SEQ ID NO: 2), e.g., the recombinant adenovirus comprises, in a 5' to 3' orientation, CTGACCTC (SEQ ID NO: 3), the first therapeutic transgene, and TCACCAGG (SEQ ID NO: 2).

In certain embodiments, the E3 insertion site comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or about 3000 to about 3185 nucleotides. In certain embodiments, the E3 insertion site is located between the stop codon of E3-10.5K and the stop codon of E3-14.7K. In certain embodiments, the E3 insertion site comprises a deletion of from about 500 to about 1551, from about 500 to about 1500, from about 500 to about 1000, from about 1000 to about 1551, from about 1000 to about 1500, or from about 1500 to about 1551 nucleotides adjacent the stop codon of E3-10.5K. In certain embodiments, the E3 insertion site comprises a deletion of about 1050 nucleotides adjacent the stop codon of E3-10.5K, e.g., the E3 insertion site comprises a deletion of 1063 nucleotides adjacent the stop codon of E3-10.5K. In certain embodiments, the E3 insertion site comprises a deletion corresponding to the Ad5 dl309 E3 deletion. In certain embodiments, the E3 insertion site comprises a deletion corresponding to nucleotides 29773-30836 of the Ad5 genome (SEQ ID NO: 1), or the second therapeutic transgene is inserted between nucleotides corresponding to 29773 and 30836 of the Ad5 genome (SEQ ID NO: 1). In certain embodiments, the E3 insertion site comprises a deletion corresponding to nucleotides 27199-30622 of the Ad35 genome (SEQ ID NO: 41).

In certain embodiments, an E4 insertion site comprises any one of the ORF of the E4 gene, i.e., between the start codon of ORF1 to the stop codon of ORF6/7. For example, a nucleotide sequence can be inserted in E4 ORF1, and/or E4 ORF2. In certain embodiments, portions of or the entire E4 region may be deleted. In certain embodiments, in any of the foregoing viruses, the recombinant adenovirus further comprises an E4 deletion. In certain embodiments, the E4 deletion is located between the start site of E4-ORF6/7 (i.e., the nucleotide sequence encoding the start codon of E4-ORF6/7, e.g., corresponding to nucleotides 34075-34077 of SEQ ID NO: 1) and the right inverted terminal repeat (ITR; e.g., corresponding to nucleotides 35836-35938 of SEQ ID NO: 1). In certain embodiments, the E4 deletion is located between the start site of E4-ORF6/7 and the start site of E4-ORF1 (i.e., the nucleotide sequence encoding the start codon of E4-ORF1, e.g., corresponding to nucleotides 35524-35526 of SEQ ID NO: 1). In certain embodiments, the E4 deletion comprises a deletion of a nucleotide sequence between the start site of E4-ORF6/7 and the start site of E4-ORF1. In certain embodiments, the E4 deletion comprises a deletion of from about 500 to about 2500, from about 500 to about 2000, from about 500 to about 1500, from about 500 to about 1000, from about 1000 to about 2500, from about 1000 to about 2000, from about 1000 to about 1500, from about 1500 to about 2500, from about 1500 to about 2000, or from about 2000 to about 2500 nucleotides. In certain embodiments, the E4 deletion comprises a deletion of from about 250 to about 1500, from about 250 to about 1250, from about 250 to about 1000, from about 250 to about 750, from about 250 to about 500, from 500 to about 1500, from about 500 to about 1250, about 500 to about 1000, from about 500 to about 750, from 750 to about 1500, from about 750 to about 1250, from about 750 to about 1000, from about 1000 to about 1500, or from about 1000 to about 1250 nucleotides adjacent the start site of E4-ORF6/7. In certain embodiments, the E4 deletion comprises a deletion of about 1450 nucleotides adjacent the start site of E4-ORF6/7, e.g., the E4 deletion comprises a deletion of about 1449 nucleotides adjacent the start site of E4-ORF6/7. In certain embodiments, the E4 deletion comprises a deletion corresponding to nucleotides 34078-35526 or 34083-35541 of the Ad5 genome (SEQ ID NO: 1). In certain embodiments, the E4 deletion comprises a deletion corresponding to nucleotides 33004-34422 or 31827-34415 of the Ad35 genome (SEQ ID NO: 41).

B. Modified Transcriptional Control Region

Previously developed oncolytic viruses include the oncolytic serotype 5 adenovirus (Ad5) referred to as TAV-255 in PCT Publication No. WO2010/101921 which is transcriptionally attenuated in normal cells but transcriptionally active in cancer cells. It is believed that the mechanism by which the TAV-255 vector achieves this tumor selectivity is through targeted deletion of three transcriptional factor (TF) binding sites for the transcription factors Pea3 and E2F, proteins that regulate adenovirus expression of E1a, the earliest gene to be transcribed after virus entry into the host cell, through binding to specific DNA sequences. These three Pea3 and E2F deletions attenuate replication in growth-arrested, normal cells but not in malignant ones, indicating that these DNA sequences are only dispensable for transcriptional regulation and growth in cancer cells.

In certain embodiments, any of the foregoing recombinant adenoviruses comprises a modified E1a regulatory sequence. In certain embodiments, the recombinant adenovirus comprises an E1a promoter having a deletion of a functional Pea3 binding site. For example, the virus may comprise a deletion of nucleotides corresponding to about −300 to about −250 upstream of the initiation site of E1a or a deletion of nucleotides corresponding to −305 to −255 upstream of the initiation site of E1a. In certain embodiments, the deletion comprises a deletion of nucleotides corresponding to 195-244 of the Ad5 genome (SEQ ID NO: 1), and/or the E1a promoter comprises the sequence GGTGTTTTGG (SEQ ID NO: 4).

In certain embodiments, the recombinant adenovirus comprises a modified TATA box-based promoter operably linked to a gene, wherein the modified TATA box-based promoter lacks a functional TATA box and permits selective expression of the gene in a hyperproliferative cell and/or a modified CAAT box-based promoter operably linked to a gene, wherein the modified CAAT box-based promoter lacks a functional CAAT box and permits selective expression of the gene in a hyperproliferative cell.

In certain embodiments, wherein the modified TATA box-based promoter is an early gene promoter. In certain embodiments, the modified TATA box-based promoter is an E1a promoter, E1b promoter, or E4 promoter. In certain embodiments, the modified TATA box-based promoter is an E1a promoter.

In certain embodiments, the modification included in the modified TATA box-based promoter comprises a deletion of the entire TATA box. In certain embodiments, the recombinant adenovirus comprises a deletion of nucleotides corresponding to −27 to −24, −31 to −24, −44 to +54, or −146 to +54 of the E1a promoter. In certain embodiments, the deletion comprises a deletion of nucleotides corresponding to 472 to 475, 468 to 475, 455 to 552, or 353 to 552 of the Ad5 genome (SEQ ID NO: 1). In certain embodiments, the deletion comprises a deletion of nucleotides corresponding 477 to 484 of the Ad35 genome (SEQ ID NO: 41).

In certain embodiments, the recombinant adenovirus comprises a polynucleotide deletion that results in a virus comprising the sequence CTAGGACTG (SEQ ID NO: 5), AGTGCCCG (SEQ ID NO: 44) and/or TATTCCCG (SEQ ID NO: 45).

In certain embodiments, the modified CAAT box-based promoter is an early gene promoter. In certain embodiments, the modified CAAT box-based promoter is an E1a promoter, E1b promoter, or E4 promoter. In certain embodiments, the modified CAAT box-based promoter is an E1a promoter.

In certain embodiments, the modification included in the modified CAAT box-based promoter comprises a deletion of the entire CAAT box. In certain embodiments, the recombinant adenovirus comprises a deletion of nucleotides corresponding to −76 to −68 of the E1a promoter.

In certain embodiments, the recombinant adenovirus comprises a deletion of nucleotides corresponding to 423 to 431 of the Ad5 genome (SEQ ID NO: 1). In certain embodiments, the recombinant adenovirus comprises a polynucleotide deletion that results in a virus comprising the sequence TTCCGTGGCG (SEQ ID NO: 46). In certain embodiments, the recombinant adenovirus comprises a deletion of nucleotides corresponding to 477 to 484 of the Ad35 genome (SEQ ID NO: 41).

In certain embodiments, the invention provides a method of expressing two therapeutic transgenes, when expressed, produce a single polypeptide chain, which may be cleaved posttranslationally into two polypeptide chains. In certain embodiments, the recombinant adenovirus further comprises the nucleotide sequence comprises a first nucleotide sequence comprising a first transgene and a second nucleotide sequence comprising a second transgene, wherein the first nucleotide sequence and the second nucleotide sequence are separated by a linker. In certain embodiments, the linker encodes a peptide cleavable by a protease or proteases. In certain embodiments, the linker encodes an internal ribosome entry site (IRES). The IRES may, e.g., be selected from the group consisting of the encephalomyocarditis virus IRES, the foot-and-mouth disease virus IRES, and the poliovirus IRES. In certain embodiments, the nucleotide sequence is inserted in the IX-E2 insertion or the L5-E4 insertion site, wherein the recombinant adenovirus further comprise a third nucleotide sequence inserted in an E1b-19K insertion site, an E3 insertion site, or an E4 insertion site.

In certain embodiments, the virus has one or more modifications to a regulatory sequence or promoter. A modification to a regulatory sequence or promoter comprises a deletion, substitution, or addition of one or more nucleotides compared to the wild-type sequence of the regulatory sequence or promoter.

In one embodiment, the modification of a regulatory sequence or promoter comprises a modification of sequence of a transcription factor binding site to reduce affinity for the transcription factor, for example, by deleting a portion thereof, or by inserting a single point mutation into the binding site. In certain embodiments, the additional modified regulatory sequence enhances expression in neoplastic cells but attenuates expression in normal cells.

The E1a regulatory sequence contains five binding sites for the transcription factor Pea3, designated Pea3 I, Pea3 II, Pea3 III, Pea3 IV, and Pea3 V, where Pea3 I is the Pea3 binding site most proximal to the E1a start site, and Pea3 V is most distal. The E1a regulatory sequence also contains binding sites for the transcription factor E2F, hereby designated E2F I and E2F II, where E2F I is the E2F binding site most proximal to the E1a start site, and E2F II is more distal. From the E1a start site, the binding sites are arranged: Pea3 I, E2F I, Pea3 II, E2F II, Pea3 III, Pea3 IV, and Pea3 V.

In one embodiment, at least one of these seven binding sites, or a functional binding site, is deleted. As used herein, a "functional binding site" refers to a binding site that is capable of binding to a respective binding partner, e.g., a transcription factor, e.g., a binding site that has at least 100%, at least 90%, at least 80%, at least 70%, at least 60%, at least 50%, or at least 40%, of the binding activity of a corresponding wild-type binding site sequence. As used herein, a "non-functional binding site" refers to a binding site that, e.g., has less than 30%, less than 20%, less than 10%, or 0% of the binding activity of a corresponding wild-type binding site sequence.

In certain embodiments, the recombinant adenovirus comprises an E1a promoter having a deletion of a functional Pea3 binding site, e.g., the deletion of an entire Pea3 binding site. As used herein, a "functional Pea3 binding site" refers to a Pea3 binding site that is capable of binding to its respective transcription factor (e.g., Pea3), e.g., a Pea3 binding site that has at least 100%, at least 90%, at least 80%, at least 70%, at least 60%, at least 50%, or at least 40%, of the Pea3 binding activity of a corresponding wild-type Pea3 binding site sequence. As used herein, a "non-functional Pea3 binding site" refers to a Pea3 binding site that, e.g., has less than 30%, less than 20%, less than 10%, or 0% of the Pea3 binding activity of a corresponding wild-type Pea3 binding site sequence. Assays for determining whether a Pea3 binding site binds to Pea3 are known in the art. Exemplary binding assays include electrophoretic mobility shift assays, chromatin immunoprecipitation assays, and DNAse footprinting assays.

In one embodiment, at least one Pea3 binding site, or a functional Pea3 binding site, is deleted. The deleted Pea3 binding site can be Pea3 I, Pea3 II, Pea3 III, Pea3 IV, and/or Pea3 V. In one embodiment, the deleted Pea3 binding site is Pea3 II, Pea3 III, Pea3 IV, and/or Pea3 V. In another embodiment, the deleted Pea3 binding site is Pea3 IV and/or Pea3 V. In another embodiment, the deleted Pea3 binding site is Pea3 II and/or Pea3 III. In another embodiment, the deleted Pea3 binding site is both Pea3 II and Pea3 III. In another embodiment, the Pea3 I binding site, or a functional Pea3 I binding site, is retained.

In one embodiment, at least one E2F binding site, or a functional E2F binding site, is deleted. In another embodiment, at least one E2F binding site, or a functional E2F binding site, is retained. In one embodiment, the retained E2F binding site is E2F I and/or E2F II. In another embodiment, the retained E2F binding site is E2F II. In another embodiment, the total deletion consists essentially of one or more of Pea3 II, Pea3 III, Pea3 IV, and/or Pea3 V. In one embodiment, the virus has a deletion of a 50 base pair region located from −305 to −255 upstream of the E1a initiation site, e.g., corresponding to 195-244 of the Ad5 genome (SEQ ID NO: 1), hereafter referred to as the TAV-255 deletion. In certain embodiments, the TAV-255 deletion results in an E1a promoter that comprises the sequence GGTGTTTTGG (SEQ ID NO: 4).

In one embodiment, the recombinant adenovirus has the same or similar E1a modification as in the oncolytic serotype 5 adenovirus (Ad5) called TAV-255 described in PCT Publication No. WO2010101921 and US Publication No. 20160017294A1, each of which is incorporated by reference herein in its entirety. It is believed that the mechanism by which the TAV-255 vector achieves this tumor selectivity is through targeted deletion of three transcriptional factor (TF) binding sites for the transcription factors Pea3 and E2F, proteins that regulate adenovirus expression of E1 a, the earliest gene to be transcribed after virus entry into the host cell, through binding to specific DNA sequences. These three Pea3 and E2F deletions attenuate replication in growth-arrested, normal cells but not in malignant ones, indicating that these DNA sequences are only dispensable for transcriptional regulation and growth in cancer cells.

In certain embodiments, the recombinant adenovirus comprises an E1a promoter having one or more deletions of a functional Pea3 binding site. In certain embodiments, the deletion comprises a deletion of nucleotides corresponding to about −300 to about −250 upstream of the initiation site of E1a. In certain embodiments, wherein the deletion comprises a deletion of nucleotides corresponding to −305 to −255 upstream of the initiation site of E1a. In certain embodiments, the deletion comprises a deletion of nucleotides corresponding to 195-244 of the Ad5 genome (SEQ ID NO: 1). In certain embodiments, the E1a promoter comprises the sequence GGTGTTTTGG (SEQ ID NO: 4).

In one embodiment, the recombinant adenovirus comprises one or more Pea3 transcription binding site deletions without one or more E2F transcription binding site deletions in the E1A region. In other embodiment, the recombinant adenovirus comprises one or more E2F transcription binding site deletions without one or more Pea3 transcription binding site deletions in the E1A region.

In certain embodiments, the recombinant oncolytic adenovirus comprises a modified TATA box-based promoter operably linked to a gene, wherein the modified TATA box-based promoter lacks a functional TATA box and permits selective expression of the gene in a hyperproliferative and/or non-growth arrested cell. As used herein, a "functional TATA box" refers to a TATA box that is capable of binding to a TATA box binding protein (TBP), e.g., a TATA box that has at least 100%, at least 90%, at least 80%, at least 70%, at least 60%, at least 50%, or at least 40%, of the TBP binding activity of a corresponding wild-type TATA box sequence. As used herein, a "non-functional TATA box" refers to a TATA box that, e.g., has less than 30%, less than 20%, less than 10%, or 0% of the TBP binding activity of a corresponding wild-type TATA box sequence. Assays for determining whether a TBP binds to a TATA box are known in the art. Exemplary binding assays include electrophoretic mobility shift assays, chromatin immunoprecipitation assays, and DNAse footprinting assays.

As used herein, a "modified TATA box" refers to a TATA box that has a deletion, substitution, or addition of one or more nucleotides relative to a wild-type TATA box sequence.

For example, the virus may comprise a deletion of nucleotides corresponding to −29 to −26, −33 to −26, −44 to +52, or −148 to +52 upstream of the initiation site of E1a. In certain embodiments, the deletion comprises a deletion of nucleotides corresponding to 353-552 of the Ad5 genome (SEQ ID NO: 1). In certain embodiments, the TATA box deletion results in an E1a promoter that comprises the sequence CTAGGACTG (SEQ ID NO: 5), AGTGCCCG (SEQ ID NO: 44) and/or TATTCCCG (SEQ ID NO: 45).

In certain embodiments, the recombinant oncolytic adenovirus comprises a modified CAAT box-based promoter operably linked to a gene, wherein the modified CAAT box-based promoter lacks a functional CAAT box and permits selective expression of the gene in a hyperproliferative cell and/or non-growth arrested. The TATA box-based promoter and the CAAT box-based promoter may be the same promoter (e.g., the Ad5 E1a promoter), or may be different promoters.

As used herein, "CAAT box" refers to a nucleotide sequence that is capable of binding to a C/EBP or NF-Y protein. A CAAT box typically comprises a consensus sequence of GG(T/C)CAATCT.

As used herein, a "modified CAAT box" refers to a CAAT box that has a deletion, substitution, or addition of one or more nucleotides relative to a wild-type CAAT box sequence.

As used herein, a "functional CAAT box" refers to a CAAT box that is capable of binding to a C/EBP or NF-Y protein, e.g., a CAAT box that has at least 100%, at least 90%, at least 80%, at least 70%, at least 60%, at least 50%, or at least 40%, of the a C/EBP or NF-Y binding activity of a corresponding wild-type CAAT box sequence. As used herein, a "non-functional CAAT box" refers to a CAAT box that, e.g., has less than 30%, less than 20%, less than 10%, or 0% of the a C/EBP or NF-Y binding activity of a corresponding wild-type CAAT box sequence. Assays for determining whether a C/EBP or NF-Y protein binds to a CAAT box are known in the art. Exemplary binding assays include electrophoretic mobility shift assays, chromatin immunoprecipitation assays, and DNAse footprinting assays.

As used herein, "CAAT box-based promoter" refers to any gene promoter that contains a CAAT box.

As used herein, a "modified CAAT box-based promoter" refers to a CAAT box-based promoter that has been modified by a deletion, substitution, or addition of one or more nucleotides relative to a wild-type CAAT box-based promoter. In certain embodiments, the modification included in the modified CAAT box-based promoter comprises a deletion of one or more nucleotides of the wild-type CAAT box-based promoter sequence. In certain embodiments, the modification included in the modified CAAT box-based promoter consists of a deletion of one or more nucleotides of the wild-type CAAT box-based promoter sequence. In certain embodiments, the modification included in the modified CAAT box-based promoter comprises a deletion of the entire CAAT box of the wild-type CAAT box-based promoter sequence. In certain embodiments, the modification included in the modified CAAT box-based promoter consists of a deletion of the entire CAAT box of the wild-type CAAT box-based promoter sequence. In certain embodiments, the modification included in the modified CAAT box-based promoter comprises a deletion of the entire CAAT box-based promoter. In certain embodiments, the modification included in the modified CAAT box-based promoter consists of a deletion of the entire CAAT box-based promoter. In certain embodiments, the modification included in the modified CAAT box-based promoter does not comprise an addition of or a substitution with a separate, functional promoter sequence.

Nucleic acids encoding viral genes can be incorporated into plasmids and introduced into host cells through conventional transfection or transformation techniques. Specific production and purification conditions will vary depending upon the virus and the production system employed. For adenovirus, the traditional method for the generation of viral particles is co-transfection followed by subsequent in vivo recombination of a shuttle plasmid (usually containing a small subset of the adenoviral genome and optionally containing a potential transgene an expression cassette) and an adenoviral helper plasmid (containing most of the entire adenoviral genome). Alternative technologies for the generation of adenovirus include utilization of the bacterial artificial chromosome (BAC) system, in vivo bacterial recombination in a recA+ bacterial strain utilizing two plasmids containing complementary adenoviral sequences, and the yeast artificial chromosome (YAC) system.

In certain embodiments, a recombinant adenovirus of the invention is an oncolytic virus, e.g., a virus that exhibits tumor-selective replication and/or viral mediated lysis. In certain embodiments, a recombinant adenovirus of the invention exhibits selective expression of a therapeutic transgene in a hyperproliferative cell, e.g., a cancer cell, a tumor cell, relative to a nonhyperproliferative cell. In certain embodiments, the expression of a therapeutic transgene in a non-hyperproliferative cell is about 90%, about 80%, about 70%, about 60%, about 50%, about 40%, about 30%, about 20%, about 10%, or about 5% of the expression of the gene in the hyperproliferative cell. In certain embodiments, the virus exhibits no detectable expression of a therapeutic transgene in a non-hyperproliferative cell. Therapeutic transgene expression may be determined by any appropriate method known in the art, e.g., Western blot or ELISA. The hyperproliferative cell may be a cancer cell, e.g., a carcinoma, sarcoma, leukemia, lymphoma, prostate cancer, lung cancer, gastrointestinal tract cancer, colorectal cancer, pancreatic cancer, breast cancer, ovarian cancer, cervical cancer, stomach cancer, thyroid cancer, mesothelioma, liver cancer, kidney cancer, skin cancer, head and neck cancer, or brain cancer cell.

C. Transgenes

The recombinant adenovirus disclosed herein comprise one or more exogenous nucleotide sequences inserted in any of the foregoing insertion sites, e.g., an IX-E2 insertion site, an L5-E4 insertion site, an E1b-19K insertion site, an E3 insertion site, or an E4 insertion site.

In certain embodiments, the nucleotide sequence comprises at least one transgene. In certain embodiments, the nucleotide sequence further comprises a promoter, wherein the transgene is operably linked to the promoter.

In certain embodiments, the recombinant adenovirus comprises, in a 5' to 3' orientation: (i) a first polyadenylation signal; (ii) a promoter; (iii) a transgene; (iv) a second polyadenylation signal; and (v) a third polyadenylation signal; wherein the transgene is operably linked to the promoter. In some embodiments, the nucleotide sequence, the first nucleotide sequence, and/or the second nucleotide sequence is inserted between the first polyadenylation signal and the third polyadenylation signal. In certain embodiments, wherein the second polyadenylation signal is in the opposite transcriptional direction of the third polyadenylation signal. In certain embodiments, the nucleotide sequence is inserted in the L5-E4 insertion site, and the first polyadenylation signal is the polyadenylation signal of the L5 transcription unit, the second polyadenylation signal is the polyadenylation signal of the transgene, and the third polyadenylation signal is the polyadenylation signal of the E4 transcription unit. In certain embodiments, the nucleotide sequence is inserted in the IX-E2 insertion site, and the first polyadenylation signal is the polyadenylation signal of the IX transcription unit, the second polyadenylation signal is the polyadenylation signal of the transgene, and the third polyadenylation signal is the polyadenylation signal of the adenovirus IVa2 gene.

In certain embodiments, the recombinant adenovirus comprises, in a 5' to 3' orientation: (i) a first polyadenylation signal; (ii) a second polyadenylation signal; (iii) a promoter; (iv) a transgene; (v) a third polyadenylation signal; and (vi) a fourth polyadenylation signal, and the transgene is operably linked to the promoter. In some embodiments, the nucleotide sequence, the first nucleotide sequence, and/or the second nucleotide sequence is inserted between the first polyadenylation signal and the fourth polyadenylation signal. In certain embodiments, wherein the second polyadenylation signal is in the opposite transcriptional direction of the first polyadenylation signal. In certain embodiments, wherein the fourth polyadenylation signal is in the opposite transcriptional direction of the third polyadenylation signal. In certain embodiments, the nucleotide sequence is inserted in the L5-E4 insertion site, and the first polyadenylation signal is the polyadenylation signal of the L5 transcription unit, the third polyadenylation signal is the polyadenylation signal of the transgene, and the fourth polyadenylation signal is the polyadenylation signal of the E4 transcription unit. In certain embodiments, the nucleotide sequence is inserted in the IX-E2 insertion site, and the first polyadenylation signal is the polyadenylation signal of the IX transcription unit, the third polyadenylation signal is the polyadenylation signal of the transgene, and the fourth polyadenylation signal is the polyadenylation signal of the adenovirus IVa2 gene.

In certain embodiments, the recombinant adenovirus further comprises the nucleotide sequence comprises a first nucleotide sequence comprising a first transgene and a second nucleotide sequence comprising a second transgene, wherein the first nucleotide sequence and the second nucleotide sequence are separated by a linker.

In certain embodiments, the nucleotide sequence comprises, in a 5' to 3' orientation: (i) a first polyadenylation signal; (ii) a promoter; (iii) a first nucleotide sequence comprising a first transgene; (iv) a linker; (v) a second nucleotide sequence comprising a second transgene; (vi) a second polyadenylation signal; and (vii) a third polyadenylation signal; wherein the transgene is operably linked to the promoter. In certain embodiments, wherein the second polyadenylation signal is in the opposite transcriptional direction of the third polyadenylation signal. In certain embodiments, the nucleotide sequence comprises, in a 5' to 3' orientation: (i) a first polyadenylation signal; (ii) a second polyadenylation signal; (iii) a promoter; (iv) a first nucleotide sequence comprising a first transgene; (v) a linker; (vi) a second nucleotide sequence comprising a second transgene; (vii) a third polyadenylation signal; and (viii) a fourth polyadenylation signal; wherein the transgene is operably linked to the promoter. In certain embodiments, wherein the second polyadenylation signal is in the opposite transcriptional direction of the first polyadenylation signal. In certain embodiments, wherein the fourth polyadenylation signal is in the opposite transcriptional direction of the third polyadenylation signal.

In certain embodiments, the linker encodes a peptide cleavable by a protease or proteases. In certain embodiments, the linker encodes internal ribosome entry site (IRES) or a self-cleaving 2A peptide. The IRES may, e.g., be selected from the group consisting of the encephalomyocarditis virus IRES, the foot-and-mouth disease virus IRES, and the poliovirus IRES. In certain embodiments, wherein the nucleotide sequence is inserted in the IX-E2 insertion or the L5-E4 insertion site, wherein the recombinant adenovirus further comprise a third nucleotide sequence inserted in an E1b-19K insertion site, an E3 insertion site, or an E4 insertion site.

In certain embodiments, one or more of the nucleotide sequence, the first nucleotide sequence, the second nucleotide sequence, and the third nucleotide sequence comprises one or more transgenes.

In certain embodiments, one or more of the nucleotide sequence, the first nucleotide sequence, the second nucleotide sequence, and the third nucleotide sequence comprises:
  a) a transcriptional initiation region;
  b) a nucleotide sequence comprising a transgene, wherein the transgene is under transcriptional control of the transcriptional initiation region; and
  c) a transcriptional termination region.

In some embodiments, the transcriptional initiation region comprises a promoter.

In certain embodiments, one or more of the transgenes, the first transgene, and the second transgene encodes a monomeric, dimeric, trimeric, tetrameric, or multimeric protein, or a part thereof. In certain embodiments, one or more of the transgene, the first transgene, and the second transgene encodes a RNA that has a therapeutic activity. In certain embodiments, one or more of the transgene, the first transgene, and the second transgene encodes a fusion protein comprising at least one binding domain.

In certain embodiments, one or more of the transgene, the first transgene, and the second transgene encodes an immunomodulatory molecule. In certain embodiments, the immunomodulatory molecule is a costimulatory ligand, a cytokine, or a cytokine receptor. In certain embodiments, the immunomodulatory molecule is selected from the group consisting of IL-1, IL-2, IL-3, IL-4, IL-5, IL-6, IL-7, IL-8, IL-9, IL-7, IL-10, IL-10 trap, IL-10R, IL-12A/p35, IL-12B/p40, IL-15, IL-23A/p19, IL-24, IL-27, IL-33, IL-35, IL-15, an IL-15 receptor fusion protein, TGF-β, a TGF-β trap, an IL-10 trap, VEGF, VEGF trap, indoleamin-2,3-dioxygenase (IDO), inducible T-cell co-stimulator ligand (ICOS-L), CD80, CD137L, TNF-α, IFN-α, IFN-β, IFN-γ, GM-CSF, GITR ligand (GITRL), OX40 ligand (OX40L), CD40 ligand (CD40L)/CD154, CD70, CD86, CD137, CD137L, BORIS/CTCFL, bone morphogenetic protein (BMP), TNFSF9, FGF, ICAM, Podocalyxin, functional fragments thereof, and derivatives thereof.

In certain embodiments, the transgene encodes a fusion protein that comprise, in an N- to C-terminal orientation: a soluble portion of an extracellular domain of a cytokine receptor; an amino acid linker; an immunoglobulin (Ig) hinge region; and an immunoglobulin (Ig) Fc domain. In some embodiments, the cytokine receptor is TGFβ type II (TβRII) receptor.

In certain embodiments, a nucleotide sequence encoding CD80 or a functional fragment thereof is inserted in the IX-E2 insertion site, and a nucleotide sequence encoding CD137L or a functional fragment thereof is inserted in the L5-E4 insertion site. In certain embodiments, a nucleotide sequence encoding CD137L or a functional fragment thereof is inserted in the IX-E2 insertion site, and a nucleotide sequence encoding CD80 or a functional fragment thereof is inserted in the L5-E4 insertion site.

In certain embodiments, the recombinant adenovirus comprises a nucleotide sequence encoding IL-12A/p35 or a functional fragment thereof, a nucleotide sequence encoding IL-12B/p40 or a functional fragment thereof, and a nucleotide sequence encoding IFN-α or a functional fragment thereof. These nucleotide sequences may be inserted in the IX-E2 insertion site, the L5-E4 insertion site, the E1b-19K insertion site, the E3 insertion site, and/or the E4 insertion site.

In certain embodiments, one or more of the transgenes, the first transgene, and/or the second transgene encodes an antigen-binding molecule. In certain embodiments, the antigen-binding molecule is an anti-PD-1 antibody, an anti-TGF-β antibody, an anti-PD-L1 antibody, and an anti-CTLA-4 antibody, or functional fragments thereof. Exemplary anti-PD-1 antibodies include nivolumab (Bristol-Myers Squibb Co.), pembrolizumab (KEYTRUDA®, Merck & Co.) and Atezolizumab (formerly MPDL3280A), MEDI4736, Avelumab, and PDR001.

In certain embodiments, one or more of the transgenes, the first transgene, and the second transgene encodes an antigen or a ligand to the antigen. In certain embodiments, the antigen is selected from the group consisting of CAIX, CEA, CD5, CD7, CD10, CD19, CD20, CD22, CD30, CD33, CD34, CD38, CD41, CD44, CD49f, CD56, CD74, CD80, CD133, CD135 (Flt3), Flt3I, CD138, a cytomegalovirus (CMV) infected cell antigen, 4-1BB, EGP-2, EGP-40, EpCAM, erbB2, erbB3, erbB4, FBP, Fetal acetylcholine receptor, KRAS, HPV E6, E7, BING-4, EphA3, calcium activated chloride channel-2, cyclin B1, 9D7, SAP-1, PRAME, SSX-2, immature laminin receptor, folate receptor-a, telomerase, tyrosinase, melan-A, NY-ESO-1, GD2, GD3, hTERT, IL13R-a2, x-light chain, KDR, LeY, LI cell adhesion molecule, MAGE-A1, MAGE-A3, MART1, MART2, MUC1, Mesothelin, HER-2/neu, EGFRvIII, NKG2D ligands, NY-ESO-1, gp100, TRP-1/-2, TRP-1/-2, P polypeptide, MC1R, prostate specific antigen, BRAF, androgen-receptor, β-catenin, BRCA1/2, CDK4, CML66, fibronectin, p53, T cell receptor, oncofetal antigen, 5T4, PSCA, PSMA, ROR1, TAG-72, VEGF-R2, WT-1, functional fragments thereof, and derivatives thereof.

In certain embodiments, one or more of the transgene, the first transgene, and the second transgene encodes a toxin. In certain embodiments, the toxin is pseudomonas exotoxin, ricin toxin, or diphtheria toxin.

In certain embodiments, one or more of the transgene, the first transgene, and the second transgene encodes an enzyme. In certain embodiments, the enzyme is selected from the group consisting of beta-glucuronidase, beta-galactosidase, beta-glucosidase, carboxypeptidase, beta-lactamase, esterase, metalloproteinase, relaxin, collagenase, streptokinase, arginase, NOS-2, fragments thereof, and derivatives thereof.

In certain embodiments, one or more of the transgene, the first transgene, and the second transgene encodes a cell cycle control agent, a growth factor, an anticoagulant, a pro-drug activating gene, a tumor suppressor gene, an apoptotic gene, an anti-platelet agent, a clotting factor, a cystic fibrosis transmembrane conductance regulator (CFTR) protein, fragments thereof, or derivatives thereof.

In certain embodiments, one or more of the transgene, the first transgene, and the second transgene encodes angiostatin, endostatin, acetylcholine, DKK1/Wnt, Ox40L, GITRL, secreted flagellin, thymidine kinase, functional fragments thereof, or derivatives thereof.

II. Methods of Treatment

In another aspect, the invention provides a method of inhibiting proliferation of a tumor cell comprising exposing the tumor cell to an effective amount of any of the foregoing recombinant adenoviruses to inhibit proliferation of the tumor cell.

In another aspect, the invention provides a method of inhibiting tumor growth in a subject in need thereof, wherein the method comprising administering to the subject to an effective amount of any of the foregoing recombinant adenoviruses to inhibit tumor growth. In some embodiments, the tumor is a HER2/neu positive tumor, and wherein the recombinant adenovirus comprises an E1a promoter having no more than one deletion of a functional Pea3 binding site. In some embodiments, the HER2/neu positive tumor is from breast cancer, gastric cancer, ovarian cancer, bladder cancer, salivary gland cancer, endometrial cancer, pancreatic cancer, or non-small-cell lung cancer (NSCLC).

In certain embodiments, the tumor is selected from the group consisting of melanoma, squamous cell carcinoma of the skin, basal cell carcinoma, head and neck tumor, breast tumor, anal cancer, cervical cancer, non-small cell lung cancer, mesothelioma, small cell lung tumor, renal cell carcinoma, prostate tumor, gastroesophageal tumor, colorectal tumor, testicular tumor, bladder tumor, ovarian tumor, hepatocellular carcinoma, cholangiocarcinoma, brain tumor, endometrial tumor, neuroendocrine tumor, merkel cell carcinoma, gastrointestinal stromal tumor, a sarcoma, and pancreatic tumor.

The recombinant adenoviruses disclosed herein can be can be used to treat various medical indications, for example, cancers. As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans In one aspect, the invention provides a method of treating a hyperproliferative disease, in a subject. The method comprises administering to the subject an effective amount of a recombinant virus described herein to treat the hyperproliferative disease in the subject. In certain embodiments, the hyperproliferative disease is selected from the group consisting of cancer, atherosclerosis, rheumatoid arthritis, psoriasis, lupus, idiopathic pulmonary fibrosis, scleroderma and cirrhosis. In certain embodiments, the hyperproliferative disease is cancer.

In some embodiments, the invention provides a method of treating cancer in a subject. The method comprises administering to the subject an effective amount of a recombinant adenoviruses described herein to treat the cancer disease in the subject.

Examples of cancers include solid tumors, soft tissue tumors, hematopoietic tumors and metastatic lesions. Examples of hematopoietic tumors include, leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), e.g., transformed CLL, diffuse large B-cell lymphomas (DLBCL), follicular lymphoma, hairy cell leukemia, myelodysplastic syndrome (MDS), a lymphoma, Hodgkin's disease, a malignant lymphoma, non-Hodgkin's lymphoma, Burkitt's lymphoma, multiple myeloma, or Richter's Syndrome (Richter's Transformation). Examples of solid tumors include malignancies, e.g., sarcomas, adenocarcinomas, and carcinomas, of the various organ systems, such as those affecting head and neck (including pharynx), thyroid, lung (small cell or non-small cell lung carcinoma (NSCLC)), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), or skin (e.g., melanoma).

In certain embodiments, the cancer is selected from melanoma, squamous cell carcinoma of the skin, basal cell carcinoma, head and neck cancer, breast cancer, anal cancer, cervical cancer, non-small cell lung cancer, mesothelioma, small cell lung cancer, renal cell carcinoma, prostate cancer, gastroesophageal cancer, colorectal cancer, testicular cancer, bladder cancer, ovarian cancer, hepatocellular carcinoma, cholangiocarcinoma, brain cancer, endometrial cancer, neuroendocrine cancer, and pancreatic cancer.

In certain embodiments, the cancer is selected from nasopharyngeal cancer, basal cell carcinoma, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, neuroendocrine, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

In some aspects, the invention provides a method of inhibiting proliferation of a tumor cell comprising exposing the tumor cell to an effective amount of any of the foregoing recombinant adenoviruses.

In another aspect, the invention provides a method of inhibiting tumor growth in a subject in need thereof, wherein the method comprising administering to the subject to an effective amount of any of the foregoing recombinant adenoviruses. In certain embodiments, the tumor is selected from the group consisting of melanoma, squamous cell carcinoma of the skin, basal cell carcinoma, head and neck tumor, breast tumor, anal cancer, cervical cancer, non-small cell lung cancer, mesothelioma, small cell lung tumor, renal cell carcinoma, prostate tumor, gastroesophageal tumor, colorectal tumor, testicular tumor, bladder tumor, ovarian tumor, hepatocellular carcinoma, cholangiocarcinoma, brain tumor, endometrial tumor, neuroendocrine tumor, merkel cell carcinoma, gastrointestinal stromal tumor, a sarcoma, and pancreatic tumor.

In another aspect, the invention provides a method of treating a disease or condition in a subject in need thereof, wherein the method comprising administering to the subject to an effective amount of any of the foregoing recombinant adenoviruses. In certain embodiments, the disease or condition is selected from the group consisting of an infection, diabetic retinopathy, psoriasis, rheumatoid arthritis, endometriosis, macular degenerative disorders and benign growth disorders such as prostate enlargement and lipomas, a vascular disorder, a cardiovascular disease, an infection, cirrhosis of the liver, a connective tissue disorder, a tumor, a vascular lesion, an ulcerative lesion, an inflammation, thrombosis, and neointima formation.

In certain embodiments, the subject is a mammal. In certain embodiments, the subject is a human. In certain embodiments, the subject is a pediatric human. In certain embodiments, the subject is an adult human.

In certain embodiments, the recombinant adenovirus is administered by intramuscular, intravenous, intraarterial, or intratumoral injection. In certain embodiments, the recombinant adenovirus is administered by intradermal, inhalation, transdermal, topical, eye drops, intranasal, transmucosal, and rectal administration.

In certain embodiments, the foregoing recombinant adenoviruses are administered to the subject in combination with one or more therapies selected from the group consisting of surgery, radiation, chemotherapy, immunotherapy, hormone therapy, and virotherapy.

In certain embodiments, the recombinant adenoviruses of the invention are administered in combination with a tyrosine kinase inhibitor, e.g., erlotinib.

In certain embodiments, the recombinant adenoviruses of the invention are administered in combination with one or more immune checkpoint modulators. In certain embodiments, the immune checkpoint modulator is an inhibitor, an antagonist, or an agonist of one or more molecules selected from the group consisting of PD-1, PD-L1, PD-L2, 2B4, TIGIT, LAG3, Tim3, BTLA, CD160, GITR, KIR, 4-1BB, and CTLA4. In some embodiments the immune checkpoint modulators are antibodies to PD-1, PD-L1, PD-L2, 2B4, TIGIT, LAG3, Tim3, BTLA, CD160, GITR, KIR, 4-1BB, and/or CTLA4. Exemplary anti-PD-1 antibodies include nivolumab (Bristol-Myers Squibb Co.), pembrolizumab (KEYTRUDA®, Merck & Co.) and Atezolizumab (formerly MPDL3280A), MEDI4736, Avelumab, and PDR001.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

The term "effective amount" as used herein refers to the amount of an active component (e.g., the amount of a recombinant virus of the present invention) sufficient to effect beneficial or desired results. An effective amount can be administered in one or more administrations, applications or dosages and is not intended to be limited to a particular formulation or administration route.

In certain embodiments, a therapeutically effective amount of active component is in the range of 0.1 mg/kg to 100 mg/kg, e.g., 1 mg/kg to 100 mg/kg, 1 mg/kg to 10 mg/kg. In certain embodiments, a therapeutically effective amount of a recombinant virus is in the range of $10^2$ to $10^{15}$ plaque forming units (pfus), e.g., $10^2$ to $10^{10}$, $10^2$ to $10^5$, $10^5$ to $10^{15}$, $10^5$ to $10^{10}$, or $10^{10}$ to $10^{15}$ plaque forming units. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the virus, and the disease being treated. Exemplary dosing frequencies are once per day, once per week and once every two weeks. One route of administration is parenteral, e.g., intravenous infusion. Formulation of virus-based drugs is within ordinary skill in the art. In certain embodiments, a recombinant virus is lyophilized, and then reconstituted in buffered saline, at the time of administration.

The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

III. Pharmaceutical Composition/Formulation

The present disclosure also provides a pharmaceutical composition comprising any of the foregoing recombinant adenoviruses and at least one pharmaceutically acceptable carrier or diluent. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration.

Pharmaceutical compositions and formulations containing the recombinant adenoviruses disclosed herein can be formulated to be compatible with its intended route of administration. Examples of routes of administration are intramuscular, intravenous, intraarterial, or intratumoral intradermal, inhalation, transdermal, topical, transmucosal, and rectal administration.

In one aspect, the present disclosure provides an adenovirus formulation for the stabilization and storage of recombinant adenoviruses. In some embodiments, the invention provides a formulation for adenoviruses comprising:
  e) one or more of any of the foregoing recombinant adenoviruses;
  f) at least one buffer;
  g) at least one tonicity modifier;
  h) at least one sugar or at least one stabilizing agent, or both; and
wherein the formulation has a pH ranging between about 7.0 and about 9.0.

In certain embodiments, the stabilizing agent is glycerol. In certain embodiments, the stabilizing agent is at about 2% to about 5% (v/v).

In certain embodiments, the buffer is Tris (includes Tris-HCl and/or mono-Tris), TES, HEPES, brucine tetrahydrate, EPPS, tricine, or histidine. In certain embodiments, the buffer is at concentration of about 1 mM to about 30 mM.

In some embodiments, the tonicity modifier is $MgCl_2$, $MnCl_2$, $CaCl_2$, $ZnI_2$, NaCl, or KCl. In one embodiment, the tonicity modifier is NaCl. In one embodiment, the tonicity modifier is at concentration of about 0.1 mM to about 5 mM. In one embodiment, the tonicity modifier is at concentration of about 10 mM to about 250 mM. In one embodiment, the the tonicity modifier is at concentration of about 25 mM to about 100 mM. In one embodiment, the tonicity modifier is at concentration of about 25 mM.

In certain embodiments, the formulation comprises a first tonicity modifier and a second tonicity modifier, wherein the first tonicity modifier is a monovalent cation, and wherein the second tonicity modifier is a divalent cation. In certain embodiments, the monovalent cation is NaCl or KCl. In certain embodiments, the divalent cation is $MgCl_2$, $MnCl_2$, $CaCl_2$, or $ZnCl_2$. In certain embodiments, the tonicity modifier or the divalent cation is at a concentration of about 0.1 mM to about 5 mM.

In some embodiments, the sugar is sucrose or trehalose. In one embodiment, the sugar is sucrose. In one embodiment, the sugar is at weight to volume percentage from about 2% to about 8%. In one embodiment, the sugar is at weight to volume percentage from about 3% to about 5%. In one embodiment, the sugar is at weight to volume percentage of about 5%.

In certain embodiments, any of the foregoing formulations further comprise at least one non-ionic surfactant. In certain embodiments, the non-ionic surfactant is polysorbate-80 or polysorbate-40. In one embodiment, the non-ionic surfactant is at a concentration of about 0.001% to about 1%. In one embodiment, the non-ionic surfactant is at a concentration of about 0.02%.

In certain embodiments, any of the foregoing formulations further comprise at least one inhibitor of free radical oxidation. In certain embodiments, the inhibitor of free radical oxidation is EDTA. In one embodiment, the inhibitor of free radical oxidation is at a concentration of about 0.01 mM to about 5 mM. In one embodiment, the inhibitor of free radical oxidation is at a concentration of about 0.05 mM to about 2 mM. In one embodiment, the inhibitor of free radical oxidation is at a concentration of about 0.1 mM.

In certain embodiments, any of the foregoing formulations further comprise at least one cryoprotectant. In certain embodiments, the cryoprotectant is EtOH. In some embodiments, the cryoprotectant is a concentration of about 0.01% to 5%. In some embodiments, the cryoprotectant is a concentration of about 0.1% to 2%. In one embodiment, the cryoprotectant is at a concentration of about 0.5%.

In some embodiments, the formulation has an osmolarity of about 200 mOs/L to about 800 mOs/L. In some embodiments, the formulation has an osmolarity of about 300 mOs/L to about 600 mOs/L. In some embodiments, the formulation has an osmolarity of about 400 mOs/L to about 500 mOs/L.

In certain embodiments, the recombinant oncolytic adenovirus in any of the foregoing formulations is at concentration from about $1\times10^7$ vp/mL to $1\times10^{13}$ vp/mL.

In certain embodiments, the formulation comprises about 20 mM Tris, about 25 mM NaCl, about 2.5% glycerol, and wherein the formulation has a pH of about 8.0. In certain embodiments, the formulation comprises about 20 mM Tris, about 25 mM NaCl, about 3-5% sucrose, and wherein the formulation has a pH of about 8.0. In certain embodiments, the formulation comprises about 10 mM Tris, about 75 mM NaCl, about 5% sucrose, about 0.02% polysorbate-80, about 1 mM MgCl2, about 0.1 mM EDTA, about 0.5% EtOH, and wherein the formulation has a pH of about 8.0.

In certain embodiments, any of the foregoing formulations further comprise at least one immunoadjuvant. In certain embodiments, the immunoadjuvant is selected from 1) Alum, 2) Saponins, 3) non-ionic polymer surfactants, 4) monophosphoryl lipid A, 5) muramyl dipeptides, and 6) cytokines.

In certain embodiments, any of the foregoing formulations further comprise at least one dye. In certain embodiments, any of the foregoing formulations further comprise at least one reversible protease inhibitor. In certain embodiments, the reversible protease inhibitor is an inhibitor of an L3/p23 cysteine protease. In certain embodiments, any of the foregoing formulations further comprise an antioxidant. In certain embodiments, the antioxidant is vitamin A, vitamin C, vitamin E, vitamin B6, vitamin B12, folic acid, or folate.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following working examples are illustrative and are not intended to be limiting and it will be readily understood by one of skill in the art that other embodiments may be utilized.

Example 1

The nucleotide sequence of an exemplary IX-E2 insertion site (nucleotide 4029 to 4093 numbering according to NCBI Reference Sequence AC_000008.1 (SEQ ID NO: 1)) is as follows. The stop codon of adenovirus IX gene ("TAA" on left; SEQ ID NO: 8) and the stop codon of adenovirus IVa2 gene ("TTA" on the right; SEQ ID NO: 9) are underlined.

(SEQ ID NO: 6)
<u>TAA</u>AACATAAATAAAAAACCAGACTCTGTTT

GGATTTGGATCAAGCAAGTGTCTTGCTGTCT

<u>TTA</u>

Example 2

The nucleotide sequence of an exemplary L5-E4 insertion site (nucleotide 32785 to 32916 numbering according to NCBI Reference Sequence AC_000008.1 (SEQ ID NO: 1)) is as follows. The stop codon of adenovirus fiber gene ("TAA" on left; SEQ ID NO: 8) and the stop codon of ORF6/7 of adenovirus E4 gene ("TCA" on the right; SEQ ID NO: 10) are underlined.

(SEQ ID NO: 7)
<u>TAA</u>AGAATCGTTTGTGTTATGTTTCAACGTG

TTTATTTTTCAATTGCAGAAAATTTCAAGTC

-continued
```
ATTTTTCATTCAGTAGTATAGCCCCACCACC

ACATAGCTTATACAGATCACCGTACCTTAAT

CAAACTCA
```

Example 3

To generate viruses with transgenes cloned into an expression cassette in the L5-E4 site, a plasmid with adenoviral nucleotide sequence (which contained deletions of the RIDα, RIDβ, and 14.7 k genes in the E3 region and the ORF1-ORF4 genes in the E4 region) was modified by inserting into the L5-E4 site an expression cassette with the SV40 promoter and terminator with an intervening SwaI restriction site ("ATTTAAAT" SEQ ID NO: 11). The nucleotide sequence of this modification, from the polyadenylation signal of the L5 transcription unit ("AATAAA" SEQ ID NO: 12) to the polyadenylation signal of the E4 transcription unit ("TTTATT" SEQ ID NO: 13) is:

```
[L5 initial Empty]
                          SEQ ID NO: 14
AATAAAGAATCGTTTGTGTTATGTTTCAACC

TGTGGAATGTGTGTCAGTTAGGGTGTGGAAA

GTCCCCAGGCTCCCCAGCAGGCAGAAGTATG

CAAAGCATGCATCTCAATTAGTCAGCAACCA

GGTGTGGAAAGTCCCCAGGCTCCCCAGCAGG

CAGAAGTATGCAAAGCATGCATCTCAATTAG

TCAGCAACCATAGTCCCGCCCCTAACTCCGC

CCATCCCGCCCCTAACTCCGCCCAGTTCCGC

CCATTCTCCGCCCCATGGCTGACTAATTTTT

TTTATTTATGCAGAGGCCGAGGCCGCCTCTG

CCTCTGAGCTATTCCAGAAGTAGTGAGGAGG

CTTTTTTGGAGGCCTAGGCTTTTGCAAAAAG

CTTTGCAAAGATTTAAATAACTTGTTTATTG

CAGCTTATAATGGTTACAAATAAAGCAATAG

CATCACAAATTTCACAAATAAAGCATTTTTT

TCACTGCATTCTAGTTGTGGTTTGTCCAAAC

TCATCAATGTATCTTATCATGTCTGGTGTTT

ATT
```

In SEQ ID NO: 14, the polyadenylation signals of the L5 and E4 transcription units, and the nucleotides of the SwaI restriction site, are underlined.

A transgene encoding the mouse GMCSF was then cloned into the SwaI site, generating the sequence:

```
[L5 initial mGMCSF]
                          SEQ ID NO: 15
AATAAAGAATCGTTTGTGTTATGTTTCAACC

TGTGGAATGTGTGTCAGTTAGGGTGTGGAAA

GTCCCCAGGCTCCCCAGCAGGCAGAAGTATG

CAAAGCATGCATCTCAATTAGTCAGCAACCA

GGTGTGGAAAGTCCCCAGGCTCCCCAGCAGG

CAGAAGTATGCAAAGCATGCATCTCAATTAG

TCAGCAACCATAGTCCCGCCCCTAACTCCGC

CCATCCCGCCCCTAACTCCGCCCAGTTCCGC

CCATTCTCCGCCCCATGGCTGACTAATTTTT

TTTATTTATGCAGAGGCCGAGGCCGCCTCTG

CCTCTGAGCTATTCCAGAAGTAGTGAGGAGG

CTTTTTTGGAGGCCTAGGCTTTTGCAAAAAG

CTTTGCAAAGATTTATGTGGCTGCAGAACCT

GCTGTTCCTGGGCATCGTGGTGTACAGCCTG

AGCGCCCCCACCAGATCCCCCATCACCGTGA

CCAGACCCTGGAAGCACGTGGAAGCCATCAA

AGAGGCCCTGAACCTGCTGGACGACATGCCC

GTGACCCTGAACGAAGAGGTGGAAGTGGTGT

CCAACGAGTTCAGCTTCAAGAAACTGACCTG

CGTGCAGACCAGACTGAAGATCTTCGAGCAG

GGCCTGAGAGGCAACTTCACCAAGCTGAAGG

GCGCTCTGAACATGACCGCCAGCTACTACCA

GACCTACTGCCCTCCCACACCCGAGACAGAC

TGCGAGACACAGGTCACAACCTACGCCGACT

TCATCGACAGCCTGAAAACCTTCCTGACCGA

CATCCCCTTCGAGTGCAAGAAACCCGGCCAG

AAGTGAAAATAACTTGTTTATTGCAGCTTAT

AATGGTTACAAATAAAGCAATAGCATCACAA

ATTTCACAAATAAAGCATTTTTTTCACTGCA

TTCTAGTTGTGGTTTGTCCAAACTCATCAAT

GTATCTTATCATGTCTGGTGTTTATT
```

In SEQ ID NO: 15, the polyadenylation signals of the L5 and E4 transcription units, and the residual nucleotides of the SwaI restriction site are underlined, and the transgene encoding the mouse GMCSF are bolded.

The virus TAV-(L5-E4)mGMCSF was generated to carry the following modifications (compared to the d1309 strain of adenovirus type 5): the TAV-255 deletion in the E1A promoter to confer selective replication in cancerous cells, a deletion of the 5' end of the viral E1B-19K gene which does not extend into the viral E1B-55K gene, a deletion of the E3 RIDβ, RIDβ, and 14.7k genes, the sequence of SEQ ID NO: 15, and a deletion of the E4 ORF1-ORF4 genes.

Figure 2:
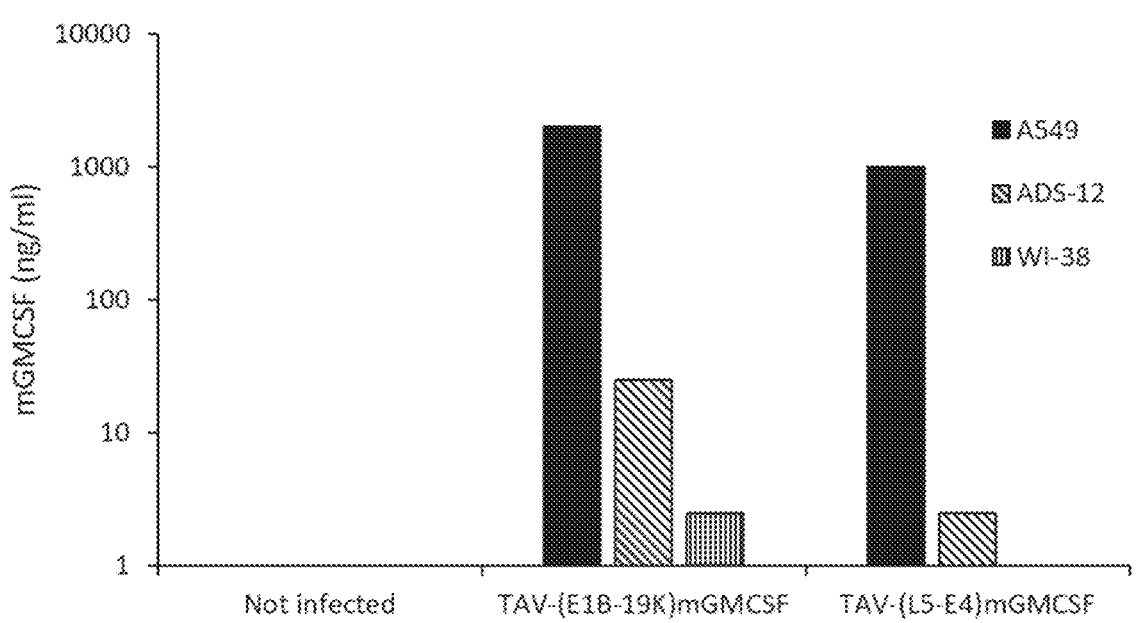
FIG. 2 depicts the mouse GMCSF expression level from A549, ADS-12, and WI-38 cells infected with the virus TAV-(E1B-19K)mGMCSF or TAV-(L5-E4)mGMCSF or kept as non-infected controls. Mouse GMCSF expression was measured in their conditioned media.

To test for mGMCSF expression: A549 cells (human cancer cell line), ADS-12 cells (mouse cancer cell line), and WI38 cells (human normal cell line) were infected with TAV-(L5-E4)mGMCSF at an MOI (multiplicity of infection) of 5. As a control, additional cells were cultured without infection or were infected with the virus TAV-(E1B-19K) mGMCSF which carries the following modifications compared to the dl309 strain of adenovirus type 5: the TAV-255 deletion in the E1A promoter, and the mGMCSF gene replacing the 5' end of the E1B-19K gene without disrupting the E1B-55K gene. Four days after infection, the conditioned media was used in an ELISA to measure mouse GMCSF expression. Results are shown in FIG. 2: both viruses gave high levels of expression in A549 cells, moderate expression in ADS-12 cells, and low levels of expression in WI38 cells.

Example 4

To investigate an expression cassette insertion at the IX-E2 site, initially, we inserted an expression cassette with the cytomegalovirus immediate early promoter (CMV promoter) and the transcription terminator of bovine growth hormone (BGH terminator) including a NotI restriction site ("GCGGCCGC" SEQ ID NO: 16) between the promoter and terminator to facilitate insertion of a transgene. Its nucleotide sequence from the polyadenylation signal of IX ("AATAAA" SEQ ID NO: 12) to the polyadenylation signal of the E2 transcription unit ("TTTATT" SEQ ID NO: 13) is:

[IX initial Empty]
SEQ ID NO: 17
AATAAAAAACCAGACTCTGTTTGGATTTGGA

TCAAGCAAGTGTCTTGCTGTCTTACGGTAAA

TGGCCCGCCTGGCTGACCGCCCAACGACCCC

CGCCCATTGACGTCAATAATGACGTATGTTC

CCATAGTAACGCCAATAGGGACTTTCCATTG

ACGTCAATGGGTGGAGTATTTACGGTAAACT

GCCCACTTGGCAGTACATCAAGTGTATCATA

TGCCAAGTACGCCCCCTATTGACGTCAATGA

CGGTAAATGGCCCGCCTGGCATTATGCCCAG

TACATGACCTTATGGGACTTTCCTACTTGGC

AGTACATCTACGTATTAGTCATCGCTATTAC

CATGGTGATGCGGTTTTGGCAGTACATCAAT

GGGCGTGGATAGCGGTTTGACTCACGGGGAT

TTCCAAGTCTCCACCCCATTGACGTCAATGG

GAGTTTGTTTTGGCACCAAAATCAACGGGAC

TTTCCAAAATGTCGTAACAACTCCGCCCCAT

TGACGCAAATGGGCGGTAGGCGTGTACGGTG

GGAGGTCTATATAAGCAGAGCTCTCTGGCTA

ACTAGAGAACCCACTGCTTACTGGCTTATCG

AAATTAATACGACTCACTATAGGGAGACCCG

CGGCCGCCTGTGCCTTCTAGTTGCCAGCCAT

CTGTTGTTTGCCCCTCCCCCGTGCCTTCCTT

GACCCTGGAAGGTGCCACTCCCACTGTCCTT

TCCTAATAAAATGAGGAAATTGCATCGCATT

GTCTGAGTAGGTGTCATTCTATTCTGGGGGG

-continued
TGGGGTGGGGCAGGACAGCAAGGGGGAGGAT

TGGGAAGACAATAGCAGGCATGCTGGGGATG

CGGTGGGCTCTATGGTTTATT

The polyadenylation signals of the IX and E2 transcripts, and the NotI restriction site, are underlined.

The virus TAV IX-WT LS-Empty carried the TAV-255 deletion in the E1A promoter, wild-type viral sequence in the IX-E2 site, and the sequence SEQ ID NO: 14 (the empty expression cassette in the L5-E4 site). The virus TAV IX-WT LS-IL7 carried the TAV-255 deletion in the E1A promoter, wild-type viral sequence in the IX-E2 site, and the sequence SEQ ID NO: 18 (see below with capital letters indicating the mouse IL-7 gene and lower case letters representing flanking nucleotides from the L5-E4 expression cassette including underlined residual nucleotides from the SwaI restriction site) cloned into the L5-E4 cassette of SEQ ID NO: 14.

[L5 mIL7]
SEQ ID NO: 18
gctttgcaaagatttATGTTCCATGTTTCTT

TTAGATATATCTTTGGAATTCCTCCACTGAT

CCTTGTTCTGCTGCCTGTCACATCATCTGAG

TGCCACATTAAAGACAAAGAAGGTAAAGCAT

ATGAGAGTGTACTGATGATCAGCATCGATGA

ATTGGACAAAATGACAGGAACTGATAGTAAT

TGCCCGAATAATGAACCAAACTTTTTTAGAA

AACATGTATGTGATGATACAAAGGAAGCTGC

TTTTCTAAATCGTGCTGCTCGCAAGTTGAAG

CAATTTCTTAAAATGAATATCAGTGAAGAAT

TCAATGTCCACTTACTAACAGTATCACAAGG

CACACAAACACTGGTGAACTGCACAAGTAAG

GAAGAAAAAAACGTAAAGGAACAGAAAAAGA

ATGATGATGTTTCCTAAAGAGACTACTGAG

AGAAATAAAAACTTGTTGGAATAAAATTTTG

AAGGGCAGTATATAAaaataacttgtttatt gcag

The virus TAV IX-WT L5-GMCSF carried the TAV-255 deletion in the E1A promoter, wild-type viral sequence in the IX-E2 site, and the sequence SEQ ID NO: 19 (with capital letters indicating the mouse GMCSF gene and lower case letters representing flanking nucleotides from the L5-E4 expression cassette including underlined residual nucleotides from the SwaI restriction site) cloned into the L5-E4 cassette of SEQ ID NO: 14. This virus carries wild-type mouse GMCSF and not the codon-optimized form of mouse GMCSF used in the virus TAV-(L5-E4)mGMCSF shown in SEQ ID NO: 15.

[L5 wt mGMCSF]
SEQ ID NO: 19
gctttgcaaag<u>atttATGTGGCTGCAGAATT</u>

TACTTTTCCTGGGCATTGTGGTCTACAGCCT

CTCAGCACCCACCCGCTCACCCATCACTGTC

ACCCGGCCTTGGAAGCATGTAGAGGCCATCA

AAGAAGCCCTGAACCTCCTGGATGACATGCC

TGTCACGTTGAATGAAGAGGTAGAAGTCGTC

TCTAACGAGTTCTCCTTCAAGAAGCTAACAT

GTGTGCAGACCCGCCTGAAGATATTCGAGCA

GGGTCTACGGGGCAATTTCACCAAACTCAAG

GGCGCCTTGAACATGACAGCCAGCTACTACC

AGACATACTGCCCCCCAACTCCGGAAACGGA

CTGTGAAACACAAGTTACCACCTATGCGGAT

TTCATAGACAGCCTTAAAACCTTTCTGACTG

ATATCCCCTTTGAATGCAAAAAACCAGGCCA

AAAATGA<u>aaat aact</u>tgtttattgcag

The virus TAV IX-GMCSF L5-IL7 carried the TAV-255 deletion in the E1A promoter, the sequence SEQ ID NO: 20 (with capital letters indicating the mouse GMCSF gene and lower case letters representing the flanking nucleotides of the IX-E2 expression cassette including underlined residual nucleotides from the NotI restriction site) cloned into the IX-E2 cassette of SEQ ID NO: 17, and mouse IL-7 cloned into the L5-E4 cassette as depicted in SEQ ID NO: 18 and SEQ ID NO: 14. The sequence of mouse GMCSF was identical in the viruses TAV IX-WT L5-GMCSF and TAV IX-GMCSF L5-IL7 but was inserted in the IX-E2 expression cassette of one virus and the L5-E4 expression cassette in the other virus.

[IX wt mGMCSF]
SEQ ID NO: 20
atagggagaccc<u>gcggcc</u>ATGTGGCTGCAGAATTT

ACTTTTCCTGGGCATTGTGGTCTACAGCCTCTCAG

CACCCACCCGCTCACCCATCACTGTCACCCGGCCT

TGGAAGCATGTAGAGGCCATCAAAGAAGCCCTGAA

CCTCCTGGATGACATGCCTGTCACGTTGAATGAAG

AGGTAGAAGTCGTCTCTAACGAGTTCTCCTTCAAG

AAGCTAACATGTGTGCAGACCCGCCTGAAGATATT

CGAGCAGGGTCTACGGGGCAATTTCACCAAACTCA

AGGGCGCCTTGAACATGACAGCCAGCTACTACCAG

ACATACTGCCCCCCAACTCCGGAAACGGACTGTGA

AACACAAGTTACCACCTATGCGGATTTCATAGACA

GCCTTAAAACCTTTCTGACTGATATCCCCTTTGAA

TGCAAAAAACCAGGCCAAAAATGA<u>ggccgc</u>tgtgc cttctagt

Figure 3:
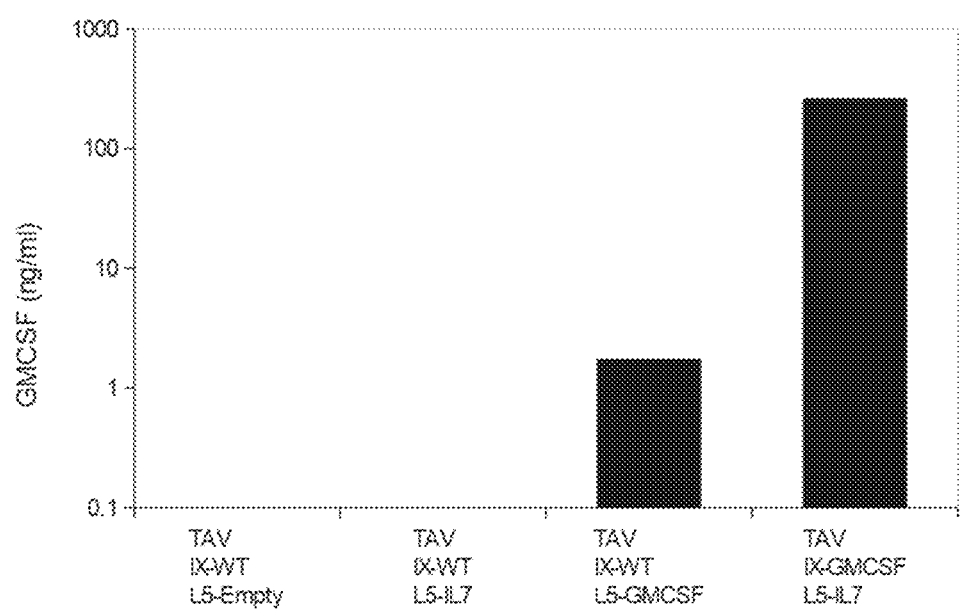
FIG. 3 depicts GMCSF expression level from A549 cells infected with virus TAV IX-WT LS-Empty, TAV IX-WT LS-IL7, TAV IX-WT LS-GMCSF, or TAV IX-GMCSF LS-IL7. GMCSF expression was measured in the conditioned media. Higher expression was seen when GMCSF was expressed from the IX-E2 expression cassette than from the L5-E4 expression cassette.

To test for transgene expression from these viruses, A549 cells were infected with the viruses at an MOI of 5 and four days later the conditioned media was collected and used in ELISAs for IL-7 and GMCSF. The ELISA for GMCSF showed substantially higher expression from the cassette in the IX-E2 site driven by the CMV promoter than from the cassette in the L5-E4 site driven by the SV40 promoter, as depicted in FIG. 3.

Example 5

Figure 4:
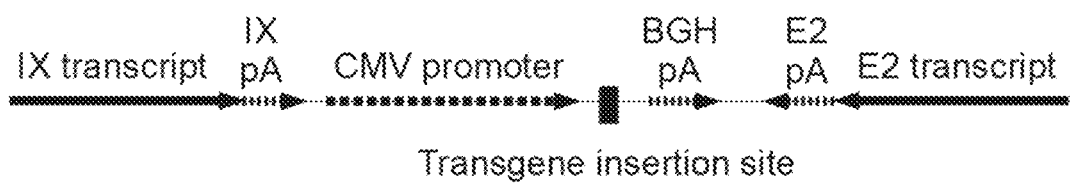
FIG. 4 depicts the initial design and revised design of the IX-E2 insertion site.
Figure 4:
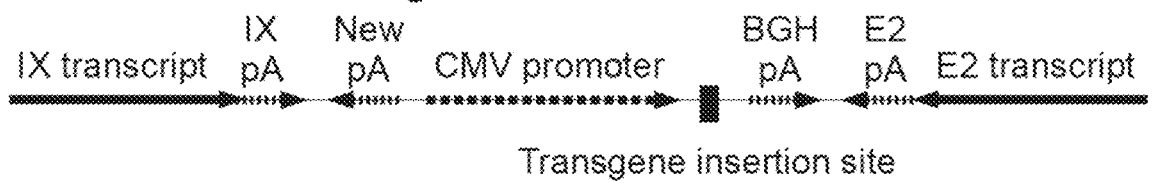

In viruses of the initial IX-E2 design (FIG. 4), we suspected that viral growth could be further optimized by blocking any potential for the CMV promoter driving transcription in the opposite direction from what was intended (Seila et al., Science. (2008) 322(5909):1849-51). We therefore revised the insert in this site so both the 5' and 3' ends of the insert contain polyadenylation signals oriented to polyadenylate transcripts going both into the insert from the normal viral genes and out of the insert toward the normal viral genes. See the revised IX-E2 design in FIG. 4.

The nucleotide sequence of the revised insert, from the polyadenylation signal of the IX transcript to the polyadenylation signal of the E2 transcript, is:

[IX revised Empty]
SEQ ID NO: 21
<u>AATAAA</u>ATACACCTTTTTTCGATTGTACGTAT<u>TTT</u>

<u>TATTT</u>ACGGTAAATGGCCCGCCTGGCTGACCGCCC

AACGACCCCCGCCCATTGACGTCAATAATGACGTA

TGTTCCCATAGTAACGCCAATAGGGACTTTCCATT

GACGTCAATGGGTGGAGTATTTACGGTAAACTGCC

CACTTGGCAGTACATCAAGTGTATCATATGCCAAG

TACGCCCCCTATTGACGTCAATGACGGTAAATGGC

CCGCCTGGCATTATGCCCAGTACATGACCTTATGG

GACTTTCCTACTTGGCAGTACATCTACGTATTAGT

CATCGCTATTACCATGGTGATGCGGTTTTGGCAGT

ACATCAATGGGCGTGGATAGCGGTTTGACTCACGG

GGATTTCCAAGTCTCCACCCCATTGACGTCAATGG

GAGTTTGTTTTGGCACCAAAATCAACGGGACTTTC

CAAAATGTCGTAACAACTCCGCCCCATTGACGCAA

ATGGGCGGTAGGCGTGTACGGTGGGAGGTCTATAT

AAGCAGAGCTCTCTGGCTAACTAGAGAACCCACTG

CTTACTGGCTTATCGAAATTAATACGACTCACTAT

AGGGAGACCC<u>GCGGCCGC</u>TGTGCCTTCTAGTTGCC

AGCCATCTGTTGTTTGCCCCTCCCCCGTGCCTTCC

TTGACCCTGGAAGGTGCCACTCCCACTGTCCTTTC

CTA<u>ATAAAA</u>ACCAGACTCTGTTTGGATTTGGATC

AAGCAAGTGTCTTGCTGTC<u>TTTATT</u>

Each forward polyadenylation signal ("AATAAA" SEQ ID NO: 12) and reverse polyadenylation signal ("TTTATT" SEQ ID NO: 13), and the NotI site ("GCGGCCGC" SEQ ID NO: 16), are underlined. Viruses carrying the expression cassette with the revised IX-E2 design grew more efficiently than the viruses with the initial IX-E2 design.

Example 6

The virus TAV-IXrL5-Empty carried the TAV-255 deletion in the viral E1A promoter, SEQ ID NO: 21 (the empty expression cassette of the revised IX-E2 design) and SEQ ID NO: 14 (the empty expression cassette in the L5-E4 site). The virus TAV-IXrL5-hIL12 carries the TAV-255 deletion in the viral E1A promoter, a gene encoding the human IL12A chain in the revised IX-E2 expression cassette (depicted in SEQ ID NO: 22), and a gene encoding the human IL12B chain in the L5-E4 expression cassette (depicted in SEQ ID NO: 23). In SEQ ID NO: 22, each forward polyadenylation signal ("AATAAA" SEQ ID NO: 12) and reverse polyadenylation signal ("TTTATT" SEQ ID NO: 13), and the residual nucleotides from the NotI site are underlined, and the gene encoding the human IL12A chain are bolded. In SEQ ID NO: 23, the polyadenylation signals of the L5 and E4 transcription units, and the residual nucleotides of the SwaI restriction site are underlined, and the gene encoding the human IL12B chain are bolded.

```
[IX revised hIL12A]
                                    SEQ ID NO: 22
AATAAAATACACCTTTTTTCGATTGTACGTATTTT

TATTTACGGTAAATGGCCCGCCTGGCTGACCGCCC

AACGACCCCCGCCCATTGACGTCAATAATGACGTA

TGTTCCCATAGTAACGCCAATAGGGACTTTCCATT

GACGTCAATGGGTGGAGTATTTACGGTAAACTGCC

CACTTGGCAGTACATCAAGTGTATCATATGCCAAG

TACGCCCCCTATTGACGTCAATGACGGTAAATGGC

CCGCCTGGCATTATGCCCAGTACATGACCTTATGG

GACTTTCCTACTTGGCAGTACATCTACGTATTAGT

CATCGCTATTACCATGGTGATGCGGTTTTGGCAGT

ACATCAATGGGCGTGGATAGCGGTTTGACTCACGG

GGATTTCCAAGTCTCCACCCCATTGACGTCAATGG

GAGTTTGTTTTGGCACCAAAATCAACGGGACTTTC

CAAAATGTCGTAACAACTCCGCCCCATTGACGCAA

ATGGGCGGTAGGCGTGTACGGTGGGAGGTCTATAT

AAGCAGAGCTCTCTGGCTAACTAGAGAACCCACTG

CTTACTGGCTTATCGAAATTAATACGACTCACTAT

AGGGAGACCCGCGGCCATGTGGCCCCCTGGGTCAG

CCTCCCAGCCACCGCCCTCACCTGCCGCGGCCACA

GGTCTGCATCCAGCGGCTCGCCCTGTGTCCCTGCA

GTGCCGGCTCAGCATGTGTCCAGCGCGCAGCCTCC

TCCTTGTGGCTACCCTGGTCCTCCTGGACCACCTC

AGTTTGGCCAGAAACCTCCCCGTGGCCACTCCAGA

CCCAGGAATGTTCCCATGCCTTCACCACTCCCAAA

ACCTGCTGAGGGCCGTCAGCAACATGCTCCAGAAG

GCCAGACAAACTCTAGAATTTTACCCTTGCACTTC

TGAAGAGATTGATCATGAAGATATCACAAAAGATA

AAACCAGCACAGTGGAGGCCTGTTTACCATTGGAA

TTAACCAAGAATGAGAGTTGCCTAAATTCCAGAGA

GACCTCTTTCATAACTAATGGGAGTTGCCTGGCCT

CCAGAAAGACCTCTTTTATGATGGCCCTGTGCCTT

AGTAGTATTTATGAAGACTTGAAGATGTACCAGGT

GGAGTTCAAGACCATGAATGCAAAGCTTCTGATGG

ATCCTAAGAGGCAGATCTTTCTAGATCAAAACATG

CTGGCAGTTATTGATGAGCTGATGCAGGCCCTGAA

TTTCAACAGTGAGACTGTGCCACAAAAATCCTCCC

TTGAAGAACCGGATTTTTATAAAACTAAAATCAAG

CTCTGCATACTTCTTCATGCTTTCAGAATTCGGGC

AGTGACTATTGATAGAGTGATGAGCTATCTGAATG

CTTCCTAAGGCCGCTGTGCCTTCTAGTTGCCAGCC

ATCTGTTGTTTGCCCCTCCCCCGTGCCTTCCTTGA

CCCTGGAAGGTGCCACTCCCACTGTCCTTTCCTAA

TAAAAAACCAGACTCTGTTTGGATTTGGATCAAGC

AAGTGTCTTGCTGTCTTTATT

[L5 initial hIL12B]
                                    SEQ ID NO: 23
AATAAAGAATCGTTTGTGTTATGTTTCAACCTGTG

GAATGTGTGTCAGTTAGGGTGTGGAAAGTCCCCAG

GCTCCCCAGCAGGCAGAAGTATGCAAAGCATGCAT

CTCAATTAGTCAGCAACCAGGTGTGGAAAGTCCCC

AGGCTCCCCAGCAGGCAGAAGTATGCAAAGCATGC

ATCTCAATTAGTCAGCAACCATAGTCCCGCCCCTA

ACTCCGCCCATCCCGCCCCTAACTCCGCCCAGTTC

CGCCCATTCTCCGCCCCATGGCTGACTAATTTTTT

TTATTTATGCAGAGGCCGAGGCCGCCTCTGCCTCT

GAGCTATTCCAGAAGTAGTGAGGAGGCTTTTTTGG

AGGCCTAGGCTTTTGCAAAAAGCTTTGCAAAGATT

TATGTGTCACCAGCAGTTGGTCATCTCTTGGTTTT

CCCTGGTTTTTCTGGCATCTCCCCTCGTGGCCATA

TGGGAACTGAAGAAAGATGTTTATGTCGTAGAATT

GGATTGGTATCCGGATGCCCCTGGAGAAATGGTGG

TCCTCACCTGTGACACCCCTGAAGAAGATGGTATC

ACCTGGACCTTGGACCAGAGCAGTGAGGTCTTAGG

CTCTGGCAAAACCCTGACCATCCAAGTCAAAGAGT

TTGGAGATGCTGGCCAGTACACCTGTCACAAAGGA

GGCGAGGTTCTAAGCCATTCGCTCCTGCTGCTTCA

CAAAAAGGAAGATGGAATTTGGTCCACTGATATTT

TAAAGGACCAGAAAGAACCCAAAAATAAGACCTTT
```

```
CTAAGATGCGAGGCCAAGAATTATTCTGGACGTTT

CACCTGCTGGTGGCTGACGACAATCAGTACTGATT

TGACATTCAGTGTCAAAAGCAGCAGAGGCTCTTCT

GACCCCCAAGGGGTGACGTGCGGAGCTGCTACACT

CTCTGCAGAGAGAGTCAGAGGGGACAACAAGGAGT

ATGAGTACTCAGTGGAGTGCCAGGAGGACAGTGCC

TGCCCAGCTGCTGAGGAGAGTCTGCCCATTGAGGT

CATGGTGGATGCCGTTCACAAGCTCAAGTATGAAA

ACTACACCAGCAGCTTCTTCATCAGGGACATCATC

AAACCTGACCCACCCAAGAACTTGCAGCTGAAGCC

ATTAAAGAATTCTCGGCAGGTGGAGGTCAGCTGGG

AGTACCCTGACACCTGGAGTACTCCACATTCCTAC

TTCTCCCTGACATTCTGCGTTCAGGTCCAGGGCAA

GAGCAAGAGAGAAAAGAAAGATAGAGTCTTCACGG

ACAAGACCTCAGCCACGGTCATCTGCCGCAAAAAT

GCCAGCATTAGCGTGCGGGCCCAGGACCGCTACTA

TAGCTCATCTTGGAGCGAATGGGCATCTGTGCCCT

GCAGTTAGAAATAACTTGTTTATTGCAGCTTATAA

TGGTTACAAATAAAGCAATAGCATCACAAATTTCA

CAAATAAAGCATTTTTTTCACTGCATTCTAGTTGT

GGTTTGTCCAAACTCATCAATGTATCTTATCATGT

CTGGTGTTTATT
```

The virus WT-IXrL5-hIL12 was created with an identical genomic structure as TAV-IXrL5-hIL12 except that it carries a wild-type E1A promoter instead of carrying the TAV-255 deletion in the E1A promoter. Each of these viruses also has a deletion of the E3 RIDα, RIDβ, and 14.7 k genes and a deletion of the E4 ORF1-ORF4 genes.

To compare this design approach with another strategy to incorporate IL12 into an oncolytic adenovirus, we tested an adenovirus carrying a gene encoding the human IL12A and IL12B chains linked by a furin cleavage site (amino acids RAKR; SEQ ID NO: 24) carried in the E1B-19K site. When the fusion protein was synthesized by the cell, the furin site was cleaved between the final R of the RAKR sequence and the next amino acid (the first amino acid of mature IL12A) by the enzyme furin in the Golgi. We previously found that using a furin cleavage site as a linker led to high level expression of the heterodimeric IL12 protein. The nucleic acid sequence of that fusion gene (capitalized), the flanking SalI and XhoI restriction sites used for cloning (underlined), and the adenoviral nucleotides indicating the site where it was inserted in the adenoviral genome (lower case) is:

```
[hIL12 furin]
                              SEQ ID NO: 25
atctgacctcgtcgaATGTGTCACCAGCAGTTGG

TCATCTCTTGGTTTTCCCTGGTTTTTCTGGCATCT

CCCCTCGTGGCCATATGGGAACTGAAGAAAGATGT

TTATGTCGTAGAATTGGATTGGTATCCGGATGCCC

CTGGAGAAATGGTGGTCCTCACCTGTGACACCCCT

GAAGAAGATGGTATCACCTGGACCTTGGACCAGAG

CAGTGAGGTCTTAGGCTCTGGCAAAACCCTGACCA

TCCAAGTCAAAGAGTTTGGAGATGCTGGCCAGTAC

ACCTGTCACAAAGGAGGCGAGGTTCTAAGCCATTC

GCTCCTGCTGCTTCACAAAAAGGAAGATGGAATTT

GGTCCACTGATATTTTAAAGGACCAGAAAGAACCC

AAAAATAAGACCTTTCTAAGATGCGAGGCCAAGAA

TTATTCTGGACGTTTCACCTGCTGGTGGCTGACGA

CAATCAGTACTGATTTGACATTCAGTGTCAAAAGC

AGCAGAGGCTCTTCTGACCCCCAAGGGGTGACGTG

CGGAGCTGCTACACTCTCTGCAGAGAGAGTCAGAG

GGGACAACAAGGAGTATGAGTACTCAGTGGAGTGC

CAGGAGGACAGTGCCTGCCCAGCTGCTGAGGAGAG

TCTGCCCATTGAGGTCATGGTGGATGCCGTTCACA

AGCTCAAGTATGAAAACTACACCAGCAGCTTCTTC

ATCAGGGACATCATCAAACCTGACCCACCCAAGAA

CTTGCAGCTGAAGCCATTAAAGAATTCTCGGCAGG

TGGAGGTCAGCTGGGAGTACCCTGACACCTGGAGT

ACTCCACATTCCTACTTCTCCCTGACATTCTGCGT

TCAGGTCCAGGGCAAGAGCAAGAGAGAAAAGAAAG

ATAGAGTCTTCACGGACAAGACCTCAGCCACGGTC

ATCTGCCGCAAAAATGCCAGCATTAGCGTGCGGGC

CCAGGACCGCTACTATAGCTCATCTTGGAGCGAAT

GGGCATCTGTGCCCTGCAGTCGTGCTAAGCGAAGA

AACCTCCCGTGGCCACTCCAGACCCAGGAATGTT

CCCATGCCTTCACCACTCCCAAAACCTGCTGAGGG

CCGTCAGCAACATGCTCCAGAAGGCCAGACAAACT

CTAGAATTTTACCCTTGCACTTCTGAAGAGATTGA

TCATGAAGATATCACAAAAGATAAAACCAGCACAG

TGGAGGCCTGTTTACCATTGGAATTAACCAAGAAT

GAGAGTTGCCTAAATTCCAGAGAGACCTCTTTCAT

AACTAATGGGAGTTGCCTGGCCTCCAGAAAGACCT

CTTTTATGATGGCCCTGTGCCTTAGTAGTATTTAT

GAAGACTTGAAGATGTACCAGGTGGAGTTCAAGAC

CATGAATGCAAAGCTTCTGATGGATCCTAAGAGGC

AGATCTTTCTAGATCAAAACATGCTGGCAGTTATT

GATGAGCTGATGCAGGCCCTGAATTTCAACAGTGA

GACTGTGCCACAAAAATCCTCCCTTGAAGAACCGG

ATTTTTATAAAACTAAAATCAAGCTCTGCATACTT
```

-continued
```
CTTCATGCTTTCAGAATTCGGGCAGTGACTATTGA

TAGAGTGATGAGCTATCTGAATGCTTCCTAATAAc tcgagtcaccaggcg
```

The virus TAV-hIL12-furin carries the TAV-255 deletion in the E1A promoter and SEQ ID NO: 25 in the E1B-19K region. The control virus TAV-Δ19k carries the TAV-255 deletion in the E1A promoter and a deletion of the E1B-19K region.

Figure 5:
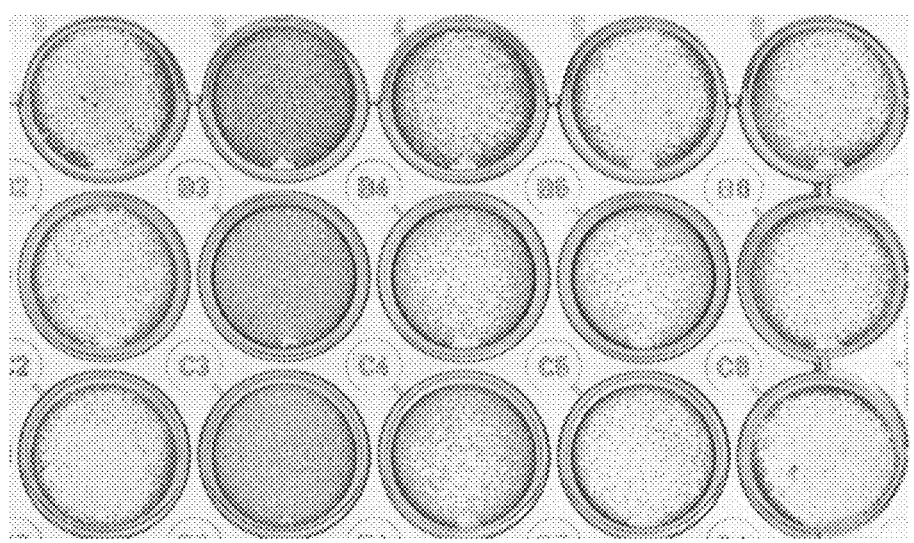
FIG. 5 depicts A549 cells infected virus (TAV-Δ19k, TAV-hIL12-furin, TAV-TAV-IXrL5-Empty, WT-IXrL5-hIL12, or TAV-IXrL5-hIL12) in triplicate and stained with crystal violet (staining live cells purple) four days after infection.

To test for oncolytic activity and IL12 expression, A549 cells were infected with TAV-Δ19k, TAV-hIL12-furin, TAV-TAV-IXrL5-Empty, and TAV-IXrL5-hIL12 at an MOI of 5 in triplicate. Four days after infection, the conditioned media was collected and IL12 was measured in an ELISA that detects only the assembled IL12A-IL12B heterodimer, and the remaining cells were stained with crystal violet. As shown in FIG. 5, TAV-hIL12-furin was slightly less lytic than the corresponding control virus TAV-Δ19k which is in agreement with our general experience when transgenes are inserted in the E1B-19K region, while TAV-IXrL5-hIL12 was as lytic as TAV-IXrL5-Empty and TAV-Δ19k. This demonstrated that insertion of expression cassettes in the IX-E2 and L5-E4 regions has minimal impact on viral fitness and may be superior to insertion of transgenes in the E1B-19K region in this regard.

Figure 6:
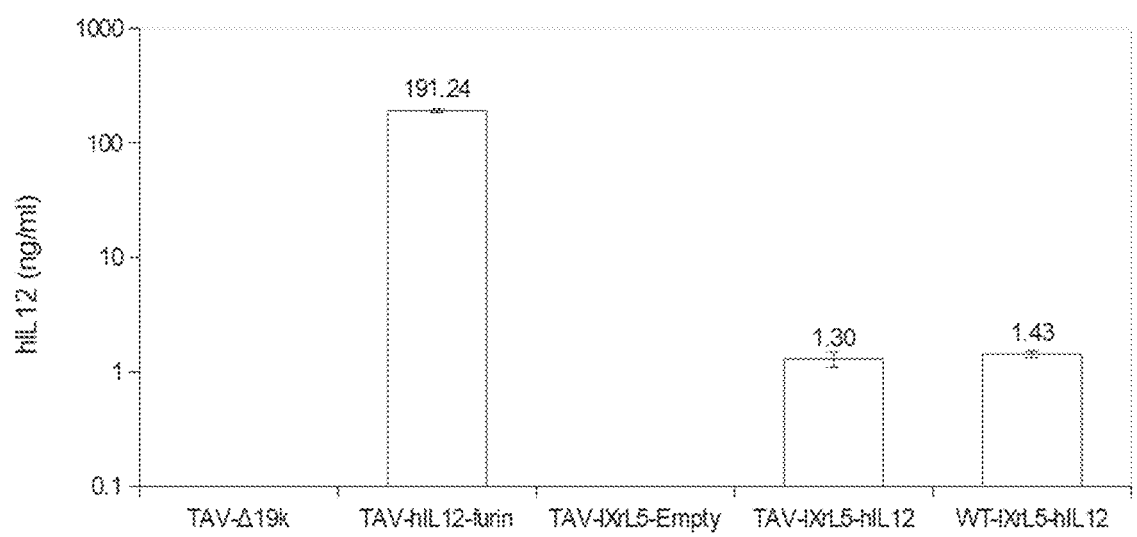
FIG. 6 depicts IL-12 expression level from A549 cells infected with virus (TAV-Δ19k, TAV-hIL12-furin, TAV-TAV-IXrL5-Empty, WT-IXrL5-hIL12, or TAV-IXrL5-hIL12). The A549 cells were infected with the indicated virus in triplicate, and IL12 in the conditioned media was measured with an ELISA four days after infection.

As shown in FIG. 6, TAV-hIL12-furin expressed higher levels of IL12 than the viruses using IX-E2 and L5-E4 cassettes. This suggested that at least one of the two expression cassettes may be suboptimal and prompted further investigation into improving the design. However, the IL12 protein generated from TAV-hIL12-furin contains a non-native RAKR sequence (the remaining furin recognition site) at the C-terminus of the IL12B chain which might lead to undesirable in vivo effects such as immunogenicity against the transgene or against native IL12, whereas the IL12 generated by TAV-IXrL5-hIL12 has the advantage that it is completely native.

Example 7

Based on the relatively low expression from the L5-E4 cassette compared to the IX-E2 cassette observed, we hypothesized that the L5-E4 cassette was the cause of the low expression of the IL-12 heterodimer. We revised the L5-E4 region to include bidirectional polydenylation signals at both ends, similar to the approach that was used for the IX-E2 region.

The nucleotide sequence SEQ ID NO: 26 was cloned into the L5-E4 region, showing the polyadenylation signals of the L5 and E4 transcripts at the 5' and 3' ends and all polyadenylation signals and the SwaI restriction site underlined.

```
[L5 revised SV40]
                                    SEQ ID NO: 26
AATAAAAGGTTTATTCTGTGGAATGTGTGTCAGTT

AGGGTGTGGAAAGTCCCCAGGCTCCCCAGCAGGCA

GAAGTATGCAAAGCATGCATCTCAATTAGTCAGCA

ACCAGGTGTGGAAAGTCCCCAGGCTCCCCAGCAGG

CAGAAGTATGCAAAGCATGCATCTCAATTAGTCAG
```
-continued
```
CAACCATAGTCCCGCCCCTAACTCCGCCCATCCCG

CCCCTAACTCCGCCCAGTTCCGCCCATTCTCCGCC

CCATGGCTGACTAATTTTTTTTATTTATGCAGAGG

CCGAGGCCGCCTCTGCCTCTGAGCTATTCCAGAAG

TAGTGAGGAGGCTTTTTTGGAGGCCTAGGCTTTTG

CAAAAAGCTTTGCAAAGATTTAAATAACTTGTTTA

TTGCAGCTTATAATGGTTACAAATAAAGAATCGTT

TGTGTTATGTTTCAACGTGTTTATT
```

The virus TAV-(IXr)Empty-(L5r)Empty was made with the TAV-255 deletion in the E1A promoter, the revised IX-E2 cassette without a transgene in the IX-E2 region shown in SEQ ID NO: 21, and the revised L5-E4 cassette without a transgene in the L5-E4 region shown in SEQ ID NO: 26.

The virus TAV-(IXr)mIL7-(L5r)mGMCSF contained the TAV-255 deletion in the E1A promoter, the revised IX-E2 cassette shown in SEQ ID NO: 21 with the mouse GMCSF gene cloned into the NotI site as shown in SEQ ID NO: 20, and the revised L5-E4 cassette shown in SEQ ID NO: 26 with the mouse IL-7 gene cloned into the SwaI site as shown in SEQ ID NO: 18.

The virus TAV-(IXr)mGMCSF-(L5r)mIL7 contained the TAV-255 deletion in the E1A promoter, the revised IX-E2 cassette shown in SEQ ID NO: 21 with the mouse IL-7 gene cloned into the NotI site as shown in SEQ ID NO: 27, and the revised L5-E4 cassette shown in SEQ ID NO: 26 with the mouse GMCSF gene cloned into the SwaI site as shown in SEQ ID NO: 19. Thus, the viruses TAV-(IXr)mGMCSF-(L5r)mIL7 and TAV-(IXr)mIL7-(L5r)mGMCSF differed only in which gene of IL-7 and GMCSF was inserted into which site: the revised IX-E2 or the revised L5-E4 site.

```
[IX mIL7]
                                    SEQ ID NO: 27
atagggagacccgcggccATGTTCCATGTTTCTTT

TAGATATATCTTTGGAATTCCTCCACTGATCCTTG

TTCTGCTGCCTGTCACATCATCTGAGTGCCACATT

AAAGACAAAGAAGGTAAAGCATATGAGAGTGTACT

GATGATCAGCATCGATGAATTGGACAAAATGACAG

GAACTGATAGTAATTGCCCGAATAATGAACCAAAC

TTTTTTAGAAAACATGTATGTGATGATACAAAGGA

AGCTGCTTTTCTAAATCGTGCTGCTCGCAAGTTGA

AGCAATTTCTTAAAATGAATATCAGTGAAGAATTC

AATGTCCACTTACTAACAGTATCACAAGGCACACA

AACACTGGTGAACTGCACAAGTAAGGAAGAAAAAA

ACGTAAAGGAACAGAAAAAGAATGATGCATGTTTC

CTAAAGAGACTACTGAGAGAAATAAAAACTTGTTG

GAATAAAATTTTGAAGGGCAGTATATAAggccgct gtgccttctagt
```

To test transgene expression from these viruses, A549 cells were infected with each virus at an MOI of 5 in triplicate. Conditioned media was collected four days later and GMCSF and IL-7 were measured in ELISAs. For both IL-7 and GMCSF, expression was higher from the virus carrying the gene in the revised IX-E2 site than the revised L5-E4 site. This confirmed the previous finding that the expression cassette at IX-E2 using the CMV promoter expressed at higher levels than the cassette at L5-E4 using the SV40 promoter and this was not affected by revising the L5-E4 site to include bidirectional polyadenylation signals.

Example 8

We next investigated further improving the promoter in the L5-E4 site. The SV40 promoter that was initially used had a point mutation of G (in the wild-type SV40 sequence) to T (in the L5-E4 insert) at the major transcription start site, so we generated an L5-E4 insert with that nucleotide changed back to the wild-type G as shown in SEQ ID NO: 28 with the previously mutated nucleotide, the polyadenylation signals, and the SwaI restriction site underlined. We also investigated using a different promoter, and generated an L5-E4 insert that used the human EF1A promoter instead of the SV40 promoter. SEQ ID NO: 29 shows the L5-E4 insert using the human EF1A promoter, shown from the polyadenylation signal from the L5 transcript to the polyadenylation signal of the E4 transcript, with the polyadenylation signals and the SwaI restriction site underlined.

[LS revised SV40 wt Empty]
SEQ ID NO: 28
A<u>ATAAA</u>AGGTTTATTCTGTGGAATGTGTGTCAGTT

AGGGTGTGGAAAGTCCCCAGGCTCCCCAGCAGGCA

GAAGTATGCAAAGCATGCATCTCAATTAGTCAGCA

ACCAGGTGTGGAAAGTCCCCAGGCTCCCCAGCAGG

CAGAAGTATGCAAAGCATGCATCTCAATTAGTCAG

CAACCATAGTCCCGCCCCTAACTCCGCCCATCCCG

CCCCTAACTCCGCCCAGTTCCGCCCATTCTCCGCC

CCATGGCTGACTAATTTTTTTATTTATGCAGAGG

CCGAGGCCGCCTC<u>G</u>GCCTCTGAGCTATTCCAGAAG

TAGTGAGGAGGCTTTTTTGGAGGCCTAGGCTTTTG

CAAAAAGCTTTGCAAAGATTTAAATAACTTGTTTA

TTGCAGCTTATAATGGTTAC<u>AATAAA</u>GAATCGTT

TGTGTTATGTTTCAACGTG<u>TTTATT</u>

[LS revised EF1A Empty]
SEQ ID NO: 29
A<u>ATAAA</u>AGGTTTATTAGGCGGCCTCCCCGTCACCA

CCCCCCCCAACCCGCCCCGACCGGAGCTGAGAGTA

ATTCATACAAAAGGACTCGCCCCTGCCTTGGGGAA

TCCCAGGGACCGTCGTTAAACTCCCACTAACGTAG

AACCCAGAGATCGCTGCGTTCCCGCCCCCTCACCC

GCCCGCTCTCGTCATCACTGAGGTGGAGAAGAGCA

TGCGTGAGGCTCCGGTGCCCGTCAGTGGGCAGAGC

GCACATCGCCCACAGTCCCCGAGAAGTTGGGGGGA

GGGGTCGGCAATTGAACCGGTGCCTAGAGAAGGTG

GCGCGGGGTAAACTGGGAAAGTGATGTCGTGTACT

GGCTCCGCCTTTTTCCCGAGGGTGGGGGAGAACCG

TATATAAGTGCAGTAGTCGCCGTGAACGTTCTTTT

TCGCAACGGGTTTGCCGCCAGAACACA<u>AATTAAAT</u>

AACTTGTTTATTGCAGCTTATAATGGTTAC<u>AAATA</u>

<u>A</u>AGAATCGTTTGTGTTATGTTTCAACGTG<u>TTTATT</u>

To test these revised expression cassettes in L5-E4, we generated viruses carrying the mouse IL-7 gene in the IX-E2 site and the mouse GMCSF gene in the new L5-E4 sites. The mouse IL-7 gene used in the IX-E2 site was modified by introducing a silent mutations in two regions near the 3' end of the gene with sequence AATAAA that might by processed as a polyadenylation signal to lead to reduced expression, substituting synonymous sequences that would not change the encoded protein sequence but would eliminate the internal AATAAA sequences; SEQ ID NO: 30 shows that nucleotide sequence with the IL-7 coding nucleotides capitalized and the mutations underlined, and the flanking nucleotides of the IX-E2 cassette in lower case with the residual nucleotides from the NotI site underlined. To attempt to improve expression of the mouse GMCSF gene in the L5-E4 sites, a consensus Kozak sequence (nucleotides GCCACC) was included between the residual nucleotides of the SwaI site and the start codon of the GMCSF gene; SEQ ID NO: 31 shows the nucleotide sequence with the mouse GMCSF gene and the Kozak sequence capitalized with the Kozak sequence underlined, and with the flanking nucleotides of the L5-E4 cassette in lower case with the residual nucleotides from the SwaI site underlined.

[mIL7 no poly-A]
SEQ ID NO: 30
atagggagaccc<u>gcggcc</u>ATGTTCCATGTTTCTTT

TAGATATATCTTTGGAATTCCTCCACTGATCCTTG

TTCTGCTGCCTGTCACATCATCTGAGTGCCACATT

AAAGACAAAGAAGGTAAAGCATATGAGAGTGTACT

GATGATCAGCATCGATGAATTGGACAAAATGACAG

GAACTGATAGTAATTGCCCGAATAATGAACCAAAC

TTTTTTAGAAAACATGTATGTGATGATACAAAGGA

AGCTGCTTTTCTAAATCGTGCTGCTCGCAAGTTGA

AGCAATTTCTTAAAATGAATATCAGTGAAGAATTC

AATGTCCACTTACTAACAGTATCACAAGGCACACA

AACACTGGTGAACTGCACAAGTAAGGAAGAAAAA

ACGTAAAGGAACAGAAAAAGAATGATGCATGTTTC

CTAAAGAGACTACTGAGAGAAAT<u>C</u>AAAACTTGTTG

GAA<u>C</u>AAAATTTTGAAGGGCAGTATATAAggccgct gtgccttctagt

-continued

[mGMCSF Kozak]

SEQ ID NO: 31 atttGCCACCATGTGGCTGCAGAATTTACTTTTCC

TGGGCATTGTGGTCTACAGCCTCTCAGCACCCACC

CGCTCACCCATCACTGTCACCCGGCCTTGGAAGCA

TGTAGAGGCCATCAAAGAAGCCCTGAACCTCCTGG

ATGACATGCCTGTCACGTTGAATGAAGAGGTAGAA

GTCGTCTCTAACGAGTTCTCCTTCAAGAAGCTAAC

ATGTGTGCAGACCCGCCTGAAGATATTCGAGCAGG

GTCTACGGGGCAATTTCACCAAACTCAAGGGCGCC

TTGAACATGACAGCCAGCTACTACCAGACATACTG

CCCCCCAACTCCGGAAACGGACTGTGAAACACAAG

TTACCACCTATGCGGATTTCATAGACAGCCTTAAA

ACCTTTCTGACTGATATCCCCTTTGAATGCAAAAA

ACCAGGCCAAAAATGAaaataacttgtttattgca g

The virus TAV-(IXr)mIL7noPA-(L5SV40wt)KozakmGMCSF contained the TAV-255 deletion in the E1A promoter, the revised IX-E2 insert shown in SEQ ID NO: 21 with the mouse IL-7 gene with synonymous mutations at the potential internal polyadenylation sites cloned into the NotI site as shown in SEQ ID NO: 30, and the L5-E4 insert with the wild-type SV40 promoter shown in SEQ ID NO: 28 with the mouse GMCSF gene including a consensus Kozak sequence cloned into the SwaI site as shown in SEQ ID NO: 31. The virus TAV-(IXr)mIL7noPA-(L5EF1A)KozakmGMCSF contains the TAV-255 deletion in the E1A promoter, the revised IX-E2 insert shown in SEQ ID NO: 21 with the mouse IL-7 gene with synonymous mutations at the potential internal polyadenylation sites cloned into the NotI site as shown in SEQ ID NO: 30, and the L5-E4 insert with the human EF1A promoter shown in SEQ ID NO: 29 with the mouse GMCSF gene including a consensus Kozak sequence cloned into the SwaI site as shown in SEQ ID NO: 31.

Figure 7:
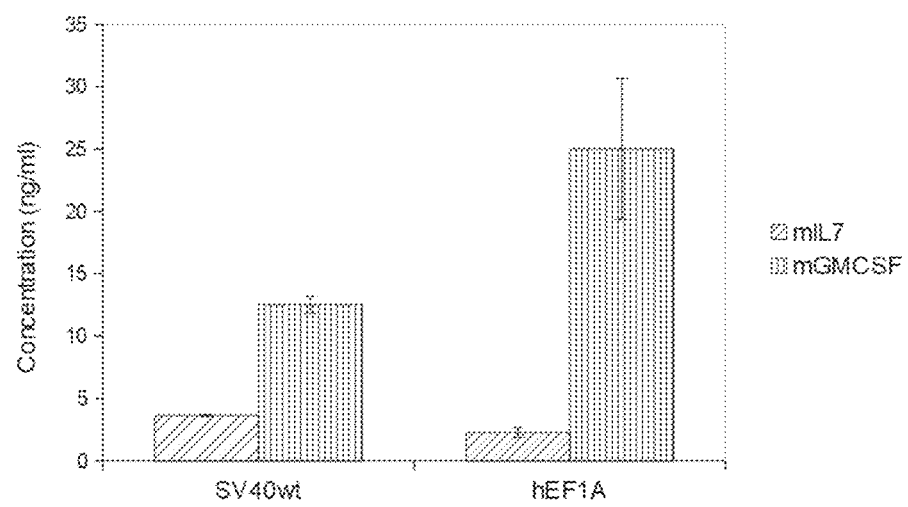
FIG. 7 depicts IL-17 and GMCSF expression level from A549 cells infected with either TAV-(IXr)mIL7noPA-(L5SV40wt)KozakmGMCSF (labeled SV40wt) or TAV-(IXr)mIL7noPA-(L5EF1A)KozakmGMCSF (labeled hEF1A).

To test these viruses for transgene expression, A549 cells were infected with the two viruses in triplicate at an MOI of 5. Four days later, conditioned media was collected and used in ELISAs to measure IL-7 and GMCSF expression. Results are shown in FIG. 7. The human EF1A promoter had moderately higher expression and was chosen for further development. The virus TAV-(IXr)mIL7noPA-(L5EF1A)KozakmGMCSF was prepared as a pharmaceutical agent for mouse experiments by amplifying the virus in serum-free suspension culture of SF-BMAdR 281 cells (derived from A549 cells), lysing the cells, purifying the virus with chromatography, and dialyzing into a buffer with 25 mM NaCl, 20 mM Tris, 2.5% glycerol at pH 8. The virus thus prepared had a viral particle concentration of $5.8 \times 10^{11}$ vp/ml and an infectious titer of $3.0 \times 10^{10}$ IU/ml.

Example 9

We further investigated whether deletion of the adenoviral death protein (ADP) could improve expression of the transgenes. ADP is expressed late during viral replication and lyses the host cell to release progeny virions, so its removal might allow cells to live and express the transgenes longer before they are killed. The nucleotide sequence of the ADP gene in the context of the E3 RIDα, RIDβ, and 14.7K deletion used in the TAV-(IXr)mIL7noPA-(L5EF1A)KozakmGMCSF virus is shown in SEQ ID NO: 32 with the nucleotides encoding ADP capitalized, the site of the E3 RIDα, RIDβ, and 14.7K deletion as a hyphen, and the flanking adenoviral nucleotides in lowercase. To create the AADP deletion, the underlined nucleotides within SEQ ID NO: 32 were deleted.

[ADP]

SEQ ID NO: 32

Gaaaatgccttaatttactaagttacaaagctaat gtcaccactaactgctttactcgctgcttgcaaaa caaattcaaaaagttagcattataattagaatagg atttaaaccccccggtcatttcctgctcaatacca ttcccctgaacaattgactctatgtgggatatgct ccagcgctacaaccttgaagtcaggcttcctggat gtcagcatctgactttggccagcacctgtcccgcg gatttgttccagtccaactacagcgacccacccta acagagATGACCAACACAACCAACGCGGCCGCCGC

TACCGGACTTACATCTACCACAAATACACCCCAAG

TTTCTGCCTTTGTCAATAACTGGGATAACTTGGGC

ATGTGGTGGTTCTCCATAGCGCTTATGTTTGTATG

CCTTATTATTATGTGGCTCATCTGCTGCCTAAAGC

GCAAACGCGCCCGACCACCCATCTATAGTCCCATC

ATTGTGCTACACCCAAACAATGATGGAATCCATAG

ATTGGACGGACTGAAACACATGTTCTTTTCTCTTA

CAGTATGAtaataaaaaaaaataataaagca

The virus TAV-(IXr)mIL7noPA-(L5EF1A)KozakmGMCSF-AADP was created with an identical genome to TAV-(IXr)mIL7noPA-(L5EF1A)KozakmGMCSF except that it also contains a deletion of the nucleotides of the ADP gene as underlined of SEQ ID NO: 32.

Figure 8:
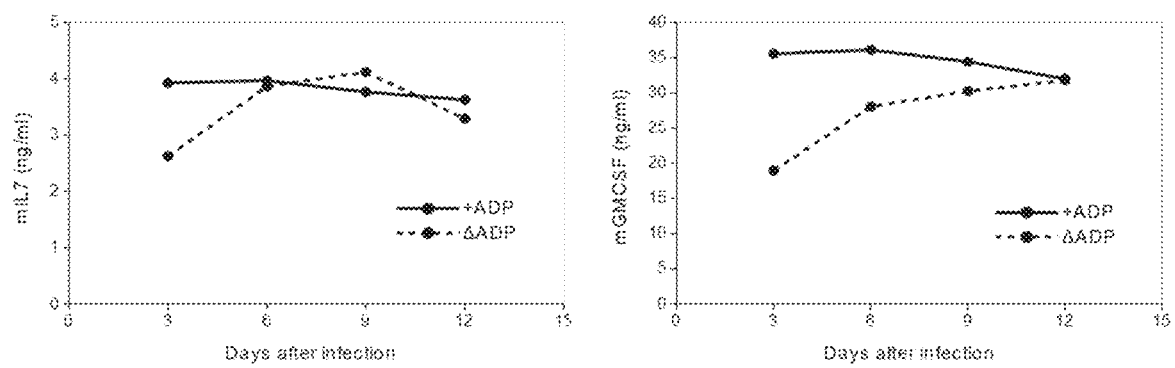
FIG. 8 depicts IL-17 and GMCSF expression level from A549 cells infected with ethe ADP gene intact [TAV-(IXr) mIL7noPA-(L5EF1A)KozakmGMCSF, labeled as +ADP] or deleted [TAV-(IXr)mIL7noPA-(L5EF1A)KozakmGMCSF-AADP, labeled as ΔADP]. Conditioned media was collected at the indicated times after infection and IL-7 and GMCSF were measured in ELISAs.
Figure 9:
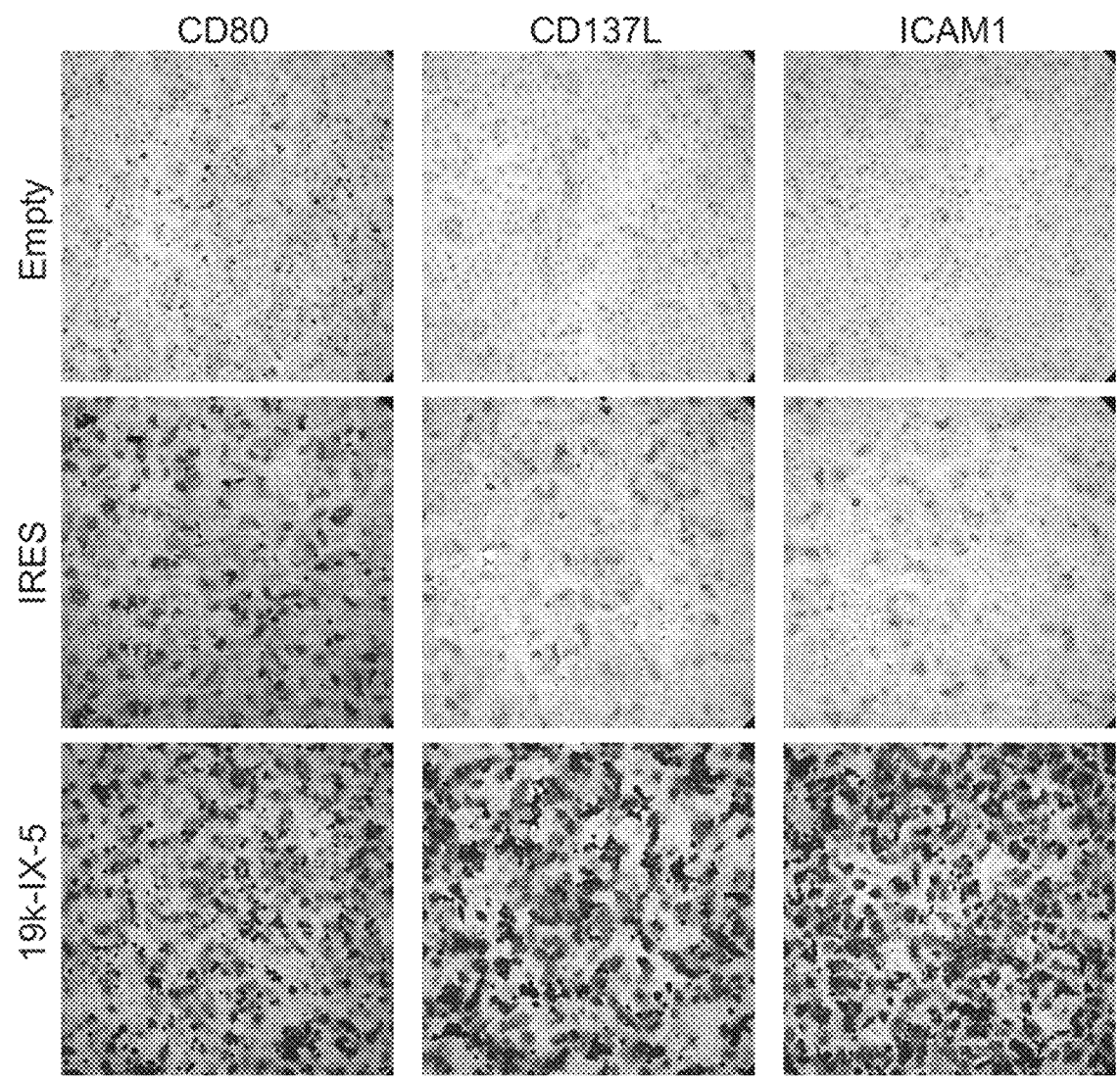
FIG. 9 depicts CD80, CD137L, and ICAM1 staining in A549 cells infected with virus [TAV-mCD80(IRES) mCD137L(IRES)mICAM1, labeled as IRES], [TAV-(19k) mCD80-(IX)mCD137L-(L5)mICAM1, labeled as 19K-IX-5], or the control virus [TAV-(19k)Empty-(IX)Empty-(L5) Empty, labeled as Empty].
Figure 10:
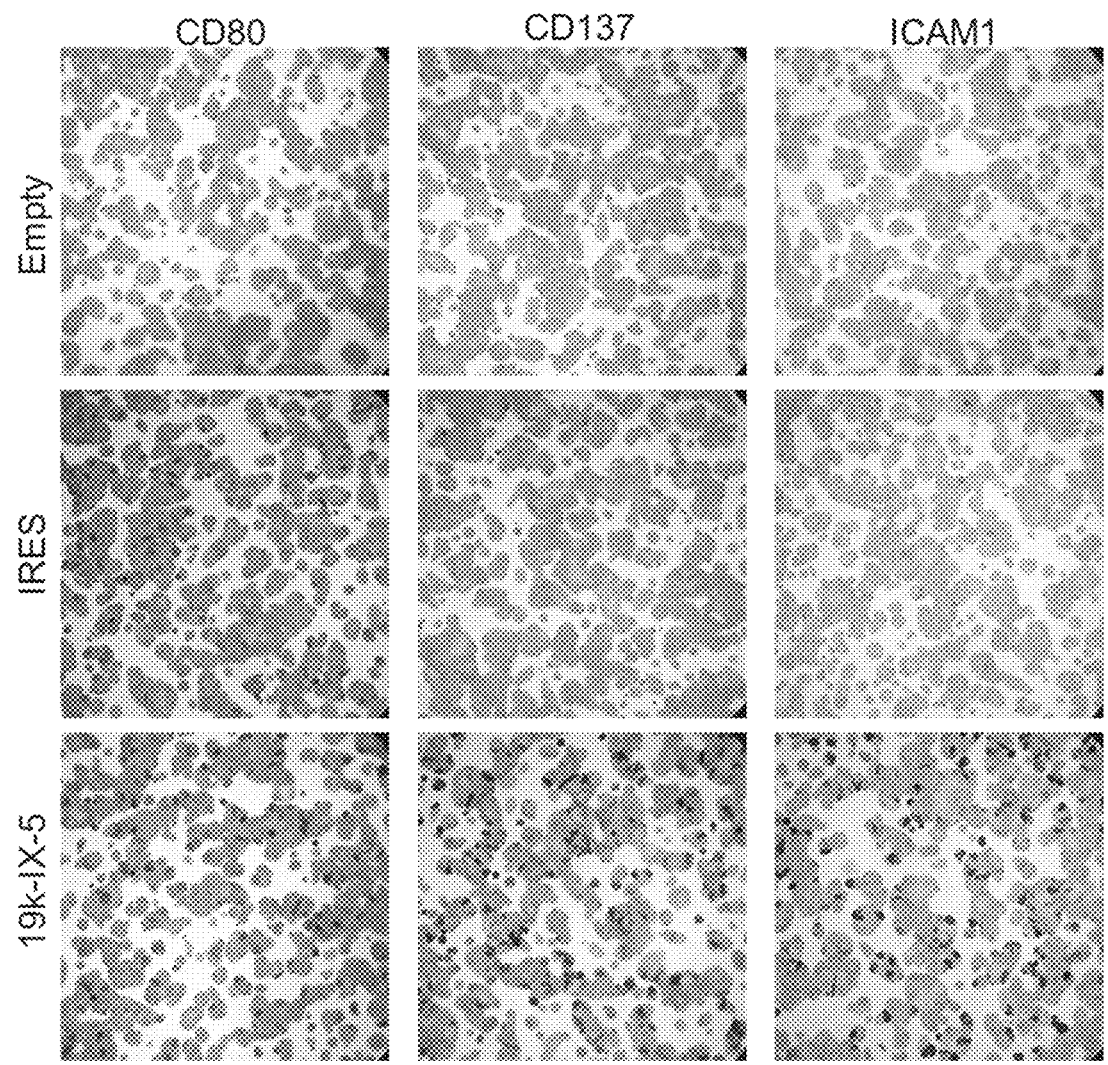
FIG. 10 depicts CD80, CD137L, and ICAM1 staining in HT29 cells infected with virus [TAV-mCD80(IRES) mCD137L(IRES)mICAM1, labeled as IRES], [TAV-(19k) mCD80-(IX)mCD137L-(L5)mICAM1, labeled as 19K-IX-5], or the control virus [TAV-(19k)Empty-(IX)Empty-(L5) Empty, labeled as Empty].
Figure 11:
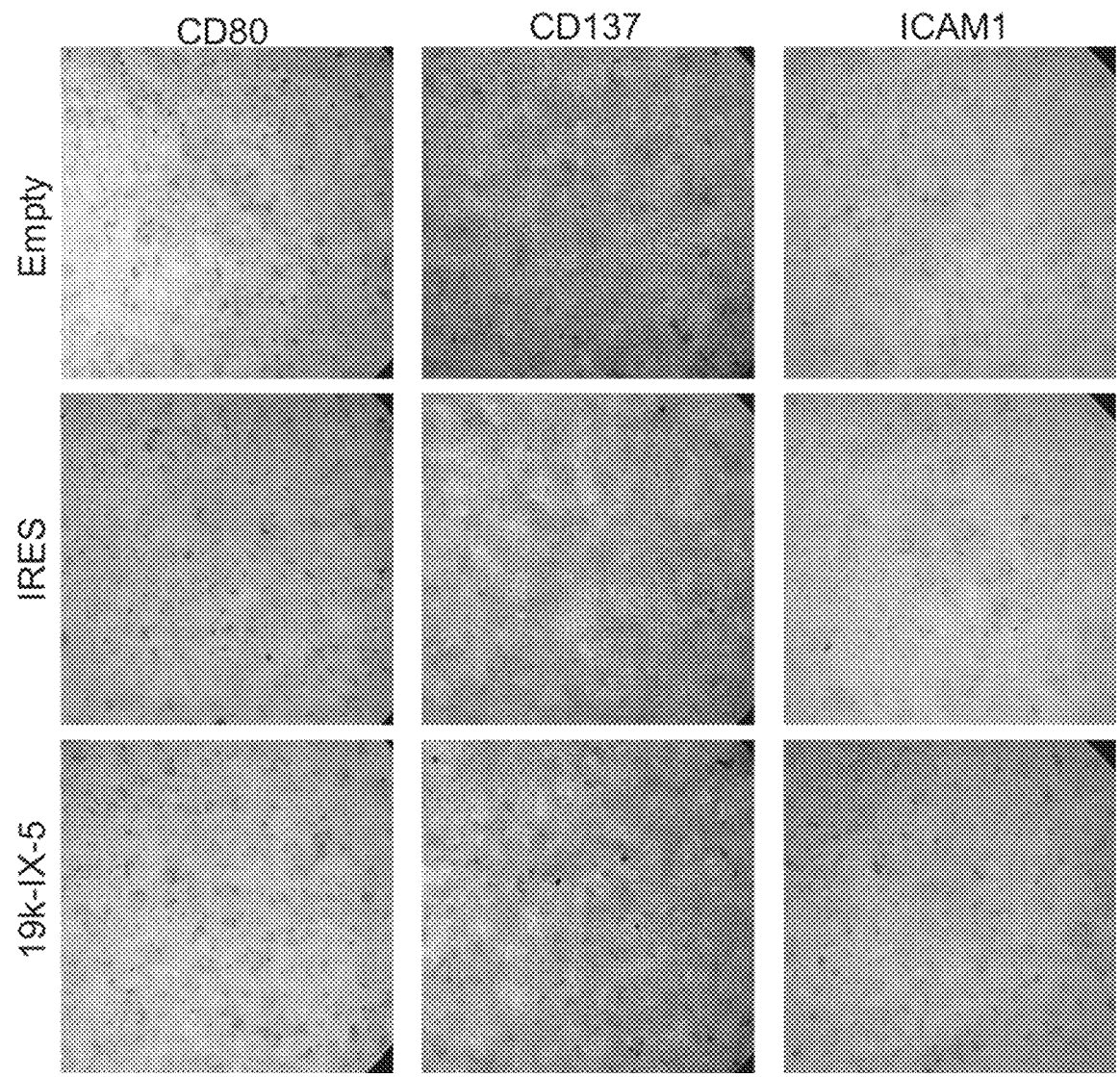
FIG. 11 depicts CD80, CD137L, and ICAM1 staining in ADS12 cells infected with virus [TAV-mCD80(IRES) mCD137L(IRES)mICAM1, labeled as IRES], [TAV-(19k) mCD80-(IX)mCD137L-(L5)mICAM1, labeled as 19K-IX-5], or the control virus [TAV-(19k)Empty-(IX)Empty-(L5) Empty, labeled as Empty].
Figure 12:
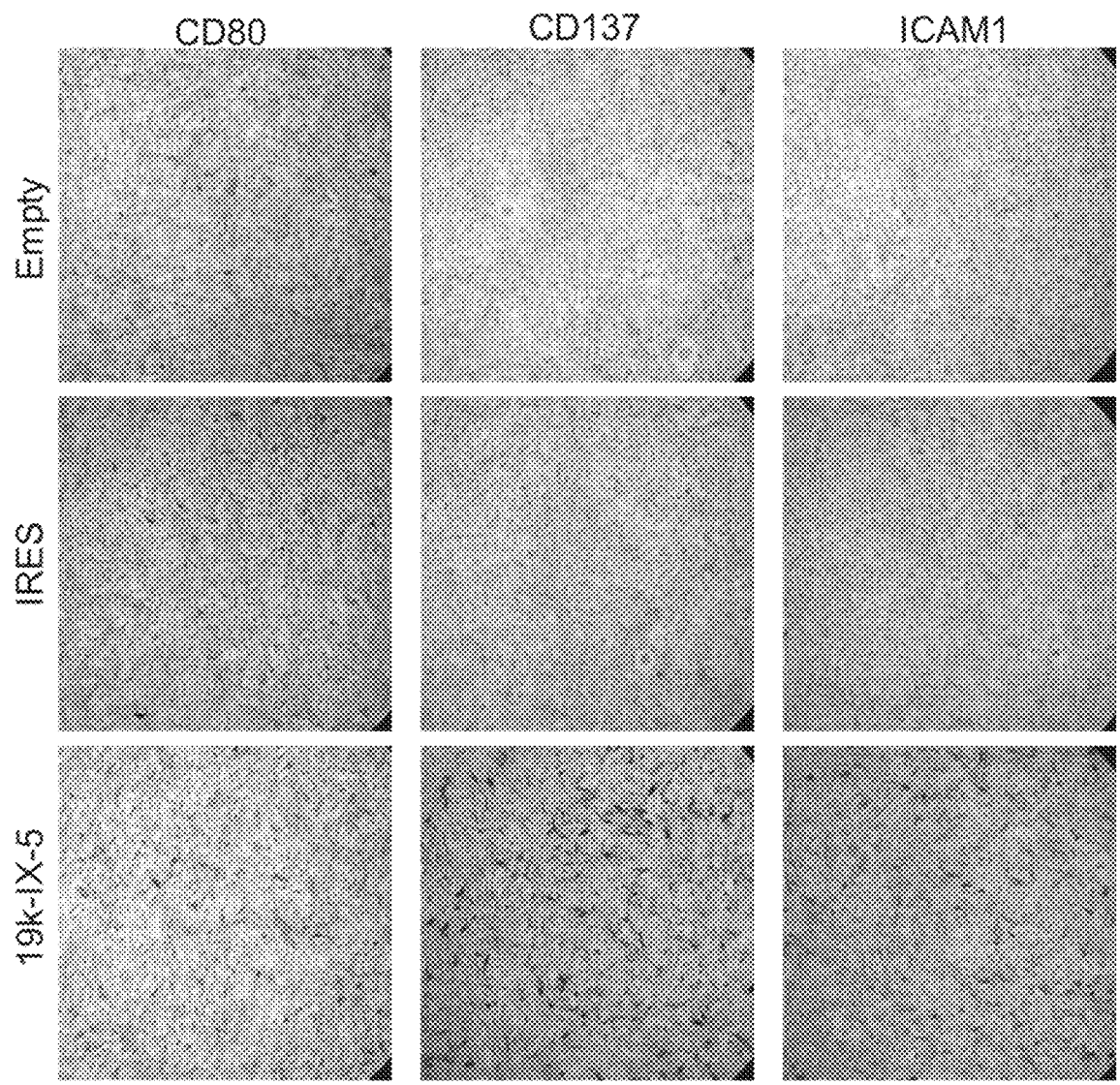
FIG. 12 depicts CD80, CD137L, and ICAM1 staining in F244 cells infected with virus [TAV-mCD80(IRES) mCD137L(IRES)mICAM1, labeled as IRES], [TAV-(19k)

To test whether ADP deletion leads to longer term and higher transgene expression, A549 cells were infected with TAV-(IXr)mIL7noPA-(L5EF1A)KozakmGMCSF and TAV-(IXr)mIL7noPA-(L5EF1A)KozakmGMCSF-AADP at an MOI of 5, and every three days after infection the conditioned media was collected to measure IL-7 and GMCSF in an ELISA. Results are shown in FIG. 8. There was no convincing difference in transgene expression levels between the two viruses, although the cells were observed during the course of the experiment and cell death was delayed from about 3 days after infection with TAV-(IXr)mIL7noPA-(L5EF1A)KozakmGMCSF to about 9 days after infection with TAV-(IXr)mIL7noPA-(L5EF1A)KozakmGMCSF-AADP. So although expression of the soluble cytokines as in this experiment was not enhanced, for some applications such as expression of costimulatory molecules on the infected cell's surface, it might be advantageous to delete ADP so the cell survives longer and the costimulatory molecule on its surface can activate target cells over a longer period of time.

Example 10

We then used the IX-E2 and L5-E4 sites as part of the design of a virus expressing three transgenes: the costimulatory molecules CD80 and CD137L and the adhesion molecule ICAM1. We previously created a virus carrying all three of these transgenes in place of the 5' end of the viral E1B-19K gene with an IRES between each of the three transgenes. The nucleotide sequence of that virus in the E1B-19K region is shown in SEQ ID NO: 33, with 5' flanking adenoviral nucleotide sequence and a SalI restriction site used for cloning (lower case), mouse CD80 (capitalized), the IRES from encephalomyocarditis virus (lower case), mouse CD137L (capitalized), the IRES from foot and mouth disease virus (lower case), mouse ICAM1 (capitalized), and 3' flanking adenoviral nucleotide sequence including an XhoI restriction site used for cloning. That virus, TAV-mCD80(IRES)mCD137L(IRES)mICAM1, contains the TAV-255 deletion in the E1A promoter, SEQ ID NO: 33 in the E1B-19K site, and deletions of the E3 region ADP, RIDα, RIDβ, and 14.7K genes and the E4 region ORF1-4 genes.

```
[Costim IRES]
                                            SEQ ID NO: 33
atctgacctcgtcgacATGGCTTGCAATTGTCAGT

TGATGCAGGATACACCACTCCTCAAGTTTCCATGT

CCAAGGCTCATTCTTCTCTTTGTGCTGCTGATTCG

TCTTTCACAAGTGTCTTCAGATGTTGATGAACAAC

TGTCCAAGTCAGTGAAAGATAAGGTATTGCTGCCT

TGCCGTTACAACTCTCCTCATGAAGATGAGTCTGA

AGACCGAATCTACTGGCAAAAACATGACAAAGTGG

TGCTGTCTGTCATTGCTGGGAAACTAAAAGTGTGG

CCCGAGTATAAGAACCGGACTTTATATGACAACAC

TACCTACTCTCTTATCATCCTGGGCCTGGTCCTTT

CAGACCGGGGCACATACAGCTGTGTCGTTCAAAAG

AAGGAAAGAGGAACGTATGAAGTTAAACACTTGGC

TTTAGTAAAGTTGTCCATCAAAGCTGACTTCTCTA

CCCCCAACATAACTGAGTCTGGAAACCCATCTGCA

GACACTAAAAGGATTACCTGCTTTGCTTCCGGGGG

TTTCCCAAAGCCTCGCTTCTCTTGGTTGGAAAATG

GAAGAGAATTACCTGGCATCAATACGACAATTTCC

CAGGATCCTGAATCTGAATTGTACACCATTAGTAG

CCAACTAGATTTCAATACGACTCGCAACCACACCA

TTAAGTGTCTCATTAAATATGGAGATGCTCACGTG

TCAGAGGACTTCACCTGGGAAAAACCCCCAGAAGA

CCCTCCTGATAGCAAGAACACACTTGTGCTCTTTG

GGGCAGGATTCGGCGCAGTAATAACAGTCGTCGTC

ATCGTTGTCATCATCAAATGCTTCTGTAAGCACAG

AAGCTGTTTCAGAAGAAATGAGGCAAGCAGAGAAA
```

-continued

```
CAAACAACAGCCTTACCTTCGGGCCTGAAGAAGCA

TTAGCTGAACAGACCGTCTTCCTTTAGtaacgtta ctggccgaagccgcttggaataaggccggtgtgcg tttgtctatatgttattttccaccatattgccgtc ttttggcaatgtgagggcccggaaacctggccctg tcttcttgacgagcattcctaggggtctttcccct ctcgccaaaggaatgcaaggtctgttgaatgtcgt gaaggaagcagttcctctggaagcttcttgaagac aaacaacgtctgtagcgaccctttgcaggcagcgg aaccccccacctggcgacaggtgcctctgcggcca aaagccacgtgtataagatacacctgcaaaggcgg cacaaccccagtgccacgttgtgagttggatagtt gtggaaagagtcaaatggctctcctcaagcgtatt caacaaggggctgaaggatgcccagaaggtacccc attgtatgggatctgatctggggcctcggtgcaca tgctttacatgtgtttagtcgaggttaaaaaacgt ctaggccccccgaaccacggggacgtggttttcct ttgaaaaacacgatgataatATGGACCAGCACACA

CTTGATGTGGAGGATACCGCGGATGCCAGACATCC

AGCAGGTACTTCGTGCCCCTCGGATGCGGCGCTCC

TCAGAGATACCGGGCTCCTCGCGGACGCTGCGCTC

CTCTCAGATACTGTGCGCCCCACAAATGCCGCGCT

CCCCACGGATGCTGCCTACCCTGCGGTTAATGTTC

GGGATCGCGAGGCCGCGTGGCCGCCTGCACTGAAC

TTCTGTTCCCGCCACCCAAAGCTCTATGGCCTAGT

CGCTTTGGTTTTGCTGCTTCTGATCGCCGCCTGTG

TTCCTATCTTCACCCGCACCGAGCCTCGGCCAGCG

CTCACAATCACCACCTCGCCCAACCTGGGTACCCG

AGAGAATAATGCAGACCAGGTCACCCCTGTTTCCC

ACATTGGCTGCCCCAACACTACACAACAGGGCTCT

CCTGTGTTCGCCAAGCTACTGGCTAAAAACCAAGC

ATCGTTGTGCAATACAACTCTGAACTGGCACAGCC

AAGATGGAGCTGGGAGCTCATACCTATCTCAAGGT

CTGAGGTACGAAGAAGACAAAAAGGAGTTGGTGGT

AGACAGTCCCGGGCTCTACTACGTATTTTTGGAAC

TGAAGCTCAGTCCAACATTCACAAACACAGGCCAC

AAGGTGCAGGGCTGGGTCTCTCTTGTTTTGCAAGC

AAAGCCTCAGGTAGATGACTTTGACAACTTGGCCC

TGACAGTGGAACTGTTCCCTTGCTCCATGGAGAAC

AAGTTAGTGGACCGTTCCTGGAGTCAACTGTTGCT

CCTGAAGGCTGGCCACCGCCTCAGTGTGGGTCTGA
```

-continued

```
GGGCTTATCTGCATGGAGCCCAGGATGCATACAGA
GACTGGGAGCTGTCTTATCCCAACACCACCAGCTT
TGGACTCTTTCTTGTGAAACCCGACAACCCATGGG
AATGAggtttccacaactgataaaactcgtgcaac
ttgaaactccgcctggtctttccaggtctagaggg
gttacactttgtactgtgctcgactccacgcccgg
tccactggcgggtgttagtagcagcactgttgttt
cgtagcggagcatggtggccgtgggaactcctcct
tggtgacaagggcccacggggccgaaagccacgtc
cagacggacccaccatgtgtgcaaccccagcacgg
caactttactgcgaacaccaccttaaggtgacac
tggtactggtactcggtcactggtgacaggctaag
gatgcccttcaggtaccccgaggtaacacgggaca
ctcgggatctgagaagggattgggacttctttaa
aagtgcccagtttaaaaagcttctacgcctgaata
ggcgaccggaggccggcgcctttccattacccact
actaaatccATGGCTTCAACCCGTGCCAAGCCCAC
GCTACCTCTGCTCCTGGCCCTGGTCACCGTTGTGA
TCCCTGGGCCTGGTGATGCTCAGGTATCCATCCAT
CCCAGAGAAGCCTTCCTGCCCCAGGGTGGGTCCGT
GCAGGTGAACTGTTCTTCCTCATGCAAGGAGGACC
TCAGCCTGGGCTTGGAGACTCAGTGGCTGAAAGAT
GAGCTCGAGAGTGGACCCAACTGGAAGCTGTTTGA
GCTGAGCGAGATCGGGGAGGACAGCAGTCCGCTGT
GCTTTGAGAACTGTGGCACCGTGCAGTCGTCCGCT
TCCGCTACCATCACCGTGTATTCGTTTCCGGAGAG
TGTGGAGCTGAGACCTCTGCCAGCCTGGCAGCAAG
TAGGCAAGGACCTCACCCTGCGCTGCCACGTGGAT
GGTGGAGCACCGCGGACCCAGCTCTCAGCAGTGCT
GCTCCGTGGGGAGGAGATACTGAGCCGCCAGCCAG
TGGGTGGGCACCCCAAGGACCCCAAGGAGATCACA
TTCACGGTGCTGGCTAGCAGAGGGGACCACGGAGC
CAATTTCTCATGCCGCACAGAACTGGATCTCAGGC
CGCAAGGGCTGGCATTGTTCTCTAATGTCTCCGAG
GCCAGGAGCCTCCGGACTTTCGATCTTCCAGCTAC
CATCCCAAAGCTCGACACCCCTGACCTCCTGGAGG
TGGGCACCCAGCAGAAGTTGTTTTGCTCCCTGGAA
GGCCTGTTTCCTGCCTCTGAAGCTCGGATATACCT
GGAGCTGGGAGGCCAGATGCCGACCCAGGAGAGCA
CAAACAGCAGTGACTCTGTGTCAGCCACTGCCTTG
```

-continued

```
GTAGAGGTGACTGAGGAGTTCGACAGAACCCTGCC
GCTGCGCTGCGTTTTGGAGCTAGCGGACCAGATCC
TGGAGACGCAGAGGACCTTAACAGTCTACAACTTT
TCAGCTCCGGTCCTGACCCTGAGCCAGCTGGAGGT
CTCGGAAGGGAGCCAAGTAACTGTGAAGTGTGAAG
CCCACAGTGGGTCGAAGGTGGTTCTTCTGAGCGGC
GTCGAGCCTAGGCCACCCACCCCGCAGGTCCAATT
CACACTGAATGCCAGCTCGGAGGATCACAAACGAA
GCTTCTTTTGCTCTGCCGCTCTGGAGGTGGCGGGA
AAGTTCCTGTTTAAAAACCAGACCCTGGAACTGCA
CGTGCTGTATGGTCCTCGGCTGGACGAGACGGACT
GCTTGGGGAACTGGACCTGGCAAGAGGGGTCTCAG
CAGACTCTGAAATGCCAGGCCTGGGGGAACCCATC
TCCTAAGATGACCTGCAGACGGAAGGCAGATGGTG
CCCTGCTGCCCATCGGGGTGGTGAAGTCTGTCAAA
CAGGAGATGAATGGTACATACGTGTGCCATGCCTT
TAGCTCCCATGGGAATGTCACCAGGAATGTGTACC
TGACAGTACTGTACCACTCTCAAAATAACTGGACT
ATAATCATTCTGGTGCCAGTACTGCTGGTCATTGT
GGGCCTCGTGATGGCAGCCTCTTATGTTTATAACC
GCCAGAGAAAGATCAGGATATACAAGTTACAGAAG
GCTCAGGAGGAGGCCATAAAACTCAAGGGACAAGC
CCCACCTCCCTGActcgagtcaccaggcg
```

We found that expression of genes after an IRES has generally been poor compared to genes where translation is not initiated by an IRES, so we investigated using the IX-E2 and L5-E4 sites as an alternative strategy. We generated the virus TAV-(19k)mCD80-(IX)mCD137L-(L5)mICAM1 carrying mouse CD80 in the E1B-19K site as shown in SEQ ID NO: 34 the CD80 gene capitalized and the flanking adenoviral sequence and restriction sites lower case (this used a Bsu36I restriction site instead of the SalI and XhoI restriction sites used in the other viruses), the mouse CD137L gene in the IX-E2 site of SEQ ID NO: 21 with the CD137L gene inserted in the NotI site as shown in SEQ ID NO: 35 with the CD137L gene capitalized and the flanking expression cassette sequence and residual NotI restriction site in lowercase, and the mouse ICAM1 gene in the L5-E4 site of SEQ ID NO: 29 with the ICAM1 gene inserted in the SwaI site as shown in SEQ ID NO: 36 with the ICAM1 gene capitalized and the flanking expression cassette sequence and residual SwaI site in lowercase. This virus also contains the TAV-255 deletion in the E1A promoter, deletion of the E3 region ADP, RIDα, RIDβ, and 14.7K genes, and deletion of the E4 region ORF1-4 genes.

[19k mCD80]

SEQ ID NO: 34

```
atctgacctcATGGCTTGCAATTGTCAGTTGATGC
AGGATACACCACTCCTCAAGTTTCCATGTCCAAGG
```

```
CTCATTCTTCTCTTTGTGCTGCTGATTCGTCTTTC
ACAAGTGTCTTCAGATGTTGATGAACAACTGTCCA
AGTCAGTGAAAGATAAGGTATTGCTGCCTTGCCGT
TACAACTCTCCTCATGAAGATGAGTCTGAAGACCG
AATCTACTGGCAAAAACATGACAAAGTGGTGCTGT
CTGTCATTGCTGGGAAACTAAAAGTGTGGCCCGAG
TATAAGAACCGGACTTTATATGACAACACTACCTA
CTCTCTTATCATCCTGGGCCTGGTCCTTTCAGACC
GGGGCACATACAGCTGTGTCGTTCAAAAGAAGGAA
AGAGGAACGTATGAAGTTAAACACTTGGCTTTAGT
AAAGTTGTCCATCAAAGCTGACTTCTCTACCCCCA
ACATAACTGAGTCTGGAAACCCATCTGCAGACACT
AAAAGGATTACCTGCTTTGCTTCCGGGGGTTTCCC
AAAGCCTCGCTTCTCTTGGTTGGAAAATGGAAGAG
AATTACCTGGCATCAATACGACAATTTCCCAGGAT
CCTGAATCTGAATTGTACACCATTAGTAGCCAACT
AGATTTCAATACGACTCGCAACCACACCATTAAGT
GTCTCATTAAATATGGAGATGCTCACGTGTCAGAG
GACTTCACCTGGGAAAAACCCCAGAAGACCCTCC
TGATAGCAAGAACACACTTGTGCTCTTTGGGGCAG
GATTCGGCGCAGTAATAACAGTCGTCGTCATCGTT
GTCATCATCAAATGCTTCTGTAAGCACAGAAGCTG
TTTCAGAAGAAATGAGGCAAGCAGAGAAACAAACA
ACAGCCTTACCTTCGGGCCTGAAGAAGCATTAGCT
GAACAGACCGTCTTCCTTTAGtcaggtgaatctgg
gtcacc
[IX mCD137L]
                    SEQ ID NO: 35
atagggagaccccgcggccATGGACCAGCACACACT
TGATGTGGAGGATACCGCGGATGCCAGACATCCAG
CAGGTACTTCGTGCCCCTCGGATGCGGCGCTCCTC
AGAGATACCGGGCTCCTCGCGGACGCTGCGCTCCT
CTCAGATACTGTGCGCCCCACAAATGCCGCGCTCC
CCACGGATGCTGCCTACCCTGCGGTTAATGTTCGG
GATCGCGAGGCCGCGTGGCCGCCTGCACTGAACTT
CTGTTCCCGCCACCCAAAGCTCTATGGCCTAGTCG
CTTTGGTTTTGCTGCTTCTGATCGCCGCCTGTGTT
CCTATCTTCACCCGCACCGAGCCTCGGCCAGCGCT
CACAATCACCACCTCGCCCAACCTGGGTACCCGAG
AGAATAATGCAGACCAGGTCACCCCTGTTTCCCAC
ATTGGCTGCCCCAACACTACACAACAGGGCTCTCC
TGTGTTCGCCAAGCTACTGGCTAAAAACCAAGCAT
CGTTGTGCAATACAACTCTGAACTGGCACAGCCAA
GATGGAGCTGGGAGCTCATACCTATCTCAAGGTCT
GAGGTACGAAGAAGACAAAAAGGAGTTGGTGGTAG
ACAGTCCCGGGCTCTACTACGTATTTTTGGAACTG
AAGCTCAGTCCAACATTCACAAACACAGGCCACAA
GGTGCAGGGCTGGGTCTCTCTTGTTTTGCAAGCAA
AGCCTCAGGTAGATGACTTTGACAACTTGGCCCTG
ACAGTGGAACTGTTCCCTTGCTCCATGGAGAACAA
GTTAGTGGACCGTTCCTGGAGTCAACTGTTGCTCC
TGAAGGCTGGCCACCGCCTCAGTGTGGGTCTGAGG
GCTTATCTGCATGGAGCCCAGGATGCATACAGAGA
CTGGGAGCTGTCTTATCCCAACACCACCAGCTTTG
GACTCTTTCTTGTGAAACCCGACAACCCATGGGAA
TGAggccgctgtgccttctagt
[L5 mICAM1]
                    SEQ ID NO: 36
cgccagaacacatttATGGCTTCAACCCGTGCCAA
GCCCACGCTACCTCTGCTCCTGGCCCTGGTCACCG
TTGTGATCCCTGGGCCTGGTGATGCTCAGGTATCC
ATCCATCCCAGAGAAGCCTTCCTGCCCCAGGGTGG
GTCCGTGCAGGTAACTGTTCTTCCTCATGCAAGG
AGGACCTCAGCCTGGGCTTGGAGACTCAGTGGCTG
AAAGATGAGCTCGAGAGTGGACCCAACTGGAAGCT
GTTTGAGCTGAGCGAGATCGGGGAGGACAGCAGTC
CGCTGTGCTTTGAGAACTGTGGCACCGTGCAGTCG
TCCGCTTCCGCTACCATCACCGTGTATTCGTTTCC
GGAGAGTGTGGAGCTGAGACCTCTGCCAGCCTGGC
AGCAAGTAGGCAAGGACCTCACCCTGCGCTGCCAC
GTGGATGGTGGAGCACCGCGGACCCAGCTCTCAGC
AGTGCTGCTCCGTGGGGAGGAGATACTGAGCCGCC
AGCCAGTGGGTGGGCACCCCAAGGACCCCAAGGAG
ATCACATTCACGGTGCTGGCTAGCAGAGGGGACCA
CGGAGCCAATTTCTCATGCCGCACAGAACTGGATC
TCAGGCCGCAAGGGCTGGCATTGTTCTCTAATGTC
TCCGAGGCCAGGAGCCTCCGGACTTTCGATCTTCC
AGCTACCATCCCAAAGCTCGACACCCCTGACCTCC
TGGAGGTGGGCACCCAGCAGAAGTTGTTTTGCTCC
CTGGAAGGCCTGTTTCCTGCCTCTGAAGCTCGGAT
ATACCTGGAGCTGGGAGGCCAGATGCCGACCCAGG
AGAGCACAAACAGCAGTGACTCTGTGTCAGCCACT
GCCTTGGTAGAGGTGACTGAGGAGTTCGACAGAAC
```

-continued

CCTGCCGCTGCGCTGCGTTTTGGAGCTAGCGGACC

AGATCCTGGAGACGCAGAGGACCTTAACAGTCTAC

AACTTTTCAGCTCCGGTCCTGACCCTGAGCCAGCT

GGAGGTCTCGGAAGGGAGCCAAGTAACTGTGAAGT

GTGAAGCCCACAGTGGGTCGAAGGTGGTTCTTCTG

AGCGGCGTCGAGCCTAGGCCACCCACCCCGCAGGT

CCAATTCACACTGAATGCCAGCTCGGAGGATCACA

AACGAAGCTTCTTTTGCTCTGCCGCTCTGGAGGTG

GCGGGAAAGTTCCTGTTTAAAAACCAGACCCTGGA

ACTGCACGTGCTGTATGGTCCTCGGCTGGACGAGA

CGGACTGCTTGGGGAACTGGACCTGGCAAGAGGGG

TCTCAGCAGACTCTGAAATGCCAGGCCTGGGGGAA

CCCATCTCCTAAGATGACCTGCAGACGGAAGGCAG

ATGGTGCCCTGCTGCCCATCGGGGTGGTGAAGTCT

GTCAAACAGGAGATGAATGGTACATACGTGTGCCA

TGCCTTTAGCTCCCATGGGAATGTCACCAGGAATG

TGTACCTGACAGTACTGTACCACTCTCAAAATAAC

TGGACTATAATCATTCTGGTGCCAGTACTGCTGGT

CATTGTGGGCCTCGTGATGGCAGCCTCTTATGTTT

ATAACCGCCAGAGAAAGATCAGGATATACAAGTTA

CAGAAGGCTCAGGAGGAGGCCATAAAACTCAAGGG

ACAAGCCCCACCTCCCTGAaaataacttgtttatt gcag

To test for expression from these two viruses: A549 cells, HT29 cells, ADS12 cells, and F244 cells were infected at an MOI of 3 with TAV-mCD80(IRES)mCD137L(IRES)mI-CAM1, TAV-(19k)mCD80-(IX)mCD137L-(L5)mICAM1, or the control virus TAV-(19k)Empty-(IX)Empty-(L5) Empty which has the same structure as TAV-(19k)mCD80-(IX)mCD137L-(L5)mICAM1 but without the transgenes. Two days later, the cells were stained for CD80, CD137L, and ICAM1 and results are shown in FIG. 9-FIG. 12. While there was poor expression of the CD137L and ICAM1 genes when expressed after the IRESes in TAV-mCD80(IRES) mCD137L(IRES)mICAM1, there was robust expression of those genes from the IX-E2 and L5-E4 sites with TAV-(19k) mCD80-(IX)mCD137L-(L5)mICAM1.

Example 11

While the experiments described above used an adenovirus based on human adenovirus type 5, other adenoviruses have a very similar structure and have clearly identifiable sites homologous to the IX-E2 and L5-E4 sites described above. For example, human adenovirus type 35 has the sequence in the IX-E2 site shown in SEQ ID NO: 37 and has the sequence in the L5-E4 site shown in SEQ ID NO: 38 where the polyadenylation signals are underlined in each sequence.

[Ad35 wt IX-E2]
SEQ ID NO: 37
AATAAAAAAAATTCCAGAATCAATGAATAAATAAA

CGAGCTTGTTGTTGATTTAAAATCAAGTGTT

TTTATT

[Ad35 wt L5-E4]
SEQ ID NO: 38
AATAAAGTTTAAGTGTTTTTATT

To determine whether expression cassettes could be inserted into these sites, the IX-E2 site was modified with the same sequence used in the adenovirus type 5 revised IX-E2 site as shown in SEQ ID NO: 39 (the expression cassette was inserted in the opposite orientation as with adenovirus type 5, so the flanking viral sequence in lower-case is the reverse complement of conventional annotation which is shown in SEQ ID NO: 37, and the L5-E4 site was modified with the same sequence used in the adenovirus type 5 site with the EF1A promoter as shown in SEQ ID NO: 40. An adenovirus type 35 carrying both of those expression cassettes in site IX-E2 and L5-E4 as well as deletions in the E3 RIDα, RIDβ, and 14.7K genes and the E4 ORF1-4 genes was rescued, demonstrating that these sites can be used for insertion of expression cassettes in other serotypes of adenovirus. The strategy of inserting an expression cassette between two adjacent transcription units with polyadenylation sites facing each other is not in principle restricted to adenoviruses and could potentially be applied to other viruses as well.

[Ad35 IX-E2 cassette]
SEQ ID NO: 39
tcgagatcggtggtccagggcataccgtgcgcgaa aaatgaaataaaATACACCTTTTTTCGATTGTACG

TATTTTTATTTACGGTAAATGGCCCGCCTGGCTGA

CCGCCCAACGACCCCCGCCCATTGACGTCAATAAT

GACGTATGTTCCCATAGTAACGCCAATAGGGACTT

TCCATTGACGTCAATGGGTGGAGTATTTACGGTAA

ACTGCCCACTTGGCAGTACATCAAGTGTATCATAT

GCCAAGTACGCCCCCTATTGACGTCAATGACGGTA

AATGGCCCGCCTGGCATTATGCCCAGTACATGACC

TTATGGGACTTTCCTACTTGGCAGTACATCTACGT

ATTAGTCATCGCTATTACCATGGTGATGCGGTTTT

GGCAGTACATCAATGGGCGTGGATAGCGGTTTGAC

TCACGGGATTTCCAAGTCTCCACCCCATTGACGT

CAATGGGAGTTTGTTTTGGCACCAAAATCAACGGG

ACTTTCCAAAATGTCGTAACAACTCCGCCCCATTG

ACGCAAATGGGCGGTAGGCGTGTACGGTGGGAGGT

CTATATAAGCAGAGCTCTCTGGCTAACTAGAGAAC

CCACTGCTTACTGGCTTATCGAAATTAATACGACT

CACTATAGGGAGACCCGCGGCCGCTGTGCCTTCTA

GTTGCCAGCCATCTGTTGTTTGCCCCTCCCCCGTG

```
CCTTCCTTGACCCTGGAAGGTGCCACTCCCACTGT

CCTTTCCTAATAAAaacacttgattttaaatcaac aacaagctcgtttatttat

[Ad35 L5-E4 cassette]
                                        SEQ ID NO: 40
tttcttttcttacattacagaagacgacaactaaa ataaaAGGTTTATTAGGCGGCCTCCCCGTCACCAC

CCCCCCCAACCCGCCCCGACCGGAGCTGAGAGTAA

TTCATACAAAAGGACTCGCCCCTGCCTTGGGGAAT

CCCAGGGACCGTCGTTAAACTCCCACTAACGTAGA

ACCCAGAGATCGCTGCGTTCCCGCCCCCTCACCCG

CCCGCTCTCGTCATCACTGAGGTGGAGAAGAGCAT

GCGTGAGGCTCCGGTGCCCGTCAGTGGGCAGAGCG

CACATCGCCCACAGTCCCCGAGAAGTTGGGGGGAG

GGGTCGGCAATTGAACCGGTGCCTAGAGAAGGTGG

CGCGGGGTAAACTGGGAAAGTGATGTCGTGTACTG

GCTCCGCCTTTTTCCCGAGGGTGGGGGAGAACCGT

ATATAAGTGCAGTAGTCGCCGTGAACGTTCTTTTT

CGCAACGGGTTTGCCGCCAGAACACAATTTAAATA

ACTTGTTTATTGCAGCTTATAATGGTTACAaataa agtttaagtgttttatttaaaatcacaaaattcg
```

Example 12

We used the revised IX-E2 and L5-E4 sites to generate a virus carrying the mouse IL12A and IL12B genes for use as a model in preclinical experiments. The gene for mouse IL12A was cloned into the NotI restriction site of the revised IX-E2 site with an expression cassette shown in SEQ ID NO: 21 to generate the sequence of SEQ ID NO: 42, with the residual nucleotides of the NotI restriction site underlined. The gene for mouse IL12B was cloned into the SwaI restriction site of the L5-E4 site with an expression cassette using the EF1A promoter shown in SEQ ID NO: 29 to generate the sequence of SEQ ID NO: 43, with the residual nucleotides of the SwaI restriction site underlined.

SEQ ID NO: 42

CTATAGGGAGACCCGCGGCCATGTGTCAATCACGC
TACCTCCTCTTTTTGGCCACCCTTGCCCTCCTAAA
CCACCTCAGTTTGGCCAGGGTCATTCCAGTCTCTG
GACCTGCCAGGTGTCTTAGCCAGTCCCGAAACCTG
CTGAAGACCACAGATGACATGGTGAAGACGGCCAG
AGAAAAACTGAAACATTATTCCTGCACTGCTGAAG
ACATCGATCATGAAGACATCACACGGGACCAAACC
AGCACATTGAAGACCTGTTTACCACTGGAACTACA
CAAGAACGAGAGTTGCCTGGCTACTAGAGAGACTT

-continued

CTTCCACAACAAGAGGGAGCTGCCTGCCCCCACAG
AAGACGTCTTTGATGATGACCCTGTGCCTTGGTAG
CATCTATGAGGACTTGAAGATGTACCAGACAGAGT
TCCAGGCCATCAACGCAGCACTTCAGAATCACAAC
CATCAGCAGATCATTCTAGACAAGGGCATGCTGGT
GGCCATCGATGAGCTGATGCAGTCTCTGAATCATA
ATGGCGAGACTCTGCGCCAGAAACCTCCTGTGGGA
GAAGCAGACCCTTACAGAGTGAAAATGAAGCTCTG
CATCCTGCTTCACGCCTTCAGCACCCGCGTCGTGA
CCATCAACAGGGTGATGGGCTATCTGAGCTCCGCC
TGAGGCCGCTGTGCCTTCTAGTT

SEQ ID NO: 43

TTGCCGCCAGAACACAATTTATGTGTCCTCAGAAG
CTAACCATCTCCTGGTTTGCCATCGTTTTGCTGGT
GTCTCCACTCATGGCCATGTGGGAGCTGGAGAAAG
ACGTTTATGTTGTAGAGGTGGACTGGACTCCCGAT
GCCCCTGGAGAAACAGTGAACCTCACCTGTGACAC
GCCTGAAGAAGATGACATCACCTGGACCTCAGACC
AGAGACATGGAGTCATAGGCTCTGGAAAGACCCTG
ACCATCACTGTCAAAGAGTTTCTAGATGCTGGCCA
GTACACCTGCCACAAAGGAGGCGAGACTCTGAGCC
ACTCACATCTGCTGCTCCACAAGAAGGAAAATGGA
ATTTGGTCCACTGAAATTTTAAAAAATTTCAAAAA
CAAGACTTTCCTGAAGTGTGAAGCACCAAATTACT
CCGGACGGTTCACGTGCTCATGGCTGGTGCAAAGA
AACATGGACTTGAAGTTCAACATCAAGAGCAGTAG
CAGTTCCCCTGACTCTCGGGCAGTGACATGTGGAA
TGGCGTCTCTGTCTGCAGAGAAGGTCACACTGGAC
CAAAGGGACTATGAGAAGTATTCAGTGTCCTGCCA
GGAGGATGTCACCTGCCCAACTGCCGAGGAGACCC
TGCCCATTGAACTGGCGTTGGAAGCACGGCAGCAG
AATAAATATGAGAACTACAGCACCAGCTTCTTCAT
CAGGGACATCATCAAACCAGACCCGCCCAAGAACT
TGCAGATGAAGCCTTTGAAGAACTCACAGGTGGAG
GTCAGCTGGGAGTACCCTGACTCCTGGAGCACTCC
CCATTCCTACTTCTCCCTCAAGTTCTTTGTTCGAA
TCCAGCGCAAGAAAGAAAAGATGAAGGAGACAGAG
GAGGGGTGTAACCAGAAAGGTGCGTTCCTCGTAGA
GAAGACATCTACCGAAGTCCAATGCAAAGGCGGGA
ATGTCTGCGTGCAAGCTCAGGATCGCTATTACAAT

TCCTCATGCAGCAAGTGGGCATGTGTTCCCTGCAG

GGTCCGATCCTAGAAATAACTTGTTTATTGCAG

The virus TAV-IX5-Empty was generated carrying the TAV-255 deletion in the E1A promoter, the IX-E2 expression cassette without a transgene shown in SEQ ID NO: 21, and the L5-E4 expression cassette without a transgene shown in SEQ ID NO: 29. The virus TAV-IX5-mIL12 was generated carrying the TAV-255 deletion in the E1A promoter, the IX-E2 expression cassette including the mouse IL12A gene of SEQ ID NO: 42, and the L5-E4 expression cassette including the mouse IL12B gene of SEQ ID NO: 43.

To test these viruses for oncolysis, A549 cells were infected with the TAV-IX5-Empty or TAV-IX5-mIL12 viruses at an MOI of 5 or kept as non-infected controls, and wells were stained with crystal violet every two days after infection. As shown in FIG. 13, both the empty control virus and the virus carrying mouse IL-12 were lytic within 4-6 days.

To test for transgene expression, A549 cells were infected with the TAV-IX5-Empty or TAV-IX5-mIL12 viruses at an MOI of 5 in triplicate and conditioned media was collected five days after infection to measure mouse IL-12 with an ELISA detecting only the heterodimer with both the mouse IL12A and mouse IL12B chains. As shown in FIG. 14, TAV-IX5-mIL12 induced expression of high levels of the IL-12 heterodimer.

```
Human adenovirus 5, complete genome
NCBI Reference Sequence: AC900008.1
>AC_000008.1 Human adenovirus 5,
complete genome
                            (SEQ ID NO: 1)
CATCATCAATAATATACCTTATTTTGGATTGAAGCC

AATATGATAATGAGGGGGTGGAGTTTGTGACGTGG

CGCGGGGCGTGGGAACGGGGCGGGTGACGTAGTAG

TGTGGCGGAAGTGTGATGTTGCAAGTGTGGCGGAA

CACATGTAAGCGACGGATGTGGCAAAAGTGACGTT

TTTGGTGTGCGCCGGTGTACACAGGAAGTGACAAT

TTTCGCGCGGTTTTAGGCGGATGTTGTAGTAAATT

TGGGCGTAACCGAGTAAGATTTGGCCATTTTCGCG

GGAAAACTGAATAAGAGGAAGTGAAATCTGAATAA

TTTTGTGTTACTCATAGCGCGTAATATTTGTCTAG

GGCCGCGGGACTTTGACCGTTTACGTGGAGACTC

GCCCAGGTGTTTTTCTCAGGTGTTTTCCGCGTTCC

GGGTCAAAGTTGGCGTTTTATTATTATAGTCAGCT

GACGTGTAGTGTATTTATACCCGGTGAGTTCCTCA

AGAGGCCACTCTTGAGTGCCAGCGAGTAGAGTTTT

CTCCTCCGAGCCGCTCCGACACCGGGACTGAAAAT

GAGACATATTATCTGCCACGGAGGTGTTATTACCG

AAGAAATGGCCGCCAGTCTTTTGGACCAGCTGATC

GAAGAGGTACTGGCTGATAATCTTCCACCTCCTAG

CCATTTTGAACCACCTACCCTTCACGAACTGTATG

ATTTAGACGTGACGGCCCCCGAAGATCCCAACGAG

GAGGCGGTTTCGCAGATTTTTCCCGACTCTGTAAT

GTTGGCGGTGCAGGAAGGGATTGACTTACTCACTT

TTCCGCCGGCGCCCGGTTCTCCGGAGCCGCCTCAC

CTTTCCCGGCAGCCCGAGCAGCCGGAGCAGAGAGC

CTTGGGTCCGGTTTCTATGCCAAACCTTGTACCGG

AGGTGATCGATCTTACCTGCCACGAGGCTGGCTTT

CCACCCAGTGACGACGAGGATGAAGAGGGTGAGGA

GTTTGTGTTAGATTATGTGGAGCACCCCGGGCACG

GTTGCAGGTCTTGTCATTATCACCGGAGGAATACG

GGGGACCCAGATATTATGTGTTCGCTTTGCTATAT

GAGGACCTGTGGCATGTTTGTCTACAGTAAGTGAA

AATTATGGGCAGTGGGTGATAGAGTGGTGGGTTTG

GTGTGGTAATTTTTTTTTTAATTTTTACAGTTTTG

TGGTTTAAAGAATTTTGTATTGTGATTTTTTTAAA

AGGTCCTGTGTCTGAACCTGAGCCTGAGCCCGAGC

CAGAACCGGAGCCTGCAAGACCTACCCGCCGTCCT

AAAATGGCGCCTGCTATCCTGAGACGCCCGACATC

ACCTGTGTCTAGAGAATGCAATAGTAGTACGGATA

GCTGTGACTCCGGTCCTTCTAACACACCTCCTGAG

ATACACCCGGTGGTCCCGCTGTGCCCCATTAAACC

AGTTGCCGTGAGAGTTGGTGGGCGTCGCCAGGCTG

TGGAATGTATCGAGGACTTGCTTAACGAGCCTGGG

CAACCTTTGGACTTGAGCTGTAAACGCCCCAGGCC

ATAAGGTGTAAACCTGTGATTGCGTGTGTGGTTAA

CGCCTTTGTTTGCTGAATGAGTTGATGTAAGTTTA

ATAAAGGGTGAGATAATGTTTAACTTGCATGGCGT

GTTAAATGGGGCGGGGCTTAAAGGGTATATAATGC

GCCGTGGGCTAATCTTGGTTACATCTGACCTCATG

GAGGCTTGGGAGTGTTTGGAAGATTTTTCTGCTGT

GCGTAACTTGCTGGAACAGAGCTCTAACAGTACCT

CTTGGTTTTGGAGGTTTCTGTGGGGCTCATCCCAG

GCAAAGTTAGTCTGCAGAATTAAGGAGGATTACAA

GTGGGAATTTGAAGAGCTTTTGAAATCCTGTGGTG

AGCTGTTTGATTCTTTGAATCTGGGTCACCAGGCG

CTTTTCCAAGAGAAGGTCATCAAGACTTTGGATTT

TTCCACACCGGGGCGCGCTGCGGCTGCTGTTGCTT

TTTTGAGTTTTATAAAGGATAAATGGAGCGAAGAA

ACCCATCTGAGCGGGGGGTACCTGCTGGATTTTCT

GGCCATGCATCTGTGGAGAGCGGTTGTGAGACACA
```

```
AGAATCGCCTGCTACTGTTGTCTTCCGTCCGCCCG
GCGATAATACCGACGGAGGAGCAGCAGCAGCAGCA
GGAGGAAGCCAGGCGGCGGCGGCAGGAGCAGAGCC
CATGGAACCCGAGAGCCGGCCTGGACCCTCGGGAA
TGAATGTTGTACAGGTGGCTGAACTGTATCCAGAA
CTGAGACGCATTTTGACAATTACAGAGGATGGGCA
GGGGCTAAAGGGGGTAAAGAGGGAGCGGGGGGCTT
GTGAGGCTACAGAGGAGGCTAGGAATCTAGCTTTT
AGCTTAATGACCAGACACCGTCCTGAGTGTATTAC
TTTTCAACAGATCAAGGATAATTGCGCTAATGAGC
TTGATCTGCTGGCGCAGAAGTATTCCATAGAGCAG
CTGACCACTTACTGGCTGCAGCCAGGGGATGATTT
TGAGGAGGCTATTAGGGTATATGCAAAGGTGGCAC
TTAGGCCAGATTGCAAGTACAAGATCAGCAAACTT
GTAAATATCAGGAATTGTTGCTACATTTCTGGGAA
CGGGGCCGAGGTGGAGATAGATACGGAGGATAGGG
TGGCCTTTAGATGTAGCATGATAAATATGTGGCCG
GGGGTGCTTGGCATGGACGGGGTGGTTATTATGAA
TGTAAGGTTTACTGGCCCCAATTTTAGCGGTACGG
TTTTCCTGGCCAATACCAACCTTATCCTACACGGT
GTAAGCTTCTATGGGTTTAACAATACCTGTGTGGA
AGCCTGGACCGATGTAAGGGTTCGGGGCTGTGCCT
TTTACTGCTGCTGGAAGGGGGTGGTGTGTCGCCCC
AAAAGCAGGGCTTCAATTAAGAAATGCCTCTTTGA
AAGGTGTACCTTGGGTATCCTGTCTGAGGGTAACT
CCAGGGTGCGCCACAATGTGGCCTCCGACTGTGGT
TGCTTCATGCTAGTGAAAAGCGTGGCTGTGATTAA
GCATAACATGGTATGTGGCAACTGCGAGGACAGGG
CCTCTCAGATGCTGACCTGCTCGGACGGCAACTGT
CACCTGCTGAAGACCATTCACGTAGCCAGCCACTC
TCGCAAGGCCTGGCCAGTGTTTGAGCATAACATAC
TGACCCGCTGTTCCTTGCATTTGGGTAACAGGAGG
GGGGTGTTCCTACCTTACCAATGCAATTTGAGTCA
CACTAAGATATTGCTTGAGCCCGAGAGCATGTCCA
AGGTGAACCTGAACGGGGTGTTTGACATGACCATG
AAGATCTGGAAGGTGCTGAGGTACGATGAGACCCG
CACCAGGTGCAGACCCTGCGAGTGTGGCGGTAAAC
ATATTAGGAACCAGCCTGTGATGCTGGATGTGACC
GAGGAGCTGAGGCCCGATCACTTGGTGCTGGCCTG
CACCCGCGCTGAGTTTGGCTCTAGCGATGAAGATA

CAGATTGAGGTACTGAAATGTGTGGGCGTGGCTTA
AGGGTGGGAAAGAATATATAAGGTGGGGGTCTTAT
GTAGTTTTGTATCTGTTTTGCAGCAGCCGCCGCCG
CCATGAGCACCAACTCGTTTGATGGAAGCATTGTG
AGCTCATATTTGACAACGCGCATGCCCCCATGGGC
CGGGGTGCGTCAGAATGTGATGGGCTCCAGCATTG
ATGGTCGCCCCGTCCTGCCCGCAAACTCTACTACC
TTGACCTACGAGACCGTGTCTGGAACGCCGTTGGA
GACTGCAGCCTCCGCCGCCGCTTCAGCCGCTGCAG
CCACCGCCCGCGGGATTGTGACTGACTTTGCTTTC
CTGAGCCCGCTTGCAAGCAGTGCAGCTTCCCGTTC
ATCCGCCCGCGATGACAAGTTGACGGCTCTTTTGG
CACAATTGGATTCTTTGACCCGGGAACTTAATGTC
GTTTCTCAGCAGCTGTTGGATCTGCGCCAGCAGGT
TTCTGCCCTGAAGGCTTCCTCCCCTCCCAATGCGG
TTTAAAACATAAATAAAAAACCAGACTCTGTTTGG
ATTTGGATCAAGCAAGTGTCTTGCTGTCTTTATTT
AGGGGTTTTGCGCGCGCGGTAGGCCCGGGACCAGC
GGTCTCGGTCGTTGAGGGTCCTGTGTATTTTTTCC
AGGACGTGGTAAAGGTGACTCTGGATGTTCAGATA
CATGGGCATAAGCCCGTCTCTGGGGTGGAGGTAGC
ACCACTGCAGAGCTTCATGCTGCGGGGTGGTGTTG
TAGATGATCCAGTCGTAGCAGGAGCGCTGGGCGTG
GTGCCTAAAAATGTCTTTCAGTAGCAAGCTGATTG
CCAGGGGCAGGCCCTTGGTGTAAGTGTTTACAAAG
CGGTTAAGCTGGGATGGGTGCATACGTGGGGATAT
GAGATGCATCTTGGACTGTATTTTTAGGTTGGCTA
TGTTCCCAGCCATATCCCTCCGGGGATTCATGTTG
TGCAGAACCACCAGCACAGTGTATCCGGTGCACTT
GGGAAATTTGTCATGTAGCTTAGAAGGAAATGCGT
GGAAGAACTTGGAGACGCCCTTGTGACCTCCAAGA
TTTTCCATGCATTCGTCCATAATGATGGCAATGGG
CCCACGGGCGGCGGCCTGGGCGAAGATATTTCTGG
GATCACTAACGTCATAGTTGTGTTCCAGGATGAGA
TCGTCATAGGCCATTTTTACAAAGCGCGGGCGGAG
GGTGCCAGACTGCGGTATAATGGTTCCATCCGGCC
CAGGGGCGTAGTTACCCTCACAGATTTGCATTTCC
CACGCTTTGAGTTCAGATGGGGGGATCATGTCTAC
CTGCGGGGCGATGAAGAAAACGGTTTCCGGGGTAG
GGGAGATCAGCTGGGAAGAAAGCAGGTTCCTGAGC
AGCTGCGACTTACCGCAGCCGGTGGGCCCGTAAAT
```

CACACCTATTACCGGGTGCAACTGGTAGTTAAGAG

AGCTGCAGCTGCCGTCATCCCTGAGCAGGGGGCC

ACTTCGTTAAGCATGTCCCTGACTCGCATGTTTTC

CCTGACCAAATCCGCCAGAAGGCGCTCGCCGCCCA

GCGATAGCAGTTCTTGCAAGGAAGCAAAGTTTTTC

AACGGTTTGAGACCGTCCGCCGTAGGCATGCTTTT

GAGCGTTTGACCAAGCAGTTCCAGGCGGTCCCACA

GCTCGGTCACCTGCTCTACGGCATCTCGATCCAGC

ATATCTCCTCGTTTCGCGGGTTGGGGCGGCTTTCG

CTGTACGGCAGTAGTCGGTGCTCGTCCAGACGGGC

CAGGGTCATGTCTTTCCACGGGCGCAGGGTCCTCG

TCAGCGTAGTCTGGGTCACGGTGAAGGGGTGCGCT

CCGGGCTGCGCGCTGGCCAGGGTGCGCTTGAGGCT

GGTCCTGCTGGTGCTGAAGCGCTGCCGGTCTTCGC

CCTGCGCGTCGGCCAGGTAGCATTTGACCATGGTG

TCATAGTCCAGCCCCTCCGCGGCGTGGCCCTTGGC

GCGCAGCTTGCCCTTGGAGGAGGCGCCGCACGAGG

GGCAGTGCAGACTTTTGAGGGCGTAGAGCTTGGGC

GCGAGAAATACCGATTCCGGGGAGTAGGCATCCGC

GCCGCAGGCCCCGCAGACGGTCTCGCATTCCACGA

GCCAGGTGAGCTCTGGCCGTTCGGGGTCAAAAACC

AGGTTTCCCCCATGCTTTTTGATGCGTTTCTTACC

TCTGGTTTCCATGAGCCGGTGTCCACGCTCGGTGA

CGAAAAGGCTGTCCGTGTCCCCGTATACAGACTTG

AGAGGCCTGTCCTCGAGCGGTGTTCCGCGGTCCTC

CTCGTATAGAAACTCGGACCACTCTGAGACAAAGG

CTCGCGTCCAGGCCAGCACGAAGGAGGCTAAGTGG

GAGGGGTAGCGGTCGTTGTCCACTAGGGGGTCCAC

TCGCTCCAGGGTGTGAAGACACATGTCGCCCTCTT

CGGCATCAAGGAAGGTGATTGGTTTGTAGGTGTAG

GCCACGTGACCGGGTGTTCCTGAAGGGGGCTATA

AAAGGGGGTGGGGCGCGTTCGTCCTCACTCTCTT

CCGCATCGCTGTCTGCGAGGGCCAGCTGTTGGGGT

GAGTACTCCCTCTGAAAAGCGGGCATGACTTCTGC

GCTAAGATTGTCAGTTTCCAAAAACGAGGAGGATT

TGATATTCACCTGGCCCGCGGTGATGCCTTTGAGG

GTGGCCGCATCCATCGGTCAGAAAAGACAATCTT

TTTGTTGTCAAGCTTGGTGGCAAACGACCCGTAGA

GGGCGTTGGACAGCAACTTGGCGATGGAGCGCAGG

GTTTGGTTTTTGTCGCGATCGGCGCGCTCCTTGGC

CGCGATGTTTAGCTGCACGTATTCGCGCGCAACGC

ACCGCCATTCGGGAAAGACGGTGGTGCGCTCGTCG

GGCACCAGGTGCACGCGCCAACCGCGGTTGTGCAG

GGTGACAAGGTCAACGCTGGTGGCTACCTCTCCGC

GTAGGCGCTCGTTGGTCCAGCAGAGGCGGCCGCCC

TTGCGCGAGCAGAATGGCGGTAGGGGGTCTAGCTG

CGTCTCGTCCGGGGGTCTGCGTCCACGGTAAAGA

CCCCGGGCAGCAGGCGCGCGTCGAAGTAGTCTATC

TTGCATCCTTGCAAGTCTAGCGCCTGCTGCCATGC

GCGGGCGGCAAGCGCGCGCTCGTATGGGTTGAGTG

GGGGACCCCATGGCATGGGTGGGTGAGCGCGGAG

GCGTACATGCCGCAAATGTCGTAAACGTAGAGGGG

CTCTCTGAGTATTCCAAGATATGTAGGGTAGCATC

TTCCACCGCGGATGCTGGCGCGCACGTAATCGTAT

AGTTCGTGCGAGGGAGCGAGGAGGTCGGGACCGAG

GTTGCTACGGGCGGGCTGCTCTGCTCGGAAGACTA

TCTGCCTGAAGATGGCATGTGAGTTGGATGATATG

GTTGGACGCTGGAAGACGTTGAAGCTGGCGTCTGT

GAGACCTACCGCGTCACGCACGAAGGAGGCGTAGG

AGTCGCGCAGCTTGTTGACCAGCTCGGCGGTGACC

TGCACGTCTAGGGCGCAGTAGTCCAGGGTTTCCTT

GATGATGTCATACTTATCCTGTCCCTTTTTTTTCC

ACAGCTCGCGGTTGAGGACAAACTCTTCGCGGTCT

TTCCAGTACTCTTGGATCGGAAACCCGTCGGCCTC

CGAACGGTAAGAGCCTAGCATGTAGAACTGGTTGA

CGGCCTGGTAGGCGCAGCATCCCTTTTCTACGGGT

AGCGCGTATGCCTGCGCGGCCTTCCGGAGCGAGGT

GTGGGTGAGCGCAAAGGTGTCCCTGACCATGACTT

TGAGGTACTGGTATTTGAAGTCAGTGTCGTCGCAT

CCGCCCTGCTCCCAGAGCAAAAAGTCCGTGCGCTT

TTTGGAACGCGGATTTGGCAGGGCGAAGGTGACAT

CGTTGAAGAGTATCTTTCCCGCGCGAGGCATAAAG

TTGCGTGTGATGCGGAAGGGTCCCGGCACCTCGGA

ACGGTTGTTAATTACCTGGGCGGCGAGCACGATCT

CGTCAAAGCCGTTGATGTTGTGCCCACAATGTAA

AGTTCCAAGAAGCGCGGGATGCCCTTGATGGAAGG

CAATTTTTTAAGTTCCTCGTAGGTGAGCTCTTCAG

GGGGAGCTGAGCCCGTGCTCTGAAAGGGCCCAGTCT

GCAAGATGAGGGTTGGAAGCGACGAATGAGCTCCA

CAGGTCACGGGCCATTAGCATTTGCAGGTGGTCGC

GAAAGGTCCTAAACTGGCGACCTATGGCCATTTTT

```
TCTGGGGTGATGCAGTAGAAGGTAAGCGGGTCTTG

TTCCCAGCGGTCCCATCCAAGGTTCGCGGCTAGGT

CTCGCGCGGCAGTCACTAGAGGCTCATCTCCGCCG

AACTTCATGACCAGCATGAAGGGCACGAGCTGCTT

CCCAAAGGCCCCCATCCAAGTATAGGTCTCTACAT

CGTAGGTGACAAAGAGACGCTCGGTGCGAGGATGC

GAGCCGATCGGGAAGAACTGGATCTCCCGCCACCA

ATTGGAGGAGTGGCTATTGATGTGGTGAAAGTAGA

AGTCCCTGCGACGGGCCGAACACTCGTGCTGGCTT

TTGTAAAAACGTGCGCAGTACTGGCAGCGGTGCAC

GGGCTGTACATCCTGCACGAGGTTGACCTGACGAC

CGCGCACAAGGAAGCAGAGTGGGAATTTGAGCCCC

TCGCCTGGCGGGTTTGGCTGGTGGTCTTCTACTTC

GGCTGCTTGTCCTTGACCGTCTGGCTGCTCGAGGG

GAGTTACGGTGGATCGGACCACCACGCCGCGCGAG

CCCAAAGTCCAGATGTCCGCGCGCGGCGGTCGGAG

CTTGATGACAACATCGCGCAGATGGGAGCTGTCCA

TGGTCTGGAGCTCCCGCGGCGTCAGGTCAGGCGGG

AGCTCCTGCAGGTTTACCTCGCATAGACGGGTCAG

GGCGCGGGCTAGATCCAGGTGATACCTAATTTCCA

GGGGCTGGTTGGTGGCGGCGTCGATGGCTTGCAAG

AGGCCGCATCCCCGCGGCGCGACTACGGTACCGCG

CGGCGGGCGGTGGGCCGCGGGGGTGTCCTTGGATG

ATGCATCTAAAAGCGGTGACGCGGGCGAGCCCCCG

GAGGTAGGGGGGGCTCCGGACCCGCCGGGAGAGGG

GGCAGGGGCACGTCGGCGCCGCGCGCGGGCAGGAG

CTGGTGCTGCGCGCGTAGGTTGCTGGCGAACGCGA

CGACGCGGCGGTTGATCTCCTGAATCTGGCGCCTC

TGCGTGAAGACGACGGGCCCGGTGAGCTTGAGCCT

GAAAGAGAGTTCGACAGAATCAATTTCGGTGTCGT

TGACGGCGGCCTGGCGCAAAATCTCCTGCACGTCT

CCTGAGTTGTCTTGATAGGCGATCTCGGCCATGAA

CTGCTCGATCTCTTCCTCCTGGAGATCTCCGCGTC

CGGCTCGCTCCACGGTGGCGGCGAGGTCGTTGGAA

ATGCGGGCCATGAGCTGCGAGAAGGCGTTGAGGCC

TCCCTCGTTCCAGACGCGGCTGTAGACCACGCCCC

CTTCGGCATCGCGGGCGCGCATGACCACCTGCGCG

AGATTGAGCTCCACGTGCCGGGCGAAGACGGCGTA

GTTTCGCAGGCGCTGAAAGAGGTAGTTGAGGGTGG

TGGCGGTGTGTTCTGCCACGAAGAAGTACATAACC

CAGCGTCGCAACGTGGATTCGTTGATATCCCCCAA

GGCCTCAAGGCGCTCCATGGCCTCGTAGAAGTCCA

CGGCGAAGTTGAAAAACTGGGAGTTGCGCGCCGAC

ACGGTTAACTCCTCCTCAGAAGACGGATGAGCTC

GGCGACAGTGTCGCGCACCTCGCGCTCAAAGGCTA

CAGGGGCCTCTTCTTCTTCTTCAATCTCCTCTTCC

ATAAGGGCCTCCCCTTCTTCTTCTTCTGGCGGCGG

TGGGGGAGGGGGGACACGGCGGCGACGACGGCGCA

CCGGGAGGCGGTCGACAAAGCGCTCGATCATCTCC

CCGCGGCGACGGCGCATGGTCTCGGTGACGGCGCG

GCCGTTCTCGCGGGGGCGCAGTTGGAAGACGCCGC

CCGTCATGTCCCGGTTATGGGTTGGCGGGGGGCTG

CCATGCGGCAGGGATACGGCGCTAACGATGCATCT

CAACAATTGTTGTGTAGGTACTCCGCCGCCGAGGG

ACCTGAGCGAGTCCGCATCGACCGGATCGGAAAAC

CTCTCGAGAAAGGCGTCTAACCAGTCACAGTCGCA

AGGTAGGCTGAGCACCGTGGCGGGCGGCAGCGGGC

GGCGGTCGGGGTTGTTTCTGGCGGAGGTGCTGCTG

ATGATGTAATTAAAGTAGGCGGTCTTGAGACGGCG

GATGGTCGACAGAAGCACCATGTCCTTGGGTCCGG

CCTGCTGAATGCGCAGGCGGTCGGCCATGCCCCAG

GCTTCGTTTTGACATCGGCGCAGGTCTTTGTAGTA

GTCTTGCATGAGCCTTTCTACCGGCACTTCTTCTT

CTCCTTCCTCTTGTCCTGCATCTCTTGCATCTATC

GCTGCGGCGGCGGCGGAGTTTGGCCGTAGGTGGCG

CCCTCTTCCTCCCATGCGTGTGACCCCGAAGCCCC

TCATCGGCTGAAGCAGGGCTAGGTCGGCGACAACG

CGCTCGGCTAATATGGCCTGCTGCACCTGCGTGAG

GGTAGACTGGAAGTCATCCATGTCCACAAAGCGGT

GGTATGCGCCCGTGTTGATGGTGTAAGTGCAGTTG

GCCATAACGGACCAGTTAACGGTCTGGTGACCCGG

CTGCGAGAGCTCGGTGTACCTGAGACGCGAGTAAG

CCCTCGAGTCAAATACGTAGTCGTTGCAAGTCCGC

ACCAGGTACTGGTATCCCACCAAAAAGTGCGGCGG

CGGCTGGCGGTAGAGGGGCCAGCGTAGGGTGGCCG

GGGCTCCGGGGGCGAGATCTTCCAACATAAGGCGA

TGATATCCGTAGATGTACCTGGACATCCAGGTGAT

GCCGGCGGCGGTGGTGGAGGCGCGCGGAAAGTCGC

GGACGCGGTTCCAGATGTTGCGCAGCGGCAAAAAG

TGCTCCATGGTCGGGACGCTCTGGCCGGTCAGGCG

CGCGCAATCGTTGACGCTCTAGACCGTGCAAAAGG
```

-continued

AGAGCCTGTAAGCGGGCACTCTTCCGTGGTCTGGT

GGATAAATTCGCAAGGGTATCATGGCGGACGACCG

GGGTTCGAGCCCCGTATCCGGCCGTCCGCCGTGAT

CCATGCGGTTACCGCCCGCGTGTCGAACCCAGGTG

TGCGACGTCAGACAACGGGGAGTGCTCCTTTTGG

CTTCCTTCCAGGCGCGGCGGCTGCTGCGCTAGCTT

TTTTGGCCACTGGCCGCGCGCAGCGTAAGCGGTTA

GGCTGGAAAGCGAAAGCATTAAGTGGCTCGCTCCC

TGTAGCCGGAGGGTTATTTTCCAAGGGTTGAGTCG

CGGGACCCCCGGTTCGAGTCTCGGACCGGCCGGAC

TGCGGCGAACGGGGTTTGCCTCCCCGTCATGCAA

GACCCCGCTTGCAAATTCCTCCGGAAACAGGGACG

AGCCCCTTTTTGCTTTTCCCAGATGCATCCGGTG

CTGCGGCAGATGCGCCCCCCTCCTCAGCAGCGGCA

AGAGCAAGAGCAGCGGCAGACATGCAGGGCACCCT

CCCCTCCTCCTACCGCGTCAGGAGGGGCGACATCC

GCGGTTGACGCGGCAGCAGATGGTGATTACGAACC

CCCGCGGCGCCGGGCCCGGCACTACCTGGACTTGG

AGGAGGGCGAGGGCCTGGCGCGGCTAGGAGCGCCC

TCTCCTGAGCGGTACCCAAGGGTGCAGCTGAAGCG

TGATACGCGTGAGGCGTACGTGCCGCGGCAGAACC

TGTTTCGCGACCGCGAGGGAGAGGAGCCCGAGGAG

ATGCGGGATCGAAAGTTCCACGCAGGGCGCGAGCT

GCGGCATGGCCTGAATCGCGAGCGGTTGCTGCGCG

AGGAGGACTTTGAGCCCGACGCGCGAACCGGGATT

AGTCCCGCGCGCACACGTGGCGGCCGCCGACCT

GGTAACCGCATACGAGCAGACGGTGAACCAGGAGA

TTAACTTTCAAAAAAGCTTTAACAACCACGTGCGT

ACGCTTGTGGCGCGCGAGGAGGTGGCTATAGGACT

GATGCATCTGTGGGACTTTGTAAGCGCGCTGGAGC

AAAACCCAAATAGCAAGCGCTCATGGCGCAGCTG

TTCCTTATAGTGCAGCACAGCAGGGACAACGAGGC

ATTCAGGGATGCGCTGCTAAACATAGTAGAGCCCG

AGGGCCGCTGGCTGCTCGATTTGATAAACATCCTG

CAGAGCATAGTGGTGCAGGAGCGCAGCTTGAGCCT

GGCTGACAAGGTGGCCGCCATCAACTATTCCATGC

TTAGCCTGGGCAAGTTTTACGCCCGCAAGATATAC

CATACCCCTTACGTTCCCATAGACAAGGAGGTAAA

GATCGAGGGGTTCTACATGCGCATGGCGCTGAAGG

TGCTTACCTTGAGCGACGACCTGGGCGTTTATCGC

-continued

AACGAGCGCATCCACAAGGCCGTGAGCGTGAGCCG

GCGGCGCGAGCTCAGCGACCGCGAGCTGATGCACA

GCCTGCAAAGGGCCCTGGCTGGCACGGGCAGCGGC

GATAGAGAGGCCGAGTCCTACTTTGACGCGGGCGC

TGACCTGCGCTGGGCCCCAAGCCGACGCGCCCTGG

AGGCAGCTGGGGCCGGACCTGGGCTGGCGGTGGCA

CCCGCGCGCGCTGGCAACGTCGGCGGCGTGGAGGA

ATATGACGAGGACGATGAGTACGAGCCAGAGGACG

GCGAGTACTAAGCGGTGATGTTTCTGATCAGATGA

TGCAAGACGCAACGGACCCGGCGGTGCGGGCGGCG

CTGCAGAGCCAGCCGTCCGGCCTTAACTCCACGGA

CGACTGGCGCCAGGTCATGGACCGCATCATGTCGC

TGACTGCGCGCAATCCTGACGCGTTCCGGCAGCAG

CCGCAGGCCAACCGGCTCTCCGCAATTCTGGAAGC

GGTGGTCCCGGCGCGCGCAAACCCCACGCACGAGA

AGGTGCTGGCGATCGTAAACGCGCTGGCCGAAAAC

AGGGCCATCCGGCCCGACGAGGCCGCCTGGTCTA

CGACGCGCTGCTTCAGCGCGTGGCTCGTTACAACA

GCGGCAACGTGCAGACCAACCTGGACCGGCTGGTG

GGGGATGTGCGCGAGGCCGTGGCGCAGCGTGAGCG

CGCGCAGCAGCAGGGCAACCTGGGCTCCATGGTTG

CACTAAACGCCTTCCTGAGTACACAGCCCGCCAAC

GTGCCGCGGGACAGGAGGACTACACCAACTTTGT

GAGCGCACTGCGGCTAATGGTGACTGAGACACCGC

AAAGTGAGGTGTACCAGTCTGGGCCAGACTATTTT

TTCCAGACCAGTAGACAAGGCCTGCAGACCGTAAA

CCTGAGCCAGGCTTTCAAAAACTTGCAGGGGCTGT

GGGGGGTGCGGGCTCCCACAGGCGACCGCGCGACC

GTGTCTAGCTTGCTGACGCCCAACTCGCGCCTGTT

GCTGCTGCTAATAGCGCCCTTCACGGACAGTGGCA

GCGTGTCCCGGGACACATACCTAGGTCACTTGCTG

ACACTGTACCGCGAGGCCATAGGTCAGGCGCATGT

GGACGAGCATACTTTCCAGGAGATTACAAGTGTCA

GCCGCGCGCTGGGGCAGGAGGACACGGGCAGCCTG

GAGGCAACCCTAAACTACCTGCTGACCAACCGGCG

GCAGAAGATCCCCTCGTTGCACAGTTTAAACAGCG

AGGAGGAGCGCATTTTGCGCTACGTGCAGCAGAGC

GTGAGCCTTAACCTGATGCGCGACGGGGTAACGCC

CAGCGTGGCGCTGGACATGACCGCGCGCAACATGG

AACCGGGCATGTATGCCTCAAACCGGCCGTTTATC

AACCGCCTAATGGACTACTTGCATCGCGCGGCCGC

-continued

```
CGTGAACCCCGAGTATTTCACCAATGCCATCTTGA

ACCCGCACTGGCTACCGCCCCTGGTTTCTACACC

GGGGGATTCGAGGTGCCCGAGGGTAACGATGGATT

CCTCTGGGACGACATAGACGACAGCGTGTTTTCCC

CGCAACCGCAGACCCTGCTAGAGTTGCAACAGCGC

GAGCAGGCAGAGGCGGCGCTGCGAAAGGAAAGCTT

CCGCAGGCCAAGCAGCTTGTCCGATCTAGGCGCTG

CGGCCCCGCGGTCAGATGCTAGTAGCCCATTTCCA

AGCTTGATAGGGTCTCTTACCAGCACTCGCACCAC

CCGCCCGCGCCTGCTGGGCGAGGAGGAGTACCTAA

ACAACTCGCTGCTGCAGCCGCAGCGCGAAAAAAAC

CTGCCTCCGGCATTTCCCAACAACGGATAGAGAG

CCTAGTGGACAAGATGAGTAGATGGAAGACGTACG

CGCAGGAGCACAGGGACGTGCCAGGCCCGCGCCCG

CCCACCCGTCGTCAAAGGCACGACCGTCAGCGGGG

TCTGGTGTGGGAGGACGATGACTCGGCAGACGACA

GCAGCGTCCTGGATTTGGGAGGGAGTGGCAACCCG

TTTGCGCACCTTCGCCCCAGGCTGGGGAGAATGTT

TTAAAAAAAAAAAAGCATGATGCAAAATAAAAAAC

TCACCAAGGCCATGGCACCGAGCGTTGGTTTTCTT

GTATTCCCCTTAGTATGCGGCGCGCGGCGATGTAT

GAGGAAGGTCCTCCTCCCTCCTACGAGAGTGTGGT

GAGCGCGGCGCCAGTGGCGGCGGCGCTGGGTTCTC

CCTTCGATGCTCCCCTGGACCCGCCGTTTGTGCCT

CCGCGGTACCTGCGGCCTACCGGGGGGAGAAACAG

CATCCGTTACTCTGAGTTGGCACCCCTATTCGACA

CCACCCGTGTGTACCTGGTGGACAACAAGTCAACG

GATGTGGCATCCCTGAACTACCAGAACGACCACAG

CAACTTTCTGACCACGGTCATTCAAAACAATGACT

ACAGCCCGGGGAGGCAAGCACACAGACCATCAAT

CTTGACGACCGGTCGCACTGGGGCGGCGACCTGAA

AACCATCCTGCATACCAACATGCCAAATGTGAACG

AGTTCATGTTTACCAATAAGTTTAAGGCGCGGGTG

ATGGTGTCGCGCTTGCCTACTAAGGACAATCAGGT

GGAGCTGAAATACGAGTGGGTGGAGTTCACGCTGC

CCGAGGGCAACTACTCCGAGACCATGACCATAGAC

CTTATGAACAACGCGATCGTGGAGCACTACTTGAA

AGTGGGCAGACAGAACGGGGTTCTGGAAAGCGACA

TCGGGGTAAAGTTTGACACCCGCAACTTCAGACTG

GGGTTTGACCCCGTCACTGGTCTTGTCATGCCTGG
```

-continued

```
GGTATATACAAACGAAGCCTTCCATCCAGACATCA

TTTTGCTGCCAGGATGCGGGGTGGACTTCACCCAC

AGCCGCCTGAGCAACTTGTTGGGCATCCGCAAGCG

GCAACCCTTCCAGGAGGGCTTTAGGATCACCTACG

ATGATCTGGAGGGTGGTAACATTCCCGCACTGTTG

GATGTGGACGCCTACCAGGCGAGCTTGAAAGATGA

CACCGAACAGGGCGGGGGTGGCGCAGGCGGCAGCA

ACAGCAGTGGCAGCGGCGCGAAGAGAACTCCAAC

GCGGCAGCCGCGGCAATGCAGCCGGTGGAGGACAT

GAACGATCATGCCATTCGCGGCGACACCTTTGCCA

CACGGGCTGAGGAGAAGCGCGCTGAGGCCGAAGCA

GCGGCCGAAGCTGCCGCCCCGCTGCGCAACCCGA

GGTCGAGAAGCCTCAGAAGAAACCGGTGATCAAAC

CCCTGACAGAGGACAGCAAGAAACGCAGTTACAAC

CTAATAAGCAATGACAGCACCTTCACCCAGTACCG

CAGCTGGTACCTTGCATACAACTACGGCGACCCTC

AGACCGGAATCCGCTCATGGACCCTGCTTTGCACT

CCTGACGTAACCTGCGGCTCGGAGCAGGTCTACTG

GTCGTTGCCAGACATGATGCAAGACCCCGTGACCT

TCCGCTCCACGCGCCAGATCAGCAACTTTCCGGTG

GTGGGCGCCGAGCTGTTGCCCGTGCACTCCAAGAG

CTTCTACAACGACCAGGCCGTCTACTCCCAACTCA

TCCGCCAGTTTACCTCTCTGACCCACGTGTTCAAT

CGCTTTCCCGAGAACCAGATTTTGGCGCGCCCGCC

AGCCCCCACCATCACCACCGTCAGTGAAAACGTTC

CTGCTCTCACAGATCACGGGACGCTACCGCTGCGC

AACAGCATCGGAGGAGTCCAGCGAGTGACCATTAC

TGACGCCAGACGCCGCACCTGCCCCTACGTTTACA

AGGCCCTGGGCATAGTCTCGCCGCGCGTCCTATCG

AGCCGCACTTTTTGAGCAAGCATGTCCATCCTTAT

ATCGCCCAGCAATAACACAGGCTGGGGCCTGCGCT

TCCCAAGCAAGATGTTTGGCGGGGCCAAGAAGCGC

TCCGACCAACACCCAGTGCGCGTGCGCGGGCACTA

CCGCGCGCCCTGGGGCGCGCACAAACGCGGCCGCA

CTGGGCGCACCACCGTCGATGACGCCATCGACGCG

GTGGTGGAGGAGGCGCGCAACTACACGCCCACGCC

GCCACCAGTGTCCACAGTGGACGCGGCCATTCAGA

CCGTGGTGCGCGGAGCCCGGCGCTATGCTAAAATG

AAGAGACGGCGGAGGCGCGTAGCACGTCGCCACCG

CCGCCGACCCGGCACTGCCGCCCAACGCGCGGCGG

CGGCCCTGCTTAACCGCGCACGTCGCACCGGCCGA
```

-continued

CGGGCGGCCATGCGGGCCGCTCGAAGGCTGGCCGC

GGGTATTGTCACTGTGCCCCCCAGGTCCAGGCGAC

GAGCGGCCGCCGCAGCAGCCGCGGCCATTAGTGCT

ATGACTCAGGGTCGCAGGGGCAACGTGTATTGGGT

GCGCGACTCGGTTAGCGGCCTGCGCGTGCCCGTGC

GCACCCGCCCCCCGCGCAACTAGATTGCAAGAAAA

AACTACTTAGACTCGTACTGTTGTATGTATCCAGC

GGCGGCGGCGCGCAACGAAGCTATGTCCAAGCGCA

AAATCAAAGAAGAGATGCTCCAGGTCATCGCGCCG

GAGATCTATGGCCCCCGAAGAAGGAAGAGCAGGA

TTACAAGCCCCGAAAGCTAAAGCGGGTCAAAAGA

AAAAGAAAGATGATGATGATGAACTTGACGACGAG

GTGGAACTGCTGCACGCTACCGCGCCCAGGCGACG

GGTACAGTGGAAAGGTCGACGCGTAAAACGTGTTT

TGCGACCCGGCACCACCGTAGTCTTTACGCCCGGT

GAGCGCTCCACCCGCACCTACAAGCGCGTGTATGA

TGAGGTGTACGGCGACGAGGACCTGCTTGAGCAGG

CCAACGAGCGCCTCGGGGAGTTTGCCTACGAAAG

CGGCATAAGGACATGCTGGCGTTGCCGCTGGACGA

GGGCAACCCAACACCTAGCCTAAAGCCCGTAACAC

TGCAGCAGGTGCTGCCCGCGCTTGCACCGTCCGAA

GAAAAGCGCGGCCTAAAGCGCGAGTCTGGTGACTT

GGCACCCACCGTGCAGCTGATGGTACCCAAGCGCC

AGCGACTGGAAGATGTCTTGGAAAAAATGACCGTG

GAACCTGGGCTGGAGCCCGAGGTCCGCGTGCGGCC

AATCAAGCAGGTGGCGCCGGGACTGGGCGTGCAGA

CCGTGGACGTTCAGATACCCACTACCAGTAGCACC

AGTATTGCCACCGCCACAGAGGGCATGGAGACACA

AACGTCCCCGGTTGCCTCAGCGGTGGCGGATGCCG

CGGTGCAGGCGGTCGCTGCGGCCGCGTCCAAGACC

TCTACGGAGGTGCAAACGGACCCGTGGATGTTTCG

CGTTTCAGCCCCCGGCGCCCGCGCGGTTCGAGGA

AGTACGGCGCCGCCAGCGCGCTACTGCCCGAATAT

GCCCTACATCCTTCCATTGCGCCTACCCCCGGCTA

TCGTGGCTACACCTACCGCCCAGAAGACGAGCAA

CTACCCGACGCCGAACCACCACTGGAACCCGCCGC

CGCCGTCGCCGTCGCCAGCCCGTGCTGGCCCCGAT

TTCCGTGCGCAGGGTGGCTCGCGAAGGAGGCAGGA

CCCTGGTGCTGCCAACAGCGCGCTACCACCCCAGC

ATCGTTTAAAAGCCGGTCTTTGTGGTTCTTGCAGA

-continued

TATGGCCCTCACCTGCCGCCTCCGTTTCCCGGTGC

CGGGATTCCGAGGAAGAATGCACCGTAGGAGGGGC

ATGGCCGGCCACGGCCTGACGGGCGGCATGCGTCG

TGCGCACCACCGGCGGCGGCGCGCGTCGCACCGTC

GCATGCGCGGCGGTATCCTGCCCCTCCTTATTCCA

CTGATCGCCGCGGCGATTGGCGCCGTGCCCGGAAT

TGCATCCGTGGCCTTGCAGGCGCAGAGACACTGAT

TAAAAACAAGTTGCATGTGGAAAAATCAAAATAAA

AAGTCTGGACTCTCACGCTCGCTTGGTCCTGTAAC

TATTTTGTAGAATGGAAGACATCAACTTTGCGTCT

CTGGCCCCGCGACACGGCTCGCGCCCGTTCATGGG

AAACTGGCAAGATATCGGCACCAGCAATATGAGCG

GTGGCGCCTTCAGCTGGGGCTCGCTGTGGAGCGGC

ATTAAAAATTTCGGTTCCACCGTTAAGAACTATGG

CAGCAAGGCCTGGAACAGCAGCACAGGCCAGATGC

TGAGGGATAAGTTGAAAGAGCAAAATTTCCAACAA

AAGGTGGTAGATGGCCTGGCCTCTGGCATTAGCGG

GGTGGTGGACCTGGCCAACCAGGCAGTGCAAAATA

AGATTAACAGTAAGCTTGATCCCCGCCCTCCCGTA

GAGGAGCCTCCACCGGCCGTGGAGACAGTGTCTCC

AGAGGGGCGTGGCGAAAAGCGTCCGCGCCCCGACA

GGGAAGAAACTCTGGTGACGCAAATAGACGAGCCT

CCCTCGTACGAGGAGGCACTAAAGCAAGGCCTGCC

CACCACCCGTCCCATCGCGCCCATGGCTACCGGAG

TGCTGGGCCAGCACACACCCGTAACGCTGGACCTG

CCTCCCCCCGCCGACACCCAGCAGAAACCTGTGCT

GCCAGGCCCGACCGCCGTTGTTGTAACCCGTCCTA

GCCGCGCGTCCTGCGCCGCGCCGCCAGCGGTCCG

CGATCGTTGCGGCCCGTAGCCAGTGGCAACTGGCA

AAGCACACTGAACAGCATCGTGGGTCTGGGGGTGC

AATCCCTGAAGCGCCGACGATGCTTCTGAATAGCT

AACGTGTCGTATGTGTGTCATGTATGCGTCCATGT

CGCCGCCAGAGGAGCTGCTGAGCCGCCGCGCGCCC

GCTTTCCAAGATGGCTACCCCTTCGATGATGCCGC

AGTGGTCTTACATGCACATCTCGGGCCAGGACGCC

TCGGAGTACCTGAGCCCCGGGCTGGTGCAGTTTGC

CCGCGCCACCGAGACGTACTTCAGCCTGAATAACA

AGTTTAGAAACCCCACGGTGGCGCCTACGCACGAC

GTGACCACAGACCGGTCCCAGCGTTTGACGCTGCG

GTTCATCCCTGTGGACCGTGAGGATACTGCGTACT

CGTACAAGGCGCGGTTCACCCTAGCTGTGGGTGAT

```
AACCGTGTGCTGGACATGGCTTCCACGTACTTTGA
CATCCGCGGCGTGCTGGACAGGGGCCCTACTTTTA
AGCCCTACTCTGGCACTGCCTACAACGCCCTGGCT
CCCAAGGGTGCCCCAAATCCTTGCGAATGGGATGA
AGCTGCTACTGCTCTTGAAATAAACCTAGAAGAAG
AGGACGATGACAACGAAGACGAAGTAGACGAGCAA
GCTGAGCAGCAAAAAACTCACGTATTTGGGCAGGC
GCCTTATTCTGGTATAAATATTACAAAGGAGGGTA
TTCAAATAGGTGTCGAAGGTCAAACACCTAAATAT
GCCGATAAAACATTTCAACCTGAACCTCAAATAGG
AGAATCTCAGTGGTACGAAACTGAAATTAATCATG
CAGCTGGGAGAGTCCTTAAAAAGACTACCCCAATG
AAACCATGTTACGGTTCATATGCAAAACCCACAAA
TGAAAATGGAGGGCAAGGCATTCTTGTAAAGCAAC
AAAATGGAAAGCTAGAAAGTCAAGTGGAAATGCAA
TTTTTCTCAACTACTGAGGCGACCGCAGGCAATGG
TGATAACTTGACTCCTAAAGTGGTATTGTACAGTG
AAGATGTAGATATAGAAACCCCAGACACTCATATT
TCTTACATGCCCACTATTAAGGAAGGTAACTCACG
AGAACTAATGGGCCAACAATCTATGCCCAACAGGC
CTAATTACATTGCTTTTAGGGACAATTTTATTGGT
CTAATGTATTACAACAGCACGGGTAATATGGGTGT
TCTGGCGGGCCAAGCATCGCAGTTGAATGCTGTTG
TAGATTTGCAAGACAGAAACACAGAGCTTTCATAC
CAGCTTTTGCTTGATTCCATTGGTGATAGAACCAG
GTACTTTTCTATGTGGAATCAGGCTGTTGACAGCT
ATGATCCAGATGTTAGAATTATTGAAAATCATGGA
ACTGAAGATGAACTTCCAAATTACTGCTTTCCACT
GGGAGGTGTGATTAATACAGAGACTCTTACCAAGG
TAAAACCTAAAACAGGTCAGGAAAATGGATGGGAA
AAAGATGCTACAGAATTTTCAGATAAAAATGAAAT
AAGAGTTGGAAATAATTTTGCCATGGAAATCAATC
TAAATGCCAACCTGTGGAGAAATTTCCTGTACTCC
AACATAGCGCTGTATTTGCCCGACAAGCTAAAGTA
CAGTCCTTCCAACGTAAAAATTTCTGATAACCCAA
ACACCTACGACTACATGAACAAGCGAGTGGTGGCT
CCCGGGTTAGTGGACTGCTACATTAACCTTGGAGC
ACGCTGGTCCCTTGACTATATGGACAACGTCAACC
CATTTAACCACCACCGCAATGCTGGCCTGCGCTAC
CGCTCAATGTTGCTGGGCAATGGTCGCTATGTGCC

CTTCCACATCCAGGTGCCTCAGAAGTTCTTTGCCA
TTAAAAACCTCCTTCTCCTGCCGGGCTCATACACC
TACGAGTGGAACTTCAGGAAGGATGTTAACATGGT
TCTGCAGAGCTCCCTAGGAAATGACCTAAGGGTTG
ACGGAGCCAGCATTAAGTTTGATAGCATTTGCCTT
TACGCCACCTTCTTCCCCATGGCCCACAACACCGC
CTCCACGCTTGAGGCCATGCTTAGAAACGACACCA
ACGACCAGTCCTTTAACGACTATCTCTCCGCCGCC
AACATGCTCTACCCTATACCCGCCAACGCTACCAA
CGTGCCCATATCCATCCCCTCCCGCAACTGGGCGG
CTTTCCGCGGCTGGGCCTTCACGCGCCTTAAGACT
AAGGAAACCCCATCACTGGGCTCGGGCTACGACCC
TTATTACACCTACTCTGGCTCTATACCCTACCTAG
ATGGAACCTTTTACCTCAACCACACCTTTAAGAAG
GTGGCCATTACCTTTGACTCTTCTGTCAGCTGGCC
TGGCAATGACCGCCTGCTTACCCCCAACGAGTTTG
AAATTAAGCGCTCAGTTGACGGGAGGGTTACAAC
GTTGCCCAGTGTAACATGACCAAAGACTGGTTCCT
GGTACAAATGCTAGCTAACTACAACATTGGCTACC
AGGGCTTCTATATCCCAGAGAGCTACAAGGACCGC
ATGTACTCCTTCTTTAGAAACTTCCAGCCCATGAG
CCGTCAGGTGGTGGATGATACTAAATACAAGGACT
ACCAACAGGTGGGCATCCTACACCAACACAACAAC
TCTGGATTTGTTGGCTACCTTGCCCCCACCATGCG
CGAAGGACAGGCCTACCCTGCTAACTTCCCCTATC
CGCTTATAGGCAAGACCGCAGTTGACAGCATTACC
CAGAAAAAGTTTCTTTGCGATCGCACCCTTTGGCG
CATCCCATTCTCCAGTAACTTTATGTCCATGGGCG
CACTCACAGACCTGGGCAAAACCTTCTCTACGCC
AACTCCGCCCACGCGCTAGACATGACTTTTGAGGT
GGATCCCATGGACGAGCCCACCCTTCTTTATGTTT
TGTTTGAAGTCTTTGACGTGGTCCGTGTGCACCGG
CCGCACCGCGGCGTCATCGAAACCGTGTACCTGCG
CACGCCCTTCTCGGCCGGCAACGCCACAACATAAA
GAAGCAAGCAACATCAACAACAGCTGCCGCCATGG
GCTCCAGTGAGCAGGAACTGAAAGCCATTGTCAAA
GATCTTGGTTGTGGGCCATATTTTTTGGGCACCTA
TGACAAGCGCTTTCCAGGCTTTGTTTCTCCACACA
AGCTCGCCTGCGCCATAGTCAATACGGCCGGTCGC
GAGACTGGGGCGTACACTGGATGGCCTTTGCCTG
GAACCCGCACTCAAAAACATGCTACCTCTTTGAGC
```

CCTTTGGCTTTTCTGACCAGCGACTCAAGCAGGTT

TACCAGTTTGAGTACGAGTCACTCCTGCGCCGTAG

CGCCATTGCTTCTTCCCCCGACCGCTGTATAACGC

TGGAAAAGTCCACCCAAAGCGTACAGGGGCCCAAC

TCGGCCGCCTGTGGACTATTCTGCTGCATGTTTCT

CCACGCCTTTGCCAACTGGCCCCAAACTCCCATGG

ATCACAACCCCACCATGAACCTTATTACCGGGGTA

CCCAACTCCATGCTCAACAGTCCCCAGGTACAGCC

CACCCTGCGTCGCAACCAGGAACAGCTCTACAGCT

TCCTGGAGCGCCACTCGCCCTACTTCCGCAGCCAC

AGTGCGCAGATTAGGAGCGCCACTTCTTTTTGTCA

CTTGAAAAACATGTAAAAATAATGTACTAGAGACA

CTTTCAATAAAGGCAAATGCTTTTATTTGTACACT

CTCGGGTGATTATTTACCCCCACCCTTGCCGTCTG

CGCCGTTTAAAAATCAAAGGGGTTCTGCCGCGCAT

CGCTATGCGCCACTGGCAGGGACACGTTGCGATAC

TGGTGTTTAGTGCTCCACTTAAACTCAGGCACAAC

CATCCGCGGCAGCTCGGTGAAGTTTTCACTCCACA

GGCTGCGCACCATCACCAACGCGTTTAGCAGGTCG

GGCGCCGATATCTTGAAGTCGCAGTTGGGGCCTCC

GCCCTGCGCGCGCGAGTTGCGATACACAGGGTTGC

AGCACTGGAACACTATCAGCGCCGGGTGGTGCACG

CTGGCCAGCACGCTCTTGTCGGAGATCAGATCCGC

GTCCAGGTCCTCCGCGTTGCTCAGGGCGAACGGAG

TCAACTTTGGTAGCTGCCTTCCCAAAAAGGGCGCG

TGCCCAGGCTTTGAGTTGCACTCGCACCGTAGTGG

CATCAAAAGGTGACCGTGCCCGGTCTGGGCGTTAG

GATACAGCGCCTGCATAAAAGCCTTGATCTGCTTA

AAAGCCACCTGAGCCTTTGCGCCTTCAGAGAAGAA

CATGCCGCAAGACTTGCCGGAAAACTGATTGGCCG

GACAGGCCGCGTCGTGCACGCAGCACCTTGCGTCG

GTGTTGGAGATCTGCACCACATTTCGGCCCCACCG

GTTCTTCACGATCTTGGCCTTGCTAGACTGCTCCT

TCAGCGCGCGCTGCCCGTTTTCGCTCGTCACATCC

ATTTCAATCACGTGCTCCTTATTTATCATAATGCT

TCCGTGTAGACACTTAAGCTCGCCTTCGATCTCAG

CGCAGCGGTGCAGCCACAACGCGCAGCCCGTGGGC

TCGTGATGCTTGTAGGTCACCTCTGCAAACGACTG

CAGGTACGCCTGCAGGAATCGCCCCATCATCGTCA

CAAAGGTCTTGTTGCTGGTGAAGGTCAGCTGCAAC

CCGCGGTGCTCCTCGTTCAGCCAGGTCTTGCATAC

GGCCGCCAGAGCTTCCACTTGGTCAGGCAGTAGTT

TGAAGTTCGCCTTTAGATCGTTATCCACGTGGTAC

TTGTCCATCAGCGCGCGCGCAGCCTCCATGCCCTT

CTCCCACGCAGACACGATCGGCACACTCAGCGGGT

TCATCACCGTAATTTCACTTTCCGCTTCGCTGGGC

TCTTCCTCTTCCTCTTGCGTCCGCATACCACGCGC

CACTGGGTCGTCTTCATTCAGCCGCCGCACTGTGC

GCTTACCTCCTTTGCCATGCTTGATTAGCACCGGT

GGGTTGCTGAAACCCACCATTTGTAGCGCCACATC

TTCTCTTTCTTCCTCGCTGTCCACGATTACCTCTG

GTGATGGCGGCGCTCGGGCTTGGGAGAAGGGCGC

TTCTTTTTCTTCTTGGGCGCAATGGCCAAATCCGC

CGCCGAGGTCGATGGCCGCGGGCTGGGTGTGCGCG

GCACCAGCGCGTCTTGTGATGAGTCTTCCTCGTCC

TCGGACTCGATACGCCGCCTCATCCGCTTTTTTGG

GGGCGCCCGGGGAGGCGGCGGCGACGGGGACGGGG

ACGACACGTCCTCCATGGTTGGGGGACGTCGCGCC

GCACCGCGTCCGCGCTCGGGGGTGGTTTCGCGCTG

CTCCTCTTCCCGACTGGCCATTTCCTTCTCCTATA

GGCAGAAAAAGATCATGGAGTCAGTCGAGAAGAAG

GACAGCCTAACCGCCCCCTCTGAGTTCGCCACCAC

CGCCTCCACCGATGCCGCCAACGCGCCTACCACCT

TCCCCGTCGAGGCACCCCCGCTTGAGGAGGAGGAA

GTGATTATCGAGCAGGACCCAGGTTTTGTAAGCGA

AGACGACGAGGACCGCTCAGTACCAACAGAGGATA

AAAAGCAAGACCAGGACAACGCAGAGGCAAACGAG

GAACAAGTCGGGCGGGGGACGAAAGGCATGGCGA

CTACCTAGATGTGGGAGACGACGTGCTGTTGAAGC

ATCTGCAGCGCCAGTGCGCCATTATCTGCGACGCG

TTGCAAGAGCGCAGCGATGTGCCCCTCGCCATAGC

GGATGTCAGCCTTGCCTACGAACGCCACCTATTCT

CACCGCGCGTACCCCCCAAACGCCAAGAAAACGGC

ACATGCGAGCCCAACCCGCGCCTCAACTTCTACCC

CGTATTTGCCGTGCCAGAGGTGCTTGCCACCTATC

ACATCTTTTTCCAAAACTGCAAGATACCCCTATCC

TGCCGTGCCAACCGCAGCCGAGCGGACAAGCAGCT

GGCCTTGCGGCAGGGCGCTGTCATACCTGATATCG

CCTCGCTCAACGAAGTGCCAAAAATCTTTGAGGGT

CTTGGACGCGACGAGAAGCGCGCGGCAAACGCTCT

GCAACAGGAAAACAGCGAAAATGAAAGTCACTCTG

```
GAGTGTTGGTGGAACTCGAGGGTGACAACGCGCGC
CTAGCCGTACTAAAACGCAGCATCGAGGTCACCCA
CTTTGCCTACCCGGCACTTAACCTACCCCCCAAGG
TCATGAGCACAGTCATGAGTGAGCTGATCGTGCGC
CGTGCGCAGCCCCTGGAGAGGGATGCAAATTTGCA
AGAACAAACAGAGGAGGGCCTACCCGCAGTTGGCG
ACGAGCAGCTAGCGCGCTGGCTTCAAACGCGCGAG
CCTGCCGACTTGGAGGAGCGACGCAAACTAATGAT
GGCCGCAGTGCTCGTTACCGTGGAGCTTGAGTGCA
TGCAGCGGTTCTTTGCTGACCCGGAGATGCAGCGC
AAGCTAGAGGAAACATTGCACTACACCTTTCGACA
GGGCTACGTACGCCAGGCCTGCAAGATCTCCAACG
TGGAGCTCTGCAACCTGGTCTCCTACCTTGGAATT
TTGCACGAAAACCGCCTTGGGCAAAACGTGCTTCA
TTCCACGCTCAAGGGCGAGGCGCGCCGCGACTACG
TCCGCGACTGCGTTTACTTATTTCTATGCTACACC
TGGCAGACGGCCATGGGCGTTTGGCAGCAGTGCTT
GGAGGAGTGCAACCTCAAGGAGCTGCAGAAACTGC
TAAAGCAAAACTTGAAGGACCTATGGACGGCCTTC
AACGAGCGCTCCGTGGCCGCGCACCTGGCGGACAT
CATTTTCCCCGAACGCCTGCTTAAAACCCTGCAAC
AGGGTCTGCCAGACTTCACCAGTCAAAGCATGTTG
CAGAACTTTAGGAACTTTATCCTAGAGCGCTCAGG
AATCTTGCCCGCCACCTGCTGTGCACTTCCTAGCG
ACTTTGTGCCCATTAAGTACCGCGAATGCCCTCCG
CCGCTTTGGGGCCACTGCTACCTTCTGCAGCTAGC
CAACTACCTTGCCTACCACTCTGACATAATGGAAG
ACGTGAGCGGTGACGGTCTACTGGAGTGTCACTGT
CGCTGCAACCTATGCACCCCGCACCGCTCCCTGGT
TTGCAATTCGCAGCTGCTTAACGAAAGTCAAATTA
TCGGTACCTTTGAGCTGCAGGGTCCCTCGCCTGAC
GAAAAGTCCGCGGCTCCGGGGTTGAAACTCACTCC
GGGGCTGTGGACGTCGGCTTACCTTCGCAAATTTG
TACCTGAGGACTACCACGCCCACGAGATTAGGTTC
TACGAAGACCAATCCCGCCCGCCAAATGCGGAGCT
TACCGCCTGCGTCATTACCCAGGGCCACATTCTTG
GCCAATTGCAAGCCATCAACAAAGCCCGCCAAGAG
TTTCTGCTACGAAAGGGACGGGGGGTTTACTTGGA
CCCCCAGTCCGGCGAGGAGCTCAACCCAATCCCCC
CGCCGCCGCAGCCCTATCAGCAGCAGCCGCGGGCC
CTTGCTTCCCAGGATGGCACCCAAAAAGAAGCTGC
AGCTGCCGCCGCCACCCACGGACGAGGAGGAATAC
TGGGACAGTCAGGCAGAGGAGGTTTTGGACGAGGA
GGAGGAGGACATGATGGAAGACTGGGAGAGCCTAG
ACGAGGAAGCTTCCGAGGTCGAAGAGGTGTCAGAC
GAAACACCGTCACCCTCGGTCGCATTCCCCTCGCC
GGCGCCCCAGAAATCGGCAACCGGTTCCAGCATGG
CTACAACCTCCGCTCCTCAGGCGCCGCCGGCACTG
CCCGTTCGCCGACCCAACCGTAGATGGGACACCAC
TGGAACCAGGGCCGGTAAGTCCAAGCAGCCGCCGC
CGTTAGCCCAAGAGCAACAACAGCGCCAAGGCTAC
CGCTCATGGCGCGGGCACAAGAACGCCATAGTTGC
TTGCTTGCAAGACTGTGGGGGCAACATCTCCTTCG
CCCGCCGCTTTCTTCTCTACCATCACGGCGTGGCC
TTCCCCCGTAACATCCTGCATTACTACCGTCATCT
CTACAGCCCATACTGCACCGGCGGCAGCGGCAGCG
GCAGCAACAGCAGCGGCCACACAGAAGCAAAGGCG
ACCGGATAGCAAGACTCTGACAAAGCCCAAGAAAT
CCACAGCGGCGGCAGCAGCAGGAGGAGGAGCGCTG
CGTCTGGCGCCCAACGAACCCGTATCGACCCGCGA
GCTTAGAAACAGGATTTTTCCCACTCTGTATGCTA
TATTTCAACAGAGCAGGGGCCAAGAACAAGAGCTG
AAAATAAAAAACAGGTCTCTGCGATCCCTCACCCG
CAGCTGCCTGTATCACAAAAGCGAAGATCAGCTTC
GGCGCACGCTGGAAGACGCGGAGGCTCTCTTCAGT
AAATACTGCGCGCTGACTCTTAAGGACTAGTTTCG
CGCCCTTTCTCAAATTTAAGCGCGAAAACTACGTC
ATCTCCAGCGGCCACACCCGGCGCCAGCACCTGTC
GTCAGCGCCATTATGAGCAAGGAAATTCCCACGCC
CTACATGTGGAGTTACCAGCCACAAATGGGACTTG
CGGCTGGAGCTGCCCAAGACTACTCAACCCGAATA
AACTACATGAGCGCGGGACCCCACATGATATCCCG
GGTCAACGGAATCCGCGCCCACCGAAACCGAATTC
TCTTGGAACAGGCGGCTATTACCACCACACCTCGT
AATAACCTTAATCCCCGTAGTTGGCCCGCTGCCCT
GGTGTACCAGGAAAGTCCCGCTCCCACCACTGTGG
TACTTCCCAGAGACGCCCAGGCCGAAGTTCAGATG
ACTAACTCAGGGGCGCAGCTTGCGGGCGGCTTTCG
TCACAGGGTGCGGTCGCCCGGGCAGGGTATAACTC
ACCTGACAATCAGAGGGCGAGGTATTCAGCTCAAC
GACGAGTCGGTGAGCTCCTCGCTTGGTCTCCGTCC
```

-continued

```
GGACGGGACATTTCAGATCGGCGGCGCCGGCCGTC
CTTCATTCACGCCTCGTCAGGCAATCCTAACTCTG
CAGACCTCGTCCTCTGAGCCGCGCTCTGGAGGCAT
TGGAACTCTGCAATTTATTGAGGAGTTTGTGCCAT
CGGTCTACTTTAACCCCTTCTCGGGACCTCCCGGC
CACTATCCGGATCAATTTATTCCTAACTTTGACGC
GGTAAAGGACTCGGCGGACGGCTACGACTGAATGT
TAAGTGGAGAGGCAGAGCAACTGCGCCTGAAACAC
CTGGTCCACTGTCGCCGCCACAAGTGCTTTGCCCG
CGACTCCGGTGAGTTTGCTACTTTGAATTGCCCG
AGGATCATATCGAGGGCCCGGCGCACGGCGTCCGG
CTTACCGCCCAGGGAGAGCTTGCCCGTAGCCTGAT
TCGGGAGTTTACCCAGCGCCCCTGCTAGTTGAGC
GGGACAGGGGACCCTGTGTTCTCACTGTGATTTGC
AACTGTCCTAACCTTGGATTACATCAAGATCTTTG
TTGCCATCTCTGTGCTGAGTATAATAAATACAGAA
ATTAAAATATACTGGGGCTCCTATCGCCATCCTGT
AAACGCCACCGTCTTCACCCGCCCAAGCAAACCAA
GGCGAACCTTACCTGGTACTTTTAACATCTCTCCC
TCTGTGATTTACAACAGTTTCAACCCAGACGGAGT
GAGTCTACGAGAGAACCTCTCCGAGCTCAGCTACT
CCATCAGAAAAAACACCACCCTCCTTACCTGCCGG
GAACGTACGAGTGCGTCACCGGCCGCTGCACCACA
CCTACCGCCTGACCGTAAACCAGACTTTTTCCGGA
CAGACCTCAATAACTCTGTTTACCAGAACAGGAGG
TGAGCTTAGAAAACCCTTAGGGTATTAGGCCAAAG
GCGCAGCTACTGTGGGGTTTATGAACAATTCAAGC
AACTCTACGGGCTATTCTAATTCAGGTTTCTCTAG
AATCGGGGTTGGGGTTATTCTCTGTCTTGTGATTC
TCTTTATTCTTATACTAACGCTTCTCTGCCTAAGG
CTCGCCGCCTGCTGTGTGCACATTTGCATTTATTG
TCAGCTTTTTAAACGCTGGGGTCGCCACCCAAGAT
GATTAGGTACATAATCCTAGGTTTACTCACCCTTG
CGTCAGCCCACGGTACCACCCAAAAGGTGGATTTT
AAGGAGCCAGCCTGTAATGTTACATTCGCAGCTGA
AGCTAATGAGTGCACCACTCTTATAAAATGCACCA
CAGAACATGAAAAGCTGCTTATTCGCACAAAAAC
AAAATTGGCAAGTATGCTGTTTATGCTATTTGGCA
GCCAGGTGACACTACAGAGTATAATGTTACAGTTT
TCCAGGGTAAAAGTCATAAAACTTTTATGTATACT
```

-continued

```
TTTCCATTTTATGAAATGTGCGACATTACCATGTA
CATGAGCAAACAGTATAAGTTGTGGCCCCCACAAA
ATTGTGTGGAAAACACTGGCACTTTCTGCTGCACT
GCTATGCTAATTACAGTGCTCGCTTTGGTCTGTAC
CCTACTCTATATTAAATACAAAAGCAGACGCAGCT
TTATTGAGGAAAAGAAAATGCCTTAATTTACTAAG
TTACAAAGCTAATGTCACCACTAACTGCTTTACTC
GCTGCTTGCAAAACAAATTCAAAAAGTTAGCATTA
TAATTAGAATAGGATTTAAACCCCCCGGTCATTTC
CTGCTCAATACCATTCCCCTGAACAATTGACTCTA
TGTGGGATATGCTCCAGCGCTACAACCTTGAAGTC
AGGCTTCCTGGATGTCAGCATCTGACTTTGGCCAG
CACCTGTCCCGCGGATTTGTTCCAGTCCAACTACA
GCGACCCACCCTAACAGAGATGACCAACACAACCA
ACGCGGCCGCCGCTACCGGACTTACATCTACCACA
AATACACCCCAAGTTTCTGCCTTTGTCAATAACTG
GGATAACTTGGGCATGTGGTGGTTCTCCATAGCGC
TTATGTTTGTATGCCTTATTATTATGTGGCTCATC
TGCTGCCTAAAGCGCAAACGCGCCCGACCACCCAT
CTATAGTCCCATCATTGTGCTACACCCAAACAATG
ATGGAATCCATAGATTGGACGGACTGAAACACATG
TTCTTTTCTCTTACAGTATGATTAAATGAGACATG
ATTCCTCGAGTTTTTATATTACTGACCCTTGTTGC
GCTTTTTTGTGCGTGCTCCACATTGGCTGCGGTTT
CTCACATCGAAGTAGACTGCATTCCAGCCTTCACA
GTCTATTTGCTTTACGGATTTGTCACCCTCACGCT
CATCTGCAGCCTCATCACTGTGGTCATCGCCTTTA
TCCAGTGCATTGACTGGGTCTGTGTGCGCTTTGCA
TATCTCAGACACCATCCCCAGTACAGGGACAGGAC
TATAGCTGAGCTTCTTAGAATTCTTTAATTATGAA
ATTTACTGTGACTTTTCTGCTGATTATTTGCACCC
TATCTGCGTTTTGTTCCCCGACCTCCAAGCCTCAA
AGACATATATCATGCAGATTCACTCGTATATGGAA
TATTCCAAGTTGCTACAATGAAAAAGCGATCTTT
CCGAAGCCTGGTTATATGCAATCATCTCTGTTATG
GTGTTCTGCAGTACCATCTTAGCCCTAGCTATATA
TCCCTACCTTGACATTGGCTGGAAACGAATAGATG
CCATGAACCACCCAACTTTCCCCGCGCCCGCTATG
CTTCCACTGCAACAAGTTGTTGCCGGCGGCTTTGT
CCCAGCCAATCAGCCTCGCCCCACTTCTCCCACCC
CCACTGAAATCAGCTACTTTAATCTAACAGGAGGA
```

-continued

```
GATGACTGACACCCTAGATCTAGAAATGGACGGAA

TTATTACAGAGCAGCGCCTGCTAGAAAGACGCAGG

GCAGCGGCCGAGCAACAGCGCATGAATCAAGAGCT

CCAAGACATGGTTAACTTGCACCAGTGCAAAAGGG

GTATCTTTTGTCTGGTAAAGCAGGCCAAAGTCACC

TACGACAGTAATACCACCGGACACCGCCTTAGCTA

CAAGTTGCCAACCAAGCGTCAGAAATTGGTGGTCA

TGGTGGGAGAAAAGCCCATTACCATAACTCAGCAC

TCGGTAGAAACCGAAGGCTGCATTCACTCACCTTG

TCAAGGACCTGAGGATCTCTGCACCCTTATTAAGA

CCCTGTGCGGTCTCAAAGATCTTATTCCCTTTAAC

TAATAAAAAAAATAATAAAGCATCACTTACTTAA

AATCAGTTAGCAAATTTCTGTCCAGTTTATTCAGC

AGCACCTCCTTGCCCTCCTCCCAGCTCTGGTATTG

CAGCTTCCTCCTGGCTGCAAACTTTCTCCACAATC

TAAATGGAATGTCAGTTTCCTCCTGTTCCTGTCCA

TCCGCACCCACTATCTTCATGTTGTTGCAGATGAA

GCGCGCAAGACCGTCTGAAGATACCTTCAACCCCG

TGTATCCATATGACACGGAAACCGGTCCTCCAACT

GTGCCTTTTCTTACTCCTCCCTTTGTATCCCCCAA

TGGGTTTCAAGAGAGTCCCCCTGGGGTACTCTCTT

TGCGCCTATCCGAACCTCTAGTTACCTCCAATGGC

ATGCTTGCGCTCAAAATGGGCAACGGCCTCTCTCT

GGACGAGGCCGGCAACCTTACCTCCCAAAATGTAA

CCACTGTGAGCCCACCTCTCAAAAAAACCAAGTCA

AACATAAACCTGGAAATATCTGCACCCCTCACAGT

TACCTCAGAAGCCCTAACTGTGGCTGCCGCCGCAC

CTCTAATGGTCGCGGGCAACACACTCACCATGCAA

TCACAGGCCCCGCTAACCGTGCACGACTCCAAACT

TAGCATTGCCACCCAAGGACCCCTCACAGTGTCAG

AAGGAAAGCTAGCCCTGCAAACATCAGGCCCCCTC

ACCACCACCGATAGCAGTACCCTTACTATCACTGC

CTCACCCCCTCTAACTACTGCCACTGGTAGCTTGG

GCATTGACTTGAAAGAGCCCATTTATACACAAAAT

GGAAAACTAGGACTAAAGTACGGGGCTCCTTTGCA

TGTAACAGACGACCTAAACACTTTGACCGTAGCAA

CTGGTCCAGGTGTGACTATTAATAATACTTCCTTG

CAAACTAAAGTTACTGGAGCCTTGGGTTTTGATTC

ACAAGGCAATATGCAACTTAATGTAGCAGGAGGAC

TAAGGATTGATTCTCAAAACAGACGCCTTATACTT
```

-continued

```
GATGTTAGTTATCCGTTTGATGCTCAAAACCAACT

AAATCTAAGACTAGGACAGGGCCCTCTTTTTATAA

ACTCAGCCCACAACTTGGATATTAACTACAACAAA

GGCCTTTACTTGTTTACAGCTTCAAACAATTCCAA

AAAGCTTGAGGTTAACCTAAGCACTGCCAAGGGGT

TGATGTTTGACGCTACAGCCATAGCCATTAATGCA

GGAGATGGGCTTGAATTTGGTTCACCTAATGCACC

AAACACAAATCCCCTCAAAACAAAAATTGGCCATG

GCCTAGAATTTGATTCAAACAAGGCTATGGTTCCT

AAACTAGGAACTGGCCTTAGTTTTGACAGCACAGG

TGCCATTACAGTAGGAAACAAAAATAATGATAAGC

TAACTTTGTGGACCACACCAGCTCCATCTCCTAAC

TGTAGACTAAATGCAGAGAAAGATGCTAAACTCAC

TTTGGTCTTAACAAAATGTGGCAGTCAAATACTTG

CTACAGTTTCAGTTTTGGCTGTTAAAGGCAGTTTG

GCTCCAATATCTGGAACAGTTCAAAGTGCTCATCT

TATTATAAGATTTGACGAAAATGGAGTGCTACTAA

ACAATTCCTTCCTGGACCCAGAATATTGGAACTTT

AGAAATGGAGATCTTACTGAAGGCACAGCCTATAC

AAACGCTGTTGGATTTATGCCTAACCTATCAGCTT

ATCCAAAATCTCACGGTAAAACTGCCAAAAGTAAC

ATTGTCAGTCAAGTTTACTTAAACGGAGACAAAAC

TAAACCTGTAACACTAACCATTACACTAAACGGTA

CACAGGAAACAGGAGACACAACTCCAAGTGCATAC

TCTATGTCATTTTCATGGGACTGGTCTGGCCACAA

CTACATTAATGAAATATTTGCCACATCCTCTTACA

CTTTTTCATACATTGCCCAAGAATAAAGAATCGTT

TGTGTTATGTTTCAACGTGTTTATTTTTCAATTGC

AGAAAATTTCAAGTCATTTTTCATTCAGTAGTATA

GCCCCACCACCACATAGCTTATACAGATCACCGTA

CCTTAATCAAACTCACAGAACCCTAGTATTCAACC

TGCCACCTCCCTCCCAACACACAGAGTACACAGTC

CTTTCTCCCCGGCTGGCCTTAAAAAGCATCATATC

ATGGGTAACAGACATATTCTTAGGTGTTATATTCC

ACACGGTTTCCTGTCGAGCCAAACGCTCATCAGTG

ATATTAATAAACTCCCCGGGCAGCTCACTTAAGTT

CATGTCGCTGTCCAGCTGCTGAGCCACAGGCTGCT

GTCCAACTTGCGGTTGCTTAACGGGCGGCGAAGGA

GAAGTCCACGCCTACATGGGGGTAGAGTCATAATC

GTGCATCAGGATAGGGCGGTGGTGCTGCAGCAGCG

CGCGAATAAACTGCTGCCGCCGCCGCTCCGTCCTG
```

CAGGAATACAACATGGCAGTGGTCTCCTCAGCGAT

GATTCGCACCGCCCGCAGCATAAGGCGCCTTGTCC

TCCGGGCACAGCAGCGCACCCTGATCTCACTTAAA

TCAGCACAGTAACTGCAGCACAGCACCACAATATT

GTTCAAAATCCCACAGTGCAAGGCGCTGTATCCAA

AGCTCATGGCGGGGACCACAGAACCCACGTGGCCA

TCATACCACAAGCGCAGGTAGATTAAGTGGCGACC

CCTCATAAACACGCTGGACATAAACATTACCTCTT

TTGGCATGTTGTAATTCACCACCTCCCGGTACCAT

ATAAACCTCTGATTAAACATGGCGCCATCCACCAC

CATCCTAAACCAGCTGGCCAAAACCTGCCCGCCGG

CTATACACTGCAGGGAACCGGGACTGGAACAATGA

CAGTGGAGAGCCCAGGACTCGTAACCATGGATCAT

CATGCTCGTCATGATATCAATGTTGGCACAACACA

GGCACACGTGCATACACTTCCTCAGGATTACAAGC

TCCTCCCGCGTTAGAACCATATCCCAGGGAACAAC

CCATTCCTGAATCAGCGTAAATCCCACACTGCAGG

GAAGACCTCGCACGTAACTCACGTTGTGCATTGTC

AAAGTGTTACATTCGGGCAGCAGCGGATGATCCTC

CAGTATGGTAGCGCGGGTTTCTGTCTCAAAAGGAG

GTAGACGATCCCTACTGTACGGAGTGCGCCGAGAC

AACCGAGATCGTGTTGGTCGTAGTGTCATGCCAAA

TGGAACGCCGGACGTAGTCATATTTCCTGAAGCAA

AACCAGGTGCGGGCGTGACAAACAGATCTGCGTCT

CCGGTCTCGCCGCTTAGATCGCTCTGTGTAGTAGT

TGTAGTATATCCACTCTCTCAAAGCATCCAGGCGC

CCCCTGGCTTCGGGTTCTATGTAAACTCCTTCATG

CGCCGCTGCCCTGATAACATCCACCACCGCAGAAT

AAGCCACACCCAGCCAACCTACACATTCGTTCTGC

GAGTCACACACGGGAGGAGCGGGAAGAGCTGGAAG

AACCATGTTTTTTTTTTATTCCAAAAGATTATCC

AAAACCTCAAAATGAAGATCTATTAAGTGAACGCG

CTCCCCTCCGGTGGCGTGGTCAAACTCTACAGCCA

AAGAACAGATAATGGCATTTGTAAGATGTTGCACA

ATGGCTTCCAAAAGGCAAACGGCCCTCACGTCCAA

GTGGACGTAAAGGCTAAACCCTTCAGGGTGAATCT

CCTCTATAAACATTCCAGCACCTTCAACCATGCCC

AAATAATTCTCATCTCGCCACCTTCTCAATATATC

TCTAAGCAAATCCCGAATATTAAGTCCGGCCATTG

TAAAAATCTGCTCCAGAGCGCCCTCCACCTTCAGC

CTCAAGCAGCGAATCATGATTGCAAAAATTCAGGT

TCCTCACAGACCTGTATAAGATTCAAAAGCGGAAC

ATTAACAAAAATACCGCGATCCCGTAGGTCCCTTC

GCAGGGCCAGCTGAACATAATCGTGCAGGTCTGCA

CGGACCAGCGCGGCCACTTCCCCGCCAGGAACCAT

GACAAAAGAACCCACACTGATTATGACACGCATAC

TCGGAGCTATGCTAACCAGCGTAGCCCCGATGTAA

GCTTGTTGCATGGGCGGCGATATAAAATGCAAGGT

GCTGCTCAAAAAATCAGGCAAAGCCTCGCGCAAAA

AAGAAAGCACATCGTAGTCATGCTCATGCAGATAA

AGGCAGGTAAGCTCCGGAACCACCACAGAAAAAGA

CACCATTTTTCTCTCAAACATGTCTGCGGGTTTCT

GCATAAACACAAAATAAAATAACAAAAAAACATTT

AAACATTAGAAGCCTGTCTTACAACAGGAAAAACA

ACCCTTATAAGCATAAGACGGACTACGGCCATGCC

GGCGTGACCGTAAAAAAACTGGTCACCGTGATTAA

AAAGCACCACCGACAGCTCCTCGGTCATGTCCGGA

GTCATAATGTAAGACTCGGTAAACACATCAGGTTG

ATTCACATCGGTCAGTGCTAAAAAGCGACCGAAAT

AGCCCGGGGGAATACATACCCGCAGGCGTAGAGAC

AACATTACAGCCCCCATAGGAGGTATAACAAAATT

AATAGGAGAGAAATACACATAAACACCTGAAAAAC

CCTCCTGCCTAGGCAAAATAGCACCCTCCCGCTCCA

GAACAACATACAGCGCTTCCACAGCGGCAGCCATA

ACAGTCAGCCTTACCAGTAAAAAAGAAAACCTATT

AAAAAAACACCACTCGACACGGCACCAGCTCAATC

AGTCACAGTGTAAAAAAGGGCCAAGTGCAGAGCGA

GTATATATAGGACTAAAAAATGACGTAACGGTTAA

AGTCCACAAAAAACACCCAGAAAACCGCACGCGAA

CCTACGCCCAGAAACGAAAGCCAAAAAACCCACAA

CTTCCTCAAATCGTCACTTCCGTTTTCCCACGTTA

CGTAACTTCCCATTTTAAGAAAACTACAATTCCCA

ACACATACAAGTTACTCCGCCCTAAAACCTACGTC

ACCCGCCCCGTTCCCACGCCCCGCGCCACGTCACA

AACTCCACCCCCTCATTATCATATTGGCTTCAATC

CAAAATAAGGTATATTATTGATGATG

Human Adenovirus 35, Complete Genome
NCIB Reference Sequence: AC_000019.1 see SEQ ID NO: 41.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

The invention claimed is:

1. A recombinant adenovirus comprising a nucleotide sequence inserted in an IX-E2 insertion site, wherein the IX-E2 insertion site is located between the stop codon of adenovirus IX gene and the stop codon of adenovirus IVa2 gene, wherein the nucleotide sequence comprises a promoter, a transgene, and a second polyadenylation signal and the recombinant adenovirus comprises in a 5' to 3' orientation:
   (i) a first polyadenylation signal;
   (ii) a fourth polyadenylation signal;
   (iii) the promoter;
   (iv) the transgene;
   (v) the second polyadenylation signal; and
   (vi) a third polyadenylation signal;
   wherein the transgene is operably linked to the promoter,
   wherein the second polyadenylation signal is the polyadenylation signal of the transgene, and
   wherein the fourth polyadenylation signal is in the opposite transcriptional direction of the first polyadenylation signal.

2. The recombinant adenovirus of claim 1, wherein the nucleotide sequence is inserted between nucleotides corresponding to 4029 and 4093 of the Ad5 genome (SEQ ID NO: 1) or between nucleotides corresponding to 3899 and 3970 of the Ad35 genome (SEQ ID NO: 41).

3. The recombinant adenovirus of claim 1, wherein the first polyadenylation signal comprises the polyadenylation signal of the IX gene and the third polyadenylation signal is the polyadenylation signal of the adenovirus IVa2 gene.

4. The recombinant adenovirus of claim 1, wherein the recombinant adenovirus further comprises a nucleotide sequence inserted in an E1b-19K insertion site, an E3 insertion site, or an E4 insertion site.

5. The recombinant adenovirus of claim 1, wherein the recombinant adenovirus further comprises a nucleotide sequence inserted in an L5-E4 insertion site, wherein the L5-E4 insertion site is located between the stop codon of adenovirus fiber gene and the stop codon of ORF6 or ORF6/7 of adenovirus E4 gene.

6. The recombinant adenovirus of claim 1, wherein the recombinant adenovirus is capable of selectively replicating in a hyperproliferative cell.

7. The recombinant adenovirus of claim 3, wherein the recombinant adenovirus is capable of selectively expressing the transgene in a hyperproliferative cell.

8. A recombinant adenovirus comprising a first nucleotide sequence inserted in an IX-E2 insertion site and a second nucleotide sequence inserted in an L5-E4 insertion site, wherein the IX-E2 insertion site is located between the stop codon of adenovirus IX gene and the stop codon of adenovirus IVa2 gene, and wherein the L5-E4 insertion site is located between the stop codon of adenovirus fiber gene and the stop codon of ORF6 or ORF6/7 of adenovirus E4 gene, wherein the first nucleotide sequence comprises a first promoter, a first transgene, and a third polyadenylation signal and the recombinant adenovirus comprises in a 5' to 3' orientation:
   (i) a first polyadenylation signal;
   (ii) a fourth polyadenylation signal;
   (iii) the first promoter;
   (iv) the first transgene;
   (v) the second polyadenylation signal; and
   (vi) a third polyadenylation signal;
   wherein the first transgene is operably linked to the first promoter,
   wherein the second polyadenylation signal is the polyadenylation signal of the first transgene, and wherein the fourth polyadenylation signal is in the opposite transcriptional direction of the first polyadenylation signal.

9. The recombinant adenovirus of claim 8, wherein the first nucleotide sequence is inserted between nucleotides corresponding to 4029 and 4093 of the Ad5 genome (SEQ ID NO: 1) or between nucleotides corresponding to 3899 and 3970 of the Ad35 genome (SEQ ID NO: 41).

10. The recombinant adenovirus of claim 8, wherein the second nucleotide sequence is inserted between nucleotides corresponding to 32785 to 32916 of the Ad5 genome (SEQ ID NO: 1) or between nucleotides corresponding to 31799 and 31821 of the Ad35 genome (SEQ ID NO: 41).

11. The recombinant adenovirus of claim 8, wherein the first polyadenylation signal is the polyadenylation signal of the IX gene and the third polyadenylation signal is the polyadenylation signal of the adenovirus IVa2 gene.

12. The recombinant adenovirus of claim 8, wherein the second nucleotide sequence comprises a second promoter, a second transgene, and a sixth polyadenylation signal and the recombinant adenovirus comprises, in a 5' to 3' orientation:
 (i) a fifth polyadenylation signal;
 (ii) the second promoter;
 (iii) the second transgene;
 (iv) the sixth polyadenylation signal; and
 (v) a seventh polyadenylation signal;

wherein the second transgene is operably linked to the second promoter, and wherein the sixth polyadenylation signal is the polyadenylation signal of the second transgene.

13. The recombinant adenovirus of claim 12, wherein the fifth polyadenylation signal is the polyadenylation signal of the fiber (L5) gene and the seventh polyadenylation signal is the polyadenylation signal of the ORF6 or ORF6/7 of the adenovirus E4 gene.

14. The recombinant adenovirus of claim 12, further comprising an eighth polyadenylation signal between the fifth polyadenylation signal and the second promoter, wherein the eighth polyadenylation signal is in the opposite transcriptional direction of the fifth polyadenylation signal.

15. The recombinant adenovirus of claim 8, wherein the recombinant adenovirus further comprises a third nucleotide sequence inserted in an E1b-19K insertion site, an E3 insertion site, or an E4 insertion site.

16. The recombinant adenovirus of claim 8, wherein the recombinant adenovirus is capable of selectively replicating in a hyperproliferative cell.

17. The recombinant adenovirus of claim 12, wherein the recombinant adenovirus is capable of selectively expressing the first transgene and the second transgene in a hyperproliferative cell.

* * * * *

```
                              SEQUENCE LISTING

<160> NUMBER OF SEQ ID NOS: 46

<210> SEQ ID NO 1
<211> LENGTH: 35938
<212> TYPE: DNA
<213> ORGANISM: Human adenovirus 5

<400> SEQUENCE: 1
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttttg    180 gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tatttgtcta gggccgcggg     360
gactttgacc gtttacgtgg agactcgccc aggtgttttt ctcaggtgtt ttccgcgttc     420
cgggtcaaag ttggcgtttt attattatag tcagctgacg tgtagtgtat ttatacccgg     480
tgagttcctc aagaggccac tcttgagtgc cagcgagtag agttttctcc tccgagccgc     540
tccgacaccg ggactgaaaa tgagacatat tatctgccac ggaggtgtta ttaccgaaga     600
aatggccgcc agtcttttgg accagctgat cgaagaggta ctggctgata atcttccacc     660
tcctagccat tttgaaccac ctaccttca cgaactgtat gatttagacg tgacggcccc     720
cgaagatccc aacgaggagg cggtttcgca gatttttccc gactctgtaa tgttggcggt     780
gcaggaaggg attgacttac tcactttcc gccggcgccc ggttctccgg agccgcctca     840
cctttcccgg cagcccgagc agccggagca gagagccttg ggtccggttt ctatgccaaa     900
ccttgtaccg gaggtgatcg atcttacctg ccacgaggct ggctttccac ccagtgacga     960
cgaggatgaa gagggtgagg agtttgtgtt agattatgtg gagcaccccg ggcacggttg    1020
caggtcttgt cattatcacc ggaggaatac gggggaccca gatattatgt gttcgctttg    1080
ctatatgagg acctgtggca tgtttgtcta cagtaagtga aaattatggg cagtgggtga    1140
tagagtggtg ggtttggtgt ggtaattttt tttttaattt ttacagtttt gtggtttaaa    1200
gaattttgta ttgtgatttt tttaaaaggt cctgtgtctg aacctgagcc tgagcccgag    1260
ccagaaccgg agcctgcaag acctacccgc cgtcctaaaa tggcgcctgc tatcctgaga    1320
cgcccgacat cacctgtgtc tagagaatgc aatagtagta cggatagctg tgactccggt    1380
ccttctaaca cacctcctga gatacacccg gtggtcccgc tgtgccccat taaaccagtt    1440
gccgtgagag ttggtgggcg tcgccaggct gtggaatgta tcgaggactt gcttaacgag    1500
cctgggcaac ctttggactt gagctgtaaa cgccccaggc cataaggtgt aaacctgtga    1560
ttgcgtgtgt ggttaacgcc tttgtttgct gaatgagttg atgtaagttt aataaagggt    1620
gagataatgt ttaacttgca tggcgtgtta aatggggcgg ggcttaaagg gtatataatg    1680
cgccgtgggc taatcttggt tacatctgac ctcatggagg cttgggagtg tttggaagat    1740
ttttctgctg tgcgtaactt gctggaacag agctctaaca gtacctcttg gttttggagg    1800
tttctgtggg gctcatccca ggcaaagtta gtctgcagaa ttaaggagga ttacaagtgg    1860
gaatttgaag agcttttgaa atcctgtggt gagctgtttg attctttgaa tctgggtcac    1920
```

```
caggcgcttt tccaagagaa ggtcatcaag actttggatt tttccacacc ggggcgcgct    1980
gcggctgctg ttgcttttt gagttttata aaggataaat ggagcgaaga aacccatctg    2040 agcgggggt acctgctgga ttttctggcc atgcatctgt ggagagcggt tgtgagacac    2100
aagaatcgcc tgctactgtt gtcttccgtc cgcccggcga taataccgac ggaggagcag    2160
cagcagcagc aggaggaagc caggcggcgg cggcaggagc agagcccatg gaacccgaga    2220
gccggcctgg accctcggga atgaatgttg tacaggtggc tgaactgtat ccagaactga    2280
gacgcatttt gacaattaca gaggatgggc aggggctaaa gggggtaaag agggagcggg    2340
gggcttgtga ggctacagag gaggctagga atctagcttt tagcttaatg accagacacc    2400
gtcctgagtg tattactttt caacagatca aggataattg cgctaatgag cttgatctgc    2460
tggcgcagaa gtattccata gagcagctga ccacttactg gctgcagcca ggggatgatt    2520
ttgaggaggc tattagggta tatgcaaagg tggcacttag gccagattgc aagtacaaga    2580
tcagcaaact tgtaaatatc aggaattgtt gctacattc tgggaacggg gccgaggtgg    2640
agatagatac ggaggatagg gtggccttta gatgtagcat gataaatatg tggccggggg    2700
tgcttggcat ggacggggtg gttattatga atgtaaggtt tactggcccc aattttagcg    2760
gtacggtttt cctggccaat accaacctta tcctacacgg tgtaagcttc tatgggttta    2820
acaatacctg tgtggaagcc tggaccgatg taagggttcg gggctgtgcc ttttactgct    2880
gctggaaggg ggtggtgtgt cgccccaaaa gcagggcttc aattaagaaa tgcctctttg    2940
aaaggtgtac cttgggtatc ctgtctgagg gtaactccag ggtgcgccac aatgtggcct    3000
ccgactgtgg ttgcttcatg ctagtgaaaa gcgtggctgt gattaagcat aacatggtat    3060
gtggcaactg cgaggacagg gcctctcaga tgctgacctg ctcggacggc aactgtcacc    3120
tgctgaagac cattcacgta gccagccact ctcgcaaggc ctggcagtg tttgagcata    3180 acatactgac ccgctgttcc ttgcatttgg gtaacaggag ggggtgttc ctaccttacc    3240 aatgcaattt gagtcacact aagatattgc ttgagcccga gagcatgtcc aaggtgaacc    3300
tgaacggggt gttgacatg accatgaaga tctggaaggt gctgaggtac gatgagaccc    3360
gcaccaggtg cagaccctgc gagtgtggcg gtaaacatat taggaaccag cctgtgatgc    3420
tggatgtgac cgaggagctg aggcccgatc acttggtgct ggcctgcacc cgcgctgagt    3480
ttggctctag cgatgaagat acagattgag gtactgaaat gtgtgggcgt ggcttaaggg    3540
tgggaaagaa tatataaggt gggggtctta tgtagttttg tatctgtttt gcagcagccg    3600
ccgccgccat gagcaccaac tcgtttgatg gaagcattgt gagctcatat ttgacaacgc    3660
gcatgccccc atgggccggg gtgcgtcaga atgtgatggg ctccagcatt gatggtcgcc    3720
ccgtcctgcc cgcaaactct actaccttga cctacgagac cgtgtctgga acgccgttgg    3780
agactgcagc ctccgccgcc gcttcagccg ctgcagccac cgcccgcggg attgtgactg    3840
actttgcttt cctgagcccg cttgcaagca gtgcagcttc ccgttcatcc gcccgcgatg    3900
acaagttgac ggctcttttg gcacaattgg attctttgac ccgggaactt aatgtcgttt    3960
ctcagcagct gttggatctg cgccagcagg tttctgccct gaaggcttcc tcccctccca    4020
atgcggttta aacataaat aaaaaaccag actctgtttg gatttggatc aagcaagtgt    4080
cttgctgtct ttatttaggg gttttgcgcg cgcggtaggc ccgggaccag cggtctcggt    4140
cgttgagggt cctgtgtatt ttttccagga cgtggtaaag gtgactctgg atgttcagat    4200
acatgggcat aagcccgtct ctggggtgga ggtagcacca ctgcagagct tcatgctgcg    4260
gggtggtgtt gtagatgatc cagtcgtagc aggagcgctg ggcgtggtgc ctaaaaatgt    4320
```

```
ctttcagtag caagctgatt gccaggggca ggcccttggt gtaagtgttt acaaagcggt    4380
taagctggga tgggtgcata cgtggggata tgagatgcat cttggactgt attttaggt    4440 tggctatgtt cccagccata tccctccggg gattcatgtt gtgcagaacc accagcacag    4500
tgtatccggt gcacttggga aatttgtcat gtagcttaga aggaaatgcg tggaagaact    4560
tggagacgcc cttgtgacct ccaagatttt ccatgcattc gtccataatg atggcaatgg    4620
gcccacgggc ggcggcctgg gcgaagatat ttctgggatc actaacgtca tagttgtgtt    4680
ccaggatgag atcgtcatag gccatttta caaagcgcgg gcggagggtg ccagactgcg    4740
gtataatggt tccatccggc ccaggggcgt agttaccctc acagatttgc atttcccacg    4800
ctttgagttc agatgggggg atcatgtcta cctgcggggc gatgaagaaa acggtttccg    4860
gggtagggga gatcagctgg gaagaaagca ggttcctgag cagctgcgac ttaccgcagc    4920
cggtgggccc gtaaatcaca cctattaccg ggtgcaactg gtagttaaga gagctgcagc    4980
tgccgtcatc cctgagcagg ggggccactt cgttaagcat gtccctgact cgcatgtttt    5040
ccctgaccaa atccgccaga aggcgctcgc cgcccagcga tagcagttct gcaaggaag    5100 caaagttttt caacggtttg agaccgtccg ccgtaggcat gcttttgagc gtttgaccaa    5160
gcagttccag gcggtcccac agctcggtca cctgctctac ggcatctcga tccagcatat    5220
ctcctcgttt cgcggggttgg ggcggctttc gctgtacggc agtagtcggt gctcgtccag    5280
acgggccagg gtcatgtctt ccacggggcg cagggtcctc gtcagcgtag tctgggtcac    5340
ggtgaagggg tgcgctccgg gctgcgcgct ggccagggtg cgcttgaggc tggtcctgct    5400
ggtgctgaag cgctgccggt cttcgccctg cgcgtcggcc aggtagcatt tgaccatggt    5460
gtcatagtcc agccctccg cggcgtggcc cttggcgcgc agcttgccct tggaggaggc    5520
gccgcacgag gggcagtgca gacttttgag ggcgtagagc ttgggcgcga gaaataccga    5580
ttccggggag taggcatccg cgccgcaggc cccgcagacg gtctcgcatt ccacgagcca    5640
ggtgagctct ggccgttcgg ggtcaaaaac caggtttccc ccatgctttt tgatgcgttt    5700
cttacctctg gtttccatga gccggtgtcc acgctcggtg acgaaaaggc tgtccgtgtc    5760
cccgtataca gacttgagag gcctgtcctc gagcggtgtt ccgcggtcct cctcgtatag    5820
aaactcggac cactctgaga caaaggctcg cgtccaggcc agcacgaagg aggctaagtg    5880
ggaggggtag cggtcgttgt ccactagggg gtccactcgc tccagggtgt gaagacacat    5940
gtcgccctct tcggcatcaa ggaaggtgat tggtttgtag gtgtaggcca cgtgaccggg    6000
tgttcctgaa gggggctat aaaaggggt gggggcgcgt tcgtcctcac tctcttccgc    6060
atcgctgtct gcgagggcca gctgttgggg tgagtactcc ctctgaaaag cgggcatgac    6120
ttctgcgcta agattgtcag tttccaaaaa cgaggaggat tgatattca cctggcccgc    6180 ggtgatgcct ttgagggtgg ccgcatccat ctggtcagaa agacaatct ttttgttgtc    6240 aagcttggtg gcaaacgacc cgtagagggc gttgacagc aacttggcga tggagcgcag    6300
ggtttggttt ttgtcgcgat cggcgcgctc cttggccgcg atgtttagct gcacgtattc    6360
gcgcgcaacg caccgccatt cgggaaagac ggtggtgcgc tcgtcgggca ccaggtgcac    6420
gcgccaaccg cggttgtgca gggtgacaag gtcaacgctg gtggctacct ctccgcgtag    6480
gcgctcgttg gtccagcaga ggcggccgcc cttgcgcgag cagaatggcg taggggtc    6540 tagctgcgtc tcgtccgggg ggtctgcgtc cacggtaaag accccgggca gcaggcgcgc    6600
gtcgaagtag tctatcttgc atccttgcaa gtctagcgcc tgctgccatg cgcgggcggc    6660
```

```
aagcgcgcgc tcgtatgggt tgagtggggg accccatggc atggggtggg tgagcgcgga      6720
ggcgtacatg ccgcaaatgt cgtaaacgta gaggggctct ctgagtattc caagatatgt      6780
agggtagcat cttccaccgc ggatgctggc gcgcacgtaa tcgtatagtt cgtgcgaggg      6840
agcgaggagg tcgggaccga ggttgctacg ggcgggctgc tctgctcgga agactatctg      6900
cctgaagatg gcatgtgagt tggatgatat ggttggacgc tggaagacgt tgaagctggc      6960
gtctgtgaga cctaccgcgt cacgcacgaa ggaggcgtag gagtcgcgca gcttgttgac      7020
cagctcggcg gtgacctgca cgtctagggc gcagtagtcc agggtttcct tgatgatgtc      7080
atacttatcc tgtcccttttt ttttccacag ctcgcggttg aggacaaact cttcgcggtc      7140
tttccagtac tcttggatcg gaaacccgtc ggcctccgaa cggtaagagc ctagcatgta      7200
gaactggttg acggcctggt aggcgcagca tcccttttct acgggtagcg cgtatgcctg      7260
cgcggccttc cggagcgagg tgtgggtgag cgcaaaggtg tccctgacca tgactttgag      7320
gtactggtat ttgaagtcag tgtcgtcgca tccgccctgc tcccagagca aaaagtccgt      7380
gcgcttttg gaacgcggat ttggcagggc gaaggtgaca tcgttgaaga gtatctttcc      7440
cgcgcgaggc ataaagttgc gtgtgatgcg gaagggtccc ggcacctcgg aacggttgtt      7500
aattacctgg gcggcgagca cgatctcgtc aaagccgttg atgttgtggc ccacaatgta      7560
aagttccaag aagcgcggga tgcccttgat ggaaggcaat tttttaagtt cctcgtaggt      7620
gagctcttca ggggagctga gcccgtgctc tgaaagggcc cagtctgcaa gatgagggtt      7680
ggaagcgacg aatgagctcc acaggtcacg ggccattagc atttgcaggt ggtcgcgaaa      7740
ggtcctaaac tggcgaccta tggccatttt tctggggtg atgcagtaga aggtaagcgg       7800
gtcttgttcc cagcggtccc atccaaggtt cgcggctagg tctcgcgcgg cagtcactag      7860
aggctcatct ccgccgaact tcatgaccag catgaagggc acgagctgct tcccaaaggc      7920
ccccatccaa gtataggtct ctacatcgta ggtgacaaag agacgctcgg tgcgaggatg      7980
cgagccgatc gggaagaact ggatctcccg ccaccaattg gaggagtggc tattgatgtg      8040
gtgaaagtag aagtccctgc gacgggccga acactcgtgc tggcttttgt aaaaacgtgc      8100
gcagtactgg cagcggtgca cgggctgtac atcctgcacg aggttgacct gacgaccgcg      8160
cacaaggaag cagagtggga atttgagccc ctcgcctggc gggtttggct ggtggtcttc      8220
tacttcggct gcttgtcctt gaccgtctgg ctgctcgagg ggagttacgg tggatcggac      8280
caccacgccg cgcgagccca agtccagat gtccgcgcgc ggcggtcgga gcttgatgac       8340
aacatcgcgc agatgggagc tgtccatggt ctggagctcc cgcggcgtca ggtcaggcgg      8400
gagctcctgc aggtttacct cgcatagacg ggtcagggcg cgggctagat ccaggtgata      8460
cctaatttcc aggggctggt tggtggcggc gtcgatggct tgcaagaggc cgcatccccg      8520
cggcgcgact acggtaccgc gcggcgggcg gtgggccgcg ggggtgtcct tggatgatgc      8580
atctaaaagc ggtgacgcgg gcgagccccc ggaggtaggg ggggctccgg acccgccggg      8640
agaggggggca ggggcacgtc ggcgccgcgc gcggcagga gctggtgctg cgcgcgtagg       8700
ttgctggcga acgcgacgac gcggcggttg atctcctgaa tctggcgcct ctgcgtgaag      8760
acgacgggcc cggtgagctt gagcctgaaa gagagttcga cagaatcaat ttcggtgtcg      8820
ttgacggcgg cctggcgcaa atctcctgc acgtctcctg agttgtcttg ataggcgatc       8880
tcggccatga actgctcgat ctcttcctcc tggagatctc cgcgtccggc tcgctccacg      8940
gtggcggcga ggtcgttgga aatgcgggcc atgagctgcg agaaggcgtt gaggcctccc      9000
tcgttccaga cgcggctgta gaccacgccc ccttcggcat cgcgggcgcg catgaccacc      9060
```

```
tgcgcgagat tgagctccac gtgccgggcg aagacggcgt agtttcgcag gcgctgaaag    9120
aggtagttga gggtggtggc ggtgtgttct gccacgaaga agtacataac ccagcgtcgc    9180
aacgtggatt cgttgatatc ccccaaggcc tcaaggcgct ccatggcctc gtagaagtcc    9240
acggcgaagt tgaaaaactg ggagttgcgc gccgacacgg ttaactcctc ctccagaaga    9300
cggatgagct cggcgacagt gtcgcgcacc tcgcgctcaa aggctacagg ggcctcttct    9360
tcttcttcaa tctcctcttc cataaggccc tccccttctt cttcttctgg cggcggtggg    9420
ggagggggga cacggcggcg acgacggcgc accgggaggc ggtcgacaaa gcgctcgatc    9480
atctccccgc ggcgacggcg catggtctcg gtgacggcgc ggccgttctc gcgggggcgc    9540
agttggaaga cgccgcccgt catgtcccgg ttatgggttg gcgggggggct gccatgcggc    9600 agggatacgg cgctaacgat gcatctcaac aattgttgtg taggtactcc gccgccgagg    9660
gacctgagcg agtccgcatc gaccggatcg gaaaacctct cgagaaaggc gtctaaccag    9720
tcacagtcgc aaggtaggct gagcaccgtg gcgggcggca gcgggcggcg gtcggggttg    9780
tttctggcgg aggtgctgct gatgatgtaa ttaaagtagg cggtcttgag acggcggatg    9840
gtcgacagaa gcaccatgtc cttgggtccg gcctgctgaa tgcgcaggcg gtcggccatg    9900
ccccaggctt cgttttgaca tcggcgcagg tctttgtagt agtcttgcat gagcctttct    9960
accggcactt cttcttctcc ttcctcttgt cctgcatctc ttgcatctat cgctgcggcg   10020
gcggcggagt ttggccgtag gtggcgccct cttcctccca tgcgtgtgac cccgaagccc   10080
ctcatcggct gaagcagggc taggtcggcg acaacgcgct cggctaatat ggcctgctgc   10140
acctgcgtga gggtagactg gaagtcatcc atgtccacaa agcggtggta tgcgcccgtg   10200
ttgatggtgt aagtgcagtt ggccataacg gaccagttaa cggtctggtg acccggctgc   10260
gagagctcgg tgtacctgag acgcgagtaa gccctcgagt caaatacgta gtcgttgcaa   10320
gtccgcacca ggtactggta tcccaccaaa aagtgcggcg gcggctggcg gtagaggggc   10380
cagcgtaggg tggccggggc tccggggggcg agatcttcca acataaggcg atgatatccg   10440
tagatgtacc tggacatcca ggtgatgccg gcggcggtgg tggaggcgcg cggaaagtcg   10500
cggacgcggt tccagatgtt gcgcagcggc aaaaagtgct ccatggtcgg gacgctctgg   10560
ccggtcaggc gcgcgcaatc gttgacgctc tagaccgtgc aaaaggagag cctgtaagcg   10620
ggcactcttc cgtggtctgg tggataaatt cgcaagggta tcatggcgga cgaccggggt   10680
tcgagccccg tatccggccg tccgccgtga tccatgcggt taccgcccgc gtgtcgaacc   10740
caggtgtgcg acgtcagaca acgggggagt gctccttttg gcttccttcc aggcgcggcg   10800
gctgctgcgc tagcttttt ggccactggc cgcgcgcagc gtaagcggtt aggctggaaa   10860
gcgaaagcat taagtggctc gctccctgta gccggaggggt tattttccaa gggttgagtc   10920
gcgggacccc cggttcgagt ctcggaccgg ccggactgcg gcgaacgggg gtttgcctcc   10980
ccgtcatgca agacccgcct tgcaaattcc tccggaaaca gggacgagcc cctttttttgc   11040 ttttcccaga tgcatccggt gctgcggcag atgcgccccc ctcctcagca gcggcaagag   11100
caagagcagc ggcagacatg cagggcaccc tcccctcctc ctaccgcgtc aggaggggcg   11160
acatccgcgt tgacgcggc agcagatggt gattacgaac ccccgcggcg ccgggcccgg   11220
cactacctgg acttggagga gggcgagggc ctggcgcggc taggagcgcc ctctcctgag   11280
cggtacccaa gggtgcagct gaagcgtgat acgcgtgagg cgtacgtgcc gcggcagaac   11340
ctgtttcgcg accgcgaggg agaggagccc gaggagatgc gggatcgaaa gttccacgca   11400
```

```
gggcgcgagc tgcggcatgg cctgaatcgc gagcggttgc tgcgcgagga ggactttgag   11460
cccgacgcgc gaaccgggat tagtcccgcg cgcgcacacg tggcggccgc cgacctggta   11520
accgcatacg agcagacggt gaaccaggag attaactttc aaaaaagctt taacaaccac   11580
gtgcgtacgc ttgtggcgcg cgaggaggtg gctataggac tgatgcatct gtgggacttt   11640
gtaagcgcgc tggagcaaaa cccaaatagc aagccgctca tggcgcagct gttccttata   11700
gtgcagcaca gcagggacaa cgaggcattc agggatgcgc tgctaaacat agtagagccc   11760
gagggccgct ggctgctcga tttgataaac atcctgcaga gcatagtggt gcaggagcgc   11820
agcttgagcc tggctgacaa ggtggccgcc atcaactatt ccatgcttag cctgggcaag   11880
ttttacgccc gcaagatata ccatacccct tacgttccca tagacaagga ggtaaagatc   11940
gaggggttct acatgcgcat ggcgctgaag gtgcttacct tgagcgacga cctgggcgtt   12000
tatcgcaacg agcgcatcca caaggccgtg agcgtgagcc ggcggcgcga gctcagcgac   12060
cgcgagctga tgcacagcct gcaaagggcc ctggctggca cgggcagcgg cgatagagag   12120
gccgagtcct actttgacgc gggcgctgac ctgcgctggg cccaagccg acgcgccctg   12180 gaggcagctg gggccggacc tgggctggcg gtggcacccg cgcgcgctgg caacgtcggc   12240
ggcgtggagg aatatgacga ggacgatgag tacgagccag aggacggcga gtactaagcg   12300
gtgatgtttc tgatcagatg atgcaagacg caacggaccc ggcggtgcgg gcggcgctgc   12360
agagccagcc gtccggcctt aactccacgc acgactggcg ccaggtcatg gaccgcatca   12420
tgtcgctgac tgcgcgcaat cctgacgcgt tccggcagca gccgcaggcc aaccggctct   12480
ccgcaattct ggaagcggtg gtcccggcgc gcgcaaaccc cacgcacgag aaggtgctgg   12540
cgatcgtaaa cgcgctggcc gaaaacaggg ccatccggcc cgacgaggcc ggcctggtct   12600
acgacgcgct gcttcagcgc gtggctcgtt acaacagcgg caacgtgcag accaacctgg   12660
accggctggt ggggatgtg cgcgaggccg tggcgcagcg tgagcgcgcg cagcagcagg   12720
gcaacctggg ctccatggtt gcactaaacg ccttcctgag tacacagccc gccaacgtgc   12780
cgcggggaca ggaggactac accaactttg tgagcgcact gcggctaatg gtgactgaga   12840
caccgcaaag tgaggtgtac cagtctgggc cagactattt tttccagacc agtagacaag   12900
gcctgcagac cgtaaacctg agccaggctt tcaaaaactt gcaggggctg tggggggtgc   12960
gggctcccac aggcgaccgc gcgaccgtgt ctagcttgct gacgcccaac tcgcgcctgt   13020
tgctgctgct aatagcgccc ttcacggaca gtggcagcgt gtcccgggac acatacctag   13080
gtcacttgct gacactgtac cgcgaggcca taggtcaggc gcatgtggac gagcatactt   13140
tccaggagat tacaagtgtc agccgcgcgc tggggcagga ggacacgggc agcctggagg   13200
caaccctaaa ctacctgctg accaaccggc ggcagaagat cccctcgttg cacagtttaa   13260
acagcgagga ggagcgcatt ttgcgctacg tgcagcagag cgtgagcctt aacctgatgc   13320
gcgacggggc aacgcccagc gtggcgctgg acatgaccgc gcgcaacatg gaaccgggca   13380
tgtatgcctc aaaccggccg tttatcaacc gcctaatgga ctacttgcat cgcgcggccg   13440
ccgtgaaccc cgagtatttc accaatgcca tcttgaaccc gcactggcta ccgccccctg   13500
gtttctacac cggggattc gaggtgcccg agggtaacga tggattcctc tgggacgaca   13560
tagacgacag cgtgttttcc ccgcaaccgc agaccctgct agagttgcaa cagcgcgagc   13620
aggcagaggc ggcgctgcga aaggaaagct tccgcaggcc aagcagcttg tccgatctag   13680
gcgctgcggg cccgcggtca gatgctagta gcccatttcc aagcttgata gggtctctta   13740
ccagcactcg caccacccgc ccgcgcctgc tgggcgagga ggagtaccta aacaactcgc   13800
```

```
tgctgcagcc gcagcgcgaa aaaaacctgc ctccggcatt tcccaacaac gggatagaga   13860
gcctagtgga caagatgagt agatggaaga cgtacgcgca ggagcacagg gacgtgccag   13920
gcccgcgccc gcccacccgt cgtcaaaggc acgaccgtca gcggggtctg gtgtgggagg   13980
acgatgactc ggcagacgac agcagcgtcc tggatttggg agggagtggc aacccgtttg   14040
cgcaccttcg ccccaggctg gggagaatgt tttaaaaaaa aaaaagcatg atgcaaaata   14100
aaaaactcac caaggccatg gcaccgagcg ttggttttct tgtattcccc ttagtatgcg   14160
gcgcgcggcg atgtatgagg aaggtcctcc tccctcctac gagagtgtgg tgagcgcggc   14220
gccagtggcg gcgcgctgg gttctcccctt cgatgctccc ctggacccgc cgtttgtgcc   14280
tccgcggtac ctgcggccta ccggggggag aaacagcatc cgttactctg agttggcacc   14340
cctattcgac accacccgtg tgtacctggt ggacaacaag tcaacggatg tggcatccct   14400
gaactaccag aacgaccaca gcaactttct gaccacggtc attcaaaaca atgactacag   14460
cccgggggag gcaagcacac agaccatcaa tcttgacgac cggtcgcact ggggcggcga   14520
cctgaaaacc atcctgcata ccaacatgcc aaatgtgaac gagttcatgt ttaccaataa   14580
gtttaaggcg cgggtgatgg tgtcgcgctt gcctactaag gacaatcagg tggagctgaa   14640
atacgagtgg gtggagttca cgctgcccga gggcaactac tccgagacca tgaccataga   14700
ccttatgaac aacgcgatcg tggagcacta cttgaaagtg ggcagacaga acggggttct   14760
ggaaagcgac atcggggtaa agtttgacac ccgcaacttc agactgggggt ttgaccccgt   14820 cactggtctt gtcatgcctg gggtatatac aaacgaagcc ttccatccag acatcatttt   14880
gctgccagga tgcggggtgg acttcaccca cagccgcctg agcaacttgt tgggcatccg   14940
caagcggcaa cccttccagg agggctttag gatcacctac gatgatctgg agggtggtaa   15000
cattcccgca ctgttggatg tggacgccta ccaggcgagc ttgaaagatg acaccgaaca   15060
gggcgggggt ggcgcaggcg gcagcaacag cagtggcagc ggcgcggaag agaactccaa   15120
cgcggcagcc gcggcaatgc agccggtgga ggacatgaac gatcatgcca ttcgcggcga   15180
cacctttgcc acacgggctg aggagaagcg cgctgaggcc gaagcagcgg ccgaagctgc   15240
cgcccccgct gcgcaacccg aggtcgagaa gcctcagaag aaaccggtga tcaaacccct   15300
gacagaggac agcaagaaac gcagttacaa cctaataagc aatgacagca ccttcaccca   15360
gtaccgcagc tggtaccttg catacaacta cggcgaccct cagaccggaa tccgctcatg   15420
gaccctgctt tgcactcctg acgtaacctg cggctcggag caggtctact ggtcgttgcc   15480
agacatgatg caagaccccg tgaccttccg ctccacgcgc cagatcagca ctttccggt   15540 ggtgggcgcc gagctgttgc ccgtgcactc caagagcttc tacaacgacc aggccgtcta   15600
ctcccaactc atccgccagt ttacctctct gacccacgtg ttcaatcgct ttcccgagaa   15660 ccagatttg gcgcgcccgc cagcccccac catcaccacc gtcagtgaaa acgttcctgc   15720
tctcacagat cacgggacgc taccgctgcg caacagcatc ggaggagtcc agcgagtgac   15780
cattactgac gccagacgcc gcacctgccc ctacgtttac aaggccctgg gcatagtctc   15840
gccgcgcgtc ctatcgagcc gcactttttg agcaagcatg tccatcctta tatcgcccag   15900
caataacaca ggctggggcc tgcgcttccc aagcaagatg tttggcgggg ccaagaagcg   15960
ctccgaccaa cacccagtgc gcgtgcgcgg gcactaccgc gcgccctggg gcgcgcacaa   16020
acgcggccgc actgggcgca ccaccgtcga tgacgccatc gacgcggtgg tggaggaggc   16080
gcgcaactac acgcccacgc cgccaccagt gtccacagtg gacgcggcca ttcagaccgt   16140
```

```
ggtgcgcgga gcccggcgct atgctaaaat gaagagacgg cggaggcgcg tagcacgtcg    16200
ccaccgccgc cgaccggca ctgccgccca acgcgcggcg gcggccctgc ttaaccgcgc     16260
acgtcgcacc ggccgacggg cggccatgcg ggccgctcga aggctggccg cgggtattgt    16320
cactgtgccc cccaggtcca ggcgacgagc ggccgccgca gcagccgcgg ccattagtgc    16380
tatgactcag ggtcgcaggg gcaacgtgta ttgggtgcgc gactcggtta gcggcctgcg    16440
cgtgcccgtg cgcacccgcc ccccgcgcaa ctagattgca agaaaaaact acttagactc    16500
gtactgttgt atgtatccag cggcggcggc gcgcaacgaa gctatgtcca agcgcaaaat    16560
caaagaagag atgctccagg tcatcgcgcc ggagatctat ggcccccga agaaggaaga     16620 gcaggattac aagccccgaa agctaaagcg ggtcaaaaag aaaagaaag atgatgatga     16680 tgaacttgac gacgaggtgg aactgctgca cgctaccgcg cccaggcgac gggtacagtg    16740
gaaaggtcga cgcgtaaaac gtgttttgcg acccggcacc accgtagtct ttacgcccgg    16800
tgagcgctcc acccgcacct acaagcgcgt gtatgatgag gtgtacggcg acgaggacct    16860
gcttgagcag gccaacgagc gcctcgggga gtttgcctac ggaaagcggc ataaggacat    16920
gctggcgttg ccgctggacg agggcaaccc aacacctagc ctaaagcccg taacactgca    16980
gcaggtgctg cccgcgcttg caccgtccga agaaaagcgc ggcctaaagc gcgagtctgg    17040
tgacttggca cccaccgtgc agctgatggt acccaagcgc cagcgactgg aagatgtctt    17100 ggaaaaatg accgtggaac ctgggctgga gcccgaggtc cgcgtgcggc caatcaagca    17160
ggtggcgccg ggactgggcg tgcagaccgt ggacgttcag atacccacta ccagtagcac    17220
cagtattgcc accgccacag agggcatgga gacacaaacg tccccggttg cctcagcggt    17280
ggcggatgcc gcggtgcagg cggtcgctgc ggccgcgtcc aagacctcta cggaggtgca    17340
aacgaccccg tggatgtttc gcgtttcagc ccccccgcgc ccgcgcggtt cgaggaagta    17400
cggcgccgcc agcgcgctac tgcccgaata tgccctacat ccttccattg cgcctacccc    17460
cggctatcgt ggctacacct accgcccag aagacgagca actacccgac gccgaaccac     17520
cactggaacc cgccgccgcc gtcgccgtcg ccagcccgtg ctggccccga tttccgtgcg    17580
cagggtggct cgcgaaggag gcaggaccct ggtgctgcca acagcgcgct accaccccag    17640
catcgtttaa aagccggtct ttgtggttct tgcagatatg gccctcacct gccgcctccg    17700
tttcccggtg ccgggattcc gaggaagaat gcaccgtagg aggggcatgg ccggccacgg    17760
cctgacgggc ggcatgcgtc gtgcgcacca ccggcggcgg cgcgcgtcgc accgtcgcat    17820
gcgcggcggt atcctgcccc tccttattcc actgatcgcc gcggcgattg gcgccgtgcc    17880
cggaattgca tccgtggcct tgcaggcgca gagacactga ttaaaaacaa gttgcatgtg    17940
gaaaaatcaa aataaaaagt ctggactctc acgctcgctt ggtcctgtaa ctattttgta    18000
gaatggaaga catcaacttt gcgtctctgg ccccgcgaca cggctcgcgc ccgttcatgg    18060
gaaactggca agatatcggc accagcaata tgagcggtgg cgccttcagc tggggctcgc    18120
tgtggagcgg cattaaaaat ttcggttcca ccgttaagaa ctatggcagc aaggcctgga    18180
acagcagcac aggccagatg ctgagggata agttgaaaga gcaaaatttc caacaaaagg    18240
tggtagatgg cctggcctct ggcattagcg gggtggtgga cctggccaac caggcagtgc    18300
aaaataagat taacagtaag cttgatcccc gccctcccgt agaggagcct ccaccggccg    18360
tggagacagt gtctccagag gggcgtggcg aaaagcgtcc gcgccccgac agggaagaaa    18420
ctctggtgac gcaaatagac gagcctcct cgtacgagga ggcactaaag caaggcctgc     18480
ccaccacccg tcccatcgcg cccatggcta ccggagtgct gggccagcac acacccgtaa    18540
```

```
cgctggacct gcctccccc gccgacaccc agcagaaacc tgtgctgcca ggcccgaccg   18600
ccgttgttgt aacccgtcct agccgcgcgt ccctgcgccg cgccgccagc ggtccgcgat   18660
cgttgcggcc cgtagccagt ggcaactggc aaagcacact gaacagcatc gtgggtctgg   18720
gggtgcaatc cctgaagcgc cgacgatgct tctgaatagc taacgtgtcg tatgtgtgtc   18780
atgtatgcgt ccatgtcgcc gccagaggag ctgctgagcc gccgcgcgcc cgctttccaa   18840
gatggctacc ccttcgatga tgccgcagtg gtcttacatg cacatctcgg gccaggacgc   18900
ctcggagtac ctgagccccg ggctggtgca gtttgcccgc gccaccgaga cgtacttcag   18960
cctgaataac aagtttagaa accccacggt ggcgcctacg cacgacgtga ccacagaccg   19020
gtcccagcgt ttgacgctgc ggttcatccc tgtggaccgt gaggatactg cgtactcgta   19080
caaggcgcgg ttcacccctag ctgtgggtga taaccgtgtg ctggacatgg cttccacgta   19140
ctttgacatc cgcggcgtgc tggacagggg ccctactttt aagccctact ctggcactgc   19200
ctacaacgcc ctggctccca agggtgcccc aaatccttgc gaatgggatg aagctgctac   19260
tgctcttgaa ataaacctag aagaagagga cgatgacaac gaagacgaag tagacgagca   19320
agctgagcag caaaaaactc acgtatttgg gcaggcgcct tattctggta taaatattac   19380
aaaggagggt attcaaatag gtgtcgaagg tcaaacacct aaatatgccg ataaaacatt   19440
tcaacctgaa cctcaaatag gagaatctca gtggtacgaa actgaaatta atcatgcagc   19500
tgggagagtc cttaaaaaga ctaccccaat gaaaccatgt tacggttcat atgcaaaacc   19560
cacaaatgaa aatggagggc aaggcattct tgtaaagcaa caaaatggaa agctagaaag   19620
tcaagtggaa atgcaatttt tctcaactac tgaggcgacc gcaggcaatg gtgataactt   19680
gactcctaaa gtggtattgt acagtgaaga tgtagatata gaaacccag acactcatat   19740
ttcttacatg cccactatta aggaaggtaa ctcacgagaa ctaatgggcc aacaatctat   19800
gcccaacagg cctaattaca ttgcttttag ggacaatttt attggtctaa tgtattacaa   19860
cagcacgggt aatatgggtg ttctggcggg ccaagcatcg cagttgaatg ctgttgtaga   19920
tttgcaagac agaaacacag agctttcata ccagcttttg cttgattcca ttggtgatag   19980
aaccaggtac tttttctatgt ggaatcaggc tgttgacagc tatgatccag atgttagaat   20040
tattgaaaat catggaactg aagatgaact tccaaattac tgctttccac tgggaggtgt   20100
gattaataca gagactctta ccaaggtaaa acctaaaaca ggtcaggaaa atggatggga   20160
aaaagatgct acagaatttt cagataaaaa tgaaataaga gttggaaata attttgccat   20220
ggaaatcaat ctaaatgcca acctgtggag aaatttcctg tactccaaca tagcgctgta   20280
tttgcccgac aagctaaagt acagtccttc caacgtaaaa atttctgata acccaaacac   20340
ctacgactac atgaacaagc gagtggtggc tcccgggtta gtggactgct acattaacct   20400
tggagcacgc tggtcccttg actatatgga caacgtcaac ccatttaacc accaccgcaa   20460
tgctggcctg cgctaccgct caatgttgct ggcaatggt cgctatgtgc ccttccacat   20520
ccaggtgcct cagaagttct tgccattaa aaacctcctt ctcctgccgg gctcatacac   20580
ctacgagtgg aacttcagga aggatgttaa catggttctg cagagctccc taggaaatga   20640
cctaagggtt gacggagcca gcattaagtt tgatagcatt tgcctttacg ccaccttctt   20700
ccccatggcc cacaacaccg cctccacgct tgaggccatg cttagaaacg acaccaacga   20760
ccagtccttt aacgactatc tctccgccgc caacatgctc tacccatatac ccgccaacgc   20820
taccaacgtg cccatatcca tccctcccg caactgggcg gctttccgcg gctgggcctt   20880
```

```
cacgcgcctt aagactaagg aaacccatc actgggctcg ggctacgacc cttattacac    20940
ctactctggc tctataccct acctagatgg aaccttttac ctcaaccaca cctttaagaa    21000
ggtggccatt acctttgact cttctgtcag ctggcctggc aatgaccgcc tgcttacccc    21060
caacgagttt gaaattaagc gctcagttga cggggagggt tacaacgttg cccagtgtaa    21120
catgaccaaa gactggttcc tggtacaaat gctagctaac tacaacattg gctaccaggg    21180
cttctatatc ccagagagct acaaggaccg catgtactcc ttctttagaa acttccagcc    21240
catgagccgt caggtggtgg atgatactaa atacaaggac taccaacagg tgggcatcct    21300
acaccaacac aacaactctg gatttgttgg ctaccttgcc cccaccatgc gcgaaggaca    21360
ggcctaccct gctaacttcc cctatccgct tataggcaag accgcagttg acagcattac    21420
ccagaaaaag tttctttgcg atcgcaccct ttggcgcatc ccattctcca gtaactttat    21480
gtccatgggc gcactcacag acctgggcca aaaccttctc tacgccaact ccgcccacgc    21540
gctagacatg acttttgagg tggatcccat ggacgagccc accttctttt atgttttgtt    21600
tgaagtcttt gacgtggtcc gtgtgcaccg gccgcaccgc ggcgtcatcg aaaccgtgta    21660
cctgcgcacg cccttctcgg ccggcaacgc cacaacataa agaagcaagc aacatcaaca    21720
acagctgccg ccatgggctc cagtgagcag gaactgaaag ccattgtcaa agatcttggt    21780
tgtgggccat attttttggg cacctatgac aagcgctttc caggctttgt ttctccacac    21840
aagctcgcct gcgccatagt caatacggcc ggtcgcgaga ctgggggcgt acactggatg    21900
gcctttgcct ggaacccgca ctcaaaaaca tgctacctct ttgagcccct tggctttttct   21960 gaccagcgac tcaagcaggt ttaccagttt gagtacgagt cactcctgcg ccgtagcgcc    22020
attgcttctt cccccgaccg ctgtataacg ctggaaaagt ccacccaaag cgtacagggg    22080
cccaactcgg ccgcctgtgg actattctgc tgcatgtttc tccacgcctt tgccaactgg    22140
ccccaaactc ccatggatca aaccccacc atgaaccta ttaccggggt acccaactcc    22200
atgctcaaca gtccccaggt acagcccacc ctgcgtcgca accaggaaca gctctacagc    22260
ttcctggagc gccactcgcc ctacttccgc agccacagtg cgcagattag gagcgccact    22320 tcttttttgtc acttgaaaaa catgtaaaaa taatgtacta gagacacttt caataaaggc    22380
aaatgctttt atttgtacac tctcgggtga ttatttaccc ccaccttgc cgtctgcgcc    22440 gtttaaaaat caaggggttt ctgccgcgca tcgctatgcg ccactggcag ggacacgttg    22500
cgatactggt gtttagtgct ccacttaaac tcaggcacaa ccatccgcgg cagctcggtg    22560
aagttttcac tccacaggct gcgcaccatc accaacgcgt ttagcaggtc gggcgccgat    22620
atcttgaagt cgcagttggg gcctccgccc tgcgcgcgcg agttgcgata cacagggttg    22680
cagcactgga acactatcag cgccgggtgg tgcacgctgg ccagcacgct cttgtcggag    22740
atcagatccg cgtccaggtc ctccgcgttg ctcagggcga acggagtcaa ctttggtagc    22800
tgccttccca aaagggcgc gtgcccaggc tttgagttgc actcgcaccg tagtggcatc    22860
aaaaggtgac cgtgcccggt ctgggcgtta ggatacagcg cctgcataaa agccttgatc    22920
tgcttaaaag ccacctgagc ctttgcgcct tcagagaaga acatgccgca agacttgccg    22980
gaaaactgat tggccggaca ggccgcgtcg tgcacgcagc accttgcgtc ggtgttggag    23040
atctgcacca catttcggcc ccaccggttc ttcacgatct tggccttgct agactgctcc    23100
ttcagcgcgc gctgcccgtt ttcgctcgtc acatccattt caatcacgtg ctccttatttt   23160 atcataatgc ttccgtgtag acacttaagc tcgccttcga tctcagcgca gcggtgcagc    23220
cacaacgcgc agcccgtggg ctcgtgatgc ttgtaggtca cctctgcaaa cgactgcagg    23280
```

```
tacgcctgca ggaatcgccc catcatcgtc acaaaggtct tgttgctggt gaaggtcagc   23340
tgcaacccgc ggtgctcctc gttcagccag gtcttgcata cggccgccag agcttccact   23400
tggtcaggca gtagtttgaa gttcgccttt agatcgttat ccacgtggta cttgtccatc   23460
agcgcgcgcg cagcctccat gcccttctcc cacgcagaca cgatcggcac actcagcggg   23520
ttcatcaccg taatttcact ttccgcttcg ctgggctctt cctcttcctc ttgcgtccgc   23580
ataccacgcc ccactgggtc gtcttcattc agccgccgca ctgtgcgctt acctcctttg   23640
ccatgcttga ttagcaccgg tgggttgctg aaacccacca tttgtagcgc cacatcttct   23700
ctttcttcct cgctgtccac gattacctct ggtgatggcg ggcgctcggg cttgggagaa   23760
gggcgcttct ttttcttctt gggcgcaatg gccaaatccg ccgccgaggt cgatggccgc   23820
gggctgggtg tgcgcggcac cagcgcgtct tgtgatgagt cttcctcgtc ctcggactcg   23880
atacgccgcc tcatccgctt ttttgggggc gcccggggag gcggcggcga cggggacggg   23940
gacgacacgt cctccatggt tgggggacgt cgcgccgcac cgcgtccgcg ctcggggggtg   24000
gtttcgcgct gctcctcttc ccgactggcc atttccttct cctataggca gaaaaagatc   24060
atggagtcag tcgagaagaa ggacagccta accgcccccct ctgagttcgc caccaccgcc   24120
tccaccgatg ccgccaacgc gcctaccacc ttccccgtcg aggcacccccc gcttgaggag   24180
gaggaagtga ttatcgagca ggacccaggt tttgtaagcg aagacgacga ggaccgctca   24240
gtaccaacag aggataaaaa gcaagaccag gacaacgcag aggcaaacga ggaacaagtc   24300
gggcggggggg acgaaaggca tggcgactac ctagatgtgg gagacgacgt gctgttgaag   24360
catctgcagc gccagtgcgc cattatctgc gacgcgttgc aagagcgcag cgatgtgccc   24420
ctcgccatag cggatgtcag ccttgcctac gaacgccacc tattctcacc gcgcgtaccc   24480
cccaaacgcc aagaaaacgg cacatgcgag cccaacccgc gcctcaactt ctaccccgta   24540
tttgccgtgc cagaggtgct tgccacctat cacatcttttt tccaaaactg caagataccc   24600
ctatcctgcc gtgccaaccg cagccgagcg gacaagcagc tggccttgcg gcagggcgct   24660
gtcatacctg atatcgcctc gctcaacgaa gtgccaaaaa tctttgaggg tcttggacgc   24720
gacgagaagc gcgcggcaaa cgctctgcaa caggaaaaca gcgaaaatga aagtcactct   24780
ggagtgttgg tggaactcga gggtgacaac gcgcgcctag ccgtactaaa acgcagcatc   24840
gaggtcaccc actttgccta cccggcactt aacctacccc ccaaggtcat gagcacagtc   24900
atgagtgagc tgatcgtgcg ccgtgcgcag cccctggaga gggatgcaaa tttgcaagaa   24960
caaacagagg agggcctacc cgcagttggc gacgagcagc tagcgcgctg gcttcaaacg   25020
cgcgagcctg ccgacttgga ggagcgacgc aaactaatga tggccgcagt gctcgttacc   25080
gtggagcttg agtgcatgca gcggttcttt gctgacccgg agatgcagcg caagctagag   25140
gaaacattgc actacacctt tcgacagggc tacgtacgcc aggcctgcaa gatctccaac   25200
gtggagctct gcaacctggt ctcctacctt ggaattttgc acgaaaaccg ccttgggcaa   25260
aacgtgcttc attccacgct caagggcgag gcgcgccgcg actacgtccg cgactgcgtt   25320
tacttatttc tatgctacac ctggcagacg gccatgggcg tttggcagca gtgcttggag   25380
gagtgcaacc tcaaggagct gcagaaactg ctaaagcaaa acttgaagga cctatggacg   25440
gccttcaacg agcgctccgt ggccgcgcac ctggcggaca tcatttttccc cgaacgcctg   25500
cttaaaaccc tgcaacaggg tctgccagac ttcaccagtc aaagcatgtt gcagaacttt   25560
aggaacttta tcctagagcg ctcaggaatc ttgcccgcca cctgctgtgc acttcctagc   25620
```

```
gactttgtgc ccattaagta ccgcgaatgc cctccgccgc tttggggcca ctgctacctt   25680
ctgcagctag ccaactacct tgcctaccac tctgacataa tggaagacgt gagcggtgac   25740
ggtctactgg agtgtcactg tcgctgcaac ctatgcaccc cgcaccgctc cctggtttgc   25800
aattcgcagc tgcttaacga aagtcaaatt atcggtacct ttgagctgca gggtccctcg   25860
cctgacgaaa agtccgcggc tccgggggttg aaactcactc cggggctgtg acgtcggct   25920 taccttcgca aatttgtacc tgaggactac cacgcccacg agattaggtt ctacgaagac   25980
caatcccgcc cgccaaatgc ggagcttacc gcctgcgtca ttacccaggg ccacattctt   26040
ggccaattgc aagccatcaa caaagcccgc caagagtttc tgctacgaaa gggacggggg   26100
gtttacttgg accccagtc cggcgaggag ctcaacccaa tcccccgcc gccgcagccc      26160 tatcagcagc agccgcgggc ccttgcttcc caggatggca cccaaaaaga agctgcagct   26220
gccgccgcca cccacggacg aggaggaata ctgggacagt caggcagagg aggttttgga   26280
cgaggaggag gaggacatga tggaagactg ggagagccta gacgaggaag cttccgaggt   26340
cgaagaggtg tcagacgaaa caccgtcacc ctcggtcgca ttcccctcgc cggcgcccca   26400
gaaatcggca accggttcca gcatggctac aacctccgct cctcaggcgc cgccggcact   26460
gcccgttcgc cgacccaacc gtagatggga ccactggaa accagggccg gtaagtccaa   26520
gcagccgccg ccgttagccc aagagcaaca acagcgccaa ggctaccgct catggcgcgg   26580
gcacaagaac gccatagttg cttgcttgca agactgtggg ggcaacatct ccttcgcccg   26640
ccgctttctt ctctaccatc acggcgtggc cttcccccgt aacatcctgc attactaccg   26700
tcatctctac agcccatact gcaccggcgg cagcggcagc ggcagcaaca gcagcggcca   26760
cacagaagca aaggcgaccg gatagcaaga ctctgacaaa gcccaagaaa tccacagcgg   26820
cggcagcagc aggaggagga cgctgcgtc tggcgcccaa cgaacccgta tcgacccgcg   26880
agcttagaaa caggattttt cccactctgt atgctatatt tcaacagagc aggggccaag   26940
aacaagagct gaaaataaaa aacaggtctc tgcgatccct cacccgcagc tgcctgtatc   27000
acaaaagcga agatcagctt cggcgcacgc tggaagacgc ggaggctctc ttcagtaaat   27060
actgcgcgct gactcttaag gactagtttc gcgcccttc tcaaatttaa gcgcgaaaac   27120
tacgtcatct ccagcggcca cacccggcgc cagcacctgt cgtcagcgcc attatgagca   27180
aggaaattcc cacgccctac atgtggagtt accagccaca aatgggactt gcggctggag   27240
ctgcccaaga ctactcaacc cgaataaact acatgagcgc gggaccccac atgatatccc   27300
gggtcaacgg aatccgcgcc caccgaaacc gaattctctt ggaacaggcg gctattacca   27360
ccacacctcg taataacctt aatccccgta gttggcccgc tgccctggtg taccaggaaa   27420
gtcccgctcc caccactgtg gtacttccca gagacgccca ggccgaagtt cagatgacta   27480
actcaggggc gcagcttgcg ggcggctttc gtcacagggt gcggtcgccc gggcagggta   27540
taactcacct gacaatcaga gggcgaggta ttcagctcaa cgacgagtcg gtgagctcct   27600
cgcttggtct ccgtccggac gggacatttc agatcggcgg cgccggccgt ccttcattca   27660
cgcctcgtca ggcaatccta actctgcaga cctcgtcctc tgagccgcgc tctggaggca   27720
ttggaactct gcaatttatt gaggagtttg tgccatcggt ctactttaac cccttctcgg   27780
gacctcccgg ccactatccg gatcaattta ttcctaactt tgacgcggta aaggactcgg   27840
cggacggcta cgactgaatg ttaagtggag aggcagagca actgcgcctg aaacacctgg   27900
tccactgtcg ccgccacaag tgctttgccc gcgactccgg tgagttttgc actttgaat    27960 tgcccgagga tcatatcgag ggcccggcgc acggcgtccg gcttaccgcc cagggagagc   28020
```

```
ttgcccgtag cctgattcgg gagtttaccc agcgcccct gctagttgag cgggacaggg    28080
gaccctgtgt tctcactgtg atttgcaact gtcctaacct tggattacat caagatcttt   28140
gttgccatct ctgtgctgag tataataaat acagaaatta aaatatactg gggctcctat   28200
cgccatcctg taaacgccac cgtcttcacc cgcccaagca aaccaaggcg aaccttacct   28260
ggtacttta  acatctctcc ctctgtgatt tacaacagtt tcaacccaga cggagtgagt   28320
ctacgagaga acctctccga gctcagctac tccatcagaa aaacaccac  cctccttacc   28380
tgccgggaac gtacgagtgc gtcaccggcc gctgcaccac acctaccgcc tgaccgtaaa   28440
ccagactttt tccggacaga cctcaataac tctgtttacc agaacaggag gtgagcttag   28500
aaaacccctta gggtattagg ccaaaggcgc agctactgtg gggtttatga acaattcaag   28560
caactctacg ggctattcta attcaggttt ctctagaatc ggggttgggg ttattctctg   28620
tcttgtgatt ctctttattc ttatactaac gcttctctgc ctaaggctcg ccgcctgctg   28680
tgtgcacatt tgcatttatt gtcagctttt taaacgctgg ggtcgccacc caagatgatt   28740
aggtacataa tcctaggttt actcacccct gcgtcagccc acggtaccac ccaaaaggtg   28800
gattttaagg agccagcctg taatgttaca ttcgcagctg aagctaatga gtgcaccact   28860
cttataaaat gcaccacaga acatgaaaag ctgcttattc gccacaaaaa caaaattggc   28920
aagtatgctg tttatgctat ttggcagcca ggtgacacta cagagtataa tgttacagtt   28980
ttccagggta aaagtcataa aactttatg  tatacttttc cattttatga aatgtgcgac   29040
attaccatgt acatgagcaa acagtataag ttgtggcccc cacaaaattg tgtggaaaac   29100
actggcactt tctgctgcac tgctatgcta attacagtgc tcgctttggt ctgtacccta   29160
ctctatatta aatacaaaag cagacgcagc tttattgagg aaaagaaaat gccttaattt   29220
actaagttac aaagctaatg tcaccactaa ctgctttact cgctgcttgc aaaacaaatt   29280
caaaaagtta gcattataat tagaatagga tttaaacccc ccggtcattt cctgctcaat   29340
accattcccc tgaacaattg actctatgtg ggatatgctc cagcgctaca accttgaagt   29400
caggcttcct ggatgtcagc atctgacttt ggccagcacc tgtcccgcgg atttgttcca   29460
gtccaactac agcgacccac cctaacagag atgaccaaca caaccaacgc ggccgccgct   29520
accggactta catctaccac aaatacaccc caagtttctg cctttgtcaa taactgggat   29580
aacttgggca tgtggtggtt ctccatagcg cttatgtttg tatgccttat tattatgtgg   29640
ctcatctgct gcctaaagcg caaacgcgcc cgaccaccca tctatagtcc catcattgtg   29700
ctacacccaa acaatgatgg aatccataga ttggacggac tgaaacacat gttcttttct   29760
cttacagtat gattaaatga gacatgattc ctcgagtttt tatattactg acccttgttg   29820
cgctttttg  tgcgtgctcc acattggctg cggtttctca catcgaagta gactgcattc   29880
cagccttcac agtctatttg ctttacggat tgtcaccct cacgctcatc tgcagcctca   29940
tcactgtggt catcgccttt atccagtgca ttgactgggt ctgtgtgcgc tttgcatatc   30000
tcagacacca tccccagtac agggacagga ctatagctga gcttcttaga attctttaat   30060
tatgaaattt actgtgactt ttctgctgat tatttgcacc ctatctgcgt tttgttcccc   30120
gacctccaag cctcaaagac atatatcatg cagattcact cgtatatgga atattccaag   30180
ttgctacaat gaaaaaagcg atctttccga agcctggtta tatgcaatca tctctgttat   30240
ggtgttctgc agtaccatct tagccctagc tatatatccc taccttgaca ttggctggaa   30300
acgaatagat gccatgaacc acccaacttt ccccgcgccc gctatgcttc cactgcaaca   30360
```

```
agttgttgcc ggcggctttg tcccagccaa tcagcctcgc cccacttctc ccaccccac   30420
tgaaatcagc tactttaatc taacaggagg agatgactga caccctagat ctagaaatgg  30480
acggaattat tacagagcag cgcctgctag aaagacgcag ggcagcggcc gagcaacagc  30540
gcatgaatca agagctccaa gacatggtta acttgcacca gtgcaaaagg ggtatctttt  30600
gtctggtaaa gcaggccaaa gtcacctacg acagtaatac caccggacac cgccttagct  30660
acaagttgcc aaccaagcgt cagaaattgg tggtcatggt gggagaaaag cccattacca  30720
taactcagca ctcggtagaa accgaaggct gcattcactc accttgtcaa ggacctgagg  30780
atctctgcac ccttattaag accctgtgcg gtctcaaaga tcttattccc tttaactaat  30840
aaaaaaaaat aataaagcat cacttactta aaatcagtta gcaaatttct gtccagttta  30900
ttcagcagca cctccttgcc ctcctcccag ctctggtatt gcagcttcct cctggctgca  30960
aactttctcc acaatctaaa tggaatgtca gtttcctcct gttcctgtcc atccgcaccc  31020
actatcttca tgttgttgca gatgaagcgc gcaagaccgt ctgaagatac cttcaacccc  31080
gtgtatccat atgacacgga aaccggtcct ccaactgtgc cttttcttac tcctccctt   31140
gtatcccca  atgggtttca agagagtccc cctggggtac tctctttgcg cctatccgaa  31200
cctctagtta cctccaatgg catgcttgcg ctcaaaatgg gcaacggcct ctctctggac  31260
gaggccggca accttacctc ccaaaatgta accactgtga gcccacctct caaaaaaacc  31320
aagtcaaaca taaacctgga aatatctgca cccctcacag ttacctcaga gccctaact   31380
gtggctgccg ccgcacctct aatggtcgcg ggcaacacac tcaccatgca atcacaggcc  31440
ccgctaaccg tgcacgactc caaacttagc attgccaccc aaggacccct cacagtgtca  31500
gaaggaaagc tagccctgca acatcaggc cccctcacca ccaccgatag cagtaccctt   31560
actatcactg cctcaccccc tctaactact gccactggta gcttgggcat tgacttgaaa  31620
gagcccattt atacacaaaa tggaaaacta ggactaaagt acggggctcc tttgcatgta  31680
acagacgacc taaacacttt gaccgtagca actggtccag gtgtgactat taataatact  31740
tccttgcaaa ctaaagttac tggagccttg ggttttgatt cacaaggcaa tatgcaactt  31800
aatgtagcag gaggactaag gattgattct caaaacagac gccttatact tgatgttagt  31860
tatccgtttg atgctcaaaa ccaactaaat ctaagactag gacagggccc tcttttttata  31920
aactcagccc acaacttgga tattaactac aacaaaggcc tttacttgtt tacagcttca  31980
aacaattcca aaaagcttga ggttaaccta agcactgcca aggggttgat gtttgacgct  32040
acagccatag ccattaatgc aggagatggg cttgaatttg gttcacctaa tgcaccaaac  32100
acaaatcccc tcaaaacaaa aattggccat ggcctagaat ttgattcaaa caaggctatg  32160
gttcctaaac taggaactgg ccttagtttt gacagcacag gtgccattac agtaggaaac  32220
aaaaataatg ataagctaac tttgtggacc acaccagctc catctcctaa ctgtagacta  32280
aatgcagaga aagatgctaa actcactttg gtcttaacaa aatgtggcag tcaaatactt  32340
gctacagttt cagttttggc tgttaaaggc agtttggctc aatatctgg aacagttcaa  32400
agtgctcatc ttattataag atttgacgaa aatggagtgc tactaaacaa ttccttcctg  32460
gacccagaat attggaactt tagaaatgga gatcttactg aaggcacagc ctatacaaac  32520
gctgttggat ttatgcctaa cctatcagct tatccaaaat ctcacggtaa aactgccaaa  32580
agtaacattg tcagtcaagt ttacttaaac ggagacaaaa ctaaacctgt aacactaacc  32640
attacactaa acggtacaca ggaaacagga gacacaactc caagtgcata ctctatgtca  32700
tttttcatgg gactggtctgg ccacaactac attaatgaaa tatttgccac atcctcttac  32760
```

```
actttttcat acattgccca agaataaaga atcgtttgtg ttatgtttca acgtgtttat    32820
ttttcaattg cagaaaattt caagtcattt ttcattcagt agtatagccc caccaccaca    32880
tagcttatac agatcaccgt accttaatca aactcacaga accctagtat tcaacctgcc    32940
acctccctcc caacacacag agtacacagt cctttctccc cggctggcct taaaaagcat    33000
catatcatgg gtaacagaca tattcttagg tgttatattc cacacggttt cctgtcgagc    33060
caaacgctca tcagtgatat taataaactc cccgggcagc tcacttaagt tcatgtcgct    33120
gtccagctgc tgagccacag gctgctgtcc aacttgcggt tgcttaacgg gcggcgaagg    33180
agaagtccac gcctacatgg gggtagagtc ataatcgtgc atcaggatag ggcggtggtg    33240
ctgcagcagc gcgcgaataa actgctgccg ccgccgctcc gtcctgcagg aatacaacat    33300
ggcagtggtc tcctcagcga tgattcgcac cgcccgcagc ataaggcgcc ttgtcctccg    33360
ggcacagcag cgcacccctga tctcacttaa atcagcacag taactgcagc acagcaccac    33420
aatattgttc aaaatcccac agtgcaaggc gctgtatcca aagctcatgg cggggaccac    33480
agaacccacg tggccatcat accacaagcg caggtagatt aagtggcgac ccctcataaa    33540
cacgctggac ataaacatta cctctttggg catgttgtaa ttcaccaccct cccggtacca    33600 tataaacctc tgattaaaca tggcgccatc caccaccatc ctaaaccagc tggccaaaac    33660
ctgcccgccg gctatacact gcagggaacc gggactggaa caatgacagt ggagagccca    33720
ggactcgtaa ccatggatca tcatgctcgt catgatatca atgttggcac aacacaggca    33780
cacgtgcata cacttcctca ggattacaag ctcctcccgc gttagaacca tatcccaggg    33840
aacaacccat tcctgaatca gcgtaaatcc cacactgcag ggaagacctc gcacgtaact    33900
cacgttgtgc attgtcaaag tgttacattc gggcagcagc ggatgatcct ccagtatggt    33960
agcgcgggtt tctgtctcaa aaggaggtag acgatcccta ctgtacggag tgcgccgaga    34020
caaccgagat cgtgttggtc gtagtgtcat gccaaatgga acgccggacg tagtcatatt    34080
tcctgaagca aaaccaggtg cgggcgtgac aaacagatct gcgtctccgg tctcgccgct    34140
tagatcgctc tgtgtagtag ttgtagtata tccactctct caaagcatcc aggcgccccc    34200
tggcttcggg ttctatgtaa actccttcat gcgccgctgc cctgataaca tccaccaccg    34260
cagaataagc cacacccagc caacctacac attcgttctg cgagtcacac acgggaggag    34320
cgggaagagc tggaagaacc atgtttttttt ttttattcca aaagattatc caaaacctca    34380
aaatgaagat ctattaagtg aacgcgctcc cctccggtgg cgtggtcaaa ctctacagcc    34440
aaagaacaga taatggcatt tgtaagatgt tgcacaatgg cttccaaaag gcaaacggcc    34500
ctcacgtcca agtggacgta aaggctaaac ccttcagggt gaatctcctc tataaacatt    34560
ccagcacctt caaccatgcc caaataattc tcatctcgcc accttctcaa tatatctcta    34620
agcaaatccc gaatattaag tccggccatt gtaaaaatct gctccagagc gccctccacc    34680
ttcagcctca agcagcgaat catgattgca aaaattcagg ttcctcacag acctgtataa    34740
gattcaaaag cggaacatta acaaaaatac cgcgatcccg taggtcccctt cgcagggcca    34800 gctgaacata atcgtgcagg tctgcacgga ccagcgcggc cacttccccg ccaggaacca    34860
tgacaaaaga acccacactg attatgacac gcatactcgg agctatgcta accagcgtag    34920
ccccgatgta agcttgttgc atgggcggcg atataaaatg caaggtgctg ctcaaaaaat    34980
caggcaaagc ctcgcgcaaa aaagaaagca catcgtagtc atgctcatgc agataaaggc    35040
aggtaagctc cggaaccacc acagaaaaag acaccatttt tctctcaaac atgtctgcgg    35100
```

-continued

```
gtttctgcat aaacacaaaa taaaataaca aaaaaacatt taaacattag aagcctgtct    35160
tacaacagga aaaacaaccc ttataagcat aagacggact acggccatgc cggcgtgacc    35220
gtaaaaaaac tggtcaccgt gattaaaaag caccaccgac agctcctcgg tcatgtccgg    35280
agtcataatg taagactcgg taaacacatc aggttgattc acatcggtca gtgctaaaaa    35340
gcgaccgaaa tagcccgggg gaatacatac ccgcaggcgt agagacaaca ttacagcccc    35400
cataggaggt ataacaaaat taataggaga gaaaaacaca taaacacctg aaaaccctc    35460 ctgcctaggc aaaatagcac cctcccgctc cagaacaaca tacagcgctt ccacagcggc    35520
agccataaca gtcagcctta ccagtaaaaa agaaaaccta ttaaaaaaac accactcgac    35580
acggcaccag ctcaatcagt cacagtgtaa aaagggcca agtgcagagc gagtatatat    35640
aggactaaaa aatgacgtaa cggttaaagt ccacaaaaaa cacccagaaa accgcacgcg    35700
aacctacgcc cagaaacgaa agccaaaaaa cccacaactt cctcaaatcg tcacttccgt    35760
tttcccacgt tacgtaactt cccatttttaa gaaaactaca attcccaaca catacaagtt    35820
actccgccct aaaacctacg tcacccgccc cgttcccacg ccccgcgcca cgtcacaaac    35880 tccacccccct cattatcata ttggcttcaa tccaaaataa ggtatattat tgatgatg    35938
```

<210> SEQ ID NO 2
<211> LENGTH: 8
<212> TYPE: DNA
<213> ORGANISM: Human adenovirus 5

<400> SEQUENCE: 2 tcaccagg                                                              8

<210> SEQ ID NO 3
<211> LENGTH: 8
<212> TYPE: DNA
<213> ORGANISM: Human adenovirus 5

<400> SEQUENCE: 3 ctgacctc                                                              8

<210> SEQ ID NO 4
<211> LENGTH: 10
<212> TYPE: DNA
<213> ORGANISM: Artificial Sequence
<220> FEATURE:
<223> OTHER INFORMATION: Modified E1a promoter

<400> SEQUENCE: 4
ggtgttttgg                                                           10

<210> SEQ ID NO 5
<211> LENGTH: 9
<212> TYPE: DNA
<213> ORGANISM: Artificial Sequence
<220> FEATURE:
<223> OTHER INFORMATION: Modified E1a promoter

<400> SEQUENCE: 5 ctaggactg                                                             9

<210> SEQ ID NO 6
<211> LENGTH: 65
<212> TYPE: DNA
<213> ORGANISM: Human adenovirus 5

<400> SEQUENCE: 6

-continued

```
taaaacataa ataaaaaacc agactctgtt tggatttgga tcaagcaagt gtcttgctgt    60
cttta                                                                65

<210> SEQ ID NO 7
<211> LENGTH: 132
<212> TYPE: DNA
<213> ORGANISM: Human adenovirus 5

<400> SEQUENCE: 7
taaagaatcg tttgtgttat gtttcaacgt gtttattttt caattgcaga aaatttcaag    60
tcatttttca ttcagtagta tagccccacc accacatagc ttatacagat caccgtacct   120
taatcaaact ca                                                       132

<210> SEQ ID NO 8
<211> LENGTH: 3
<212> TYPE: DNA
<213> ORGANISM: Human adenovirus 5

<400> SEQUENCE: 8 taa                                                                  3

<210> SEQ ID NO 9
<211> LENGTH: 3
<212> TYPE: DNA
<213> ORGANISM: Human adenovirus 5

<400> SEQUENCE: 9 tta                                                                  3

<210> SEQ ID NO 10
<211> LENGTH: 3
<212> TYPE: DNA
<213> ORGANISM: Human adenovirus 5

<400> SEQUENCE: 10 tca                                                                  3

<210> SEQ ID NO 11
<211> LENGTH: 8
<212> TYPE: DNA
<213> ORGANISM: Unknown
<220> FEATURE:
<223> OTHER INFORMATION: SwaI restriction site

<400> SEQUENCE: 11 atttaaat                                                             8

<210> SEQ ID NO 12
<211> LENGTH: 6
<212> TYPE: DNA
<213> ORGANISM: Human adenovirus 5

<400> SEQUENCE: 12 aataaa                                                               6

<210> SEQ ID NO 13
<211> LENGTH: 6
<212> TYPE: DNA
<213> ORGANISM: Human adenovirus 5

<400> SEQUENCE: 13
```

<210> SEQ ID NO 14
<211> LENGTH: 530
<212> TYPE: DNA
<213> ORGANISM: Artificial Sequence
<220> FEATURE:
<223> OTHER INFORMATION: L5 initial Empty

<400> SEQUENCE: 14

```
aataaagaat cgtttgtgtt atgtttcaac ctgtggaatg tgtgtcagtt agggtgtgga      60
aagtccccag gctccccagc aggcagaagt atgcaaagca tgcatctcaa ttagtcagca     120
accaggtgtg gaaagtcccc aggctcccca gcaggcagaa gtatgcaaag catgcatctc     180
aattagtcag caaccatagt cccgccccta actccgccca tcccgcccct aactccgccc     240
agttccgccc attctccgcc ccatggctga ctaattttt ttatttatgc agaggccgag      300
gccgcctctg cctctgagct attccagaag tagtgaggag gcttttttgg aggcctaggc     360
ttttgcaaaa agctttgcaa agatttaaat aacttgttta ttgcagctta taatggttac     420
aaataaagca atagcatcac aaatttcaca aataaagcat ttttttcact gcattctagt     480
tgtggtttgt ccaaactcat caatgtatct tatcatgtct ggtgtttatt                530
```

<210> SEQ ID NO 15
<211> LENGTH: 956
<212> TYPE: DNA
<213> ORGANISM: Artificial Sequence
<220> FEATURE:
<223> OTHER INFORMATION: L5 initial mGMCSF

<400> SEQUENCE: 15

```
aataaagaat cgtttgtgtt atgtttcaac ctgtggaatg tgtgtcagtt agggtgtgga      60
aagtccccag gctccccagc aggcagaagt atgcaaagca tgcatctcaa ttagtcagca     120
accaggtgtg gaaagtcccc aggctcccca gcaggcagaa gtatgcaaag catgcatctc     180
aattagtcag caaccatagt cccgccccta actccgccca tcccgcccct aactccgccc     240
agttccgccc attctccgcc ccatggctga ctaattttt ttatttatgc agaggccgag      300
gccgcctctg cctctgagct attccagaag tagtgaggag gcttttttgg aggcctaggc     360
ttttgcaaaa agctttgcaa agatttatgt ggctgcagaa cctgctgttc ctgggcatcg     420
tggtgtacag cctgagcgcc cccaccagat cccccatcac cgtgaccaga ccctggaagc     480
acgtggaagc catcaaagag gccctgaacc tgctggacga catgcccgtg accctgaacg     540
aagaggtgga agtggtgtcc aacgagttca gcttcaagaa actgacctgc gtgcagacca     600
gactgaagat cttcgagcag ggcctgagag gcaacttcac caagctgaag ggcgctctga     660
acatgaccgc cagctactac cagacctact gccctcccac acccgagaca gactgcgaga     720
cacaggtcac aacctacgcc gacttcatcg acagcctgaa aaccttcctg accgacatcc     780
ccttcgagtg caagaaaccc ggccagaagt gaaaataact tgtttattgc agcttataat     840
ggttacaaat aaagcaatag catcacaaat ttcacaaata aagcattttt tcactgcat     900
tctagttgtg gtttgtccaa actcatcaat gtatcttatc atgtctggtg tttatt         956
```

<210> SEQ ID NO 16
<211> LENGTH: 8
<212> TYPE: DNA
<213> ORGANISM: Unknown
<220> FEATURE:
<223> OTHER INFORMATION: NotI restriction site

<400> SEQUENCE: 16 gcggccgc                                                                    8

<210> SEQ ID NO 17
<211> LENGTH: 858
<212> TYPE: DNA
<213> ORGANISM: Artificial Sequence
<220> FEATURE:
<223> OTHER INFORMATION: IX initial Empty

<400> SEQUENCE: 17
aataaaaaac cagactctgt ttggatttgg atcaagcaag tgtcttgctg tcttacggta      60
aatggcccgc ctggctgacc gcccaacgac ccccgcccat tgacgtcaat aatgacgtat     120
gttcccatag taacgccaat agggactttc cattgacgtc aatgggtgga gtatttacgg     180
taaactgccc acttggcagt acatcaagtg tatcatatgc caagtacgcc ccctattgac     240
gtcaatgacg gtaaatggcc cgcctggcat tatgcccagt acatgacctt atgggacttt     300
cctacttggc agtacatcta cgtattagtc atcgctatta ccatggtgat gcggttttgg     360
cagtacatca atgggcgtgg atagcggttt gactcacggg gatttccaag tctccacccc     420
attgacgtca atgggagttt gttttggcac caaaatcaac gggactttcc aaaatgtcgt     480
aacaactccg ccccattgac gcaaatgggc ggtaggcgtg tacggtggga ggtctatata     540
agcagagctc tctggctaac tagagaaccc actgcttact ggcttatcga attaatacg      600 actcactata gggagacccg cggccgcctg tgccttctag ttgccagcca tctgttgttt     660
gcccctcccc cgtgccttcc ttgaccctgg aaggtgccac tcccactgtc ctttcctaat     720
aaaatgagga aattgcatcg cattgtctga gtaggtgtca ttctattctg gggggtgggg     780
tggggcagga cagcaagggg gaggattggg aagacaatag caggcatgct ggggatgcgg     840
tgggctctat ggtttatt                                                    858

<210> SEQ ID NO 18
<211> LENGTH: 500
<212> TYPE: DNA
<213> ORGANISM: Artificial Sequence
<220> FEATURE:
<223> OTHER INFORMATION: L5 mIL7

<400> SEQUENCE: 18
gctttgcaaa gatttatgtt ccatgtttct tttagatata tctttggaat tcctccactg      60
atccttgttc tgctgcctgt cacatcatct gagtgccaca ttaaagacaa agaaggtaaa     120
gcatatgaga gtgtactgat gatcagcatc gatgaattgg acaaaatgac aggaactgat     180
agtaattgcc cgaataatga accaaacttt tttagaaaac atgtatgtga tgatacaaag     240
gaagctgctt ttctaaatcg tgctgctcgc aagttgaagc aatttcttaa aatgaatatc     300
agtgaagaat tcaatgtcca cttactaaca gtatcacaag gcacacaaac actggtgaac     360
tgcacaagta aggaagaaaa aaacgtaaag gaacagaaaa agaatgatgc atgtttccta     420
aagagactac tgagagaaat aaaaacttgt tggaataaaa ttttgaaggg cagtatataa     480
aaataacttg tttattgcag                                                  500

<210> SEQ ID NO 19
<211> LENGTH: 461
<212> TYPE: DNA
<213> ORGANISM: Artificial Sequence
<220> FEATURE:

<223> OTHER INFORMATION: L5 wt mGMCSF

<400> SEQUENCE: 19

```
gctttgcaaa gatttatgtg gctgcagaat ttacttttcc tgggcattgt ggtctacagc      60
ctctcagcac ccacccgctc acccatcact gtcacccggc cttggaagca tgtagaggcc     120
atcaaagaag ccctgaacct cctggatgac atgcctgtca cgttgaatga agaggtagaa     180
gtcgtctcta acgagttctc cttcaagaag ctaacatgtg tgcagacccg cctgaagata     240
ttcgagcagg gtctacgggg caatttcacc aaactcaagg gcgccttgaa catgacagcc     300
agctactacc agacatactg ccccccaact ccggaaacgg actgtgaaac acaagttacc     360
acctatgcgg atttcataga cagccttaaa acctttctga ctgatatccc ctttgaatgc     420
aaaaaaccag gccaaaaatg aaataacttg tttattgca g                          461
```

<210> SEQ ID NO 20
<211> LENGTH: 463
<212> TYPE: DNA
<213> ORGANISM: Artificial Sequence
<220> FEATURE:
<223> OTHER INFORMATION: IX wt mGMCSF

<400> SEQUENCE: 20

```
atagggagac ccgcggccat gtggctgcag aatttacttt tcctgggcat tgtggtctac      60
agcctctcag cacccacccg ctcacccatc actgtcaccc ggccttggaa gcatgtagag     120
gccatcaaag aagccctgaa cctcctggat gacatgcctg tcacgttgaa tgaagaggta     180
gaagtcgtct ctaacgagtt ctccttcaag aagctaacat gtgtgcagac ccgcctgaag     240
atattcgagc agggtctacg gggcaatttc accaaactca agggcgcctt gaacatgaca     300
gccagctact accagacata ctgcccccca actccggaaa cggactgtga aacacaagtt     360
accacctatg cggatttcat agacagcctt aaaacctttc tgactgatat ccccttgaa     420
tgcaaaaaac caggccaaaa atgaggccgc tgtgccttct agt                        463
```

<210> SEQ ID NO 21
<211> LENGTH: 760
<212> TYPE: DNA
<213> ORGANISM: Artificial Sequence
<220> FEATURE:
<223> OTHER INFORMATION: IX revised Empty

<400> SEQUENCE: 21

```
aataaaatac acctttttc gattgtacgt attttatt acggtaaatg gcccgcctgg        60
ctgaccgccc aacgacccc gcccattgac gtcaataatg acgtatgttc ccatagtaac     120
gccaataggg actttccatt gacgtcaatg ggtggagtat ttacggtaaa ctgcccactt     180
ggcagtacat caagtgtatc atatgccaag tacgccccct attgacgtca atgacggtaa     240
atggcccgcc tggcattatg cccagtacat gaccttatgg gactttccta cttggcagta     300
catctacgta ttagtcatcg ctattaccat ggtgatgcgg ttttggcagt acatcaatgg     360
gcgtggatag cggtttgact cacggggatt tccaagtctc cacccattg acgtcaatgg     420
gagtttgttt tggcaccaaa atcaacggga ctttccaaaa tgtcgtaaca actccgcccc     480
attgacgcaa atgggcggta ggcgtgtacg gtgggaggtc tatataagca gagctctctg     540
gctaactaga aacccactg cttactggct tatcgaaatt aatacgactc actatagga     600
gacccgcggc cgctgtgcct tctagttgcc agccatctgt tgtttgcccc tcccccgtgc     660
cttccttgac cctggaaggt gccactccca ctgtcctttc ctaataaaaa accagactct     720
```

```
gtttggattt ggatcaagca agtgtcttgc tgtctttatt                      760
```

<210> SEQ ID NO 22
<211> LENGTH: 1526
<212> TYPE: DNA
<213> ORGANISM: Artificial Sequence
<220> FEATURE:
<223> OTHER INFORMATION: IX revised hIL12A

<400> SEQUENCE: 22

```
aataaaatac acctttttc gattgtacgt attttattt acggtaaatg gcccgcctgg   60
ctgaccgccc aacgaccccc gcccattgac gtcaataatg acgtatgttc ccatagtaac  120
gccaataggg actttccatt gacgtcaatg ggtggagtat ttacggtaaa ctgcccactt  180
ggcagtacat caagtgtatc atatgccaag tacgccccct attgacgtca atgacggtaa  240
atggcccgcc tggcattatg cccagtacat gaccttatgg gactttccta cttggcagta  300
catctacgta ttagtcatcg ctattaccat ggtgatgcgg ttttggcagt acatcaatgg  360
gcgtggatag cggtttgact cacggggatt ccaagtctc caccccattg acgtcaatgg  420
gagtttgttt tggcaccaaa atcaacggga ctttccaaaa tgtcgtaaca actccgcccc  480
attgacgcaa atgggcggta ggcgtgtacg gtgggaggtc tatataagca gagctctctg  540
gctaactaga gaacccactg cttactggct tatcgaaatt aatacgactc actataggga  600
gacccgcggc catgtggccc cctgggtcag cctcccagcc accgccctca cctgccgcgg  660
ccacaggtct gcatccagcg gctcgccctg tgtccctgca gtgccggctc agcatgtgtc  720
cagcgcgcag cctcctcctt gtggctaccc tggtcctcct ggaccacctc agtttggcca  780
gaaacctccc cgtggccact ccagacccag gaatgttccc atgccttcac cactcccaaa  840
acctgctgag ggccgtcagc aacatgctcc agaaggccag acaaactcta gaattttacc  900
cttgcacttc tgaagagatt gatcatgaag atatcacaaa agataaaacc agcacagtgg  960
aggcctgttt accattggaa ttaaccaaga tgagagttg cctaaattcc agagagacct 1020
ctttcataac taatgggagt tgcctggcct ccagaaagac ctcttttatg atggccctgt 1080
gccttagtag tatttatgaa gacttgaaga tgtaccaggt ggagttcaag accatgaatg 1140
caaagcttct gatggatcct aagaggcaga tctttctaga tcaaaacatg ctggcagtta 1200
ttgatgagct gatgcaggcc ctgaatttca acagtgagac tgtgccacaa aaatcctccc 1260
ttgaagaacc ggatttttat aaaactaaaa tcaagctctg catacttctt catgctttca 1320
gaattcgggc agtgactatt gatagagtga tgagctatct gaatgcttcc taaggccgct 1380
gtgccttcta gttgccagcc atctgttgtt tgcccctccc ccgtgccttc cttgaccctg 1440
gaaggtgcca ctcccactgt cctttcctaa taaaaaacca gactctgttt ggatttggat 1500
caagcaagtg tcttgctgtc tttatt                                    1526
```

<210> SEQ ID NO 23
<211> LENGTH: 1517
<212> TYPE: DNA
<213> ORGANISM: Artificial Sequence
<220> FEATURE:
<223> OTHER INFORMATION: L5 initial hIL12B

<400> SEQUENCE: 23

```
aataaagaat cgtttgtgtt atgtttcaac ctgtggaatg tgtgtcagtt agggtgtgga   60
aagtccccag gctccccagc aggcagaagt atgcaaagca tgcatctcaa ttagtcagca  120
```

```
accaggtgtg gaaagtcccc aggctcccca gcaggcagaa gtatgcaaag catgcatctc      180
aattagtcag caaccatagt cccgcccta actccgccca tcccgcccct aactccgccc       240
agttccgccc attctccgcc ccatggctga ctaattttt ttatttatgc agaggccgag       300
gccgcctctg cctctgagct attccagaag tagtgaggag gcttttttgg aggcctaggc      360
ttttgcaaaa agctttgcaa agatttatgt gtcaccagca gttggtcatc tcttggtttt     420
ccctggtttt tctggcatct cccctcgtgg ccatatggga actgaagaaa gatgtttatg      480
tcgtagaatt ggattggtat ccggatgccc ctggagaaat ggtggtcctc acctgtgaca      540
cccctgaaga gatggtatc acctggacct tggaccagag cagtgaggtc ttaggctctg       600
gcaaaaccct gaccatccaa gtcaaagagt ttggagatgc tggccagtac acctgtcaca      660
aaggaggcga ggttctaagc cattcgctcc tgctgcttca caaaaaggaa gatggaattt      720
ggtccactga tattttaaag gaccagaaag aacccaaaaa taagaccttt ctaagatgcg      780
aggccaagaa ttattctgga cgtttcacct gctggtggct gacgacaatc agtactgatt      840
tgacattcag tgtcaaaagc agcagaggct cttctgaccc ccaaggggtg acgtgcggag      900
ctgctacact ctctgcagag agagtcagag gggacaacaa ggagtatgag tactcagtgg      960
agtgccagga ggacagtgcc tgcccagctg ctgaggagag tctgcccatt gaggtcatgg     1020
tggatgccgt tcacaagctc aagtatgaaa actacaccag cagcttcttc atcagggaca     1080
tcatcaaacc tgacccaccc aagaacttgc agctgaagcc attaaagaat ctcggcagg      1140 tggaggtcag ctgggagtac cctgacacct ggagtactcc acattcctac ttctccctga     1200
cattctgcgt tcaggtccag ggcaagagca agagagaaaa gaaagataga gtcttcacgg     1260
acaagacctc agccacggtc atctgccgca aaaatgccag cattagcgtg cgggcccagg     1320
accgctacta tagctcatct tggagcgaat gggcatctgt gccctgcagt tagaaataac     1380
ttgtttattg cagcttataa tggttacaaa taaagcaata gcatcacaaa tttcacaaat     1440 aaagcattt tttcactgca ttctagttgt ggtttgtcca aactcatcaa tgtatcttat     1500
catgtctggt gtttatt                                                    1517
```

<210> SEQ ID NO 24
<211> LENGTH: 4
<212> TYPE: PRT
<213> ORGANISM: Unknown
<220> FEATURE:
<223> OTHER INFORMATION: furin cleavage site

<400> SEQUENCE: 24

Arg Ala Lys Arg
1

<210> SEQ ID NO 25
<211> LENGTH: 1625
<212> TYPE: DNA
<213> ORGANISM: Artificial Sequence
<220> FEATURE:
<223> OTHER INFORMATION: hIL12 furin

<400> SEQUENCE: 25

```
atctgacctc gtcgacatgt gtcaccagca gttggtcatc tcttggtttt ccctggtttt       60
tctggcatct cccctcgtgg ccatatggga actgaagaaa gatgtttatg tcgtagaatt      120
ggattggtat ccggatgccc ctggagaaat ggtggtcctc acctgtgaca cccctgaaga      180
agatggtatc acctggacct tggaccagag cagtgaggtc ttaggctctg gcaaaaccct     240
```

```
gaccatccaa gtcaaagagt ttggagatgc tggccagtac acctgtcaca aaggaggcga      300
ggttctaagc cattcgctcc tgctgcttca caaaaaggaa gatggaattt ggtccactga      360
tattttaaag gaccagaaag aacccaaaaa taagacccttt ctaagatgcg aggccaagaa     420
ttattctgga cgtttcacct gctggtggct gacgacaatc agtactgatt tgacattcag      480
tgtcaaaagc agcagaggct cttctgaccc ccaagggtg acgtgcggag ctgctacact       540
ctctgcagag agagtcagag gggacaacaa ggagtatgag tactcagtgg agtgccagga     600
ggacagtgcc tgcccagctg ctgaggagag tctgcccatt gaggtcatgg tggatgccgt      660
tcacaagctc aagtatgaaa actacaccag cagcttcttc atcagggaca tcatcaaacc      720
tgacccaccc aagaacttgc agctgaagcc attaaagaat tctcggcagg tggaggtcag      780 ctggagtac cctgacacct ggagtactcc acattcctac ttctccctga cattctgcgt       840
tcaggtccag ggcaagagca agagagaaaa gaaagataga gtcttcacgg acaagacctc     900
agccacggtc atctgccgca aaaatgccag cattagcgtg cgggcccagg accgctacta     960
tagctcatct tggagcgaat gggcatctgt gccctgcagt cgtgctaagc gaagaaacct     1020
ccccgtggcc actccagacc caggaatgtt cccatgcctt caccactccc aaaacctgct    1080
gagggccgtc agcaacatgc tccagaaggc cagacaaact ctagaatttt acccttgcac     1140
ttctgaagag attgatcatg aagatatcac aaaagataaa accagcacag tggaggcctg     1200
tttaccattg gaattaacca agaatgagag ttgcctaaat tccagagaga cctctttcat     1260
aactaatggg agttgcctgg cctccagaaa gacctctttt atgatggccc tgtgccttag    1320
tagtatttat gaagacttga agatgtacca ggtggagttc aagaccatga atgcaaagct    1380
tctgatggat cctaagaggc agatctttct agatcaaaac atgctggcag ttattgatga     1440
gctgatgcag gccctgaatt tcaacagtga gactgtgcca caaaaatcct cccttgaaga    1500
accggatttt tataaaacta aaatcaagct ctgcatactt cttcatgctt tcagaattcg     1560
ggcagtgact attgatagag tgatgagcta tctgaatgct tcctaataac tcgagtcacc     1620
aggcg                                                                1625

<210> SEQ ID NO 26
<211> LENGTH: 445
<212> TYPE: DNA
<213> ORGANISM: Artificial Sequence
<220> FEATURE:
<223> OTHER INFORMATION: L5 revised SV40

<400> SEQUENCE: 26
aataaaaggt ttattctgtg gaatgtgtgt cagttagggt gtggaaagtc cccaggctcc       60
ccagcaggca gaagtatgca aagcatgcat ctcaattagt cagcaaccag gtgtggaaag     120
tccccaggct ccccagcagg cagaagtatg caaagcatgc atctcaatta gtcagcaacc     180
atagtcccgc ccctaactcc gcccatcccg ccctaactc cgcccagttc cgcccattct      240
ccgccccatg gctgactaat ttttttttatt tatgcagagg ccgaggccgc ctctgcctct    300
gagctattcc agaagtagtg aggaggcttt tttggaggcc taggcttttg caaaaagctt    360
tgcaaagatt taaataactt gtttattgca gcttataatg gttacaaata aagaatcgtt    420
tgtgttatgt ttcaacgtgt ttatt                                          445

<210> SEQ ID NO 27
<211> LENGTH: 502
<212> TYPE: DNA
<213> ORGANISM: Artificial Sequence
```

<220> FEATURE:
<223> OTHER INFORMATION: IX mIL7

<400> SEQUENCE: 27

```
atagggagac ccgcggccat gttccatgtt tcttttagat atatctttgg aattcctcca    60
ctgatccttg ttctgctgcc tgtcacatca tctgagtgcc acattaaaga caaagaaggt   120
aaagcatatg agagtgtact gatgatcagc atcgatgaat tggacaaaat gacaggaact   180
gatagtaatt gcccgaataa tgaaccaaac ttttttagaa acatgtatg tgatgataca    240
aaggaagctg cttttctaaa tcgtgctgct cgcaagttga agcaatttct taaaatgaat   300
atcagtgaag aattcaatgt ccacttacta acagtatcac aaggcacaca acactggtg    360
aactgcacaa gtaaggaaga aaaaaacgta aggaacaga aaaagaatga tgcatgtttc    420
ctaaagagac tactgagaga aataaaaact tgttggaata aaattttgaa gggcagtata   480
taaggccgct gtgccttcta gt                                             502
```

<210> SEQ ID NO 28
<211> LENGTH: 445
<212> TYPE: DNA
<213> ORGANISM: Artificial Sequence
<220> FEATURE:
<223> OTHER INFORMATION: L5 revised SV40 wt Empty

<400> SEQUENCE: 28

```
aataaaaggt ttattctgtg aatgtgtgt cagttagggt gtggaaagtc cccaggctcc     60
ccagcaggca gaagtatgca aagcatgcat ctcaattagt cagcaaccag gtgtggaaag   120
tccccaggct ccccagcagg cagaagtatg caaagcatgc atctcaatta gtcagcaacc   180
atagtcccgc ccctaactcc gcccatcccg ccctaactc cgcccagttc cgcccattct    240
ccgccccatg gctgactaat ttttttatt tatgcagagg ccgaggccgc ctcggcctct    300
gagctattcc agaagtagtg aggaggcttt tttggaggcc taggcttttg caaaaagctt   360
tgcaaagatt taaataactt gtttattgca gcttataatg gttacaaata agaatcgtt    420
tgtgttatgt ttcaacgtgt ttatt                                          445
```

<210> SEQ ID NO 29
<211> LENGTH: 525
<212> TYPE: DNA
<213> ORGANISM: Artificial Sequence
<220> FEATURE:
<223> OTHER INFORMATION: L5 revised EF1A Empty

<400> SEQUENCE: 29

```
aataaaaggt ttattaggcg gcctcccgt caccacccc cccaacccgc cccgaccgga      60
gctgagagta attcatacaa aaggactcgc ccctgccttg gggaatccca gggaccgtcg   120
ttaaactccc actaacgtag aacccagaga tcgctgcgtt cccgccccct cacccgcccg   180
ctctcgtcat cactgaggtg gagaagagca tgcgtgaggc tccggtgccc gtcagtgggc   240
agagcgcaca tcgcccacag tccccgagaa gttgggggga gggtcggca attgaaccgg   300
tgcctagaga aggtggcgcg gggtaaactg ggaaagtgat gtcgtgtact ggctccgcct   360
ttttcccgag ggtggggggag aaccgtatat aagtgcagta gtcgccgtga acgttctttt   420
tcgcaacggg tttgccgcca gaacacaatt taaataactt gtttattgca gcttataatg   480
gttacaaata agaatcgtt tgtgttatgt ttcaacgtgt ttatt                    525
```

<210> SEQ ID NO 30

```
<211> LENGTH: 502
<212> TYPE: DNA
<213> ORGANISM: Artificial Sequence
<220> FEATURE:
<223> OTHER INFORMATION: mIL7 no poly-A

<400> SEQUENCE: 30
atagggagac ccgcggccat gttccatgtt tcttttagat atatctttgg aattcctcca      60
ctgatccttg ttctgctgcc tgtcacatca tctgagtgcc acattaaaga caaagaaggt     120
aaagcatatg agagtgtact gatgatcagc atcgatgaat tggacaaaat gacaggaact     180
gatagtaatt gcccgaataa tgaaccaaac ttttttagaa acatgtatg tgatgataca      240
aaggaagctg cttttctaaa tcgtgctgct cgcaagttga agcaatttct taaaatgaat     300
atcagtgaag aattcaatgt ccacttacta acagtatcac aaggcacaca acactggtg     360
aactgcacaa gtaaggaaga aaaaaacgta aggaacaga aaagaatga tgcatgtttc      420
ctaaagagac tactgagaga atcaaaact tgttggaaca aattttgaa gggcagtata      480
taaggccgct gtgccttcta gt                                             502

<210> SEQ ID NO 31
<211> LENGTH: 456
<212> TYPE: DNA
<213> ORGANISM: Artificial Sequence
<220> FEATURE:
<223> OTHER INFORMATION: mGMCSF Kozak

<400> SEQUENCE: 31
atttgccacc atgtggctgc agaatttact tttcctgggc attgtggtct acagcctctc      60
agcacccacc cgctcaccca tcactgtcac ccggccttgg aagcatgtag aggccatcaa     120
agaagccctg aacctcctgg atgacatgcc tgtcacgttg aatgaagagg tagaagtcgt     180
ctctaacgag ttctccttca agaagctaac atgtgtgcag acccgcctga agatattcga     240
gcagggtcta cggggcaatt tcaccaaact caagggcgcc ttgaacatga cagccagcta     300
ctaccagaca tactgccccc caactccgga aacggactgt gaaacacaag ttaccaccta     360
tgcggatttc atagacagcc ttaaaaacctt tctgactgat atccccttgg aatgcaaaaa     420
accaggccaa aaatgaaaat aacttgttta ttgcag                              456

<210> SEQ ID NO 32
<211> LENGTH: 591
<212> TYPE: DNA
<213> ORGANISM: Unknown
<220> FEATURE:
<223> OTHER INFORMATION: adenoviral death protein

<400> SEQUENCE: 32
gaaaatgcct taatttacta agttacaaag ctaatgtcac cactaactgc tttactcgct      60
gcttgcaaaa caaattcaaa aagttagcat tataattaga ataggattta aaccccccgg     120
tcatttcctg ctcaatacca ttcccctgaa caattgactc tatgtgggat atgctccagc     180
gctacaacct tgaagtcagg cttcctggat gtcagcatct gactttggcc agcacctgtc     240
ccgcggattt gttccagtcc aactacagcg acccaccta acagagatga ccaacacaac     300
caacgcggcc gccgctaccg gacttacatc taccacaaat acaccccaag tttctgcctt     360
tgtcaataac tgggataact gggcatgtg gtggttctcc atagcgctta tgtttgtatg     420
ccttattatt atgtggctca tctgctgcct aaagcgcaaa cgcgcccgac cacccatcta     480
tagtcccatc attgtgctac acccaaacaa tgatggaatc catagattgg acggactgaa     540
```

```
acacatgttc ttttctctta cagtatgata ataaaaaaaa ataataaagc a         591
```

<210> SEQ ID NO 33
<211> LENGTH: 4509
<212> TYPE: DNA
<213> ORGANISM: Artificial Sequence
<220> FEATURE:
<223> OTHER INFORMATION: Costim IRES

<400> SEQUENCE: 33

```
atctgacctc gtcgacatgg cttgcaattg tcagttgatg caggatacac cactcctcaa   60
gtttccatgt ccaaggctca ttcttctctt tgtgctgctg attcgtcttt cacaagtgtc  120
ttcagatgtt gatgaacaac tgtccaagtc agtgaaagat aaggtattgc tgccttgccg  180
ttacaactct cctcatgaag atgagtctga agaccgaatc tactggcaaa acatgacaa   240
agtggtgctg tctgtcattg ctgggaaact aaaagtgtgg cccgagtata agaaccggac  300
tttatatgac aacactacct actctcttat catcctgggc ctggtccttt cagaccgggg  360
cacatacagc tgtgtcgttc aaaagaagga agaggaacg tatgaagtta aacacttggc   420
tttagtaaag ttgtccatca agctgacttc tctccccccc aacataactg agtctggaaa  480
cccatctgca gacactaaaa ggattacctg ctttgcttcc ggggttttcc caaagcctcg  540
cttctcttgg ttggaaaatg gaagagaatt acctggcatc aatacgacaa tttcccagga  600
tcctgaatct gaattgtaca ccattagtag ccaactagat ttcaatacga ctcgcaacca  660
caccattaag tgtctcatta aatatggaga tgctcacgtg tcagaggact tcacctggga  720
aaaaccccca gaagaccctc ctgatagcaa gaacacactt gtgctctttg ggcaggatt   780
cggcgcagta ataacagtcg tcgtcatcgt tgtcatcatc aaatgcttct gtaagcacag  840
aagctgtttc agaagaaatg aggcaagcag agaaacaaac aacagcctta ccttcgggcc  900
tgaagaagca ttagctgaac agaccgtctt cctttagtaa cgttactggc cgaagccgct  960
tggaataagg ccggtgtgcg tttgtctata tgttattttc caccatattg ccgtcttttg 1020
gcaatgtgag ggcccggaaa cctggccctg tcttcttgac gagcattcct aggggtcttt 1080
cccctctcgc caaaggaatg caaggtctgt tgaatgtcgt gaaggaagca gttcctctgg 1140
aagcttcttg aagacaaaca acgtctgtag cgaccctttg caggcagcgg aaccccccac 1200
ctggcgacag gtgcctctgc ggccaaaagc cacgtgtata agatacacct gcaaaggcgg 1260
cacaaccccca gtgccacgtt gtgagttgga tagttgtgga aagagtcaaa tggctctcct 1320
caagcgtatt caacaagggg ctgaaggatg cccagaaggt accccattgt atgggatctg 1380
atctggggcc tcggtgcaca tgctttacat gtgtttagtc gaggttaaaa aacgtctagg 1440
ccccccgaac cacggggacg tggttttcct ttgaaaaaca cgatgataat atggaccagc 1500
acacacttga tgtggaggat accgcggatg ccagacatcc agcaggtact cgtgcccct  1560
cggatgcggc gctcctcaga gataccgggc tcctcgcgga cgctgcgctc ctctcagata 1620
ctgtgcgccc cacaaatgcc gcgctcccca cggatgctgc ctaccctgcg gttaatgttc 1680
gggatcgcga ggccgcgtgg ccgcctgcac tgaacttctg ttcccgccac ccaaagctct 1740
atggcctagt cgctttggtt ttgctgcttc tgatcgccgc ctgtgttcct atcttcaccc 1800
gcaccgagcc tcggccagcg ctcacaatca ccacctcgcc caacctgggt acccgagaga 1860
ataatgcaga ccaggtcacc cctgtttccc acattggctg ccccaacact acacaacagg 1920
gctctcctgt gttcgccaag ctactggcta aaaaccaagc atcgttgtgc aatacaactc 1980
```

```
tgaactggca cagccaagat ggagctggga gctcatacct atctcaaggt ctgaggtacg   2040
aagaagacaa aaaggagttg gtggtagaca gtcccgggct ctactacgta tttttggaac   2100
tgaagctcag tccaacattc acaaacacag gccacaaggt gcagggctgg gtctctcttg   2160
ttttgcaagc aaagcctcag gtagatgact ttgacaactt ggccctgaca gtggaactgt   2220
tcccttgctc catggagaac aagttagtgg accgttcctg gagtcaactg ttgctcctga   2280
aggctggcca ccgcctcagt gtgggtctga ggcttatct gcatggagcc caggatgcat    2340
acagagactg ggagctgtct tatcccaaca ccaccagctt tggactcttt cttgtgaaac   2400
ccgacaaccc atgggaatga ggtttccaca actgataaaa ctcgtgcaac ttgaaactcc   2460
gcctggtctt tccaggtcta gaggggttac actttgtact gtgctcgact ccacgcccgg   2520
tccactggcg ggtgttagta gcagcactgt tgtttcgtag cggagcatgg tggccgtggg   2580
aactcctcct tggtgacaag ggcccacggg gccgaaagcc acgtccagac ggacccacca   2640
tgtgtgcaac cccagcacgg caacttttac tgcgaacacc accttaaggt gacactggta   2700
ctggtactcg gtcactggtg acaggctaag gatgcccttc aggtaccccg aggtaacacg   2760
ggacactcgg gatctgagaa ggggattggg acttctttaa aagtgcccag tttaaaaagc   2820
ttctacgcct gaataggcga ccggaggccg gcgcctttcc attcccact actaaatcca    2880
tggcttcaac ccgtgccaag cccacgctac ctctgctcct ggccctggtc accgttgtga   2940
tccctgggcc tggtgatgct caggtatcca tccatcccag agaagccttc ctgccccagg   3000
gtgggtccgt gcaggtgaac tgttcttcct catgcaagga ggacctcagc ctgggcttgg   3060
agactcagtg gctgaaagat gagctcgaga gtggacccaa ctggaagctg tttgagctga   3120
gcgagatcgg ggaggacagc agtccgctgt gctttgagaa ctgtggcacc gtgcagtcgt   3180
ccgcttccgc taccatcacc gtgtattcgt ttccggagag tgtggagctg agacctctgc   3240
cagcctggca gcaagtaggc aaggacctca ccctgcgctg ccacgtggat ggtggagcac   3300
cgcggaccca gctctcagca gtgctgctcc gtggggagga gatactgagc cgccagccag   3360
tgggtgggca ccccaaggac cccaaggaga tcacattcac ggtgctggct agcagagggg   3420
accacggagc caatttctca tgccgcacag aactggatct caggccgcaa gggctggcat   3480
tgttctctaa tgtctccgag gccaggagcc tccggacttt cgatcttcca gctaccatcc   3540
caaagctcga cacccctgac ctcctggagg tgggcaccca gcagaagttg ttttgctccc   3600
tggaaggcct gtttcctgcc tctgaagctc ggatatacct ggagctggga ggccagatgc   3660
cgacccagga gagcacaaac agcagtgact ctgtgtcagc cactgccttg gtagaggtga   3720
ctgaggagtt cgacagaacc ctgccgctgc gctgcgtttt ggagctagcg gaccagatcc   3780
tggagacgca gaggacctta acagtctaca ctttttcagc tccggtcctg accctgagcc   3840
agctggaggt ctcggaaggg agccaagtaa ctgtgaagtg tgaagcccac agtgggtcga   3900
aggtggttct tctgagcggc gtcgagccta ggccacccac cccgcaggtc caattcacac   3960
tgaatgccag ctcggaggat cacaaacgaa gcttcttttg ctctgccgct ctggaggtgg   4020
cgggaaagtt cctgtttaaa aaccagaccc tggaactgca cgtgctgtat ggtcctcggc   4080
tggacgagac ggactgcttg gggaactgga cctggcaaga ggggtctcag cagactctga   4140
aatgccaggc ctgggggaac ccatctccta agatgacctg cagacggaag gcagatggtg   4200
ccctgctgcc catcggggtg gtgaagtctg tcaaacagga gatgaatggt acatacgtgt   4260
gccatgcctt tagctcccat gggaatgtca ccaggaatgt gtacctgaca gtactgtacc   4320
actctcaaaa taactggact ataatcattc tggtgccagt actgctggtc attgtgggcc   4380
```

| | |
|---|---|
| tcgtgatggc agcctcttat gtttataacc gccagagaaa gatcaggata tacaagttac | 4440 |
| agaaggctca ggaggaggcc ataaaactca agggacaagc cccacctccc tgactcgagt | 4500 |
| caccaggcg | 4509 |

<210> SEQ ID NO 34
<211> LENGTH: 951
<212> TYPE: DNA
<213> ORGANISM: Artificial Sequence
<220> FEATURE:
<223> OTHER INFORMATION: 19k mCD80

<400> SEQUENCE: 34

| | |
|---|---|
| atctgacctc atggcttgca attgtcagtt gatgcaggat acaccactcc tcaagtttcc | 60 |
| atgtccaagg ctcattcttc tctttgtgct gctgattcgt ctttcacaag tgtcttcaga | 120 |
| tgttgatgaa caactgtcca gtcagtgaa agataaggta ttgctgcctt gccgttacaa | 180 |
| ctctcctcat gaagatgagt ctgaagaccg aatctactgg caaaaacatg acaaagtggt | 240 |
| gctgtctgtc attgctggga actaaaagt gtggcccgag tataagaacc ggactttata | 300 |
| tgacaacact acctactctc ttatcatcct gggcctggtc ctttcagacc ggggcacata | 360 |
| cagctgtgtc gttcaaaaga aggaaagagg aacgtatgaa gttaaacact ggctttagt | 420 |
| aaagttgtcc atcaaagctg acttctctac ccccaacata actgagtctg aaacccatc | 480 |
| tgcagacact aaaaggatta cctgcttgc ttccgggggt ttcccaaagc ctcgcttctc | 540 |
| ttggttggaa atggaagag aattacctgg catcaatacg acaatttccc aggatcctga | 600 |
| atctgaattg tacaccatta gtagccaact agatttcaat acgactcgca accacaccat | 660 |
| taagtgtctc attaaatatg gagatgctca cgtgtcagag gacttcacct gggaaaaacc | 720 |
| cccagaagac cctcctgata gcaagaacac acttgtgctc tttggggcag gattcggcgc | 780 |
| agtaataaca gtcgtcgtca tcgttgtcat catcaaatgc ttctgtaagc acagaagctg | 840 |
| tttcagaaga aatgaggcaa gcagagaaac aaacaacagc cttaccttcg ggcctgaaga | 900 |
| agcattagct gaacagaccg tcttcctta gtcaggtgaa tctgggtcac c | 951 |

<210> SEQ ID NO 35
<211> LENGTH: 967
<212> TYPE: DNA
<213> ORGANISM: Artificial Sequence
<220> FEATURE:
<223> OTHER INFORMATION: IX mCD137L

<400> SEQUENCE: 35

| | |
|---|---|
| atagggagac ccgcggccat ggaccagcac acacttgatg tggaggatac cgcggatgcc | 60 |
| agacatccag caggtacttc gtgccctcg gatgcggcgc tcctcagaga taccgggctc | 120 |
| ctcgcggacg ctgcgctcct ctcagatact gtgcgcccca caaatgccgc gctccccacg | 180 |
| gatgctgcct accctgcggt taatgttcgg gatcgcgagg ccgcgtggcc gcctgcactg | 240 |
| aacttctgtt ccgccaccc aaagctctat ggcctagtcg ctttggtttt gctgcttctg | 300 |
| atcgccgcct gtgttcctat cttcacccgc accgagcctc ggccagcgct cacaatcacc | 360 |
| acctcgccca acctgggtac ccgagagaat aatgcagacc aggtcacccc tgtttcccac | 420 |
| attggctgcc ccaacactac acaacagggc tctcctgtgt cgccaagct actggctaaa | 480 |
| aaccaagcat cgttgtgcaa tacaactctg aactggcaca gccaagatgg agctgggagc | 540 |
| tcataccctat ctcaaggtct gaggtacgaa gaagacaaaa aggagttggt ggtagacagt | 600 |

```
cccgggctct actacgtatt tttggaactg aagctcagtc caacattcac aaacacaggc    660
cacaaggtgc agggctgggt ctctcttgtt ttgcaagcaa agcctcaggt agatgacttt    720
gacaacttgg ccctgacagt ggaactgttc ccttgctcca tggagaacaa gttagtggac    780
cgttcctgga gtcaactgtt gctcctgaag gctggccacc gcctcagtgt gggtctgagg    840
gcttatctgc atggagccca ggatgcatac agagactggg agctgtctta tcccaacacc    900
accagctttg gactctttct tgtgaaaccc gacaacccat gggaatgagg ccgctgtgcc    960
ttctagt                                                              967
```

<210> SEQ ID NO 36
<211> LENGTH: 1649
<212> TYPE: DNA
<213> ORGANISM: Artificial Sequence
<220> FEATURE:
<223> OTHER INFORMATION: L5 mICAM1

<400> SEQUENCE: 36

```
cgccagaaca catttatggc ttcaacccgt gccaagccca cgctacctct gctcctggcc     60
ctggtcaccg ttgtgatccc tgggcctggt gatgctcagg tatccatcca tcccagagaa    120
gccttcctgc cccagggtgg gtccgtgcag gtgaactgtt cttcctcatg caaggaggac    180
ctcagcctgg gcttggagac tcagtggctg aaagatgagc tcgagagtgg acccaactgg    240
aagctgtttg agctgagcga gatcggggag gacagcagtc cgctgtgctt tgagaactgt    300
ggcaccgtgc agtcgtccgc ttccgctacc atcaccgtgt attcgtttcc ggagagtgtg    360
gagctgagac tctgccagc ctggcagcaa gtaggcaagg acctcaccct gcgctgccac    420
gtggatggtg agcaccgcg acccagctc tcagcagtgc tgctccgtgg ggaggagata    480
ctgagccgcc agccagtggg tgggcacccc aaggacccca aggagatcac attcacggtg    540
ctggctagca gaggggacca cggagccaat ttctcatgcc gcacagaact ggatctcagg    600
ccgcaagggc tggcattgtt ctctaatgtc tccgaggcca ggagcctccg gactttcgat    660
cttccagcta ccatcccaaa gctcgacacc cctgacctcc tggaggtggg cacccagcag    720
aagttgtttt gctccctgga aggcctgttt cctgcctctg aagctcggat atacctggag    780
ctgggaggcc agatgccgac ccaggagagc acaaacagca gtgactctgt gtcagccact    840
gccttggtag aggtgactga ggagttcgac agaaccctgc cgctgcgctg cgttttggag    900
ctagcggacc agatcctgga gacgcagagg accttaacag tctacaactt ttcagctccg    960
gtcctgaccc tgagccagct ggaggtctcg gaagggagcc aagtaactgt gaagtgtgaa   1020
gcccacagtg ggtcgaaggt ggttcttctg agcggcgtcg agcctaggcc acccacccg    1080 caggtccaat tcacactgaa tgccagctcg gaggatcaca aacgaagctt cttttgctct   1140
gccgctctgg aggtggcggg aaagttcctg tttaaaaacc agaccctgga actgcacgtg   1200
ctgtatggtc ctcggctgga cgagacggac tgcttgggga ctggacctg caagaggggg   1260 tctcagcaga ctctgaaatg ccaggcctgg gggaacccat ctcctaagat gacctgcaga   1320
cggaaggcag atggtgccct gctgcccatc ggggtggtga agtctgtcaa acaggagatg   1380
aatggtacat acgtgtgcca tgcctttagc tcccatggga atgtcaccag gaatgtgtac   1440
ctgacagtac tgtaccactc tcaaaataac tggactataa tcattctggt gccagtactg   1500
ctggtcattg tgggcctcgt gatggcagcc tcttatgttt ataaccgcca gagaaagatc   1560
aggatataca agttacagaa ggctcaggag gaggccataa aactcaaggg acaagcccca   1620
cctccctgaa ataaacttgt ttattgcag                                     1649
```

<210> SEQ ID NO 37
<211> LENGTH: 72
<212> TYPE: DNA
<213> ORGANISM: Human adenovirus 35

<400> SEQUENCE: 37

```
aataaaaaaa attccagaat caatgaataa ataaacgagc ttgttgttga tttaaaatca    60
agtgttttta tt                                                        72
```

<210> SEQ ID NO 38
<211> LENGTH: 23
<212> TYPE: DNA
<213> ORGANISM: Human adenovirus 35

<400> SEQUENCE: 38

```
aataaagttt aagtgttttt att                                            23
```

<210> SEQ ID NO 39
<211> LENGTH: 789
<212> TYPE: DNA
<213> ORGANISM: Artificial Sequence
<220> FEATURE:
<223> OTHER INFORMATION: Ad35 IX-E2 cassette

<400> SEQUENCE: 39

```
tcgagatcgg tggtccaggg cataccgtgc gcgaaaaatg aaataaaata cacctttttt    60
cgattgtacg tatttttatt tacggtaaat ggcccgcctg gctgaccgcc caacgacccc   120
cgcccattga cgtcaataat gacgtatgtt cccatagtaa cgccaatagg gactttccat   180
tgacgtcaat gggtggagta tttacggtaa actgcccact tggcagtaca tcaagtgtat   240
catatgccaa gtacgccccc tattgacgtc aatgacggta aatggcccgc ctggcattat   300
gcccagtaca tgaccttatg gactttcct acttggcagt acatctacgt attagtcatc    360
gctattacca tggtgatgcg gttttggcag tacatcaatg ggcgtggata gcggtttgac   420
tcacggggat ttccaagtct ccacccctt gacgtcaatg ggagtttgtt ttggcaccaa    480
aatcaacggg actttccaaa atgtcgtaac aactccgccc cattgacgca aatgggcggt   540
aggcgtgtac ggtgggaggt ctatataagc agagctctct ggctaactag agaacccact   600
gcttactggc ttatcgaaat taatacgact cactataggg agacccgcgg ccgctgtgcc   660
ttctagttgc cagccatctg ttgtttgccc ctcccccgtg ccttccttga ccctggaagg   720
tgccactccc actgtccttt cctaataaaa acacttgatt taaatcaac aacaagctcg    780 tttatttat                                                           789
```

<210> SEQ ID NO 40
<211> LENGTH: 560
<212> TYPE: DNA
<213> ORGANISM: Artificial Sequence
<220> FEATURE:
<223> OTHER INFORMATION: Ad35 L5-E4 cassette

<400> SEQUENCE: 40

```
tttcttttct tacattacag aagacgacaa ctaaaataaa aggtttatta ggcggcctcc    60
ccgtcaccac ccccccccaac ccgccccgac cggagctgag agtaattcat acaaaaggac  120
tcgcccctgc cttggggaat cccagggacc gtcgttaaac tcccactaac gtagaaccca   180
gagatcgctg cgttcccgcc ccctcacccg ccgctctcg tcatcactga ggtggagaag    240
```

| | |
|---|---|
| agcatgcgtg aggctccggt gcccgtcagt gggcagagcg cacatcgccc acagtccccg | 300 |
| agaagttggg gggaggggtc ggcaattgaa ccggtgccta gagaaggtgg cgcggggtaa | 360 |
| actgggaaag tgatgtcgtg tactggctcc gccttttttcc cgagggtggg ggagaaccgt | 420 |
| atataagtgc agtagtcgcc gtgaacgttc tttttcgcaa cgggtttgcc gccagaacac | 480 |
| aatttaaata acttgtttat tgcagcttat aatggttaca aataaagttt aagtgttttt | 540 |
| atttaaaatc acaaaattcg | 560 |

<210> SEQ ID NO 41
<211> LENGTH: 34794
<212> TYPE: DNA
<213> ORGANISM: Human adenovirus 35

<400> SEQUENCE: 41

| | |
|---|---|
| catcatcaat aatataccttt atagatggaa tggtgccaat atgtaaatga ggtgatttta | 60 |
| aaaagtgtgg gccgtgtggt gattggctgt gggggttaacg gttaaaaggg gcggcgcggc | 120 |
| cgtgggaaaa tgacgtttta tgggggtgga gttttttttgc aagttgtcgc gggaaatgtt | 180 |
| acgcataaaa aggcttcttt tctcacggaa ctacttagtt ttcccacggt atttaacagg | 240 |
| aaatgaggta gttttgaccg gatgcaagtg aaaattgctg attttcgcgc gaaaactgaa | 300 |
| tgaggaagtg ttttctgaa taatgtggta tttatggcag ggtggagtat ttgttcaggg | 360 |
| ccaggtagac tttgacccat tacgtggagg tttcgattac cgtgttttt acctgaattt | 420 |
| ccgcgtaccg tgtcaaagtc ttctgttttt acgtaggtgt cagctgatcg ctagggtatt | 480 |
| tataccctcag ggtttgtgtc aagaggccac tcttgagtgc cagcgagaag agttttctcc | 540 |
| tctgcgccgg cagtttaata ataaaaaaat gagagatttg cgatttctgc ctcaggaaat | 600 |
| aatctctgct gagactggaa atgaaatatt ggagcttgtg gtgcacgccc tgatgggaga | 660 |
| cgatccggag ccacctgtgc agcttttttga gcctcctacg cttcaggaac tgtatgattt | 720 |
| agaggtagg ggatcggagg attctaatga ggaagctgtg aatggctttt ttaccgattc | 780 |
| tatgcttttta gctgctaatg aaggattaga attagatccg cctttggaca cttttcaatac | 840 |
| tccagggtg attgtggaaa gcggtacagg tgtaagaaaa ttacctgatt tgagttccgt | 900 |
| ggactgtgat ttgcactgct atgaagacgg gttttcctccg agtgatgagg aggaccatga | 960 |
| aaaggagcag tccatgcaga ctgcagcggg tgagggagtg aaggctgcca atgttggttt | 1020 |
| tcagttggat tgcccggagc ttcctggaca tggctgtaag tcttgtgaat ttcacaggaa | 1080 |
| aaatactgga gtaaaggaac tgttatgttc gctttgttat atgagaacgc actgccactt | 1140 |
| tatttacagt aagtgtgttt aagttaaaat ttaaggaat atgctgtttt tcacatgtat | 1200 |
| attgagtgtg agttttgtgc ttcttattat aggtcctgtg tctgatgctg atgaatcacc | 1260 |
| atctcctgat tctactacct cacctcctga tattcaagca cctgttcctg tggacgtgcg | 1320 |
| caagcccatt cctgtgaagc ttaagcctgg gaaacgtcca gcagtggaga acttgaggga | 1380 |
| cttgttacag ggtggggacg gaccctttgga cttgagtaca cggaaacgtc caagacaata | 1440 |
| agtgttccat atccgtgttt acttaaggtg acgtcaatat ttgtgtgaga gtgcaatgta | 1500 |
| ataaaaatat gttaactgtt cactggtttt tattgctttt tgggcgggga ctcaggtata | 1560 |
| taagtagaag cagacctgtg tggttagctc ataggagctg gctttcatcc atggaggttt | 1620 |
| gggccattt ggaagacctt aggaagacta ggcaactgtt agagagcgct tcggacggag | 1680 |
| tctccggttt ttggagattc tggttcgcta gtgaattagc tagggtagtt tttaggataa | 1740 |
| aacaggacta taaacaagaa tttgaaaagt tgttggtaga ttgcccagga cttttttgaag | 1800 |

-continued

```
ctcttaattt gggccatcag gttcacttta agaaaaagt tttatcagtt ttagactttt      1860
caacccagg  tagaactgct gctgctgtgg cttttcttac ttttatatta gataaatgga     1920
tcccgcagac tcatttcagc aggggatacg ttttggattt catagccaca gcattgtgga     1980
gaacatggaa ggttcgcaag atgaggacaa tcttaggtta ctggccagtg cagcctttgg     2040
gtgtagcggg aatcctgagg catccaccgg tcatgccagc ggttctggag gaggaacagc    2100
aagaggacaa cccgagagcc ggcctggacc ctccagtgga ggaggcggag tagctgactt    2160
gtctcctgaa ctgcaacggg tgcttactgg atctacgtcc actggacggg atagggcgt     2220
taagagggag agggcatcca gtggtactga tgctagatct gagttggctt taagtttaat    2280
gagtcgcaga cgtcctgaaa ccatttggtg gcatgaggtt cagaaagagg aagggatga     2340
agtttctgta ttgcaggaga aatattcact ggaacaggtg aaaacatgtt ggttggagcc    2400
agaggatgat tgggcggtgg ccattaaaaa ttatgccaag atagctttga ggcctgataa    2460
acagtataag atcagtagac ggattaatat ccggaatgct tgttacatat ctggaaatgg    2520
ggctgaggtg gtaatagata ctcaagacaa gacagttatt agatgctgca tgatggatat    2580
gtggcctgga gtagtcggta tggaagcagt cacttttgta aatgttaagt ttaggggaga    2640
tggttataat ggaatagtgt ttatggccaa taccaaactt atattgcatg gttgtagctt    2700
ttttggtttc aacaatacct gtgtagatgc ctggggacag gttagtgtac ggggtgtag    2760
tttctatgcg tgttggattg ccacagctgg cagaaccaag agtcaattgt ctctgaagaa    2820
atgcatattc caaagatgta acctgggcat tctgaatgaa ggcgaagcaa gggtccgtca    2880
ctgcgcttct acagatactg gatgttttat tttaattaag ggaaatgcca gcgtaaagca    2940
taacatgatt tgtggtgctt ccgatgagag gccttatcaa atgctcactt gtgctggtgg    3000
gcattgtaat atgctggcta ctgtgcatat tgtttcccat caacgcaaaa aatggcctgt    3060
ttttgatcac aatgtgttga ccaagtgcac catgcatgca ggtgggcgta gaggaatgtt    3120
tatgccttac cagtgtaaca tgaatcatgt gaaagtgttg ttggaaccag atgccttttc    3180
cagaatgagc ctaacaggaa tctttgacat gaacacgcaa atctggaaga tcctgaggta    3240
tgatgatacg agatcgaggg tgcgcgcatg cgaatgcgga ggcaagcatg ccaggttcca    3300
gccggtgtgt gtagatgtga ccgaagatct cagaccggat catttggtta ttgcccgcac    3360
tggagcagag ttcggatcca gtggagaaga aactgactaa ggtgagtatt gggaaaactt    3420
tggggtggga ttttcagatg gacagattga gtaaaaattt gttttttctg tcttgcagct    3480
gacatgagtg gaaatgcttc ttttaagggg ggagtcttca gcccttatct gacagggcgt    3540
ctcccatcct gggcaggagt tcgtcagaat gttatgggat ctactgtgga tggaagaccc    3600
gttcaacccg ccaattcttc aacgctgacc tatgctactt taagttcttc accttttggac   3660
gcagctgcag ccgctgccgc cgcctctgtc gccgctaaca ctgtgcttgg aatgggttac    3720
tatgaaagca tcgtggctaa ttccacttcc tctaataacc cttctacact gactcaggac    3780
aagttacttg tcctttttggc ccagctggag gctttgaccc aacgtctggg tgaactttct    3840
cagcaggtgg ccgagttgcg agtacaaact gagtctgctg tcggcacggc aaagtctaaa    3900
taaaaaaat tccagaatca atgaataaat aaacgagctt gttgttgatt taaaatcaag     3960
tgttttatt tcatttttcg cgcacggtat gccctggacc accgatctcg atcattgaga    4020
actcggtgga ttttttccag aatcctatag aggtgggatt gaatgtttag atacatgggc    4080
attaggccgt ctttggggtg gagatagctc cattgaaggg attcatgctc cggggtagtg    4140
```

```
ttgtaaatca cccagtcata acaaggtcgc agtgcatggt gttgcacaat atcttttaga    4200
agtaggctga ttgccacaga taagcccttg gtgtaggtgt ttacaaaccg gttgagctgg    4260
gaggggtgca ttcgaggtga aattatgtgc attttggatt ggattttaa gttggcaata    4320
ttgccgccaa gatcccgtct tgggttcatg ttatgaagga ctaccaagac ggtgtatccg    4380
gtacatttag gaaatttatc gtgcagcttg gatggaaaag cgtggaaaaa tttggagaca    4440
cccttgtgtc ctccgagatt ttccatgcac tcatccatga taatagcaat ggggccgtgg    4500
gcagcggcgc gggcaaacac gttccgtggg tctgacacat catagttatg ttcctgagtt    4560
aaatcatcat aagccatttt aatgaatttg gggcggagcg taccagattg ggtatgaat     4620
gttccttcgg gccccggagc atagttcccc tcacagattt gcatttccca agctttcagt    4680
tctgagggtg gaatcatgtc cacctggggg gctatgaaga acaccgtttc ggggcgggg    4740
gtgattagtt gggatgatag caagtttctg agcaattgag atttgccaca tccggtgggg    4800
ccataaataa ttccgattac aggttgcagg tggtagttta gggaacggca actgccgtct    4860
tctcgaagca agggggccac ctcgttcatc atttcccttta catgcatatt ttcccgcacc    4920
aaatccatta ggaggcgctc tcctcctagt gatagaagtt cttgtagtga ggaaaagttt    4980
ttcagcggtt ttagaccgtc agccatgggc attttggaaa gagtttgctg caaaagttct    5040
agtctgttcc acagttcagt gatgtgttct atggcatctc gatccagcag acctcctcgt    5100
ttcgcgggtt tggacggctc ctggagtagg gtatgagacg atgggcgtcc agcgctgcca    5160
gggttcggtc cttccagggt ctcagtgttc gagtcagggt tgtttccgtc acagtgaagg    5220
ggtgtgcgcc tgcttgggcg cttgccaggg tgcgcttcag actcattctg ctggtggaga    5280
acttctgtcg cttggcgccc tgtatgtcgg ccaagtagca gtttaccatg agttcgtagt    5340
tgagcgcctc ggctgcgtgg cctttggcgc ggagcttacc tttggaagtt ttcttgcata    5400
ccgggcagta taggcatttc agcgcataca gcttgggcgc aaggaaaatg gattctgggg    5460
agtatgcatc cgcgccgcag gaggcgcaaa cagtttcaca ttccaccagc caggttaaat    5520
ccggttcatt ggggtcaaaa acaagttttc cgccatattt tttgatgcgt ttcttacctt    5580
tggtctccat aagttcgtgt cctcgttgag tgacaaacag gctgtccgta tctccgtaga    5640
ctgattttac aggcctcttc tccagtggag tgcctcggtc ttcttcgtac aggaactctg    5700
accactctga tacaaaggcg cgcgtccagg ccagcacaaa ggaggctatg tgggaggggt    5760
agcgatcgtt gtcaaccagg gggtccacct tttccaaagt atgcaaacac atgtcaccct    5820
cttcaacatc caggaatgtg attggcttgt aggtgtattt cacgtgacct gggggtccccg    5880
ctgggggggt ataaaagggg gcggttcttt gctcttcctc actgtcttcc ggatcgctgt    5940
ccaggaacgt cagctgttgg ggtaggtatt ccctctcgaa ggcgggcatg acctctgcac    6000
tcaggttgtc agtttctaag aacgaggagg atttgatatt gacagtgccg gttgagatgc    6060
ctttcatgag gttttcgtcc atttggtcag aaaacacaat ttttttattg tcaagtttgg    6120
tggcaaatga tccatacagg gcgttggata aagtttggc aatggatcgc atggtttggt     6180
tcttttcctt gtccgcgcgc tctttggcgg cgatgttgag ttggacatac tcgcgtgcca    6240
ggcacttcca ttcggggaag atagttgtta attcatctgg cacgattctc acttgccacc    6300
ctcgattatg caaggtaatt aaatccacac tggtggccac ctcgcctcga aggggttcat    6360
tggtccaaca gagcctacct cctttcctag aacagaaagg gggaagtggg tctagcataa    6420
gttcatcggg agggtctgca tccatggtaa agattcccgg aagtaaatcc ttatcaaaat    6480
agctgatggg agtgggggtca tctaaggcca tttgccattc tcgagctgcc agtgcgcgct    6540
```

```
catatgggtt aaggggactg ccccagggca tgggatgggt gagagcagag gcatacatgc    6600
cacagatgtc atagacgtag atgggatcct caaagatgcc tatgtaggtt ggatagcatc    6660
gcccccctct gatacttgct cgcacatagt catatagttc atgtgatggc gctagcagcc    6720
ccggacccaa gttggtgcga ttgggttttt ctgttctgta gacgatctgg cgaaagatgg    6780
cgtgagaatt ggaagagatg gtgggtcttt gaaaaatgtt gaaatgggca tgaggtagac    6840
ctacagagtc tctgacaaag tgggcataag attcttgaag cttggttacc agttcggcgg    6900
tgacaagtac gtctagggcg cagtagtcaa gtgtttcttg aatgatgtca taacctggtt    6960
ggttttctt tcccacagt tcgcggttga gaaggtattc ttcgcgatcc ttccagtact      7020
cttctagcgg aaacccgtct ttgtctgcac ggtaagatcc tagcatgtag aactgattaa    7080
ctgccttgta agggcagcag cccttctcta cgggtagaga gtatgcttga gcagttttc     7140
gtagcgaagc gtgagtaagg gcaaaggtgt ctctgaccat gactttgaga aattggtatt    7200
tgaagtccat gtcgtcacag gctccctgtt cccagagttg gaagtctacc cgtttcttgt    7260
aggcggggtt gggcaaagcg aaagtaacat cattgaagag aatcttaccg gctctgggca    7320
taaaattgcg agtgatgcgg aaaggctgtg gtacttccgc tcgattgttg atcacctggg    7380
cagctaggac gatttcgtcg aaaccgttga tgttgtgtcc tacgatgtat aattctatga    7440
aacgcggcgt gcctctgacg tgaggtagct tactgagctc atcaaaggtt aggtctgtgg    7500
ggtcagataa ggcgtagtgt tcgagagccc attcgtgcag gtgaggattt gcatgtagga    7560
atgatgacca aagatctacc gccagtgctg tttgtaactg gtcccgatac tgacgaaaat    7620
gccggccaat tgccattttt tctggagtga cacagtagaa ggttctgggg tcttgttgcc    7680
atcgatccca cttgagttta atggctagat cgtgggccat gttgacgaga cgctcttctc    7740
ctgagagttt catgaccagc atgaaaggaa ctagttgttt gccaaaggat cccatccagg    7800
tgtaagtttc cacatcgtag gtcaggaaga gtctttctgt gcgaggatga gagccgatcg    7860
ggaagaactg gatttcctgc caccagttgg aggattggct gttgatgtga tggaagtaga    7920
agtttctgcg gcgcgccgag cattcgtgtt tgtgcttgta cagacggccg cagtagtcgc    7980
agcgttgcac gggttgtatc tcgtgaatga gctgtacctg gcttcccttg acgagaaatt    8040
tcagtgggaa gccgaggcct ggcgattgta tctcgtgctc ttctatattc gctgtatcgg    8100
cctgttcatc ttctgtttcg atggtggtca tgctgacgag cccccgcggg aggcaagtcc    8160
agacctcggc gcgggagggg cggagctgaa ggacgagagc gcgcaggctg gagctgtcca    8220
gagtcctgag acgctgcgga ctcaggttag taggtaggga cagaagatta acttgcatga    8280
tcttttccag ggcgtgcggg aggttcagat ggtacttgat ttccacaggt tcgtttgtag    8340
agacgtcaat ggcttgcagg gttccgtgtc ctttgggcgc cactaccgta cctttgtttt    8400
ttcttttgat cggtggtggc tctcttgctt cttgcatgct cagaagcggt gacggggacg    8460
cgcgccgggc ggcagcggtt gttccggacc cggggggcatg gctggtagtg gcacgtcggc    8520
gccgcgcacg ggcaggttct ggtattgcgc tctgagaaga cttgcgtgcg ccaccacgcg    8580
tcgattgacg tcttgtatct gacgtctctg ggtgaaagct accggccccg tgagcttgaa    8640
cctgaaagag agttcaacag aatcaatttc ggtatcgtta acggcagctt gtctcagtat    8700
ttcttgtacg tcaccagagt tgtcctggta ggcgatctcc gccatgaact gctcgatttc    8760
ttcctcctga agatctccgc gacccgctct ttcgacggtg gccgcgaggt cattggagat    8820
acggcccatg agttgggaga atgcattcat gcccgcctcg ttccagacgc ggctgtaaac    8880
```

```
cacggcccc   tcggagtctc   ttgcgcgcat   caccacctga   gcgaggttaa   gctccacgtg    8940
tctggtgaag   accgcatagt   tgcataggcg   ctgaaaaagg   tagttgagtg   tggtggcaat    9000
gtgttcggcg   acgaagaaat   acatgatcca   tcgtctcagc   ggcatttcgc   taacatcgcc    9060
cagagcttcc   aagcgctcca   tggcctcgta   gaagtccacg   gcaaaattaa   aaaactggga    9120
gtttcgcgcg   gacacggtca   attcctcctc   gagaagacgg   atgagttcgg   ctatggtggc    9180
ccgtacttcg   cgttcgaagg   ctcccgggat   ctcttcttcc   tcttctatct   cttcttccac    9240
taacatctct   tcttcgtctt   caggcggggg   cggagggggc   acgcggcgac   gtcgacggcg    9300
cacgggcaaa   cggtcgatga   atcgttcaat   gacctctccg   cggcggcggc   gcatggtttc    9360
agtgacggcg   cggccgttct   cgcgcggtcg   cagagtaaaa   acaccgccgc   gcatctcctt    9420
aaagtggtga   ctgggaggtt   ctccgtttgg   gagggagagg   gcgctgatta   tacattttat    9480
taattggccc   gtagggactg   cgcgcagaga   tctgatcgtg   tcaagatcca   cgggatctga    9540
aaacctttcg   acgaaagcgt   ctaaccagtc   acagtcacaa   ggtaggctga   gtacggcttc    9600
ttgtgggcgg   gggtggttat   gtgttcggtc   tgggtcttct   gtttcttctt   catctcggga    9660
aggtgagacg   atgctgctgg   tgatgaaatt   aaagtaggca   gttctaagac   ggcggatggt    9720
ggcgaggagc   accaggtctt   tgggtccggc   ttgctggata   cgcaggcgat   tggccattcc    9780
ccaagcatta   tcctgacatc   tagcaagatc   tttgtagtag   tcttgcatga   gccgttctac    9840
gggcacttct   tcctcacccg   ttctgccatg   catacgtgtg   agtccaaatc   cgcgcattgg    9900
ttgtaccagt   gccaagtcag   ctacgactct   ttcggcgagg   atggcttgct   gtacttgggt    9960
aagggtggct   tgaaagtcat   caaaatccac   aaagcggtgg   taagcccctg   tattaatggt   10020
gtaagcacag   ttggccatga   ctgaccagtt   aactgtctgg   tgaccagggc   gcacgagctc   10080
ggtgtattta   aggcgcgaat   aggcgcgggt   gtcaaagatg   taatcgttgc   aggtgcgcac   10140
cagatactgg   taccctataa   gaaaatgcgg   cggtggttgg   cggtagagag   gccatcgttc   10200
tgtagctgga   gcgccagggg   cgaggtcttc   caacataagg   cggtgatagc   cgtagatgta   10260
cctggacatc   caggtgattc   ctgcggcggt   agtagaagcc   cgaggaaact   cgcgtacgcg   10320
gttccaaatg   ttgcgtagcg   gcatgaagta   gttcattgta   ggcacggttt   gaccagtgag   10380
gcgcgcgcag   tcattgatgc   tctatagaca   cggagaaaat   gaaagcgttc   agcgactcga   10440
ctccgtagcc   tggaggaacg   tgaacgggtt   gggtcgcggt   gtaccccggt   tcgagacttg   10500
tactcgagcc   ggccggagcc   gcggctaacg   tggtattggc   actcccgtct   cgacccagcc   10560
tacaaaaatc   caggatacgg   aatcgagtcg   ttttgctggt   ttccgaatgg   cagggaagtg   10620
agtcctattt   tttttttttt   tttgccgctc   agatgcatcc   cgtgctgcga   cagatgcgcc   10680
cccaacaaca   gccccctcg    cagcagcagc   agcagcaacc   acaaaaggct   gtccctgcaa   10740
ctactgcaac   tgccgccgtg   agcggtgcgg   gacagcccgc   ctatgatctg   gacttggaag   10800
agggcgaagg   actggcacgt   ctaggtgcgc   cttcgcccga   gcggcatccg   cgagttcaac   10860
tgaaaaaaga   ttctcgcgag   gcgtatgtgc   cccaacagaa   cctatttaga   gacagaagcg   10920
gcgaggagcc   ggaggagatg   cgagcttccc   gctttaacgc   gggtcgtgag   ctgcgtcacg   10980
gtttggaccg   aagacgagtg   ttgcgagacg   aggatttcga   agttgatgaa   gtgacaggga   11040
tcagtcctgc   cagggcacac   gtggctgcag   ccaaccttgt   atcggcttac   gagcagacag   11100
taaaggaaga   gcgtaacttc   caaaagtctt   ttaataatca   tgtgcgaacc   ctgattgccc   11160
gcgaagaagt   tacccttggt   ttgatgcatt   tgtgggattt   gatggaagct   atcattcaga   11220
accctactag   caaacctctg   accgcccagc   tgtttctggt   ggtgcaacac   agcagagaca   11280
```

```
atgaggcttt cagagaggcg ctgctgaaca tcaccgaacc cgaggggaga tggttgtatg   11340
atcttatcaa cattctacag agtatcatag tgcaggagcg gagcctgggc ctggccgaga   11400
aggtagctgc catcaattac tcggttttga gcttgggaaa atattacgct cgcaaaatct   11460
acaagactcc atacgttccc atagacaagg aggtgaagat agatgggttc tacatgcgca   11520
tgacgctcaa ggtcttgacc ctgagcgatg atcttggggt gtatcgcaat gacagaatgc   11580
atcgcgcggt tagcgccagc aggaggcgcg agttaagcga cagggaactg atgcacagtt   11640
tgcaaagagc tctgactgga gctggaaccg agggtgagaa ttacttcgac atgggagctg   11700
acttgcagtg gcagcctagt cgcagggctc tgagcgccgc gacggcagga tgtgagcttc   11760
cttacataga agaggcggat gaaggcgagg aggaagaggg cgagtacttg gaagactgat   11820
ggcacaaccc gtgttttttg ctagatggaa cagcaagcac cggatcccgc aatgcgggcg   11880
gcgctgcaga gccagccgtc cggcattaac tcctcggacg attggaccca ggccatgcaa   11940
cgtatcatgg cgttgacgac tcgcaacccc gaagccttta cagcaacc ccaggccaac    12000 cgtctatcgg ccatcatgga agctgtagtg ccttcccgat ctaatcccac tcatgagaag   12060
gtcctggcca tcgtgaacgc gttggtggag aacaaagcta ttcgtccaga tgaggccgga   12120
ctggtataca acgctctctt agaacgcgtg gctcgctaca acagtagcaa tgtgcaaacc   12180
aatttggacc gtatgataac agatgtacgc gaagccgtgt ctcagcgcga aaggttccag   12240
cgtgatgcca acctgggttc gctggtggcg ttaaatgctt tcttgagtac tcagcctgct   12300
aatgtgccgc gtggtcaaca ggattatact aacttttttaa gtgctttgag actgatggta   12360
tcagaagtac ctcagagcga agtgtatcag tccggtcctg attacttctt tcagactagc   12420
agacagggct tgcagacggt aaatctgagc caagctttta aaaaccttaa aggtttgtgg   12480
ggagtgcatg cccccggtagg agaaagagca accgtgtcta gcttgttaac tccgaactcc   12540
cgcctgttat tactgttggt agctcctttc accgacagcg gtagcatcga ccgtaattcc   12600
tatttgggtt acctactaaa cctgtatcgc gaagccatag ggcaaagtca ggtggacgag   12660
cagacctatc aagaaattac ccaagtcagt cgcgctttgg gacaggaaga cactggcagt   12720
ttggaagcca ctctgaactt cttgcttacc aatcggtctc aaaagatccc tcctcaatat   12780
gctcttactg cggaggagga gaggatcctt agatatgtgc agcagagcgt gggattgttt   12840
ctgatgcaag aggggcaac tccgactgca gcactggaca tgacagcgcg aaatatggag   12900
cccagcatgt atgccagtaa ccgaccttc attaacaaac tgctggacta cttgcacaga   12960
gctgccgcta tgaactctga ttatttcacc aatgccatct aaacccgca ctggctgccc    13020 ccacctggtt tctacacggg cgaatatgac atgcccgacc ctaatgacgg atttctgtgg   13080
gacgacgtga acagcgatgt ttttcacct ctttctgatc atcgcacgtg gaaaaggaa     13140 ggcggtgata gaatgcattc ttctgcatcg ctgtccgggg tcatgggtgc taccgcggct   13200
gagcccgagt ctgcaagtcc ttttcctagt ctacccttt ctctacacag tgtacgtagc    13260
agcgaagtgg gtagaataag tcgcccgagt ttaatgggcg aagaggagta cctaaacgat   13320
tccttgctca gaccggcaag agaaaaaat ttcccaaaca atggaataga aagtttggtg    13380
gataaaatga gtagatggaa gacttatgct caggatcaca gagacgagcc tgggatcatg   13440
gggactacaa gtagagcgag ccgtagacgc cagcgccatg acagacagag gggtcttgtg   13500
tgggacgatg aggattcggc cgatgatagc agcgtgttgg acttgggtgg gagaggaagg   13560
ggcaacccgt ttgctcattt gcgccctcgc ttgggtggta tgttgtgaaa aaaaataaaa   13620
```

-continued

```
aagaaaaact caccaaggcc atggcgacga gcgtacgttc gttcttcttt attatctgtg   13680
tctagtataa tgaggcgagt cgtgctaggc ggagcggtgg tgtatccgga gggtcctcct   13740
ccttcgtacg agagcgtgat gcagcagcag caggcgacgg cggtgatgca atccccactg   13800
gaggctccct ttgtgcctcc gcgatacctg gcacctacgg agggcagaaa cagcattcgt   13860
tactcggaac tggcacctca gtacgatacc accaggttgt atctggtgga caacaagtcg   13920
gcggacattg cttctctgaa ctatcagaat gaccacagca acttcttgac cacggtggtg   13980
cagaacaatg actttacccc tacggaagcc agcacccaga ccattaactt tgatgaacga   14040
tcgcggtggg gcggtcagct aaagaccatc atgcatacta acatgccaaa cgtgaacgag   14100
tatatgttta gtaacaagtt caaagcgcgt gtgatggtgt ccagaaaacc tcccgacggt   14160
gctgcagttg gggatactta tgatcacaag caggatattt tggaatatga gtggttcgag   14220
tttactttgc cagaaggcaa cttttcagtt actatgacta ttgatttgat gaacaatgcc   14280
atcatagata attacttgaa agtgggtaga cagaatggag tgcttgaaag tgacattggt   14340
gttaagttcg acaccaggaa cttcaagctg ggatgggatc ccgaaaccaa gttgatcatg   14400
cctggagtgt atacgtatga agccttccat cctgacattg tcttactgcc tggctgcgga   14460
gtggatttta ccgagagtcg tttgagcaac cttcttggta tcagaaaaaa acagccattt   14520
caagagggtt ttaagatttt gtatgaagat ttagaaggtg gtaatattcc ggccctcttg   14580
gatgtagatg cctatgagaa cagtaagaaa gaacaaaaag ccaaaataga agctgctaca   14640
gctgctgcag aagctaaggc aaacatagtt gccagcgact ctacaagggt tgctaacgct   14700
ggagaggtca gaggagacaa ttttgcgcca acacctgttc cgactgcaga atcattattg   14760
gccgatgtgt ctgaaggaac ggacgtgaaa ctcactattc aacctgtaga aaaagatagt   14820
aagaatagaa gctataatgt gttggaagac aaaatcaaca cagcctatcg cagttggtat   14880
cttcgtaca attatggcga tcccgaaaaa ggagtgcgtt cctggacatt gctcaccacc   14940
tcagatgtca cctgcggagc agagcaggtt tactggtcgc ttccagacat gatgaaggat   15000
cctgtcactt tccgctccac tagacaagtc agtaactacc ctgtggtggg tgcagagctt   15060
atgcccgtct tctcaaagag cttctacaac gaacaagctg tgtactccca gcagctccgc   15120
cagtccacct cgcttacgca cgtcttcaac cgctttcctg agaaccagat tttaatccgt   15180
ccgccggcgc ccaccattac caccgtcagt gaaaacgttc ctgctctcac agatcacggg   15240
accctgccgt tgcgcagcag tatccgggga gtccaacgtg tgaccgttac tgacgccaga   15300
cgccgcacct gtccctacgt gtacaaggca ctgggcatag tcgcaccgcg cgtcctttca   15360
agccgcactt tctaaaaaaa aaaaatgtcc attcttatct cgcccagtaa taacaccggt   15420
tggggtctgc gcgctccaag caagatgtac ggaggcgcac gcaaacgttc tacccaacat   15480
cccgtgcgtg ttcgcggaca ttttcgcgct ccatggggtg ccctcaaggg ccgcactcgc   15540
gttcgaacca ccgtcgatga tgtaatcgat caggtggttg ccgacgcccg taattatact   15600
cctactgcgc ctacatctac tgtggatgca gttattgaca gtgtagtggc tgacgctcgc   15660
aactatgctc gacgtaagag ccggcgaagg cgcattgcca gacgccaccg agctaccact   15720
gccatgcgag ccgcaagagc tctgctacga agagctagac gcgtggggcg aagagccatg   15780
cttagggcgg ccagacgtgc agcttcgggc gccagcgccg gcaggtcccg caggcaagca   15840
gccgctgtcg cagcggcgac tattgccgac atggcccaat cgcgaagagg caatgtatac   15900
tgggtgcgtg acgctgccac cggtcaacgt gtacccgtgc gcacccgtcc ccctcgcact   15960
tagaagatac tgagcagtct ccgatgttgt gtcccagcgg cgaggatgtc caagcgcaaa   16020
```

```
tacaaggaag aaatgctgca ggttatcgca cctgaagtct acggccaacc gttgaaggat    16080
gaaaaaaaac cccgcaaaat caagcgggtt aaaaaggaca aaaaagaaga ggaagatggc    16140
gatgatgggc tggcggagtt tgtgcgcgag tttgccccac ggcgacgcgt gcaatggcgt    16200
gggcgcaaag ttcgacatgt gttgagacct ggaacttcgg tggtctttac acccggcgag    16260
cgttcaagcg ctacttttaa gcgttcctat gatgaggtgt acggggatga tgatattctt    16320
gagcaggcgg ctgaccgatt aggcgagttt gcttatggca agcgtagtag aataacttcc    16380
aaggatgaga cagtgtcaat acccttggat catggaaatc ccaccccctag tcttaaaccg    16440 gtcactttgc agcaagtgtt acccgtaact ccgcgaacag gtgttaaacg cgaaggtgaa    16500
gatttgtatc ccactatgca actgatggta cccaaacgcc agaagttgga ggacgttttg    16560
gagaaagtaa aagtggatcc agatattcaa cctgaggtta aagtgagacc cattaagcag    16620
gtagcgcctg gtctgggggt acaaactgta gacattaaga ttcccactga aagtatggaa    16680
gtgcaaactg aacccgcaaa gcctactgcc acctccactg aagtgcaaac ggatccatgg    16740
atgcccatgc ctattacaac tgacgccgcc ggtcccactc gaagatcccg acgaaagtac    16800
ggtccagcaa gtctgttgat gcccaattat gttgtacacc catctattat tcctactcct    16860
ggttaccgag gcactcgcta ctatcgcagc cgaaacagta cctcccgccg tcgccgcaag    16920
acacctgcaa atcgcagtcg tcgccgtaga cgcacaagca aaccgactcc cggcgccctg    16980
gtgcggcaag tgtaccgcaa tggtagtgcg gaacctttga cactgccgcg tgcgcgttac    17040
catccgagta tcatcactta atcaatgttg ccgctgcctc cttgcagata tggccctcac    17100
ttgtcgcctt cgcgttccca tcactggtta ccgaggaaga aactcgcgcc gtagaagagg    17160
gatgttggga cgcggaatgc gacgctacag gcgacggcgt gctatccgca agcaattgcg    17220
gggtggtttt ttaccagcct taattccaat tatcgctgct gcaattggcg cgataccagg    17280
catagcttcc gtggcggttc aggcctcgca acgacattga cattggaaaa aaaacgtata    17340
aataaaaaaa aatacaatgg actctgacac tcctggtcct gtgactatgt tttcttagag    17400
atggaagaca tcaattttc atccttggct ccgcgacacg gcacgaagcc gtacatgggc    17460
acctggagcg acatcggcac gagccaactg aacgggggcg ccttcaattg gagcagtatc    17520
tggagcgggc ttaaaaattt tggctcaacc ataaaaacat acgggaacaa agcttggaac    17580
agcagtacag gacaggcgct tagaaataaa cttaaagacc agaacttcca acaaaaagta    17640
gtcgatggga tagcttccgg catcaatgga gtggtagatt tggctaacca ggctgtgcag    17700
aaaaagataa acagtcgttt ggacccgccg ccagcaaccc caggtgaaat gcaagtggag    17760
gaagaaattc ctccgccaga aaaacgaggc gacaagcgtc cgcgtcccga tttggaagag    17820
acgctggtga cgcgcgtaga tgaaccgcct tcttatgagg aagcaacgaa gcttggaatg    17880
cccaccacta gaccgatagc cccaatggcc accggggtga tgaaaccttc tcagttgcat    17940
cgacccgtca ccttggattt gccccctccc ctgctgctac tgctgtacc cgcttctaag    18000 cctgtcgctg ccccgaaacc agtcgccgta gccaggtcac gtcccggggg cgctcctcgt    18060
ccaaatgcgc actggcaaaa tactctgaac agcatcgtgg gtctaggcgt gcaaagtgta    18120
aaacgccgtc gctgcttta attaaatatg gagtagcgct taacttgcct atctgtgtat    18180
atgtgtcatt acacgccgtc acagcagcag aggaaaaaag gaagaggtcg tgcgtcgacg    18240
ctgagttact ttcaagatgg ccaccccatc gatgctgccc caatgggcat acatgcacat    18300
cgccggacag gatgcttcgg agtacctgag tccgggtctg gtgcagttcg cccgcgccac    18360
```

```
agacacctac ttcaatctgg gaaataagtt tagaaatccc accgtagcgc cgacccacga   18420
tgtgaccacc gaccgtagcc agcggctcat gttgcgcttc gtgcccgttg accgggagga   18480
caatacatac tcttacaaag tgcggtacac cctggccgtg ggcgacaaca gagtgctgga   18540
tatggccagc acgttctttg acattagggg cgtgttggac agaggtccca gtttcaaacc   18600
ctattctggt acggcttaca actctctggc tcctaaaggc gctccaaatg catctcaatg   18660
gattgcaaaa ggcgtaccaa ctgcagcagc cgcaggcaat ggtgaagaag aacatgaaac   18720
agaggagaaa actgctactt acactttgc caatgctcct gtaaaagccg aggctcaaat   18780
tacaaaagag ggcttaccaa taggtttgga gatttcagct gaaaacgaat ctaaacccat   18840
ctatgcagat aaactttatc agccagaacc tcaagtggga gatgaaactt ggactgacct   18900
agacggaaaa accgaagagt atggaggcag ggctctaaag cctactacta acatgaaacc   18960
ctgttacggg tcctatgcga agcctactaa tttaaaaggt ggtcaggcaa aaccgaaaaa   19020
ctcggaaccg tcgagtgaaa aaattgaata tgatattgac atggaatttt ttgataactc   19080
atcgcaaaga acaaacttca gtcctaaaat tgtcatgtat gcagaaaatg taggtttgga   19140
aacgccagac actcatgtag tgtacaaacc tggaacagaa gacacaagtt ccgaagctaa   19200
tttgggacaa cagtctatgc ccaacagacc caactacatt ggcttcagag ataacttat   19260 tggactcatg tactataaca gtactggtaa catggggggtg ctggctggtc aagcgtctca   19320
gttaaatgca gtggttgact tgcaggacag aaacacagaa cttcttacc aactcttgct   19380 tgactctctg ggcgacagaa ccagatactt tagcatgtgg aatcaggctg tggacagtta   19440
tgatcctgat gtacgtgtta ttgaaaatca tggtgtggaa gatgaacttc ccaactattg   19500
ttttccactg gacggcatag gtgttccaac aaccagttac aaatcaatag ttccaaatgg   19560
agaagataat aataattgga agaacctga gtaaatgga acaagtgaga tcggacaggg   19620
taatttgttt gccatggaaa ttaaccttca agccaatcta tggcgaagtt tcctttattc   19680
caatgtggct ctgtatctcc cagactcgta caaatacacc ccgtccaatg tcactcttcc   19740
agaaaacaaa aacacctacg actacatgaa cgggcgggtg gtgccgccat ctctagtaga   19800
cacctatgtg aacattggtg ccaggtggtc tctggatgcc atggacaatg tcaacccatt   19860
caaccaccac cgtaacgctg gcttgcgtta ccgatctatg cttctgggta acggacgtta   19920
tgtgcctttc cacatacaag tgcctcaaaa attcttcgct gttaaaaacc tgctgcttct   19980
cccaggctcc tacacttatg agtggaactt taggaaggat gtgaacatgg ttctacagag   20040
ttccctcggt aacgacctgc gggtagatgg cgccagcatc agtttcacga gcatcaacct   20100
ctatgctact tttttccca tggctcacaa caccgcttcc acccttgaag ccatgctgcg   20160
gaatgacacc aatgatcagt cattcaacga ctacctatct gcagctaaca tgctctaccc   20220
cattcctgcc aatgcaacca atattcccat ttccattcct tctcgcaact gggcggcttt   20280
cagaggctgg tcatttacca gactgaaaac caaagaaact ccctctttgg ggtctggatt   20340 tgaccctac tttgtctatt ctggttctat tccctacctg gatggtacct tctacctgaa   20400
ccacactttt aagaaggttt ccatcatgtt tgactcttca gtgagctggc ctggaaatga   20460
caggttacta tctcctaacg aatttgaaat aaagcgcact gtggatggcg aaggctacaa   20520
cgtagcccaa tgcaacatga ccaaagactg gttcttggta cagatgctcg ccaactacaa   20580
catcggctat cagggcttct acattccaga aggatacaaa gatcgcatgt attcatttttt   20640 cagaaacttc cagcccatga gcaggcaggt ggttgatgag gtcaattaca aagacttcaa   20700
ggccgtcgcc ataccctacc aacacaacaa ctctggcttt gtgggttaca tggctccgac   20760
```

```
catgcgccaa ggtcaaccct atcccgctaa ctatccctat ccactcattg gaacaactgc   20820
cgtaaatagt gttacgcaga aaaagttctt gtgtgacaga accatgtggc gcataccgtt   20880
ctcgagcaac ttcatgtcta tgggggccct tacagacttg ggacagaata tgctctatgc   20940
caactcagct catgctctgg acatgacctt tgaggtggat cccatggatg agcccaccct   21000
gctttatctt ctcttcgaag ttttcgacgt ggtcagagtg catcagccac accgcggcat   21060
catcgaggca gtctacctgc gtacaccgtt ctcggccggt aacgctacca cgtaagaagc   21120
ttcttgcttc ttgcaaatag cagctgcaac catggcctgc ggatcccaaa acggctccag   21180
cgagcaagag ctcagagcca ttgtccaaga cctgggttgc ggaccctatt ttttgggaac   21240
ctacgataag cgcttcccgg ggttcatggc ccccgataag ctcgcctgtg ccattgtaaa   21300
tacggccgga cgtgagacgg ggggagagca ctggttggct ttcggttgga acccacgttc   21360
taacacctgc tacctttttg atccttttgg attctcggat gatcgtctca aacagattta   21420
ccagtttgaa tatgagggtc tcctgcgccg cagcgctctt gctaccaagg accgctgtat   21480
tacgctggaa aaatctaccc agaccgtgca gggcccccgt tctgccgcct gcggactttt   21540
ctgctgcatg ttccttcacg cctttgtgca ctggcctgac cgtcccatgg acggaaaccc   21600
caccatgaaa ttgctaactg gagtgccaaa caacatgctt cattctccta aagtccagcc   21660
caccctgtgt gacaatcaaa aagcactcta ccatttcctt aatacccatt cgccttattt   21720
tcgctctcat cgtacacaca tcgaaagggc cactgcgttc gaccgtatgg atgttcaata   21780
atgactcatg taaacaacgt gttcaataaa catcacttta ttttttaca tgtatcaagg   21840 ctctggatta cttatttatt tacaagtcga atgggttctg acgagaatca gaatgacccg   21900
caggcagtga tacgttgcgg aactgatact tgggttgcca cttgaattcg ggaatcacca   21960
acttgggaac cggtatatcg ggcaggatgt cactccacag ctttctggtc agctgcaaag   22020
ctccaagcag gtcaggagcc gaaatcttga aatcacaatt aggaccagtg ctctgagcgc   22080
gagagttgcg gtacaccgga ttgcagcact gaaacaccat cagcgacgga tgtctcacgc   22140
ttgccagcac ggtgggatct gcaatcatgc ccacatccag atcttcagca ttggcaatgc   22200
tgaacggggt catcttgcag gtctgcctac ccatggcggg cacccaatta ggcttgtggt   22260
tgcaatcgca gtgcaggggg atcagtatca tcttggcctg atcctgtctg attcctggat   22320
acacggctct catgaaagca tcatattgct tgaaagcctg ctgggcttta ctaccctcgg   22380
tataaaacat cccgcaggac ctgctcgaaa actggttagc tgcacagccg gcatcattca   22440
cacagcagcg ggcgtcattg ttggctattt gcaccacact tctgccccag cggttttggg   22500
tgattttggt tcgctcggga ttctcccttta aggctcgttg tccgttctcg ctggccacat   22560
ccatctcgat aatctgctcc ttctgaatca taatattgcc atgcaggcac ttcagcttgc   22620
cctcataatc attgcagcca tgaggccaca acgcacagcc tgtacattcc caattatggt   22680
gggcgatctg agaaaaagaa tgtatcattc cctgcagaaa tcttcccatc atcgtgctca   22740
gtgtcttgtg actagtgaaa gttaactgga tgcctcggtg ctcttcgttt acgtactggt   22800
gacagatgcg cttgtattgt tcgtgttgct caggcattag tttaaaacag gttctaagtt   22860
cgttatccag cctgtacttc tccatcagca gacacatcac ttccatgcct ttctcccaag   22920
cagacaccag gggcaagcta atcggattct taacagtgca ggcagcagct cctttagcca   22980
gagggtcatc tttagcgatc ttctcaatgc ttcttttgcc atccttctca acgatgcgca   23040
cgggcgggta gctgaaaccc actgctacaa gttgcgcctc ttctcttct tcttcgctgt   23100
```

```
cttgactgat gtcttgcatg gggatatgtt tggtcttcct tggcttcttt ttgggggta    23160 tcggaggagg aggactgtcg ctccgttccg gagacaggga ggattgtgac gtttcgctca    23220
ccattaccaa ctgactgtcg gtagaagaac ctgacccac acggcgacag gtgtttttct     23280 tcggggcag aggtggaggc gattgcgaag ggctgcggtc cgacctggaa ggcggatgac      23340
tggcagaacc ccttccgcgt tcgggggtgt gctccctgtg gcggtcgctt aactgatttc    23400
cttcgcggct ggccattgtg ttctcctagg cagagaaaca acagacatgg aaactcagcc   23460
attgctgtca acatcgccac gagtgccatc acatctcgtc ctcagcgacg aggaaaagga    23520
gcagagctta agcattccac cgcccagtcc tgccaccacc tctaccctag aagataagga   23580
ggtcgacgca tctcatgaca tgcagaataa aaaagcgaaa gagtctgaga cagacatcga   23640
gcaagacccg ggctatgtga caccggtgga acacgaggaa gagttgaaac gctttctaga   23700
gagagaggat gaaaactgcc caaaacagcg agcagataac tatcaccaag atgctggaaa   23760
tagggatcag aacaccgact acctcatagg gcttgacggg gaagacgcgc tccttaaaca    23820
tctagcaaga cagtcgctca tagtcaagga tgcattattg gacagaactg aagtgcccat    23880
cagtgtggaa gagctcagct gcgcctacga gcttaacctt ttttcacctc gtactccccc    23940
caaacgtcag ccaaacggca cctgcagcc aaatcctcgc ttaaactttt atccagcttt     24000
tgctgtgcca gaagtactgg ctacctatca catctttttt aaaaatcaaa aaattccagt    24060
ctcctgccgc gctaatcgca cccgcgccga tgccctactc aatctgggac ctggttcacg    24120
cttacctgat atagcttcct tggaagaggt tccaaagatc ttcgagggtc tgggcaataa   24180
tgagactcgg gccgcaaatg ctctgcaaaa gggagaaaat ggcatggatg agcatcacag   24240
cgttctggtg gaattggaag gcgataatgc cagactcgca gtactcaagc gaagcgtcga    24300
ggtcacacac ttcgcatatc ccgctgtcaa cctgcccct aaagtcatga cggcggtcat    24360
ggaccagtta ctcattaagc gcgcaagtcc cctttcagaa gacatgcatg acccagatgc   24420
ctgtgatgag ggtaaaccag tggtcagtga tgagcagcta acccgatggc tgggcaccga    24480
ctctccccgg gatttggaag agcgtcgcaa gcttatgatg gccgtggtgc tggttaccgt    24540
agaactagag tgtctccgac gtttctttac cgattcagaa accttgcgca aactcgaaga    24600
gaatctgcac tacactttta gacacggctt tgtgcggcag gcatgcaaga tatctaacgt    24660
ggaactcacc aacctggttt cctacatggg tattctgcat gagaatcgcc taggacaaag    24720
cgtgctgcac agcaccctta aggggaagc ccgccgtgat tacatccgcg attgtgtcta     24780
tctctacctg tgccacacgt ggcaaaccgg catgggtgta tggcagcaat gtttagaaga   24840
acagaacttg aaagagcttg acaagctctt acagaaatct cttaaggttc tgtggacagg    24900
gttcgacgag cgcaccgtcg cttccgacct ggcagacctc atcttcccag agcgtctcag    24960
ggttactttg cgaaacggat tgcctgactt tatgagccag agcatgctta acaattttcg   25020
ctctttcatc ctggaacgct ccggtatcct gcccgccacc tgctgcgcac tgccctccga   25080 cttttgtgcct ctcacctacc gcgagtgccc cccgccgcta tggagtcact gctacctgtt    25140
ccgtctggcc aactatctct cctaccactc ggatgtgatc gaggatgtga gcggagacgg    25200
cttgctggag tgccactgcc gctgcaatct gtgcacgccc caccggtccc tagcttgcaa    25260 ccccccagttg atgagcgaaa cccagataat aggcaccttt gaattgcaag gccccagcag    25320
ccaaggcgat gggtcttctc ctgggcaaag tttaaaactg accccgggac tgtggacctc    25380
cgcctacttg cgcaagtttg ctccggaaga ttaccacccc tatgaaatca gttctatga     25440 ggaccaatca cagcctccaa aggccgaact ttcggcttgc gtcatcaccc aggggcaat     25500
```

```
tctggcccaa ttgcaagcca tccaaaaatc ccgccaagaa tttctactga aaaagggtaa   25560
gggggtctac cttgacccccc agaccggcga ggaactcaac acaaggttcc ctcaggatgt   25620
cccaacgacg agaaaacaag aagttgaagg tgcagccgcc gcccccagaa gatatggagg   25680
aagattggga cagtcaggca gaggaggcgg aggaggacag tctggaggac agtctggagg   25740
aagacagttt ggaggaggaa aacgaggagg cagaggaggt ggaagaagta accgccgaca   25800
aacagttatc ctcggctgcg gagacaagca acagcgctac catctccgct ccagtcgag    25860 gaacccggcg gcgtcccagc agtagatggg acgagaccgg acgcttcccg aacccaacca   25920
gcgcttccaa gaccggtaag aaggatcggc agggatacaa gtcctggcgg gggcataaga   25980
atgccatcat ctcctgcttg catgagtgcg ggggcaacat atccttcacg cggcgctact   26040
tgctattcca ccatggggtg aactttccgc gcaatgtttt gcattactac cgtcacctcc   26100
acagccccta ctatagccag caaatcccga cagtctcgac agataaagac agcggcggcg   26160
acctccaaca gaaaaccagc agcggcagtt agaaaataca caacaagtgc agcaacagga   26220
ggattaaaga ttacagccaa cgagccagcg caaacccgag agttaagaaa tcggatcttt   26280
ccaaccctgt atgccatctt ccagcagagt cggggtcaag agcaggaact gaaaataaaa   26340
aaccgatctc tgcgttcgct caccagaagt tgtttgtatc acaagagcga agatcaactt   26400
cagcgcactc tcgaggacgc cgaggctctc ttcaacaagt actgcgcgct gactcttaaa   26460
gagtaggcag cgaccgcgct tattcaaaaa aggcgggaat tacatcatcc tcgacatgag   26520
taaagaaatt cccacgcctt acatgtggag ttatcaaccc caaatgggat tggcagcagg   26580
cgcctcccag gactactcca cccgcatgaa ttggctcagc gccgggcctt ctatgatttc   26640
tcgagttaat gatatacgcg cctaccgaaa ccaaatactt ttggaacagt cagctcttac   26700
caccacgccc cgccaacacc ttaatcccag aaattggccc gccgcctag tgtaccagga    26760 aagtcccgct cccaccactg tattacttcc tcgagacgcc caggccgaag tccaaatgac   26820
taatgcaggt gcgcagttag ctggcggctc caccctatgt cgtcacaggc ctcggcataa   26880
tataaaacgc ctgatgatca gaggccgagg tatccagctc aacgacgagt cggtgagctc   26940
tccgcttggt ctacgaccag acggaatctt tcagattgcc ggctgcggga gatcttcctt   27000
cacccctcgt caggctgttc tgactttgga aagttcgtct tcgcaacccc gctcgggcgg   27060
aatcgggacc gttcaatttg tagaggagtt tactccctct gtctacttca accccttctc   27120
cggatctcct gggcactacc cggacgagtt cataccgaac ttcgacgcga ttagcgagtc   27180
agtggacggc tacgattgat gtctggtgac gcggctgagc tatctcggct gcgacatcta   27240
gaccactgcc gccgctttcg ctgctttgcc cgggaactta ttgagttcat ctacttcgaa   27300
ctccccaagg atcaccctca aggtccggcc cacgagtgc ggattactat cgaaggcaaa    27360
atagactctc gcctgcaacg aattttctcc cagcggcccg tgctgatcga gcgagaccag   27420
ggaaacacca cggtttccat ctactgcatt tgtaatcacc ccggattgca tgaaagcctt   27480
tgctgtctta tgtgtactga gtttaataaa aactgaatta agactctcct acggactgcc   27540
gcttcttcaa cccggatttt acaaccagaa gaacaaaact tttcctgtcg tccaggactc   27600
tgttaacttc acctttccta ctcacaaact agaagctcaa cgactacacc gcttttccag   27660
aagcattttc cctactaata ctactttcaa aaccggaggt gagctccacg gtctccctac   27720
agaaaaccct tgggtggaag cgggccttgt agtactagga attcttgcgg gtgggcttgt   27780
gattattctt tgctacctat acacaccttg cttcactttc ctagtggtgt tgtggtattg   27840
```

```
gtttaaaaaa tggggcccat actagtcttg cttgttttac tttcgctttt ggaaccgggt   27900
tctgccaatt acgatccatg tctagacttt gacccagaaa actgcacact tacttttgca   27960
cccgacacaa gccgcatctg tggagttctt attaagtgcg gatgggaatg caggtccgtt   28020
gaaattacac acaataacaa aacctggaac aataccttat ccaccacatg ggagccagga   28080
gttcccgagt ggtacactgt ctctgtccga ggtcctgacg gttccatccg cattagtaac   28140
aacactttca ttttttctga aatgtgcgat ctggccatgt tcatgagcaa acagtattct   28200
ctatggcctc ctagcaagga caacatcgta acgttctcca ttgcttattg cttgtgcgct   28260
tgccttctta ctgctttact gtgcgtatgc atacacctgc ttgtaaccac tcgcatcaaa   28320
aacgccaata acaaagaaaa aatgccttaa cctctttctg tttacagaca tggcttctct   28380
tacatctctc atatttgtca gcattgtcac tgccgctcac ggacaaacag tcgtctctat   28440
cccactagga cataattaca ctctcatagg accccaatc acttcagagg tcatctggac   28500
caaactggga agcgttgatt actttgatat aatctgtaac aaaacaaaac caataatagt   28560
aacttgcaac atacaaaatc ttacattgat taatgttagc aaagtttaca gcggttacta   28620
ttatggttat gacagataca gtagtcaata tagaaattac ttggttcgtg ttacccagtt   28680
gaaaaccacg aaaatgccaa atatggcaaa gattcgatcc gatgacaatt ctctagaaac   28740
ttttacatct cccaccacac ccgacgaaaa aaacatccca gattcaatga ttgcaattgt   28800
tgcagcggtg gcagtggtga tggcactaat aataatatgc atgcttttat atgcttgtcg   28860
ctacaaaaag tttcatccta aaaaacaaga tctcctacta aggcttaaca tttaatttct   28920
ttttatacag ccatggtttc cactaccaca ttccttatgc ttactagtct cgcaactctg   28980
acttctgctc gctcacacct cactgtaact ataggctcaa actgcacact aaaaggacct   29040
caaggtggtc atgtcttttg gtggagaata tatgacaatg gatggtttac aaaaccatgt   29100
gaccaacctg gtagattttt ctgcaacggc agagacctaa ccattatcaa cgtgacagca   29160
aatgacaaag gcttctatta tggaaccgac tataaaagta gtttagatta taacattatt   29220
gtactgccat ctaccactcc agcaccccgc acaactactt tctctagcag cagtgtcgct   29280
aacaatacaa tttccaatcc aacctttgcc gcgcttttaa aacgcactgt gaataattct   29340
acaacttcac atacaacaat ttccacttca acaatcagca tcatcgctgc agtgacaatt   29400
ggaatatcta ttcttgtttt taccataacc tactacgcct gctgctatag aaaagacaaa   29460
cataaaggtg atccattact tagatttgat atttaatttg ttctttttt ttatttacag   29520 tatggtgaac accaatcatg gtacctagaa atttcttctt caccatactc atctgtgctt   29580
ttaatgtttg cgctactttc acagcagtag ccacagcaac cccagactgt ataggagcat   29640
ttgcttccta tgcactttt gcttttgtta cttgcatctg cgtatgtagc atagtctgcc   29700
tggttattaa ttttttccaa cttctagact ggatccttgt gcgaattgcc tacctgcgcc   29760
accatcccga ataccgcaac caaaatatcg cggcacttct tagactcatc taaaaccatg   29820
caggctatac taccaatatt tttgcttcta ttgcttccct acgctgtctc aaccccagct   29880
gcctatagta ctccaccaga acaccttaga aaatgcaaat ccaacaaccc gtggtcattt   29940
cttgcttgct atcgagaaaa atcagaaatc ccccaaatt taataatgat tgctggaata   30000
attaatataa tctgttgcac cataatttca tttttgatat acccctatt tgattttggc   30060 tggaatgctc ccaatgcaca tgatcatcca caagacccag aggaacacat tcccccacaa   30120
aacatgcaac atcaaatagc gctaatgat tacgaaagtg aaccacaacc cccactactc   30180
cctgctatta gttacttcaa cctaaccggc ggagatgact gaaacactca ccacctccaa   30240
```

```
ttccgccgag gatctgctcg atatggacgg ccgcgtctca gaacaacgac ttgcccaact   30300
acgcatccgc cagcagcagg aacgcgtggc caaagagctc agagatgtca tccaaattca   30360
ccaatgcaaa aaaggcatat tctgtttggt aaaacaagcc aagatatcct acgagatcac   30420
cgctactgac catcgcctct cttacgaact tggcccccaa cgacaaaaat ttacctgcat   30480
ggtgggaatc aaccccatag ttatcaccca acaaagtgga gatactaagg gttgcattca   30540
ctgctcctgc gattccatcg agtgcaccta caccctgctg aagacccta gcggcctaag    30600 agacctgcta ccaatgaatt aaaaaaaaat gattaataaa aaatcactta cttgaaatca   30660
gcaataaggt ctctgttgaa attttctccc agcagcacct cacttccctc ttcccaactc   30720
tggtattcta aaccccgttc agcggcatac tttctccata ctttaaaggg gatgtcaaat   30780
tttagctcct ctcctgtacc cacaatcttc atgtctttct tcccagatga ccaagagagt   30840
ccggctcagt gactccttca accctgtcta ccctatgaa gatgaaagca cctcccaaca    30900 ccctttata  aacccagggt ttatttcccc aaatggcttc acacaaagcc cagacggagt    30960
tcttacttta aaatgtttaa ccccactaac aaccacaggc ggatctctac agctaaaagt   31020 gggagggga cttacagtgg atgacactga tggtacctta caagaaaaca tacgtgctac     31080
agcacccatt actaaaaata atcactctgt agaactatcc attggaaatg gattagaaac   31140
tcaaaacaat aaactatgtg ccaaattggg aaatgggtta aaatttaaca acggtgacat   31200
ttgtataaag gatagtatta acaccttatg gactggaata aaccctccac ctaactgtca   31260
aattgtggaa aacactaata caaatgatgg caaacttact ttagtattag taaaaaatgg   31320
agggcttgtt aatggctacg tgtctctagt tggtgtatca gacactgtga accaaatgtt   31380
cacacaaaag acagcaaaca tccaattaag attatatttt gactcttctg gaaatctatt   31440
aactgaggaa tcagacttaa aaattccact taaaaataaa tcttctacag cgaccagtga   31500
aactgtagcc agcagcaaag cctttatgcc aagtactaca gcttatccct tcaacaccac   31560
tactagggat agtgaaaact acattcatgg aatatgttac tacatgacta gttatgatag   31620
aagtctattt cccttgaaca tttctataat gctaaacagc cgtatgattt cttccaatgt   31680
tgcctatgcc atacaatttg aatggaatct aaatgcaagt gaatctccag aaagcaacat   31740
agctacgctg accacatccc ccttttttctt ttcttacatt acagaagacg acaactaaaa   31800
taaagtttaa gtgttttat ttaaaatcac aaaattcgag tagttatttt gcctccacct    31860 tcccattga cagaatacac caatctctcc ccacgcacag ctttaaacat ttggatacca    31920
ttagagatag acattgttt agattccaca ttccaaacag tttcagagcg agccaatctg    31980
gggtcagtga tagataaaaa tccatcgcga tagtctttta aagcgctttc acagtccaac   32040
tgctgcggat gcgactccgg agtttggatc acggtcatct ggaagaagaa cgatgggaat   32100
cataatccga aaacggtatc ggacgattgt gtctcatcaa acccacaagc agccgctgtc   32160
tgcgtcgctc cgtgcgactg ctgtttatgg gatcagggtc cacagtttcc tgaagcatga   32220
ttttaatagc ccttaacatc aactttctgg tgcgatgcgc gcagcaacgc attctgattt   32280
cactcaaatc tttgcagtag gtacaacaca ttattacaat attgtttaat aaaccataat   32340
taaaagcgct ccagccaaaa ctcatatctg atataatcgc cctgcatga ccatcatacc     32400 aaagtttaat ataattaaa tgacgttccc tcaaaacac actacccaca tacatgatct      32460
cttttggcat gtgcatatta acaatctgtc tgtaccatgg acaacgttgg ttaatcatgc   32520
aacccaatat aaccttccgg aaccacactg ccaacaccgc tcccccagcc atgcattgaa   32580
```

```
gtgaaccctg ctgattacaa tgacaatgaa gaacccaatt ctctcgaccg tgaatcactt    32640
gagaatgaaa aatatctata gtggcacaac atagacataa atgcatgcat cttctcataa    32700
tttttaactc ctcaggattt agaaacatat cccagggaat aggaagctct tgcagaacag    32760
taaagctggc agaacaagga agaccacgaa cacaacttac actatgcata gtcatagtat    32820
cacaatctgg caacagcggg tggtcttcag tcatagaagc tcgggtttca ttttcctcac    32880
aacgtggtaa ctgggctctg gtgtaagggt gatgtctggc gcatgatgtc gagcgtgcgc    32940
gcaaccttgt cataatggag ttgcttcctg acattctcgt attttgtata gcaaaacgcg    33000
gccctggcag aacacactct tcttcgcctt ctatcctgcc gcttagcgtg ttccgtgtga    33060
tagttcaagt acagccacac tcttaagttg gtcaaaagaa tgctggcttc agttgtaatc    33120
aaaactccat cgcatctaat tgttctgagg aaatcatcca cggtagcata tgcaaatccc    33180
aaccaagcaa tgcaactgga ttgcgtttca agcaggagag gagagggaag agacggaaga    33240
accatgttaa tttttattcc aaacgatctc gcagtacttc aaattgtaga tcgcgcagat    33300
ggcatctctc gcccccactg tgttggtgaa aaagcacagc taaatcaaaa gaatgcgat    33360 tttcaaggtg ctcaacggtg gcttccaaca aagcctccac gcgcacatcc aagaacaaaa    33420
gaataccaaa agaaggagca ttttctaact cctcaatcat catattacat tcctgcacca    33480
ttcccagata atttttcagct ttccagcctt gaattattcg tgtcagttct tgtggtaaat    33540
ccaatccaca cattacaaac aggtcccgga gggcgccctc caccaccatt cttaaacaca    33600
ccctcataat gacaaaatat cttgctcctg tgtcacctgt agcgaattga gaatggcaac    33660
atcaattgac atgcccttgg ctctaagttc ttctttaagt tctagttgta aaaactctct    33720
catattatca ccaaactgct tagccagaag ccccccggga acaagagcag gggacgctac    33780
agtgcagtac aagcgcagac ctccccaatt ggctccagca aaaacaagat tggaataagc    33840
atattgggaa ccaccagtaa tatcatcgaa gttgctggaa atataatcag gcagagtttc    33900
ttgtagaaat tgaataaaag aaaaatttgc caaaaaaaca ttcaaaacct ctgggatgca    33960
aatgcaatag gttaccgcgc tgcgctccaa cattgttagt tttgaattag tctgcaaaaa    34020
taaaaaaaaa acaagcgtca tatcatagta gcctgacgaa caggtggata aatcagtctt    34080
tccatcacaa gacaagccac agggtctcca gctcgaccct cgtaaaacct gtcatcgtga    34140
ttaaacaaca gcaccgaaag ttcctcgcgg tgaccagcat gaataagtct tgatgaagca    34200
tacaatccag acatgttagc atcagttaag gagaaaaaac agccaacata gcctttgggt    34260
ataattatgc ttaatcgtaa gtatagcaaa gccacccctc gcggatacaa agtaaaaggc    34320
acaggagaat aaaaaatata attatttctc tgctgctgtt taggcaacgt cgcccccggt    34380
ccctctaaat acacatacaa agcctcatca gccatggctt accagagaaa gtacagcggg    34440
cacacaaacc acaagctcta aagtcactct ccaacctctc cacaatatat atacacaagc    34500
cctaaactga cgtaatggga ctaaagtgta aaaaatcccg ccaaacccaa cacacacccc    34560
gaaactgcgt caccagggaa aagtacagtt tcacttccgc aatcccaaca agcgtcactt    34620
cctctttctc acggtacgtc acatcccatt aacttacaac gtcatttttcc cacggccgcg    34680 ccgccccttt taaccgttaa ccccacagcc aatcaccaca cggcccacac ttttttaaaat    34740 cacctcattt acatattggc accattccat ctataaggta tattattgat gatg          34794
```

<210> SEQ ID NO 42
<211> LENGTH: 688
<212> TYPE: DNA
<213> ORGANISM: Artificial Sequence

```
<220> FEATURE:
<223> OTHER INFORMATION: mouse IL12A cloned into the NotI restriction
      site of the revised IX-E2 site with an expression cassette

<400> SEQUENCE: 42
ctatagggag acccgcggcc atgtgtcaat cacgctacct cctcttttg gccacccttg      60 ccctcctaaa ccacctcagt ttggccaggg tcattccagt ctctggacct gccaggtgtc    120
ttagccagtc ccgaaacctg ctgaagacca cagatgacat ggtgaagacg ccagagaaa     180 aactgaaaca ttattcctgc actgctgaag acatcgatca tgaagacatc acacgggacc    240
aaaccagcac attgaagacc tgtttaccac tggaactaca aagaacgag agttgcctgg     300 ctactagaga gacttcttcc acaacaagag ggagctgcct gcccccacag aagacgtctt    360
tgatgatgac cctgtgcctt ggtagcatct atgaggactt gaagatgtac cagacagagt    420
tccaggccat caacgcagca cttcagaatc acaaccatca gcagatcatt ctagacaagg    480
gcatgctggt ggccatcgat gagctgatgc agtctctgaa tcataatggc gagactctgc    540
gccagaaacc tcctgtggga gaagcagacc cttacagagt gaaaatgaag ctctgcatcc    600
tgcttcacgc cttcagcacc cgcgtcgtga ccatcaacag ggtgatgggc tatctgagct    660
ccgcctgagg ccgctgtgcc ttctagtt                                       688

<210> SEQ ID NO 43
<211> LENGTH: 1048
<212> TYPE: DNA
<213> ORGANISM: Artificial Sequence
<220> FEATURE:
<223> OTHER INFORMATION: mouse IL12B cloned into the SwaI restriction
      site of the L5-E4 site with an expression cassette using the EF1A
      promoter

<400> SEQUENCE: 43
ttgccgccag aacacaattt atgtgtcctc agaagctaac catctcctgg tttgccatcg     60
ttttgctggt gtctccactc atggccatgt gggagctgga aaagacgtt tatgttgtag    120 aggtggactg gactcccgat gcccctggag aaacagtgaa cctcacctgt gacacgcctg    180
aagaagatga catcacctgg acctcagacc agagacatgg agtcataggc tctggaaaga    240
ccctgaccat cactgtcaaa gagtttctag atgctggcca gtacacctgc cacaaaggag    300
gcgagactct gagccactca catctgctgc tccacaagaa ggaaaatgga atttggtcca    360
ctgaaatttt aaaaaatttc aaaaacaaga cttttcctga gtgtgaagca ccaaattact    420
ccggacggtt cacgtgctca tggctggtgc aaagaaacat ggacttgaag ttcaacatca    480
agagcagtag cagttcccct gactctcggg cagtgacatg tggaatggcg tctctgtctg    540
cagagaaggt cacactggac caagggact atgagaagta ttcagtgtcc tgccaggagg    600
atgtcacctg cccaactgcc gaggagaccc tgcccattga actggcgttg gaagcacggc    660
agcagaataa atatgagaac tacagcacca gcttcttcat cagggacatc atcaaaccag    720
acccgcccaa gaacttgcag atgaagcctt tgaagaactc acaggtggag gtcagctggg    780
agtaccctga ctcctggagc actccccatt cctacttctc cctcaagttc tttgttcgaa    840
tccagcgcaa gaaagaaaag atgaaggaga cagaggaggt gtgtaaccag aaaggtgcgt    900
tcctcgtaga agacatctct ccgaagtcc aatgcaaagg cgggaatgtc tgcgtgcaag    960
ctcaggatcg ctattacaat tcctcatgca gcaagtgggc atgtgttccc tgcagggtcc   1020
gatcctagaa ataacttgtt tattgcag                                      1048
```

```
<210> SEQ ID NO 44
<211> LENGTH: 8
<212> TYPE: DNA
<213> ORGANISM: Artificial Sequence
<220> FEATURE:
<223> OTHER INFORMATION: modified TATA box

<400> SEQUENCE: 44 agtgcccg                                                                 8

<210> SEQ ID NO 45
<211> LENGTH: 8
<212> TYPE: DNA
<213> ORGANISM: Artificial Sequence
<220> FEATURE:
<223> OTHER INFORMATION: modified TATA box

<400> SEQUENCE: 45 tattcccg                                                                 8

<210> SEQ ID NO 46
<211> LENGTH: 10
<212> TYPE: DNA
<213> ORGANISM: Artificial Sequence
<220> FEATURE:
<223> OTHER INFORMATION: modified CAAT box

<400> SEQUENCE: 46
ttccgtggcg                                                              10
```